US009580427B2

(12) United States Patent
Taunton, Jr. et al.

(10) Patent No.: US 9,580,427 B2
(45) Date of Patent: Feb. 28, 2017

(54) KINASE INHIBITORS

(75) Inventors: John William Taunton, Jr., San Francisco, CA (US); Jesse McFarland, Oakland, CA (US); Shyam Krishnan, San Francisco, CA (US); Jonathan Choy, Lafayette, CA (US)

(73) Assignee: The Regents of the University of California, Oakland, CA (US)

( * ) Notice: Subject to any disclaimer, the term of this patent is extended or adjusted under 35 U.S.C. 154(b) by 289 days.

(21) Appl. No.: 14/118,541

(22) PCT Filed: May 16, 2012

(86) PCT No.: PCT/US2012/038214
§ 371 (c)(1),
(2), (4) Date: Jul. 6, 2016

(87) PCT Pub. No.: WO2012/158843
PCT Pub. Date: Nov. 22, 2012

(65) Prior Publication Data
US 2014/0323464 A1      Oct. 30, 2014

Related U.S. Application Data

(60) Provisional application No. 61/487,233, filed on May 17, 2011.

(51) Int. Cl.
| C07D 487/04 | (2006.01) |
| A61K 31/519 | (2006.01) |
| A61P 35/02 | (2006.01) |
| A61P 35/04 | (2006.01) |
| C07D 471/04 | (2006.01) |
| C07D 215/54 | (2006.01) |
| C07D 235/08 | (2006.01) |
| C07D 403/04 | (2006.01) |
| C07D 405/12 | (2006.01) |
| C07D 405/14 | (2006.01) |
| C07D 417/12 | (2006.01) |
| C07D 239/48 | (2006.01) |
| C07D 239/94 | (2006.01) |
| C07D 401/12 | (2006.01) |
| C07D 401/14 | (2006.01) |
| C07D 403/12 | (2006.01) |
| A61P 35/00 | (2006.01) |

(52) U.S. Cl.
CPC ......... *C07D 487/04* (2013.01); *C07D 215/54* (2013.01); *C07D 235/08* (2013.01); *C07D 239/48* (2013.01); *C07D 239/94* (2013.01); *C07D 401/12* (2013.01); *C07D 401/14* (2013.01); *C07D 403/04* (2013.01); *C07D 403/12* (2013.01); *C07D 405/12* (2013.01); *C07D 405/14* (2013.01); *C07D 417/12* (2013.01); *C07D 471/04* (2013.01)

(58) Field of Classification Search
CPC .......................... C07D 487/04; A61K 31/519
USPC ............................................. 544/262, 262.1
See application file for complete search history.

(56) References Cited

U.S. PATENT DOCUMENTS

| 4,721,710 A | 1/1988 | Bernhart et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 6,225,346 B1 | 5/2001 | Tang et al. |
| 6,331,555 B1 | 12/2001 | Hirth et al. |
| 6,410,486 B2 | 6/2002 | Wetterich et al. |
| 2004/0006083 A1 | 1/2004 | Hirst et al. |
| 2005/0026945 A1 | 2/2005 | Kafka et al. |
| 2005/0065176 A1 | 3/2005 | Field et al. |
| 2006/0079494 A1 | 4/2006 | Santi et al. |
| 2007/0149464 A1 | 6/2007 | Billen et al. |
| 2007/0149550 A1 | 6/2007 | Billen et al. |
| 2008/0146643 A1 | 6/2008 | Billen et al. |

(Continued)

FOREIGN PATENT DOCUMENTS

| CN | 101880243 A | 11/2010 |
| EP | 0908457 A1 | 4/1999 |

(Continued)

OTHER PUBLICATIONS

Bernhart et al., "Synthesis and Antiarrhythmic Activity of New [(Diakylamino)alkyl]pyridylacetamides", *J. Med. Chem.*, 1983, 26:451-455.

(Continued)

*Primary Examiner* — Susanna Moore
(74) *Attorney, Agent, or Firm* — Mintz Levin Cohn Ferris Glovsky and Popeo, P.C.

(57) ABSTRACT

Provided herein are compounds such as the compounds having the structure of Formula (XI)

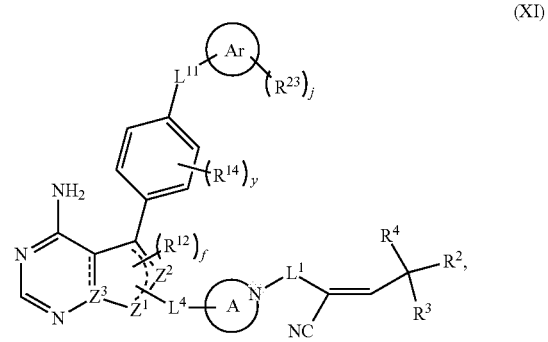

and methods of using the same, such as methods of inhibiting kinases.

12 Claims, No Drawings

(56) References Cited

U.S. PATENT DOCUMENTS

| | | |
|---|---|---|
| 2008/0176865 A1 | 7/2008 | Billen et al. |
| 2010/0152143 A1 | 6/2010 | Priebe et al. |

FOREIGN PATENT DOCUMENTS

| | | |
|---|---|---|
| EP | 2508509 A1 | 10/2012 |
| JP | 42008308 B4 | 4/1967 |
| JP | 56-063950 A | 5/1981 |
| JP | 02-001450 A | 1/1990 |
| JP | 04177244 A | 6/1992 |
| JP | 2005-239657 A | 9/2005 |
| WO | WO 96/05309 A2 | 2/1996 |
| WO | WO 03/050080 A1 | 6/2003 |
| WO | WO 03/082807 A2 | 10/2003 |
| WO | WO 2004/016259 A1 | 2/2004 |
| WO | WO 2005/023773 A1 | 3/2005 |
| WO | WO 2005/030184 A2 | 4/2005 |
| WO | WO 2006/134468 A1 | 12/2006 |
| WO | WO 2008/005954 A2 | 1/2008 |
| WO | WO 2008/039218 A2 | 4/2008 |
| WO | WO 2008/061740 A1 | 5/2008 |
| WO | WO 2008/072053 A2 | 6/2008 |
| WO | WO 2011/060440 A2 | 5/2011 |
| WO | WO 2011/068244 A1 | 6/2011 |
| WO | WO 2012/158764 A1 | 11/2012 |
| WO | WO 2012/158810 A1 | 11/2012 |

OTHER PUBLICATIONS

Burini et al., "Efficient Synthesis of 4-Cyano 2,3-Dihydrooxazoles by Direct Amination of 2-Alkylidene 3-Oxo Nitriles", *SYNLETT*, 2005, 17:2673-2675.

Elliot et al., "The Pyrethrins and Related Compounds. Part XVIII. Insecticidal 2,2-Dimethylcyclopropanecarboxylates with New Unsaturated 3-Substituents", *Journal of the Chemical Society, Perkin I*, 1974, 21:2470-2474.

Fioravanti et al., "Parallel Solution-Phase Synthesis of Acrylonitrile Scaffolds Carrying L-α-Amino Acidic or D-Glycosyl Residues", *J. Comb. Chem.*, 2006, 8:808-811.

Gyoung et al., "Regiospecific synthesis of 2-allylated-5-substituted tetrazoles via palladium-catalyzed reaction of nitriles, trimethylsilyl azide, and allyl acetates", *Tetrahedron Letters*, 2000, 4193-4196.

Kamijo et al., "Tetrazole synthesis via the palladium-catalyzed three component coupling reaction", *Molecular Diversity*, 2003, 6:181-192.

European Search Report dated Nov. 19, 2014 in European Patent Application No. 12785097.2, 7 pages.

Blair et al., "Structure-guided development of affinity probes for tyrosine kinases using chemical genetics", *Nature Chemical Biology* 2007, 3(4):229-238.

De Costa et al, "Synthesis and Biological Evaluation of Conformationally Restricted 2-(1-Pyrrolidinyl)-$N$-[2-(3,4-dicholorphenyl)ethyl]-$N$-methylethylenediamines as o Recepter Ligands. 1. Pyrrolidine, Piperidine, Homopiperidine, and Tetrahydroisoquinoline Classes", *J. Med. Chem.* 1992, 35:4334-4343.

Honigberg et al., "The Bruton tyrosine kinase inhibitor PCI-32765 blocks B-cell activation and is efficacious in models of autoimmune disease and B-cell malignancy", *Proc Natl Acad Sci* 2010, 107(29):13075-13080.

Karaman et al., "A quantitative analysis of kinase inhibitor selectivity", *Nature Biotechnology* 2008, 26(1):127-132.

Pan et al., "Discovery of Selective Irreversible Inhibitors for Bruton's Tyrosine Kinase", *ChemMedChem* 2007, 2:58-61.

Yang et al., "Kinetic and Mechanistic Studies of Geometrical Ismerism in Neutral Square-Planar Methylpalladium Complexes Bearing Unsymmetrical Bidentate Ligands of α-Aminoaldimines", *Inorganic Chemistry* 2009, 48:7639-7644.

International Preliminary Report on Patentability and Written Opinion dated Nov. 19, 2013 for International Application No. PCT/US2012/038214, 9 pages.

International Search Report and Written Opinion dated Feb. 3, 2013 for International Application No. PCT/US2012/038214, 14 pages.

KINASE INHIBITORS

CROSS-REFERENCE TO RELATED APPLICATIONS

This application claims the benefit of U.S. Provisional Application No. 61/487,233, filed May 17, 2011, which is incorporated herein by reference in its entirety and for all purposes.

FEDERALLY SPONSORED RESEARCH AND DEVELOPMENT

This invention was made with government support under grant No. GM071434 awarded by the National Institutes of Health. The government has certain rights in this invention.

FIELD OF INVENTION

Provided herein are novel compounds, pharmaceutical compositions containing the same and methods of treating diseases, including diseases mediated by kinases and methods of preparing such compounds.

BACKGROUND OF THE INVENTION

The human genome contains at least 500 genes encoding protein kinases. In fact, protein kinase genes constitute about 2% of all human genes. Protein kinases modify up to 30% of all human proteins and regulate the majority of cellular pathways, particularly those pathways involved in signal transduction.

Because of the profound effects on cells, the activities of protein kinases are highly regulated. Indeed, unregulated kinase activity frequently causes disease related to control of cell growth, cell movement and cell death, particularly cancer. A large body of research is currently being conducted to find drugs capable of inhibiting specific kinases to treat a variety of diseases. Some such drugs are already in clinical use, including Gleevec (imatinib) and Iressa (gefitinib). To increase potency and selectivity, irreversible electrophilic inhibitors, which form a covalent bond with a cysteine in the kinase active site, have been developed. Several of these irreversible kinase inhibitors are currently in clinical trials (e.g., neratinib, tovok). Inhibition of proteins through irreversible binding of an inhibitor to the protein, however, often leads to toxicity and/or immunogenic problems when used to treat diseases. Therefore, reversible kinase inhibitors are needed to inhibit kinases while minimizing the risk of toxicity. The present invention addresses these and other needs in the art.

BRIEF SUMMARY OF THE INVENTION

In a first aspect, compounds are provided having the structure of Formula I:

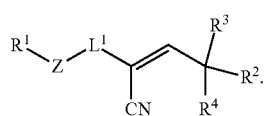

(I)

In Formula I, $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, -$L^1$-Z—$R^1$, $L^1$-$R^1$ and/or $R^1$ is/are generally designed to fit within a kinase ATP binding site and/or bind to amino acids within the kinase ATP binding site (e.g. a kinase ATP binding site moiety). In one embodiment, $R^1$ is substituted or unsubstituted alkenyl or substituted or unsubstituted alkynyl. In another embodiment, $R^1$ is substituted or unsubstituted saturated alkyl.

$L^1$ is a bond, —C(O)—, —N($L^2R^5$)C(O)—, —OC(O)—, —S(O)$_n$—, —(O$L^2R^5$)OP(O)—, —N($L^2R^5$)SO$_2$—, —(N($L^2R^5$))NP(O)—, substituted or unsubstituted alkylene, substituted or unsubstituted heteroalkylene, substituted or unsubstituted cycloalkylene, substituted or unsubstituted heterocycloalkylene,

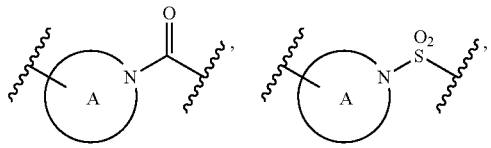

substituted or unsubstituted arylene, or substituted or unsubstituted heteroarylene. The symbol n is 0, 1 or 2. In some embodiments, $L^1$ is a bond. In another embodiment, where $L^1$ is a bond, $R^1$ is not a substituted or unsubstituted heteroaryl where the point of attachment to the remainder of the compound is a heteroatom. Ring A is substituted or unsubstituted heterocycloalkylene or substituted or unsubstituted heteroarylene. Z is a bond, —O—, —N($R^a$)—, —S—, —SO—, —SO$_2$—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. $R^a$ is hydrogen, unsubstituted alkyl. In some embodiments, where $L^1$ is —N($L^2R^5$)C(O)—, —OC(O)—, —S(O)$_n$—, —(O$L^2R^5$)OP(O)—, —N($L^2R^5$)SO$_2$—, or —(N($L^2R^5$))NP(O)—, the atom on the left hand side is attached to Z and the atom on the right hand side is attached to the α-carbon (e.g. in —N($L^2R^5$)C(O)—, N is attached to Z and C(O) is attached to the carbon substituted with cyano group).

$L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^5$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $L^1$ is —(N($L^2R^5$))NP(O)—, —N($L^2R^5$)C(O)—, or —N($L^2R^5$)SO$_2$—, and $R^5$ and $R^1$ are optionally joined together to form a substituted or unsubstituted heterocycloalkyl, or substituted or unsubstituted heteroaryl.

$R^2$ and $R^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^2$ and $R^3$ are optionally joined together (with the carbon to which they are attached) to form a substituted or unsubstituted cycloalkyl or substituted or unsubstituted heterocycloalkyl. In one embodiment, $R^2$ and $R^3$ are independently substituted or unsubstituted alkenyl or substituted or unsubstituted alkynyl. In another embodiment, $R^2$ and $R^3$ are independently substituted or unsubstituted saturated alkyl.

$R^4$ is independently hydrogen, $-NR^{4A}R^{4B}$, $-OR^{4A}$, $-SR^{4A}$, $-CN$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^4$ is independently hydrogen, $-NR^{4A}R^{4B}$, $-OR^{4A}$, $-CN$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In one embodiment, $R^4$ is substituted or unsubstituted alkenyl or substituted or unsubstituted alkynyl. In another embodiment, $R^4$ is substituted or unsubstituted saturated alkyl. $R^{4A}$ and $R^{4B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In one embodiment, $R^{4A}$ and $R^{4B}$ are independently substituted or unsubstituted alkenyl or substituted or unsubstituted alkynyl. In another embodiment, $R^{4A}$ and $R^{4B}$ are independently substituted or unsubstituted saturated alkyl.

Pharmaceutically acceptable salts of the compounds of Formula (I), and embodiments thereof, are included herein.

In another aspect, methods of inhibiting protein kinases are provided. The methods include contacting a protein kinase with an effective amount of a compound provided herein.

The compound may have the structure of Formula I (or any of the embodiments thereof described herein).

In another aspect, a method of treating a disease associated with kinase activity in a subject in need of such treatment. The method includes administering to the subject an effective amount of a compound provided herein. The compound may have the structure of Formula I (or any of the embodiments thereof described herein).

In another aspect, compound of Formula (I) (or any embodiments thereof described herein) for use as medicaments is provided.

In yet another aspect, processes for preparing compounds that form a reversible covalent bond, preferably with a cysteine residue of said kinase, is provided.

In yet another aspect, processes for preparing compounds of Formula (I) (or any embodiments thereof described herein) are provided.

DETAILED DESCRIPTION OF THE INVENTION

I. Definitions

Unless otherwise stated, the following terms used in the specification and claims are defined for the purposes of this application and have the following meaning. The abbreviations used herein have their conventional meaning within the chemical and biological arts. The chemical structures and formulae set forth herein are constructed according to the standard rules of chemical valency known in the chemical arts.

The term "alkyl," by itself or as part of another substituent, means, unless otherwise stated, a straight (i.e. unbranched) or branched chain, or combination thereof, which may be fully saturated (referred to herein as a "saturated alkyl"), mono- or polyunsaturated and can include di- and multivalent radicals, having the number of carbon atoms designated (i.e. $C_1$-$C_{10}$ means one to ten carbons, $C_1$-$C_6$ means one to six carbons). Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. The term "alkyl" includes saturated alkyl, alkenyl and alkynyl. A saturated alkyl may have from 1 to 10 or 1 to 6 carbon atoms. The term "alkenyl" by itself or as part of another substituent, means, unless otherwise stated, a straight (i.e. unbranched) or branched hydrocarbon chain (e.g. two to ten, or two to six carbon atoms) having one or more double bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), and the like. The term "alkynyl" by itself or as part of another substituent, means, unless otherwise stated, a straight (i.e. unbranched) or branched hydrocarbon chain (e.g. two to ten or two to six carbon atoms) having one or more triple bonds. Examples of alkynyl groups include, but are not limited to, ethynyl, 1- and 3-propynyl, 3-butynyl, and the like.

An "alkoxy" is an alkyl attached to the remainder of the molecule via an oxygen linker (—O—). An "alkylthio" is an alkyl attached to the remainder of the molecule via an sulfer linker (—S—).

A "haloalkoxy" is an alkoxy substituted with a halogen. When the halogen is a fluoro, it is also referred to herein as a "fluoroalkoxy."

"Alkoxycarbonyl" is an alkyl attached to the remained of the molecule via a oxycarbonyl linker (—C(O)O—) and includes methoxycarbonyl, ethoxycarbonyl, and the like.

"Aminocarbonyl" means a —CONRR' radical where R is independently hydrogen, unsubstituted alkyl, or alkyl substituted with a substituent group and R' is hydrogen, unsubstituted alkyl, unsubstituted cycloalkyl, unsubstituted cycloalkylalkyl, unsubstituted aryl, unsubstituted aralkyl, unsubstituted heteroaryl, unsubstituted heteroaralkyl, unsubstituted heterocycloalkyl, unsubstituted heterocyclylalkyl, or alkyl substituted with a substituent group, each as defined herein and wherein the aryl, heteroaryl, or heterocyclyl ring either alone or part of another group e.g., aralkyl, is optionally substituted with one, two, or three substituent group(s). Likewise, "aminosulfonyl" means a —SO$_2$NRR' radical where R and R' are as defined for aminocarbonyl.

The term "alkylene", "alkenylene, and "alkynylene" by itself or as part of another substituent means a divalent radical derived from an alkyl, alkenyl, or alkynyl as exemplified, but not limited, by methylene, ethylene, —CH$_2$CH$_2$CH$_2$CH$_2$—, vinylene and the like. Preferably an alkylene may be a unsubstituted saturated ($C_1$-$C_6$) alkylene.

The term "amino" as used herein means a —NH$_2$.

The term "carboxy" as used herein means —COOH (including pharmaceutically acceptable salts thereof).

The term "heteroalkyl," by itself or in combination with another term, means, unless otherwise stated, a stable straight or branched chain or combinations thereof, consisting of at least one carbon atom and at least one heteroatom selected from the group consisting of O, N, P, Si and S or CO and wherein the nitrogen and sulfur atoms may optionally be oxidized and the nitrogen heteroatom may optionally be quaternized. The heteroatom(s) O, N, P and S and Si or CO may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). As described above, heteroalkyl groups, as used herein, include those groups that are attached to the remainder of the molecule through a heteroatom. A heteroalkyl may be one to six carbon atoms and contains 1-3 heteroatoms independently selected from N, O, or S.

The terms "cycloalkyl" and "heterocycloalkyl," by themselves or in combination with other terms, represent, unless otherwise stated, non-aromatic cyclic versions of "alkyl" and "heteroalkyl", respectively (e.g. having 4 to 8 ring atoms or 3 to 6 carbon atoms, a heterocycloalkyl may have 4-8 ring atoms with one or two heteroatoms independently selected from N, O or S). Additionally, for heterocycloalkyl, a heteroatom can occupy the position at which the heterocycle is attached to the remainder of the molecule. Heterocycloalkyls may include one or two ring heteroatoms selected from N, O, or S(O)$_{n'}$, where n' is an integer from 0 to 2, the remaining ring atoms being carbon. The heterocycoalkyl or cycloalkyl ring is optionally fused to one or more aryl or heteroaryl rings as defined herein (e.g. where the aryl and heteroaryl rings are monocyclic). The heterocycloalkyl or cycloalkyl ring fused to monocyclic aryl or heteroaryl ring may be referred to in this application as "bicyclic heterocycloalkyl" ring or a "bicyclic cycloalkyl" ring. Additionally, one or two ring carbon atoms in the heterocycloalkyl ring can optionally be replaced by a —CO— group. More specifically the term heterocycloalkyl includes, but is not limited to, pyrrolidino, piperidino, homopiperidino, 2-oxopyrrolidinyl, 2-oxopiperidinyl, morpholino, piperazino, tetrahydropyranyl, thiomorpholino, dihydroindolyl, and the like. When the heterocycloalkyl ring is unsaturated it can contain one or two ring double bonds provided that the ring is not aromatic. When the heterocycloalkyl group contains at least one nitrogen atom, it may also be referred to herein as heterocycloamino and is a subset of the heterocycloalkyl group. When the heterocycloalkyl group is a saturated ring and is not fused to aryl or heteroaryl ring as stated above, it may be referred to herein as a saturated monocyclic heterocycloalkyl. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent means a divalent radical derived from a cycloalkyl and heterocycloalkyl, respectively.

"Heterocycloamino" as used herein means a saturated or unsaturated monovalent monocyclic group (e.g. having 4 to 8 ring atoms) in which one or more (e.g. 2) ring atoms is a heteroatom selected from N, O, or S(O)$_{n''}$, where n'' is an integer from 0 to 2, the remaining ring atoms being carbon provided that at least one of the ring atoms is nitrogen. Additionally, one or more (e.g. 2) ring carbon atoms in the heterocycloamino ring can optionally be replaced by a —CO— group. When the heterocycloamino ring is unsaturated it can contain one or more (e.g. two) ring double bonds provided that the ring is not aromatic. Unless otherwise stated, the heterocyloamino ring can optionally be substituted with one, two, or three substituents (e.g. independently selected from saturated unsubstituted alkyl, hydroxyl, saturated unsubstituted alkoxy, amino, saturated unsubstituted alkylamino, or saturated unsubstituted dialkylamino). Heterocycloamino is a subset of heterocycle defined above.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$) alkyl" is meant to include, but not be limited to, fluoromethyl, difluoromethyl, trifluoromethyl, 2,2,2-trifluoroethyl, 4-chlorobutyl, 3-bromopropyl, and the like.

The term "acyl" means —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl or substituted or unsubstituted heteroaryl.

The term "aryl" means, unless otherwise stated, an aromatic substituent which can be a single ring or multiple rings (preferably from 1 to 3 rings) which may be fused together (i.e. a fused ring aryl) or linked covalently. A fused ring aryl refers to multiple rings fused together wherein at least one of the fused rings is an aryl ring (e.g. phenyl, 1-naphthyl, 2-naphthyl, or 4-biphenyl). When two rings are fused together they may be referred to herein as fused bicylic ring. When aryl is monocyclic or fused bicyclic ring of 6 to 10 ring atoms and is completely aromatic it is referred to herein as monocyclic or fused bicyclic (C$_6$-C$_{10}$) aromatic aryl.

The term "heteroaryl" refers to aryl groups (or rings) that contain from one to more (e.g. 4) heteroatoms selected from N, O, and S, wherein the nitrogen and sulfur atoms are optionally oxidized, and the nitrogen atom(s) are optionally quaternized, the remaining ring atoms being carbon. The heteroaryl may be a monovalent monocyclic, bicyclic, or tricyclic (e.g. monocyclic or bicyclic) aromatic radical of 5 to 14 (e.g. 5 to 10) ring atoms where one or more, (e.g. one, two, or three) ring atoms are heteroatom selected from N, O, or S. Examples include, but are not limited to, thienyl, isoindolyl, benzoxazolyl, pyridazinyl, triazolyl, tetrazolyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, 2-benzimidazolyl, 5-indolyl, 1-isoquinolyl, 5-isoquinolyl, 2-quinoxalinyl, 5-quinoxalinyl, 3-quinolyl, and 6-quinolyl. Thus, the term "heteroaryl" includes fused ring heteroaryl groups (i.e. multiple rings fused together wherein at least one of the fused rings is a heteroaromatic ring). When two rings are fused together they are may be referred to herein as fused bicylic ring. A 5,6-fused ring heteroaryl refers to two rings fused together, wherein one ring has 5 members and the other ring has 6 members, and wherein at least one ring is a heteroaryl ring. Likewise, a 6,6-fused ring heteroaryl refers to two rings fused together, wherein one ring has 6 members and the other ring has 6 members, and wherein at least one ring is a heteroaryl ring. And a 6,5-fused ring heteroaryl refers to two rings fused together, wherein one ring has 6 members and the other ring has 5 members, and wherein at least one ring is a heteroaryl ring. A heteroaryl group can be attached to the remainder of the molecule through a carbon or heteroatom. The term "monocyclic or fused bicyclic 5 to 10 membered aromatic heteroaryl" as used herein means a moncyclic or fused aromatic ring(s) containing (e.g. one to three) heteroatoms independently selected from N, O or S, the remaining ring atoms being C. An "arylene" and a "heteroarylene," alone or as part of another substituent means a divalent radical derived from an aryl and heteroaryl, respectively.

The terms "arylalkyl" and "heteroarylalkyl" is meant to include those radicals in which an aryl group or a heteroaryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom. The term "carbonyl" as used herein refers to a —C(O)— group.

"Optional" or "optionally" means that the subsequently described event or circumstance may but need not occur, and that the description includes instances where the event or circumstance occurs and instances in which it does not. For example, "heterocycloalkyl group optionally substituted with an alkyl group" means that the alkyl may but need not be present, and the description includes situations where the heterocycloalkyl group is substituted with an alkyl group and situations where the heterocycloalkyl group is not substituted with alkyl.

The term "alkylsulfonyl" as used herein means a moiety having the formula —S(O$_2$)—R', where R' is an alkyl group as defined above. R' may have a specified number of carbons (e.g. "C$_1$-C$_4$ alkylsulfonyl").

Each of the above terms (e.g., "alkyl," "heteroalkyl," "aryl" and "heteroaryl") can be substituted with substituents listed below. When "alkyl," "heteroalkyl," "aryl" and "heteroaryl" are substituted they are referred to herein as "substituted alkyl", "substituted heteroalkyl", "substituted aryl" and "substituted heteroaryl". For sake of clarity, when "alkyl," "heteroalkyl," "aryl" and "heteroaryl" are unsubstituted they are referred to herein as "unsubstituted alkyl", "unsubstituted heteroalkyl", "unsubstituted aryl" and "unsubstituted heteroaryl". Additionally, since "alkyl," "heteroalkyl," "aryl" and "heteroaryl" contain saturated and unsaturated groups, they may be additionally qualified where only one of these encompassed groups is intended. For example, when "alkyl" is referred to as "unsubstituted saturated alkyl," the terms cover only alkyl which is saturated and unsubstituted. The term "unsubstituted saturated (C$_1$-C$_6$) haloalkyl" refers to "haloalkyl" that has only one to six carbon atoms, is substituted with only halogen and is saturated. Similarly, "unsubstituted saturated heteroalkyl" means heteroalkyl that is saturated and unsubstituted with substituents listed below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", R', —OC(O)R', —C(O)R', —CO$_2$R', —CONR'R", —OC(O)NR'R", —NR"C(O)R', —NR'—C(O)NR"R'", —NR"C(O)$_2$R', —NR'—C(NR'R"R'")=NR"", —NR—C(NR'R")=NR"", —S(O)R', —S(O)$_2$R', —S(O)$_2$NR'R", —NRSO$_2$R', —CN and —NO$_2$, (e.g. —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR'—C(NR'R"R'")=NR"", —NR—C(NR'R")=NR"", —S(O)R', —S(O)$_2$R', —S(O)$_2$NR'R", —NRSO$_2$R', —CN and —NO$_2$), —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR'—C(NR'R"R'")=NR"", —NR—C(NR'R")=NR"", —S(O)R', —S(O)$_2$R', —S(O)$_2$NR'R", —NRSO$_2$R', —CN and —NO$_2$, in a number ranging from zero to (2m'+1), where m' is the total number of carbon atoms in such radical. R', R", R'" and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy or thioalkoxy groups, or arylalkyl groups. Preferably R', R", R'" and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and may be selected from, for example: halogen, —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR'R", —NR"C(O)$_2$R', —NR—C(NR'R"R'")=NR"", —NR'—C(NR'R")=NR'", —S(O)R', —S(O)$_2$R', —S(O)$_2$NR'R", —NR'SO$_2$R', —CN and —NO$_2$, —R', —N$_3$, —CH(Ph)$_2$, fluoro(C$_1$-C$_4$) alkoxy, and fluoro(C$_1$-C$_4$) alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl. The term "wherein the heterocycloalkyl, aryl or heteroaryl, whether attached directly or indirectly, are substituted . . . " as used herein means that all of the above mentioned rings are included whether they are bonded directly or via a linking group (e.g., all rings whether they are attached directly or via O, N, or S . . . etc., in OR', —NR'R", or —SR' . . . etc, can be substituted).

The term "electron withdrawing group" ("EWG") refers to a chemical substituent that modifies the electrostatic forces acting on a nearby chemical reaction center by withdrawing negative charge from that chemical reaction center. Thus, electron withdrawing groups draw electrons away from a reaction center. As a result, the reaction center is fractionally more positive than it would be in the absence of the electron-withdrawing group. In some embodiments, the chemical reaction center is one of the two carbons forming the carbon-carbon double bond (olefin). In some embodiments, the chemical reaction center is the olefin carbon attached to EWG. The electron withdrawing group functions to draw charge or electrons away from this olefin carbon thereby making the olefin carbon electron deficient (relative to the absence of the electron withdrawing group). The electron deficient olefin carbon is thereby rendered more reactive toward electron rich chemical groups, such as the sulfhydryl of a kinase active site cysteine.

Unless otherwise stated, the term "heteroatom" or "ring heteroatom" is meant to include oxygen (O), nitrogen (N), sulfur (S), phosphorus (P), and silicon (Si) (e.g. nitrogen, oxygen, sulfur).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ (e.g. $C_4$-$C_8$ cycloalkyl), and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ (e.g. $C_5$-$C_7$) cycloalkyl, and each substituted or unsubstituted heterocycloalkyl is a substituted or unsubstituted 4 to 7, preferably 5 to 7 membered heterocycloalkyl.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19) and Additional information on suitable pharmaceutically acceptable salts can be found in *Remington's Pharmaceutical Sciences,* 17th ed., Mack Publishing Company, Easton, Pa., 1985, which is incorporated herein by reference). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

The present invention also includes the prodrugs of compounds of Formula (I). The term prodrug is intended to represent covalently bonded carriers, which are capable of releasing the active ingredient of Formula (I) when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (I) include compounds wherein a hydroxyl, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxyl or amino functional groups in compounds of Formula (I)), amides (e.g., trifluoroacetylamino, acetylamino, and the like), and the like. Prodrugs of compounds of Formula (I) are also within the scope of this invention.

The compounds of the present invention may have asymmetric centers and/or geometric isomers. Compounds of the present invention containing an asymmetrically substituted atom may be isolated in optically active or racemic forms. It is well known in the art how to prepare optically active forms, such as by resolution of materials. All chiral, diastereomeric, racemic forms are within the scope of this invention, unless the specific stereochemistry or isomeric form is specifically indicated. All possible tautomers and cis and trans isomers, as individual forms and mixtures thereof are within the scope of this invention. Additionally, as used herein the term alkyl includes all the possible isomeric forms of said alkyl group albeit only a few examples are set forth. Furthermore, when the cyclic groups such as aryl, heteroaryl, heterocycloalkyl are substituted, they include all the positional isomers albeit only a few examples are set forth. Furthermore, all polymorphic forms, including amorphous form, and hydrates of a compound of Formula (I) are within the scope of this invention.

Certain compounds of the present invention possess asymmetric carbon atoms (optical centers) or double bonds; the racemates, diastereomers, tautomers, geometric isomers and individual isomers are encompassed within the scope of the present invention. The compounds of the present invention do not include those which are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

Where a substituent of a compound provided herein is "R-substituted" (e.g. $R^7$-substituted), it is meant that the substituent is substituted with one or more of the named R groups (e.g. $R^7$) as appropriate. Each appearance of the substituent may be different. In some embodiments, the substituent is substituted with only one of the named R groups. Each of the numbered R substituents provided herein may be alternatively referred to as a primed number such as a first prime ('), a second prime ("), a third prime ("') and so on. For example, $R^7$ may be alternatively referred to as $R^{7'}$, $R^{7''}$, $R^{7'''}$ and so on. Unless otherwise noted, the primed number of the R substituent is accorded the same definition as the R substituent itself, but where the primed number of the R substituent is optionally different that the R substituent itself when both appear in a compound of Formula. For example, $R^7$ and $R^{7'}$, unless otherwise stated, are independently chosen form the same Markush group definition.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The terms "treating" or "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer, in inhibiting its growth and or causing remission of cancer.

An "effective amount" of a compound of Formula I is an amount sufficient to contribute to the treatment, prevention, or reduction of a symptom or symptoms of a disease, or to inhibit the activity or a protein kinase relative to the absence of the kinase inhibitor. Where recited in reference to a disease treatment, an "effective amount" may also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) a disease, or reducing the likelihood of the onset (or reoccurrence) of a disease or its symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an osteoclast or leukocyte relative to the absence of the antagonist.

The terms "kinase," "protein kinase" and the like, refer to an enzyme that transfers a phosphate group from a donor molecule (e.g. ATP) to a substrate. The process of transferring a phosphate group from a donor to a substrate is conventionally known as phosphorylation. The term "substrate" in the context of protein phosphorylation refers to a compound (e.g. protein) which accepts a phosphate group and is thus phosphorylated. The protein sequences of the known human protein kinases may be aligned using standard protein alignment techniques familiar to a person skilled in the art. Using such a sequence alignment in conjunction with structural information regarding the known binding sites of small molecule kinase inhibitors that bind to the ATP binding site of kinases, it is possible to identify the residues within each kinase that constitute the ATP binding site. Kinases may then be grouped based upon the presence of a non-conserved cysteine residue within the ATP binding site which may be targeted for reversible covalent inhibition. These cysteine residues are referred to herein as Cys 1-Cys 27. Each of these targetable cysteine residues may be found in one or more kinase sequences. Table 1 below lists the human kinases by their targetable cysteine residue Cys 1-Cys 27. The general location of each of the cysteine residues is indicated in the table below with the designated structural elements. The sequence numbers that correspond to Cys 1-Cys 27 for three representative kinase sequences are also provided.

TABLE 1

| Generic Numbering | Structural Element | Abl X-ray PDB 2GQG Seq Code P00519 | EGFR X-ray PDB 2ITV Seq Code P00533 | c-Kit X-ray PDB 1T46 Seq Code P10721 | Kinase |
|---|---|---|---|---|---|
| CYS 1 | P-loop | 250 | 720 | 597 | CK1G1, CK1G2, CK1G3, CRIK, ERK3, ZAP70 |
| CYS 2 | P-loop | 251 | 721 | 598 | ROR1 |
| CYS 3 | P-loop | 252 | 722 | 599 | FGFR1, FGFR2, FGFR3, FGFR4, FGR, LIMK1, PINK1, SRC, TNK1, YES |
| CYS 4 | P-loop | 253 | 723 | 600 | CHK2, MAP2K7, SURTK106 |
| CYS 5 | P-loop | 255 | 725 | 602 | ACTR2, ACTR2B, IRAK1, MET, NEK10, VRK1 |
| CYS 6 | beta2 | 256 | 726 | 603 | MAP3K1, MSK1_domain2, MSK2_domain2, NEK2, PLK1, PLK2, PLK3, RSK1_domain2, RSK2_domain2, RSK3_domain2, RSK4_domain2, SGK269 |
| CYS 7 | beta3 | 269 | 743 | 621 | HER3ERBB3 |
| CYS 8 | beta3 | 270 | 744 | 622 | COT, GPRK4, GPRK5, GPRK6, GPRK7, MOK, RHOK, TRB1, TRB2, TRB3, VACAMKL |
| CYS 9 | beta3 | 271 | 745 | 623 | WNK1, WNK2, WNK3, WNK4 |
| CYS 10 | C-helix | 289 | 765 | 643 | AXL, CDC7, MER, RNASEL, SNRK, TYRO3 |
| CYS 11 | C-helix | 290 | 766 | 644 | CAMK2A, CAMK2B, CAMK2D, CAMK2G, CASK, IRAK2, NIK |
| CYS 12 | C-helix | 293 | 769 | 647 | GCK, HPK1, IRAK2, IRAK4, KHS1, KHS2, LOK, MAP2K1, MAP2K2, MAP2K5, MAPKAPK5, MNK1, MNK2, MSK1domain2, MSK2 domain2, MST1, MST2, MST3, MST4, OSR1, PRPK, SGK223, SLK, SLOB, STLK3, YSK1 |
| CYS 13 | beta4 | 299 | 775 | 654 | BUBR1, EGFR, MELK, TBCK, TTBK1, TTBK2 |
| CYS 14 | hinge region | 317 | 792 | 672 | FGFR4, MAPKAPK2, MAPKAPK3, P70S6KB, TTK |
| CYS 15 | hinge region | 318 | 793 | 673 | AAK1, ANPA, ANPB, ARAF, BIKE, BRAF, CDK10, CDK5, CDK9, CDKL1, |

TABLE 1-continued

| Generic Numbering | Structural Element | Abl X-ray PDB 2GQG Seq Code P00519 | EGFR X-ray PDB 2ITV Seq Code P00533 | c-Kit X-ray PDB 1T46 Seq Code P10721 | Kinase |
|---|---|---|---|---|---|
| | | | | | CDKL4, CHK1, CLIK1, CLIK1L, CYGD, CYGF, DLK, FAK, FLT1, FLT3, FLT4, FMS, GAK, GCK, GCN2_domain2, HPK1, HRI, HSER, HUNK, IKKA, IKKB, IKKE, IRE1, IRE2, KDR, KHS1, KHS2, KIT, KSR1, KSR2, LKB1, LMR1, LMR2, LMR3, LOK, LZK, MAP3K4, MELK, MLKL, MST1, MST2, MYO3A, MYO3B, MYT1, NEK1, NEK11, NEK2, NEK3, NEK4, NEK5, NEK9, OBSCN, OBSCN_domain2, PDGFRA, PDGFRB, PEK, PKG1, PKG2, PKR, PLK1, PLK2, PLK3, PLK4, RAF1, RNASEL, ROR2, SGK494, SLK, SPEG, SPEG_domain2, STK33, TAO1, TAO2, TAO3, TBCK, TBK1, TLK1, TLK2, ULK1, ULK2, ULK3, ULK4, WEE1, WEE1B, ZC1HGK, ZC2TNIK, ZC3MINK, ZC4NRK |
| CYS 16 | hinge region | 319 | 794 | 674 | FGR, FLT3, FMS, KIT, RON, SGK396 |
| CYS 17 | hinge region | 322 | 797 | 677 | BLK, BMX, BTK, EGFR, HER2ERBB2, HER4ERBB4, ITK, JAK3_domain2, TEC, TXK |
| CYS 18 | D-helix | 330 | 804 | 759 | ABL, ARG |
| CYS 19 | D-helix | 332 | 806 | 761 | BMPR1A, CDKL3, COT, IRAK1, P38A, P38B, PKCT, TRB2 |
| CYS 20 | E-helix | 354 | 828 | 783 | AMPKA1, AMPKA2, AURA, AURB, AURC, BRSK1, BRSK2, CAMK2A, CAMK2B, CAMK2D, CASK, CCRK, CDC2, CDK2, CDK3, CDK5, CDKL1, CDKL2, CDKL4, CDKL5, CHED, CK2A1, CK2A2, CRK7, MAPKAPK5, MARK1, MARK2, MARK3, MARK4, NEK2, NUAK1, NUAK2, PCTAIRE1, PCTAIRE2, PCTAIRE3, PIM1, PIM2, PIM3, QIK, QSK, SIK, SNRK, TRB1, TRB2, TRB3, TSSK1, TSSK2, TSSK3 |
| CYS 21 | catalytic loop | 359 | 833 | 788 | ANPA, CDKL1, CDKL4, FER, FES, FGFR1, FGFR2, FGFR3, FGFR4, FLT1, FLT3, FLT4, FMS, JAK3_domain2, KDR, KIT, PDGFRA, PDGFRB, PYK2, STLK6 |
| CYS 22 | catalytic loop | 360 | 834 | 789 | BRSK1, BRSK2, GSK3A, GSK3B, SCYL3 |
| CYS 23 | DFG loop | 380 | 854 | 809 | AAK1, BIKE, CDKL1, CDKL2, CDKL3, CDKL4, CDKL5, ERK1, ERK2, ERK7, FLT1, FLT3, FLT4, FUSED, GAK, GSK3A, GSK3B, KDR, KIT, MAP2K1, MAP2K2, MAP2K3, MAP2K4, MAP2K5, MAP2K6, MAP2K7, MAPKAPK5, MNK1, MNK2, NIK, NLK, OBSCN, PBK, PDGFRA, PDGFRB, PKD1, PKD2, PKD3, PRP4, RSK1_domain2, RSK2_domain2, RSK3_domain2, RSK4_domain2, SPEG, SURTK106, TAK1, TGFBR2, ZAK |
| CYS 24 | DFG loop | 385 | 859 | 814 | AKT1, AKT2, AKT3, DMPK1, DMPK2, IRE1, IRE2, LATS1, LATS2, MELK, MOK, MRCKA, MRCKB, NDR1, NDR2, P70S6K, P70S6KB, PAK1, PAK2, PAK3, PAK4, PAK5, PAK6, PINK1, PKCA, PKCB, PKCD, PKCE, PKCG, PKCH, PKCI, PKCT, PKCZ, PKN1, PKN2, PKN3, ROCK1, ROCK2, SCYL2, SGK, SGK2, SGK3, SGK496 |
| CYS 25 | activation loop | 386 | 860 | 815 | BARK1, BARK2, DYRK1A, DYRK1B, DYRK2, DYRK3, DYRK4, HRI, MSSK1, PHKG1, PHKG2, SCYL1, SRPK1, SRPK2, TAK1 |
| CYS 26 | activation loop | 394 | 866 | 821 | IRE2, JNK2, LRRK2, MOS, PKCH, TSSK4, VRK2, VRK3 |
| CYS 27 | activation loop | 399 | 871 | 826 | HIPK1, HIPK2, HIPK3, IKKA, IKKB, ILK, JAK1, LKB1, NRBP1, ROCK1, ROCK2, RSKL1, RSKL2 |

In addition, for a representative number of kinases, Cys residue numbers and the associated UniprotKB sequence identifier are provided below.

| Internal Family ID | Kinase | UniprotKB Sequence ID | Cys Residue Number |
|---|---|---|---|
| Cys 17 | BTK | Q06187 | 481 |
| Cys 17 | JAK3_domain2 | P52333 | 909 |
| Cys 17 | ITK | Q08881 | 442 |
| Cys 17 | EGFR | P00533 | 797 |
| Cys 1 | ZAP70 | P43403 | 346 |
| Cys 12 | IRAK4 | Q9NWZ3 | 240 |
| Cys 21 | FMS | P07333 | 774 |
| Cys 21 | FLT3 | P36888 | 807 |
| Cys 21 | FGFR1 | P11362 | 619 |
| Cys 21 | PYK2 | Q14289 | 545 |
| Cys 3 | SRC | P12931 | 277 |
| Cys 3 | FGFR1 | P11362 | 488 |
| Cys 6 | RSK2_domain2 | P51812 | 15 |
| Cys 6 | NEK2 | P51955 | 22 |

II. Compounds

In a first aspect, compounds are provided having the structure of Formula I:

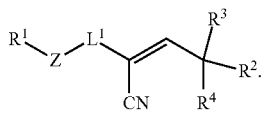

(I)

In some embodiments, the compounds are kinase inhibitors. In Formula I, $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In one embodiment, $R^1$ is substituted or unsubstituted alkenyl or substituted or unsubstituted alkynyl. In another embodiment, $R^1$ is substituted or unsubstituted saturated alkyl. $L^1$-$Z$—$R^1$, $L^1$-$R^1$ and/or $R^1$ may be designed to fit within a kinase ATP binding site and/or bind to amino acids within the kinase ATP binding site (e.g. a kinase ATP binding site moiety). In yet another embodiment, $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl provided that when $L^1$ is a bond, —C(O)—, —N($L^2R^5$)C(O)—, —OC(O)—, —S(O)$_n$—, —(OL$^2$R$^5$)OP(O)—, —N(L$^2$R$^5$)SO$_2$—, or —(N(L$^2$R$^5$))NP(O)— then $R^1$ is substituted cycloalkyl, substituted heterocycloalkyl, substituted aryl, or substituted heteroaryl. In yet another embodiment, $R^1$ is substituted saturated ($C_3$-$C_6$) cycloalkyl, substituted saturated 4 to 8 membered saturated heterocycloalkyl containing one or two heteroatoms independently selected from N, O, S, SO or SO$_2$, substituted monocyclic or fused bicyclic ($C_6$-$C_{10}$) aromatic aryl, or substituted monocyclic or fused bicyclic 5-10 membered aromatic heteroaryl.

Z is a bond, —O—, —N(R$^a$)—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

In some embodiments, Z is a bond, —O—, —N(R$^a$)—, substituted or unsubstituted alkylene or substituted or unsubstituted heterocycloalkylene. In some embodiments, Z is a bond, —O—, —N(R$^a$)—, or unsubstituted alkylene (e.g. methylene). In some embodiments, Z is a bond or unsubstituted saturated ($C_1$-$C_6$) alkylene. In some embodiments, $R^a$ is substituted or unsubstituted alkyl, substituted or unsubstituted heteroalkyl, substituted or unsubstituted cycloalkyl, substituted or unsubstituted hetercycloalkyl, substituted or unsubstituted aryl or substituted or unsubstituted heteroaryl. R' may be hydrogen or unsubstituted alkyl.

In some embodiments, Z is a bond, —O—, —N(R$^a$)—, $R^{a1}$-substituted or unsubstituted alkylene, $R^{a1}$-substituted or unsubstituted heteroalkylene, $R^{a1}$-substituted or unsubstituted cycloalkylene, $R^{a1}$-substituted or unsubstituted heterocycloalkylene, $R^{a1}$-substituted or unsubstituted arylene or $R^{a1}$-substituted or unsubstituted heteroarylene. $R^a$ may be $R^{a1}$-substituted or unsubstituted alkylene, $R^{a1}$ substituted or unsubstituted heteroalkylene, $R^{a1}$ substituted or unsubstituted cycloalkylene, $R^{a1}$-substituted or unsubstituted heterocycloalkylene, $R_{a1}$-substituted or unsubstituted arylene or $R^{a1}$-substituted or unsubstituted heteroarylene. In some embodiments, $R^a$ is $R^{a1}$-substituted or unsubstituted alkylene (e.g. $C_1$-$C_{10}$ alkylene such as methyl or ethyl).

$R^{a1}$ is halogen, —CN, —OH, —SH, —NH$_2$, —COOH, —CONH$_2$, —NO$_2$, —CF$_3$, $R^{a2}$-substituted or unsubstituted alkyl, $R^{a2}$-substituted or unsubstituted heteroalkyl, $R^{a2}$-substituted or unsubstituted cycloalkyl, $R^{a2}$-substituted or unsubstituted heterocycloalkyl, $R^{a2}$-substituted or unsubstituted aryl or $R^{a2}$-substituted or unsubstituted heteoaryl. $R^{a2}$ is halogen, —CN, —OH, —SH, —NH$_2$, —COOH, —CONH$_2$, —NO$_2$, —CF$_3$, $R^{a3}$-substituted or unsubstituted alkyl, $R^{a3}$-substituted or unsubstituted heteroalkyl, $R^{a3}$-substituted or unsubstituted cycloalkyl, $R^{a3}$-substituted or unsubstituted heterocycloalkyl, $R^{a3}$-substituted or unsubstituted aryl or $R^{a3}$-substituted or unsubstituted heteoaryl. $R^{a3}$ is halogen, —CN, —OH, —SH, —NH$_2$, —COOH, —CONH$_2$, —NO$_2$, —CF$_3$, unsubstituted alkyl, unsubstituted heteroalkyl, unsubstituted cycloalkyl, unsubstituted heterocycloalkyl, unsubstituted aryl or unsubstituted heteoraryl.

$L^1$ is a bond, —C(O)—, —N(L$^2$R$^5$)C(O)—, —OC(O)—, —S(O)$_n$—, —(OL$^2$R$^5$)OP(O)—, —N(L$^2$R$^5$)SO$_2$—,

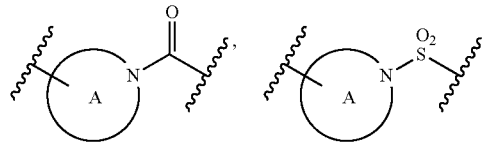

substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteoarylene. In some embodiments, $L^1$ is —C(O)—, —N(L$^2$R$^5$)C(O)—, —S(O)$_n$—, —(OL$^2$R$^5$)OP(O)—, —N(L$^2$R$^5$)SO$_2$—, —(N(L$^2$R$^5$))NP(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteoarylene. The symbol n is 0, 1 or 2. In some embodiments, n is 1 or 2. In some embodiments, $L^1$ is a bond. In another embodiment, where $L^1$ is a bond, $R^1$ is not a substituted or unsubstituted heteroaryl where the point of attachment to the remainder of the compound is a heteroatom. Ring A in

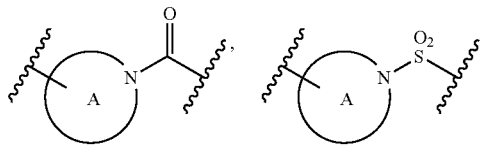

is substituted or unsubstituted heteoraryl or substituted or unsubstituted heterocycloalkyl. In some embodiments, Ring A is $R^{16}$-substituted or unsubstituted heteoraryl or $R^{16}$-substituted or unsubstituted heterocycloalkyl. In some embodiments, the —CO— and —SO$_2$— groups are attached to the —C(CN)=CHC($R^2$)($R^3$)($R^4$) moiety. Ring A may be substituted with one, two, or three substituents independently selected from hydrogen, unsubstituted saturated ($C_1$-$C_6$) alkyl, unsubstituted saturated ($C_1$-$C_6$) alkoxy, hydroxyl, cyano, nitro, halo, unsubstituted saturated ($C_1$-$C_6$) haloalkyl, unsubstituted saturated ($C_1$-$C_6$)-haloalkoxy, —S($C_1$-$C_6$) unsubstituted saturated alkyl, —SO$_2$($C_1$-$C_6$) unsubstituted saturated alkyl, carboxy, or —COO—($C_1$-$C_6$) unsubstituted saturated alkyl.

In some embodiments, $L^1$ is a bond, —C(O)—, —N($L^2R^5$)C(O)—, —S(O)$_n$—, —(O$L^2R^5$)OP(O)—, —N($L^2R^5$)SO$_2$—, —(N($L^2R^5$))NP(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In some embodiments, $L^1$ is —(N($L^2R^5$))NP(O)—, —N($L^2R^5$)C(O)—, or —N($L^2R^5$)—SO$_2$— and $R^5$ and $R^1$ are optionally joined together to form a substituted or unsubstituted heterocycloalkyl, or substituted or unsubstituted heteroaryl.

In some embodiments, $L^1$ is —N($L^2R^5$)C(O)—. In some related embodiments, $R^2$ and $R^3$ are attached to the remainder of the molecule through a carbon atom (i.e. the point of attachment of $R^2$ and $R^3$ is a carbon atom). In some embodiments, $L^1$ is —N($L^2R^5$)C(O)— and $R^2$ and $R^3$ are attached to the remainder of the molecule through a carbon atom. In some embodiments, $R^4$ is not hydrogen. In some embodiments, $L^1$ is —N($L^2R^5$)C(O)—, $R^2$ and $R^3$ are attached to the remainder of the molecule through a carbon atom, and $R^4$ is a hydrogen.

In some embodiments, $L^1$ is a bond, —C(O)—, —N($L^2R^5$)C(O)—, —OC(O)—, —S(O)$_n$—, —(O$L^2R^5$)OP(O)—, —N($L^2R^5$)SO$_2$—, —(N($L^2R^5$))NP(O)—, substituted or unsubstituted alkylene, substituted or unsubstituted arylene, substituted or unsubstituted heteroarylene, heterocycloaminosulfonyl, or heterocycloaminocarbonyl where n is 0, 1, or 2. In some embodiments, $L^1$ is —C(O)—, —N($L^2R^5$)C(O)—, —OC(O)—, —S(O)$_n$—, —N($L^2R^5$)SO$_2$—,

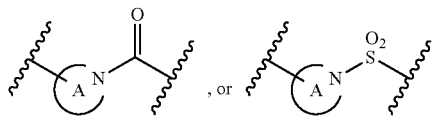

wherein n is 0, 1 or 2; $L^2$ is a bond or substituted or unsubstituted saturated ($C_1$-$C_6$) alkylene; $R^5$ is hydrogen; wherein the —CO— and —SO$_2$— groups of Ring A are attached to the —C(CN)=CHC($R^2$)($R^3$)($R^4$) moiety; and Ring A is substituted with one, two, or three substituents independently selected from hydrogen, unsubstituted saturated ($C_1$-$C_6$) alkyl, unsubstituted saturated ($C_1$-$C_6$) alkoxy, hydroxyl, cyano, nitro, halo, unsubstituted saturated ($C_1$-$C_6$) haloalkyl, unsubstituted saturated ($C_1$-$C_6$)-haloalkoxy, —S($C_1$-$C_6$) unsubstituted saturated alkyl, —SO$_2$($C_1$-$C_6$) unsubstituted saturated alkyl, carboxy, or —COO—($C_1$-$C_6$) unsubstituted saturated alkyl.

In some embodiments, $L^1$ is CO and $R^1$ is substituted saturated 4 to 8 membered saturated heterocycloalkyl containing one or two heteroatoms independently selected from N, O, S, SO or SO$_2$.

In some embodiments, $L^1$ is —CO— and $R^1$ is a pyrrolidinyl, piperidinyl, or azetidinyl where each of aforementioned ring is attached to $L^1$ via nitrogen ring atom and is: (i) substituted with one, two or three substituents where two substituents are independently selected from hydrogen, halogen, or —OR' (where R' is hydrogen or unsubstituted saturated ($C_1$-$C_6$) alkyl) and the third substituent is selected from —OR', —NR'R", or R' where R" is hydrogen or unsubstituted saturated ($C_1$-$C_6$) alkyl and R' is -unsubstituted saturated ($C_1$-$C_6$) alkylene-monocyclic or fused bicyclic ($C_6$-$C_{10}$) aromatic aryl, -unsubstituted saturated ($C_1$-$C_6$) alkylene-monocyclic or fused bicyclic 5 to 10 membered aromatic heteroaryl, monocyclic or fused bicyclic ($C_6$-$C_{10}$) aromatic aryl, or monocyclic or fused bicyclic 5 to 10 membered aromatic heteroaryl wherein the aryl and heteroaryl rings in -unsubstituted saturated ($C_1$-$C_6$) alkylene-monocyclic or fused bicyclic ($C_6$-$C_{10}$) aromatic aryl, -unsubstituted saturated ($C_1$-$C_6$) alkylene-monocyclic or fused bicyclic 5 to 10 membered aromatic heteroaryl, monocyclic or fused bicyclic ($C_6$-$C_{10}$) aromatic aryl, or monocyclic or fused bicyclic 5 to 10 membered aromatic heteroaryl are: (ii) substituted with one to three substituents independently selected from hydrogen, halogen, —OR', —NR'R", —SR', —OC(O)R', —C(O)R', —CO$_2$R', —CONR'R", —OC(O)NR'R", —NR"C(O)R', —NR'—C(O)NR'R", —NR"C(O)$_2$R', —S(O)$_2$R', —S(O)$_2$NR'R", —NR'SO$_2$R', R', —CN, —NO$_2$, unsubstituted saturated fluoro($C_1$-$C_4$) alkoxy, or unsubstituted saturated fluoro($C_1$-$C_4$) alkyl where R" is hydrogen or unsubstituted saturated ($C_1$-$C_6$) alkyl and R' is hydrogen, unsubstituted saturated ($C_1$-$C_6$) alkyl, saturated ($C_1$-$C_6$) alkyl substituted with one or two halogen, —OR', —NR'R" (where R' and R" in —OR' and —NR'R" are independently hydrogen or unsubstituted saturated ($C_1$-$C_6$) alkyl; or R' and R" are attached to the same nitrogen atom, they can be combined with the nitrogen atom to form 4-7 membered ring), unsubstituted saturated ($C_3$-$C_6$) cycloalkyl, 4 to 8 membered saturated heterocycloalkyl containing one or two heteroatoms independently selected from N, O, S, SO or SO$_2$, monocyclic or fused bicyclic ($C_6$-$C_{10}$) aromatic aryl or monocyclic or fused bicyclic 5 to 10 membered aromatic heteroaryl wherein the heterocycloalkyl, aryl or heteroaryl in (ii), whether attached directly or indirectly, are: (iii) substituted with one to three substituents independently selected from hydrogen, halogen, —OR', —NR'R", —SR', —OC(O)R', —C(O)R', —CO$_2$R', —CONR'R", —OC(O)NR'R", —NR"C(O)R', —NR'—C(O)NR'R", —NR"C(O)$_2$R', —S(O)$_2$R', —S(O)$_2$NR'R", —NR'SO$_2$R', R', —CN, —NO$_2$, unsubstituted saturated fluoro($C_1$-$C_4$) alkoxy, or unsubstituted saturated fluoro($C_1$-$C_4$) alkyl where R" is hydrogen or unsubstituted saturated ($C_1$-$C_6$) alkyl and R' is hydrogen, unsubstituted saturated ($C_1$-$C_6$) alkyl, saturated ($C_1$-$C_6$) alkyl substituted with one or two halogen, —OR', —NR'R" (where R' and R" in —OR', —NR'R" are independently hydrogen, unsubstituted saturated ($C_1$-$C_6$) alkyl, or R' and R" are attached to the same nitrogen atom, they can be combined with the nitrogen atom to form 4-7 membered ring), unsubstituted saturated ($C_3$-$C_6$) cycloalkyl, 4 to 8 membered saturated heterocycloalkyl containing one or two heteroatoms independently selected from N, O, S, SO or $SO_2$, monocyclic or fused bicyclic ($C_6$-$C_{10}$) aromatic aryl or monocyclic or fused bicyclic 5 to 10 membered aromatic heteroaryl wherein heterocycloalkyl, aryl or heteroaryl in (iii), whether attached directly or indirectly, are substituted with one to three substituents independently selected from hydrogen, halogen, unsubstituted saturated ($C_1$-$C_6$) alkyl, —OR', —NR'R", —C(O)R', —$CO_2$R', —S(O)$_2$R', —CN, unsubstituted saturated fluoro($C_1$-$C_4$) alkoxy, and unsubstituted saturated fluoro($C_1$-$C_4$) alkyl wherein R' is hydrogen or unsubstituted saturated ($C_1$-$C_6$) alkyl.

In some embodiments, where —OR', —NR'R", or R' in (i) in the preceding paragraph is attached at the 3 position of piperidinyl and at the 2 position of pyrrolidinyl and R' is -unsubstituted saturated ($C_1$-$C_6$) alkylene-5 to 10 membered aromatic heteroaryl or 5 to 10 membered aromatic heteroaryl where the monocyclic or fused bicyclic heteroaryl ring is indazolyl, quinolinyl, isoquinolinyl, quinazolinyl, benzimidazolyl, pyrimidinyl, pyridinyl, indolyl, 7-azaindolyl, or purinyl.

In some embodiments, $L^1$ is —NHCO— or —NHSO$_2$— and $R^1$ is monocyclic or fused bicyclic ($C_6$-$C_{10}$) aromatic aryl or monocyclic or fused bicyclic 5 to 10 membered aromatic heteroaryl substituted with: (i) one to three substituents independently selected from hydrogen, halogen, —OR', —NR'R", —SR', —OC(O)R', —C(O)R', —$CO_2$R', —CONR'R", OC(O)NR'R", —NR"C(O)R', —NR'—C(O)NR'R", —NR"C(O)$_2$R', —S(O)$_2$R', —S(O)$_2$NR'R", —NR'SO$_2$R', R', —CN, —NO$_2$, saturated fluoro($C_1$-$C_4$) alkoxy, or saturated fluoro($C_1$-$C_4$) alkyl where R" is hydrogen or unsubstituted saturated ($C_1$-$C_6$) alkyl and R' is hydrogen, unsubstituted saturated ($C_1$-$C_6$) alkyl, saturated ($C_1$-$C_6$) alkyl substituted with one or two halogen, —OR', —NR'R" (where R' and R" in —OR' and —NR'R" are independently hydrogen, unsubstituted saturated ($C_1$-$C_6$) alkyl, or R' and R" are attached to the same nitrogen atom, they can be combined with the nitrogen atom to form 4-7 membered saturated ring), unsubstituted saturated ($C_3$-$C_6$) cycloalkyl, 4 to 8 membered saturated heterocycloalkyl containing one or two heteroatoms independently selected from N, O, S, SO or $SO_2$, monocyclic or fused bicyclic ($C_6$-$C_{10}$) aromatic aryl, or monocyclic or fused bicyclic 5 to 10 membered aromatic heteroaryl provided at least one of the three substituent is not hydrogen and wherein heterocycloalkyl, aryl or heteroaryl in (i), whether attached directly or indirectly to $R^1$ is: (ii) substituted with one to three substituents independently selected from hydrogen, halogen, —OR', —NR'R", —SR', —OC(O)R', —C(O)R', —$CO_2$R', —CONR'R", —OC(O)NR'R", —NR"C(O)R', —NR'—C(O)NR'R", —NR"C(O)$_2$R', —S(O)$_2$R', —S(O)$_2$NR'R", —NR'SO$_2$R', R', —CN, —NO$_2$, unsubstituted saturated fluoro($C_1$-$C_4$) alkoxy, or unsubstituted saturated fluoro($C_1$-$C_4$) alkyl where R" is hydrogen or unsubstituted saturated ($C_1$-$C_6$) alkyl) and R' is hydrogen, unsubstituted saturated ($C_1$-$C_6$) alkyl, saturated ($C_1$-$C_6$) alkyl substituted with one or two halogen, —OR', —NR'R' (where R' and R" in —OR' and —NR'R" are independently hydrogen, unsubstituted saturated ($C_1$-$C_6$) alkyl, or R' and R" are attached to the same nitrogen atom, they can be combined with the nitrogen atom to form 4-7 membered ring), unsubstituted saturated ($C_3$-$C_6$) cycloalkyl, 4 to 8 membered saturated heterocycloalkyl containing one or two heteroatoms independently selected from N, O, S, SO or $SO_2$, monocyclic or fused bicyclic ($C_6$-$C_{10}$) aromatic aryl or monocyclic or fused bicyclic 5 to 10 membered aromatic heteroaryl wherein heterocycloalkyl, aryl or heteroaryl in (ii), whether attached directly or indirectly, is substituted with one to three substituents independently selected from hydrogen, halogen, unsubstituted saturated ($C_1$-$C_6$) alkyl, —OR', —NR'R", —C(O)R', —$CO_2$R', —S(O)$_2$R', —CN, unsubstituted saturated fluoro($C_1$-$C_4$) alkoxy, and unsubstituted saturated fluoro($C_1$-$C_4$) alkyl wherein R' is hydrogen or unsubstituted saturated ($C_1$-$C_6$) alkyl.

$L^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^5$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $L^1$ is —(N($L^2R^5$))NP(O)—, —N($L^2R^5$)C(O)—, or —N($L^2R^5$)SO$_2$—, and $R^5$ and $R^1$ are optionally joined together to form a substituted or unsubstituted cycloalkyl, substituted or unsubstituted heterocycloalkyl, substituted or unsubstituted aryl, or substituted or unsubstituted heteroaryl.

$R^2$ and $R^3$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^2$ and $R^3$ are optionally joined together (with the carbon to which they are attached) to form a substituted or unsubstituted cycloalkyl or substituted or unsubstituted heterocycloalkyl. In one embodiment, $R^2$ and $R^3$ are independently substituted or unsubstituted alkenyl or substituted or unsubstituted alkynyl. In another embodiment, $R^2$ and $R^3$ are independently substituted or unsubstituted saturated alkyl.

In yet another embodiment, $R^2$ and $R^3$ are independently substituted or unsubstituted saturated alkyl, unsubstituted heteroalkyl, or substituted or unsubstituted heterocycloalkyl provided that alkyl and heterocycloalkyl in $R^2$ and $R^3$ are not substituted with substituted or unsubstituted aryl, substituted or unsubstituted heteroaryl, substituted or unsubstituted cycloalkyl or substituted or unsubstituted heterocycloalkyl. In yet another embodiment, $R^2$ and $R^3$ are independently substituted or unsubstituted saturated alkyl. In yet another embodiment, $R^2$ and $R^3$ are optionally joined together to form a substituted or unsubstituted cycloalkyl, or substituted or unsubstituted heterocycloalkyl. In yet another embodiment, $R^2$ and $R^3$ are independently substituted or unsubstituted saturated ($C_1$-$C_8$) alkyl, or $R^2$ and $R^3$ are optionally joined together to form a substituted or unsubstituted ($C_3$-$C_6$)-cycloalkyl, or substituted or unsubstituted 4 to 8 membered heterocycloalkyl containing one or two heteroatoms independently selected from N, O, S, SO or $SO_2$ provided that alkyl and heterocycloalkyl in $R^2$ and $R^3$ are not substituted with substituted or unsubstituted aryl, substituted or unsubstituted heteroaryl, substituted or unsubstituted cycloalkyl or substituted or unsubstituted heterocycloalkyl. In yet another embodiment, $R^2$ and $R^3$ are independently unsubstituted saturated ($C_1$-$C_6$) alkyl and $R^4$ is hydrogen or unsubstituted saturated ($C_1$-$C_6$) alkyl. In yet another embodiment, $R^2$ and $R^3$ are independently unsubstituted saturated ($C_1$-$C_6$) alkyl and $R^4$ is saturated ($C_1$-$C_6$) alkyl substituted with one to three substituents independently selected from —OR' or —NR'R" where R' and R" are independently hydrogen or unsubstituted saturated ($C_1$-$C_6$) alkyl. In yet another embodiment, $R^2$ and $R^3$ are independently unsubstituted saturated ($C_1$-$C_6$) alkyl and $R^4$ is —$NR^{4A}R^{4B}$ or —$OR^{4A}$ where $R^{4A}$ and $R^{4B}$ are independently hydrogen, unsubstituted saturated ($C_1$-$C_6$) alkyl, or saturated ($C_1$-$C_6$) alkyl substituted with one to three substituents independently selected from —OR' or —NR'R" where R' and R" are independently hydrogen or unsubstituted saturated ($C_1$-$C_6$) alkyl. In yet another embodiment, $R^2$ and $R^3$ may independently be unsubstituted saturated ($C_1$-$C_6$) alkyl and $R^4$ is unsubstituted saturated 4-7-membered heterocycloalkyl containing one to two heteroatoms selected from N, O, S, SO or $SO_2$ or saturated 4-7-membered heterocycloalkyl containing one to two heteroatoms selected from N, O, S, SO or $SO_2$ and substituted with one or two unsubstituted saturated ($C_1$-$C_6$) alkyl, hydroxy, unsubstituted saturated —O($C_1$-$C_6$) alkyl, or fluoro. In yet another embodiment, $R^2$ and $R^3$ may be joined together to form a unsubstituted saturated ($C_3$-$C_6$) cycloalkyl, saturated ($C_3$-$C_6$) cycloalkyl substituted with one or two substituents independently selected from unsubstituted saturated ($C_1$-$C_6$) alkyl, hydroxy, unsubstituted saturated —O($C_1$-$C_6$) alkyl, or halo. In yet another embodiment, $R^2$ and $R^3$ are joined together to form an unsubstituted saturated ($C_3$-$C_6$) cycloalkyl. In yet another embodiment, $R^2$ and $R^3$ are joined together to form unsubstituted saturated 4 to 6 membered heterocycloalkyl containing one to two heteroatoms selected from N, O, S, SO or $SO_2$ or saturated 4 to 6 membered heterocycloalkyl containing one to two heteroatoms selected from N, O, S, SO or $SO_2$ substituted with one to three substituents independently selected from unsubstituted saturated ($C_1$-$C_6$) alkyl, hydroxy, unsubstituted saturated O($C_1$-$C_6$) alkyl, or halo. In yet another embodiment, $R^2$ and $R^3$ are methyl or ethyl and $R^4$ is hydrogen, methyl, ethyl, amino, methylamino, dimethylamino, diethylamino, methylethylamino, isopropylamino, butylamino, hydroxy, methoxy, ethoxy, propoxy, methoxymethyl, 2-methoxyethyl, ethoxymethyl, 2-ethoxyethyl, pyrrolidinyl, piperidinyl, piperazinyl, morpholinyl, thiomorpholinyl, tetrahydropyranyl, tetrahydrofuranyl, oxetanyl, or azetidinyl wherein each of the aforementioned ring is optionally substituted with one or two substituents independently selected from methyl, ethyl, propyl, hydroxy, methoxy, ethoxy, chloro, or fluoro. In yet another embodiment, $R^2$ and $R^3$ are joined together to form a cyclopropyl, cyclobutyl, cyclohexyl, pyrrolidinyl, piperidinyl, piperazinyl, tetrahydropyranyl, tetrahydrofuranyl, azetidinyl, or oxetanyl where pyrrolidinyl, piperidinyl, piperazinyl, or azetidinyl is optionally substituted with one or two substituents independently selected from methyl, ethyl, propyl, hydroxy, methoxy, ethoxy, chloro or fluoro and $R^4$ is hydrogen or methyl or ethyl.

In some embodiments, where $R^2$ and $R^3$ are joined together to form a substituted piperidinyl, then the substituted piperidinyl is substituted with an unsubstituted alkyl (e.g. $C_1$-$C_8$ alkyl such as a saturated alkyl) or an unsubstituted heteroalkyl (e.g. a 2-8 membered heteroalkyl). In some embodiments, where $R^2$ and $R^3$ are joined together to form a substituted piperidinyl and $R^4$ is hydrogen, then the substituted piperidinyl is substituted with an unsubstituted alkyl (e.g. $C_1$-$C_8$ alkyl such as a saturated alkyl) or an unsubstituted heteroalkyl (e.g. a 2-8 membered heteroalkyl).

In some embodiment, $R^2$ and $R^3$ are not joined together to form a substituted piperidinyl. In some embodiment where $R^4$ is hydrogen, $R^2$ and $R^3$ are not joined together to form a substituted piperidinyl.

$R^4$ is independently hydrogen, —$NR^{4A}R^{4B}$, —$OR^{4A}$, —$SR^{4A}$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^4$ is independently hydrogen, —$NR^{4A}R^{4B}$, —$OR^{4A}$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In one embodiment, $R^4$ is substituted or unsubstituted alkenyl or substituted or unsubstituted alkynyl. In another embodiment, $R^4$ is substituted or unsubstituted saturated alkyl. $R^{4A}$ and $R^{4B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In one embodiment, $R^{4A}$ and $R^{4B}$ are independently substituted or unsubstituted alkenyl or substituted or unsubstituted alkynyl. In another embodiment, $R^{4A}$ and $R^{4B}$ are independently substituted or unsubstituted saturated alkyl.

In yet another embodiment, $R^4$ is independently hydrogen, —$NR^{4A}R^{4B}$, —$OR^{4A}$, —$SR^{4A}$, —CN, substituted or unsubstituted alkyl or substituted or unsubstituted heterocycloalkyl, where $R^{4A}$ and $R^{4B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl provided that alkyl and heterocycloalkyl in $R^4$ are not substituted with substituted or unsubstituted aryl, substituted or unsubstituted heteroaryl, substituted or unsubstituted cycloalkyl or substituted or unsubstituted heterocycloalkyl. In yet another embodiment, $R^4$ is hydrogen, —$NR^{4A}R^{4B}$, —$OR^{4A}$, —$SR^{4A}$, substituted or unsubstituted alkyl or substituted or unsubstituted 4 to 8 membered heterocycloalkyl containing one or two heteroatoms independently selected from N, O, S, SO or $SO_2$ wherein $R^{4A}$ and $R^{4B}$ are independently hydrogen, substituted or unsubstituted ($C_1$-$C_6$) alkyl, or substituted or unsubstituted 4 to 8 membered heterocycloalkyl containing one or two heteroatoms independently selected from N, O, S, SO or SO2, provided that alkyl and heterocycloalkyl in $R^4$ are not substituted with substituted or unsubstituted aryl, substituted or unsubstituted heteroaryl, substituted or unsubstituted cycloalkyl or substituted or unsubstituted heterocycloalkyl. In yet another embodiment, $R^{4A}$ and $R^{4B}$ are independently hydrogen, unsubstituted saturated ($C_1$-$C_6$) alkyl, or saturated ($C_1$-$C_6$) alkyl substituted with one to three substituents independently selected from —OR' or —NR'R" where R' and R" are independently hydrogen, unsubstituted saturated ($C_1$-$C_6$) alkyl. In yet another embodiment, $R^2$ and $R^3$ are independently unsubstituted saturated ($C_1$-$C_6$) alkyl and $R^4$ is hydrogen, unsubstituted saturated ($C_1$-$C_6$) alkyl, saturated ($C_1$-$C_6$) alkyl substituted with one to three substituents independently selected from —OR' or —NR'R" (where R' and R" are independently hydrogen or unsubstituted saturated ($C_1$-$C_6$) alkyl), —$NR^{4A}R^{4B}$, —$OR^{4A}$ [where $R^{4A}$ and $R^{4B}$ are independently hydrogen, unsubstituted saturated ($C_1$-$C_6$) alkyl, or saturated ($C_1$-$C_6$) alkyl substituted with one to three substituents independently selected from —OR' or —NR'R" (where R' and R" are independently hydrogen or unsubstituted saturated ($C_1$-$C_6$) alkyl)], unsubstituted saturated 4-7-membered heterocycloalkyl containing one to two heteroatoms selected from N, O, S, SO or $SO_2$, saturated 4-7-membered heterocycloalkyl containing one to two heteroatoms selected from N, O, S, SO or $SO_2$ and substituted with one or two unsubstituted saturated ($C_1$-$C_6$) alkyl, hydroxy, unsubstituted saturated —O($C_1$-$C_6$) alkyl, or fluoro, saturated ($C_1$-$C_6$) alkyl substituted with one unsaturated 4-7-membered heterocycloalkyl containing one to two heteroatoms selected from N, O, S, SO or $SO_2$, saturated ($C_1$-$C_6$) alkyl substituted with one saturated 4-7-membered heterocycloalkyl containing one to two heteroatoms selected from N, O, S, SO or $SO_2$ and substituted with one or two unsubstituted saturated ($C_1$-$C_6$) alkyl, hydroxy, unsubstituted saturated —O($C_1$-$C_6$) alkyl, or fluoro. In yet another embodiment, $R^4$ is hydrogen or unsubstituted saturated ($C_1$-$C_6$) alkyl.

In some embodiments, the compound is not (E)-3-(1-(1H-imidazo[4,5-c]pyridin-4-yl)piperidin-4-yl)-2-cyano-N-methylacrylamide; 2-pentenenitrile, 2-(2,2-dimethyl-1-oxopropyl)-4,4-dimethyl-; 1H-benzimidazole-2-acetonitrile, α-(2,2-dimethylpropylidene)-; benzenepropanenitrile, α-(2,2-dimethylpropylidene)-β-oxo-; tetradecanoic acid, 2-[2-[[2-butyl-5-(1,1,3,3-tetramethylbutyl)phenyl]sulfonyl]-2-cyanoethenyl]-2-dodecyl-, 4-hydroxyphenyl ester; 3-butenoic acid, 4-cyano-2,2-dimethyl-4-(2-pyridinyl)-, ethyl ester; 3-butenoic acid, 2-acetyl-4-cyano-4-[(4-methylphenyl)sulfonyl]-2-nitroso-ethyl ester; 2-pyridineacetonitrile, α-(2,2-dimethylpropylidene)-; 3-butenoic acid, 2-acetyl-4-[(4-chlorophenyl)sulfonyl]-4-cyano-2-[2-(3-nitrophenyl)diazenyl]-, ethyl ester; 3-butenoic acid, 2-acetyl-2-[2-(4-chlorophenyl)diazenyl]-4-[(4-chlorophenyl)sulfonyl]-4-cyano-, ethyl ester; 3-butenoic acid, 2-acetyl-4-cyano-4-[(4-methylphenyl)sulfonyl]-2-[2-(4-nitrophenyl)diazenyl]-, ethyl ester; 3-butenoic acid, 2-acetyl-2-[2-(4-bromophenyl)diazenyl]-4-cyano-4-[(4-methylphenyl)sulfonyl]-, ethyl ester; 3-butenoic acid, 2-acetyl-2-[2-(4-chlorophenyl)diazenyl]-4-cyano-4-[(4-methylphenyl)sulfonyl]-, ethyl ester; 2-Hexenedioic acid, 2-cyano-5-hydroxy-4,4-dimethyl-5-(trifluoromethyl)-, 1-ethyl 6-methyl ester; α-D-galactopyranose, 1,2:3,4-bis-O-(1-methylethylidene)-, (2E)-2-cyano-4,4-dimethyl-2-pentenoate; L-phenylalanine, N-[(2E)-2-cyano-4,4-dimethyl-1-oxo-2-penten-1-yl]-, methyl ester; 2-nonenoic acid, 2-cyano-4,4,8-trimethyl-, phenylmethyl ester; 2,6-heptadienoic acid, 2-cyano-4,4-dimethyl-, ethyl ester; 2,5-hexadienoic acid, 2-cyano-4,4-dimethyl-6,6-diphenyl-, ethyl ester; 2H-tetrazole-5-acetonitrile, α-(2,2-dimethylpropylidene)-2-(2-propen-1-yl)-; 2-pentenoic acid, 2-cyano-4,4-dimethyl-, ethyl ester; 2-pentenoic acid, 2-cyano-4,4-dimethyl-, methyl ester; 2-pentenamide, N-[1-(4-chlorophenyl)ethyl]-2-cyano-4,4-dimethyl-; 3-butenoic acid, 4-cyano-2,2-dimethyl-4-(2-pyridinyl)-, ethyl ester; 2-pyridineacetonitrile, α-(2,2-dimethylpropylidene)-; 2-pentenoic acid, 4-bromo-2-cyano-4-methyl-, methyl ester; 2-pentenoic acid, 2-cyano-4,4-dimethyl-, ethyl ester; 2-propenoic acid, 2-cyano-3-[3-formyl-2,2-dimethylcyclopropyl]-, ethyl ester; cyclopropanecarboxylic acid, 3-[(1E)-2-cyano-2-fluoroethenyl]-2,2-dimethyl-, (2-methyl[1,1'-biphenyl]-3-yl)methyl ester; 2-propenoic acid, 2-cyano-3-cyclopropyl-, ethyl ester; cyclopropanecarboxylic acid, 2,2-dichloro-1-(2-cyano-3-methoxy-3-oxo-1-propen-1-yl)-, ethyl ester; cyclopropanecarboxylic acid, 3-[(1E)-2-cyano-3-methoxy-3-oxo-1-propen-1-yl]-2,2-dimethyl-, [5-(phenylmethyl)-3-furanyl] methyl ester; cyclopropanecarboxylic acid, 2-(2-cyano-3-methoxy-3-oxo-1-propen-1-yl)-, ethyl ester; 2-propenoic acid, 2-cyano-3-(1-methylcyclopropyl)-, methyl ester; 2-propenoic acid, 2-cyano-3-[2-(trifluoromethyl)cyclopropyl]-, methyl ester; 2-propenoic acid, 2-cyano-3-[1-(trifluoromethyl)cyclopropyl]-, methyl ester; 2-propenoic acid, 2-cyano-3-(1-methylcyclopropyl)-, ethyl ester; cyclopropanecarboxylic acid, 3-(2-carboxy-2-cyanoethenyl)-2,2-dimethyl-, 1-[[2,3,5,6-tetrafluoro-4-(methoxymethyl)phenyl]methyl]ester; cyclopropanecarboxylic acid, 3-[(1E)-2-cyano-3-(1,1-dimethylethoxy)-3-oxo-1-propen-1-yl]-2,2-dimethyl-, [2,3,5,6-tetrafluoro-4-(methoxymethyl)phenyl] methyl ester; cyclopropanecarboxylic acid, 3-[(1E)-2-cyano-3-(1-methylethoxy)-3-oxo-1-propen-1-yl]-2,2-dimethyl-, [2,3,5,6-tetrafluoro-4-(methoxymethyl)phenyl] methyl ester; cyclopropanecarboxylic acid, 3-[(1E)-2-cyano-3-oxo-3-(2-propen-1-yloxy)-1-propen-1-yl]-2,2-dimethyl-, [2,3,5,6-tetrafluoro-4-(methoxymethyl)phenyl] methyl ester; cyclopropanecarboxylic acid, 3-[(1E)-2-cyano-3-oxo-3-propoxy-1-propen-1-yl]-2,2-dimethyl-, [2,3,5,6-tetrafluoro-4-(methoxymethyl)phenyl]methyl ester; cyclopropanecarboxylic acid, 3-[(1E)-2-cyano-3-methoxy-3-oxo-1-propen-1-yl]-2,2-dimethyl-, [2,3,5,6-tetrafluoro-4-(methoxymethyl)phenyl]methyl ester; cyclopropanecarboxylic acid, 3-[(1E)-2-cyano-3-ethoxy-3-oxo-1-propen-1-yl]-2,2-dimethyl-, [2,3,5,6-tetrafluoro-4-(methoxymethyl)phenyl]methyl ester; 1,2-benzisothiazole-3-acetonitrile, α-(cyclopropylmethylene)-5-[3,6-dihydro-3-methyl-2,6-dioxo-4-(trifluoromethyl)-1(2H)-pyrimidinyl]-; 2-propenoic acid, 2-cyano-3-(2,2-dichloro-1-methylcyclopropyl)-, ethyl ester; 2-propenoic acid, 2-cyano-3-cyclopropyl-, ethyl ester; cyclopropanecarboxylic acid, 3-(2-cyano-3-ethoxy-3-oxo-1-propen-1-yl)-2,2-dimethyl-, cyano(3-phenoxyphenyl) methyl ester; cyclopropanecarboxylic acid, 3-(2-cyano-3-ethoxy-3-oxo-1-propen-1-yl)-2,2-dimethyl-, (3-phenoxyphenyl)methyl ester; cyclopropanecarboxylic acid, 3-(2-cyano-3-methoxy-3-oxo-1-propen-1-yl)-2,2-dimethyl-, (3-phenoxyphenyl)methyl ester; cyclopropanecarboxylic acid, 3-(2-cyano-3-ethoxy-3-oxo-1-propenyl)-2,2-dimethyl-, [5-(phenylmethyl)-3-furanyl]methyl ester; cyclopropanecarboxylic acid, 3-(2-cyano-3-ethoxy-3-oxo-1-propenyl)-2,2-dimethyl-, 1,1-dimethylethyl ester; cyclopropanecarboxylic acid, 3-(2-cyano-3-methoxy-3-oxo-1-propen-1-yl)-2,2-dimethyl-, 2-methyl-4-oxo-3-(2-propen-1-yl)-2-cyclopenten-1-yl ester; N-(1-(4-chlorophenyl)ethyl)-2-cyano-4,4-dimethylpent-2-enamide, N-(1-(4-chlorophenyl)ethyl)-2-cyano-4-methylpent-2-enamide, 2-(2-allyl-2H-tetrazol-5-yl)-4,4-dimethylpent-2-enenitrile, cyclopropanecarboxylic acid, 3-(2-cyano-3-methoxy-3-oxo-1-propen-1-yl)-2,2-dimethyl- or any salt thereof. In one embodiment, the compound is not a compound having a pyridinyl directly attached to the α-carbon at the pyridinyl 2-position. In another embodiment, the compound is not a compound having a pyridinyl directly attached to the α-carbon at the 2-position of the pyridinyl wherein the pyridinyl is substituted at the 4-position.

In some embodiment, the compound provided herein (e.g. the compound of Formula (I)) does not contain:
(i) a substituted or unsubstituted heteroaryl ring (e.g. unsubstituted heteroaryl ring) of formula

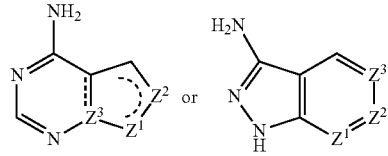

where the dashed lines are an optional bond and $Z^1$, $Z^2$, and $Z^3$ are N or C (following the normal chemical rules of valency), provided that one or two of $Z^1$, $Z^2$, and $Z^3$ are N, wherein at least one of the ring atoms is an attachment point to the remainder of the compound, and wherein the hydrogen of the NH moiety may be replaced with a bond to the remainder of the compound; or (ii) a substituted heteroaryl ring of formula

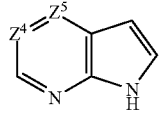

where $Z^4$ and $Z^5$ are independently N or C (following the normal rules of valency) provided that at least one of $Z^4$ and $Z^5$ is N and further provided that both $Z^4$ and $Z^5$ are not N, wherein at least one of the ring atoms is an attachment point to the remainder of the compound, and wherein the hydrogen of the NH moiety may be replaced with a bond to the remainder of the compound. The valency of N or C for $Z^1$, $Z^2$, $Z^3$, $Z^4$ and $Z^5$ is filled with a single or double bond to a neighboring ring atom, a bond to the remainder of the compound, and/or a bond to hydrogen or a substituent within the scope of the invention.

In some embodiments, $R^2$ and $R^3$ are independently unsubstituted alkyl, unsubstituted heteroalkyl, unsubstituted cycloalkyl, unsubstituted heterocycloalkyl, unsubstituted aryl or unsubstituted heteroaryl. $R^2$ and $R^3$ may also independently be unsubstituted $C_1$-$C_8$ alkyl, unsubstituted 2-8 membered heteroalkyl, unsubstituted $C_3$-$C_8$ cycloalkyl, unsubstituted 3 to 8 membered heterocycloalkyl, unsubstituted phenyl or unsubstituted 5 or 6 membered heteroaryl. $R^2$ and $R^3$ may also independently be unsubstituted $C_1$-$C_6$ alkyl, unsubstituted 2-6 membered heteroalkyl, unsubstituted $C_3$-$C_6$ cycloalkyl, unsubstituted 3 to 6 membered heterocycloalkyl, unsubstituted phenyl or unsubstituted 5 or 6 membered heteroaryl. $R^2$ and $R^3$ may also independently be unsubstituted $C_1$-$C_3$ alkyl, unsubstituted 2-3 membered heteroalkyl, unsubstituted $C_3$-$C_8$ cycloalkyl, unsubstituted 3 to 8 membered heterocycloalkyl, unsubstituted phenyl or unsubstituted 5 or 6 membered heteroaryl. $R^2$ and $R^3$ may also independently be unsubstituted $C_1$-$C_8$ alkyl (e.g. $C_1$-$C_3$ alkyl).

In some embodiments, $R^2$ and $R^3$ are methyl. In some related embodiments, $R^4$ is not hydrogen. In some related embodiments, $L^1$ is not —OC(O)—.

In some embodiments, $R^2$ and $R^3$ are joined together to form a substituted or unsubstituted $C_3$-$C_8$ cycloalkyl. In some embodiments, $R^2$ and $R^3$ are joined together to form a substituted or unsubstituted $C_3$-$C_6$ cycloalkyl. In some embodiments, $R^2$ and $R^3$ are joined together to form a substituted or unsubstituted cyclopropyl. In some related embodiments, $L^1$ is not —OC(O)—.

$R^4$ is independently hydrogen, —$NR^{4A}R^{4B}$, —$OR^{4A}$, —$SR^{4A}$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^4$ is independently hydrogen, —$NR^{4A}R^{4B}$, —$OR^{4A}$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ may also independently be hydrogen, —$NR^{4A}R^{4B}$, —$OR^{4A}$, —$SR^{4A}$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In one embodiment, $R^4$ is substituted or unsubstituted alkenyl or substituted or unsubstituted alkynyl. In another embodiment, $R^4$ is substituted or unsubstituted saturated alkyl. $R^{4A}$ and $R^{4B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In one embodiment, $R^{4A}$ and $R^{4B}$ are independently substituted or unsubstituted alkenyl or substituted or unsubstituted alkynyl. In another embodiment, $R^{4A}$ and $R^{4B}$ are independently substituted or unsubstituted saturated alkyl.

In some embodiments, $R^4$ is hydrogen, unsubstituted alkyl, unsubstituted heteroalkyl, unsubstituted cycloalkyl, unsubstituted heterocycloalkyl, unsubstituted aryl or unsubstituted heteroaryl. $R^4$ may also independently be unsubstituted $C_1$-$C_8$ alkyl, unsubstituted 2-8 membered heteroalkyl, unsubstituted $C_3$-$C_8$ cycloalkyl, unsubstituted 3 to 8 membered heterocycloalkyl, unsubstituted phenyl or unsubstituted 5 or 6 membered heteroaryl. $R^4$ may also be hydrogen, unsubstituted $C_1$-$C_6$ alkyl, unsubstituted 2-6 membered heteroalkyl, unsubstituted $C_3$-$C_6$ cycloalkyl, unsubstituted 3 to 6 membered heterocycloalkyl, unsubstituted phenyl or unsubstituted 5 or 6 membered heteroaryl. $R^4$ may also be hydrogen, unsubstituted $C_1$-$C_3$ alkyl, unsubstituted 2-3 membered heteroalkyl, unsubstituted $C_3$-$C_8$ cycloalkyl, unsubstituted 3 to 8 membered heterocycloalkyl, unsubstituted phenyl or unsubstituted 5 or 6 membered heteroaryl. $R^4$ may also be hydrogen, unsubstituted $C_1$-$C_8$ alkyl (e.g. $C_1$-$C_3$ alkyl). In some embodiments, $R^4$ is methyl. In some embodiments, $R^4$ is not hydrogen.

In some embodiments, $R^4$ is not hydrogen and $R^2$ and $R^3$ are methyl.

In one embodiment, -$L^1$-Z—$R^1$ is an electron withdrawing group. Where -$L^1$-Z—$R^1$ is an electron withdrawing group, then at least one of $L^1$, Z or —$R^1$ must be electron withdrawing (as defined below). That is one or both of $L^1$, Z, or —$R^1$ must be electron withdrawing. In some embodiments, $L^1$ is a bond or an electron withdrawing group. Where $L^1$ is a bond and Z is a bond, $R^1$ is an electron withdrawing group. In some further embodiments, an electron withdrawing group is attached to the α-carbon (described below) of the compound of Formula I. In some embodiment, the point of attachment of -$L^1$-Z—$R^1$ (or $R^1$ where $L^1$ is a bond) is not —S—. In other embodiments, an electron withdrawing groups is attached directly to the α-carbon. Acceptable electron withdrawing groups within the -$L^1$-Z—$R^1$ group include, for example, —C(O)—, —S(O)$_n$—, —N($L^2R^5$)C(O)—, —N($L^2R^5$)SO$_2$—,

(where Ring A is as defined below), substituted or unsubstituted heteroarylene (e.g. $R^{16}$-substituted or unsubstituted heteroarylene) and substituted or unsubstituted arylene (e.g. $R^{16}$-substituted or unsubstituted arylene). In some embodiments, -$L^1$-Z—$R^1$ includes one of the following heteroaryl groups (either in monovalent or divalent form): pyridinyl, pyrazolyl, indazolyl, indolyl, thienyl, pyrrolyl, imidazolyl, thiazolyl, benzothiazolyl, oxazolyl, benzimidazolyl, benzoxazolyl, isoxazolyl, benzisoxazolyl, triazolyl, benzotriazolyl, quinolinyl, isoquinolinyl, quinazolinyl, pyrimidinyl, a 5 or 6-membered heteroaryl with a C—N double bond optionally fused to a 5 or 6 membered heteroaryl, or pyridinyl N-oxide optionally substituted.

In some embodiments, $R^1$ is:

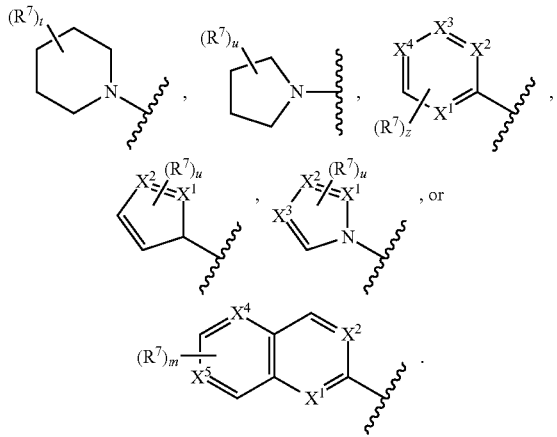

The symbol z is 0, 1, or 2. The symbol m is 0, 1, 2, or 3. The symbol u is 0, 1, 2, 3 or 4. The symbol t is 0, 1, 2, 3, 4 or 5. $X^1$, $X^2$, $X^3$, $X^4$ and $X^5$ are independently N or C(-$L^5$-$R^{7A}$). $R^7$ may independently be -$L^4$-$R^{7B}$. $R^{7A}$ and $R^{7B}$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, (e.g. where $L^1$ is —C(O)— and/or $R^1$ is piperidinyl), $R^2$ and $R^3$ are not joined together to form a substituted or unsubstituted cycloalkyl, substituted or unsubstituted heterocycloalkyl, substituted or unsubstituted aryl, or substituted or unsubstituted heteroaryl. In other embodiments (e.g. where $L^1$ is —C(O)— and/or $R^1$ is piperidinyl), $R^2$ and $R^3$ may not joined together to form a substituted or unsubstituted aryl, such as a substituted or unsubstituted phenyl.

In other embodiments, (e.g. where $L^1$ is —C(O)— and/or $R^1$ is piperidinyl) $R^2$ and $R^3$ may not joined together to form a $R^{17}$-substituted or unsubstituted aryl, such as a $R^{17}$-substituted or unsubstituted phenyl. In other embodiments, (e.g. where $L^1$ is —C(O)— and/or $R^1$ is piperidinyl) $R^2$ and $R^3$ may not joined together to form a $R^{17}$-substituted or unsubstituted aryl, such as a $R^{17}$-substituted or unsubstituted phenyl where $R^{17}$ is hydroxyl.

$L^4$ is independently a bond, —C(O)—, —C(O)N($L^6R^8$)—, —N($L^6R^8$)C(O)—, —C(O)O—, —S(O)$_w$—, —O—, —N($L^6R^8$)—, —P(O)(O$L^6R^8$)O—, —SO$_2$N($L^6R^8$)—, —N($L^6R^8$)SO$_2$—, —N($L^6R^8$)C(O)N($L^7R^9$)—, —P(O)(N($L^6R^8$))N—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. $L^4$ is independently a bond, —C(O)—, —C(O)N($L^6R^8$)—, —N($L^6R^8$)C(O)—, —C(O)O—, —S(O)$_w$—, —O—, —N($L^6R^8$)—, —SO$_2$N($L^6R^8$)—, —N($L^6R^8$)SO$_2$—, —N($L^6R^8$)C(O)N($L^7R^9$)—, substituted or unsubstituted alkylene, substituted or unsubstituted heteroalkylene, substituted or unsubstituted cycloalkylene, substituted or unsubstituted arylene, or substituted or unsubstituted heteroarylene. The symbol w is 0, 1 or 2.

$L^6$ and $L^7$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^8$ and $R^9$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^5$ is independently a bond, —C(O)—, —C(O)N($L^8R^{10}$)—, —N($L^8R^{10}$)C(O)—, —C(O)O—, —S(O)$_v$—, —O—, —N($L^8R^{10}$)—, —P(O)(O$L^8R^{10}$)O—, —SO$_2$N($L^8R^{10}$)—, —N($L^8R^{10}$)SO$_2$—, —N($L^8R^{10}$)C(O)N($L^9R^{11}$)—, —P(O)(N($L^8R^{10}$))N—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. The symbol v is 0, 1 or 2.

$L^8$ and $L^9$ are independently a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^{10}$ and $R^{11}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, $R^1$ is

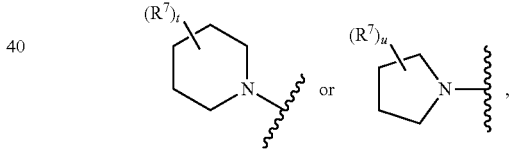

and $L^1$ is —C(O)—.

In some embodiments, $R^1$ is $R^7$-substituted or unsubstituted alkyl, $R^7$-substituted or unsubstituted heteroalkyl, $R^7$-substituted or unsubstituted cycloalkyl, $R^7$-substituted or unsubstituted heterocycloalkyl, $R^7$-substituted or unsubstituted aryl, or $R^7$-substituted or unsubstituted heteroaryl. In some embodiments, $R^1$ is substituted or unsubstituted cycloalkyl, substituted or unsubstituted heterocycloalkyl, substituted or unsubstituted aryl, or substituted or unsubstituted heteroaryl. In some embodiments, $R^1$ is $R^7$-substituted or unsubstituted cycloalkyl, $R^7$-substituted or unsubstituted heterocycloalkyl, $R^7$-substituted or unsubstituted aryl, or $R^7$-substituted or unsubstituted heteroaryl. In some embodiments, $R^1$ is substituted or unsubstituted aryl, or substituted or unsubstituted heteroaryl. In some embodiments, $R^1$ is $R^7$-substituted or unsubstituted aryl, or $R^7$-substituted or unsubstituted heteroaryl. In some embodiment, $R^1$ is an $R^7$-substituted or unsubstituted heterocycloamino.

In certain embodiments (e.g. where $L^1$ is —(N($L^2R^5$))NP(O)—, —N($L^2R^5$)C(O)—, or —N($L^2R^5$)SO$_2$—), $R^5$ and $R^1$ are joined together to form substituted or unsubstituted heterocycloalkyl or substituted or unsubstituted heteroaryl.

In certain embodiments, $R^5$ and $R^1$ are joined together to form a substituted or unsubstituted heteroaryl or substituted or unsubstituted heterocycloalkyl. In certain embodiments, $R^5$ and $R^1$ are joined together to form a $R^7$-substituted or unsubstituted heteroaryl or $R^7$-substituted or unsubstituted heterocycloalkyl. In certain embodiments, $R^5$ and $R^1$ are joined together to form a substituted or unsubstituted pyrrolidinyl or substituted or unsubstituted piperidinyl. In certain embodiments, $R^5$ and $R^1$ are joined together to form a $R^7$-substituted or unsubstituted pyrrolidinyl or $R^7$-substituted or unsubstituted piperidinyl.

$R^7$ is independently hydrogen, halogen, —CN, —OH, —SH, —$NH_2$, —COOH, —$CONH_2$, —$NO_2$, —$CF_3$, $R^{12}$-substituted or unsubstituted alkyl, $R^{12}$-substituted or unsubstituted heteroalkyl (e.g. $R^{12}$-substituted or unsubstituted alkylthio or $R^{12}$-substituted or unsubstituted alkoxy such as $R^{12}$-substituted or unsubstituted haloalkoxy or $R^{12}$-substituted or unsubstituted alkoxycarbonyl), $R^{12}$-substituted or unsubstituted cycloalkyl, $R^{12}$-substituted or unsubstituted heterocycloalkyl, $R^{12}$-substituted or unsubstituted aryl, $R^{12}$-substituted or unsubstituted heteroaryl, or -$L^4R^{7B}$. In some embodiments, $R^7$ is independently hydrogen, halogen, —CN, —OH, —SH, —$NH_2$, —COOH, or —$CF_3$. In some embodiments, $R^7$ is independently $R^{12}$-substituted or unsubstituted alkyl, or $R^{12}$-substituted or unsubstituted heteroalkyl. In some embodiments, $R^7$ is independently $R^{12}$-substituted or unsubstituted cycloalkyl, or $R^{12}$-substituted or unsubstituted heterocycloalkyl. In some embodiments, $R^7$ is independently $R^{12}$-substituted or unsubstituted aryl, or $R^{12}$-substituted or unsubstituted heteroaryl. In some embodiments, $R^7$ is independently $R^{12}$-substituted or unsubstituted heteroaryl. In some embodiments, $R^7$ is $R^{12}$-substituted alkyl, where $R^7$ is $R^{12}$-substituted or unsubstituted cycloalkyl (a cycloalkylalkyl) or $R^{12}$-substituted or unsubstituted heterocycloalkyl (a heterocycloalkylalkyl).

$R^{7A}$ is independently hydrogen, halogen, —CN, —OH, —SH, —$NH_2$, —COOH, —$CONH_2$, —$NO_2$, —$CF_3$, $R^{12}$-substituted or unsubstituted alkyl, $R^{12}$-substituted or unsubstituted heteroalkyl (e.g. $R^{12}$-substituted or unsubstituted alkylthio or $R^{12}$-substituted or unsubstituted alkoxy such as $R^{12}$-substituted or unsubstituted haloalkoxy or $R^{12}$-substituted or unsubstituted alkoxycarbonyl), $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl. $R^{7B}$ is independently hydrogen, halogen, —CN, —OH, —SH, —$NH_2$, —COOH, —$CONH_2$, —$NO_2$, —$CF_3$, $R^{12}$-substituted or unsubstituted alkyl, $R^{12}$-substituted or unsubstituted heteroalkyl, $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl.

$R^{12}$ is independently hydrogen, halogen, —CN, —OH, —SH, —$NH_2$, —COOH, —$CONH_2$, —$NO_2$, —$CF_3$, $R^{13}$-substituted or unsubstituted alkyl, $R^{13}$-substituted or unsubstituted heteroalkyl (e.g. $R^{13}$-substituted or unsubstituted alkylthio or $R^{13}$-substituted or unsubstituted alkoxy such as $R^{13}$-substituted or unsubstituted haloalkoxy or $R^{13}$-substituted or unsubstituted alkoxycarbonyl), $R^{13}$-substituted or unsubstituted cycloalkyl, $R^{13}$-substituted or unsubstituted heterocycloalkyl, $R^{13}$-substituted or unsubstituted aryl, $R^{13}$-substituted or unsubstituted heteroaryl or -$L^{10}$-$R^{13A}$. In some embodiments, $R^{12}$ is independently hydrogen, halogen, —CN, —OH, —SH, —$NH_2$, —COOH, —$CONH_2$, —$NO_2$, or —$CF_3$. In some embodiments, $R^{12}$ is independently $R^{13}$-substituted or unsubstituted alkyl, or $R^{13}$-substituted or unsubstituted heteroalkyl. In some embodiments, $R^{12}$ is independently $R^{13}$-substituted or unsubstituted cycloalkyl, or $R^{13}$-substituted or unsubstituted heterocycloalkyl. In some embodiments, $R^{12}$ is independently $R^{13}$-substituted or unsubstituted aryl, or $R^{13}$-substituted or unsubstituted heteroaryl. In some embodiments, $R^{12}$ is independently $R^{13}$-substituted or unsubstituted heteroaryl. In some embodiments, $R^{12}$ is independently —$NH_2$, —C(O)$NH_2$ or unsubstituted alkyl. $L^{10}$ is —O—, —$NR^{13C}$—, —C(O)—, —C(O)O—, —C(O)$NR^{13C}$—, —$NR^{13C}$C(O), —S(O)$_{m'}$—, —$NR^{13C}$S(O)$_2$—, or —S(O)$_2NR^{13C}$— or —$NR^{13C}$C(O)$NR^{13D}$—, $R^{13C}$-substituted or unsubstituted alkylene, $R^{13C}$-substituted or unsubstituted heteroalkylene, $R^{13C}$-substituted or unsubstituted cycloalkylene, $R^{13C}$-substituted or unsubstituted heterocycloalkylene, $R^{13C}$-substituted or unsubstituted arylene, or $R^{13C}$-substituted or unsubstituted heteroarylene. The symbol m' is 0, 1 or 2. $R^{13C}$ and $R^{13D}$ are independently hydrogen, hydrogen, halogen, —CN, —OH, —SH, —$NH_2$, —$CONH_2$, —$NO_2$, —COOH, or —$CF_3$, $R^{13E}$-substituted or unsubstituted alkyl, u $R^{13E}$-substituted or unsubstituted, $R^{13E}$-substituted or unsubstituted cycloalkyl, $R^{13E}$-substituted or unsubstituted heterocycloalkyl, $R^{13E}$-substituted or unsubstituted aryl or $R^{13E}$-substituted or unsubstituted heteroaryl. $R^{13E}$ is independently hydrogen, hydrogen, halogen, —CN, —OH, —SH, —$NH_2$, —$CONH_2$, —$NO_2$, —COOH, or —$CF_3$, unsubstituted alkyl, unsubstituted heteroalkyl, unsubstituted cycloalkyl, unsubstituted heterocycloalkyl, unsubstituted aryl, unsubstituted heteroaryl.

$R^{13}$ is independently hydrogen, halogen, —CN, —OH, —SH, —$NH_2$, —COOH, —$CONH_2$, —$NO_2$, —$CF_3$, $R^{14}$-substituted or unsubstituted alkyl, $R^{14}$-substituted or unsubstituted heteroalkyl (e.g. $R^{14}$-substituted or unsubstituted alkylthio or $R^{14}$-substituted or unsubstituted alkoxy such as $R^{14}$-substituted or unsubstituted haloalkoxy or $R^{14}$-substituted or unsubstituted alkoxycarbonyl), $R^{14}$-substituted or unsubstituted cycloalkyl, $R^{14}$-substituted or unsubstituted heterocycloalkyl, $R^{14}$-substituted or unsubstituted aryl, $R^{14}$-substituted or unsubstituted heteroaryl, or -$L^{13}$-$R^{13B}$. $L^{13}$ is —O—, —$NR^{13C}$—, —C(O)—, —C(O)O—, —C(O)$NR^{13C}$—, —$NR^{13C}$(O), —S(O)$_{w'}$—, —$NR^{13C}$S(O)$_2$—, or —S(O)$_2NR^{13C}$— or —$NR^{13C}$C(O)$NR^{13D}$—, $R^{13C}$-substituted or unsubstituted alkylene, $R^{13C}$-substituted or unsubstituted heteroalkylene, $R^{13C}$-substituted or unsubstituted cycloalkylene, $R^{13C}$-substituted or unsubstituted heterocycloalkylene, $R^{13C}$-substituted or unsubstituted arylene, or $R^{13C}$-substituted or unsubstituted heteroarylene. The symbol w' is 0, 1 or 2. $R^{13C}$ and $R^{13D}$ are independently hydrogen, unsubstituted alkyl, unsubstituted heteroalkyl, unsubstituted cycloalkyl, unsubstituted heterocycloalkyl, unsubstituted aryl or unsubstituted heteroaryl.

$R^{13A}$ and $R^{13B}$ are independently hydrogen, halogen, —CN, —OH, —SH, —$NH_2$, —COOH, —$CONH_2$, —$NO_2$, —$CF_3$, $R^{14}$-substituted or unsubstituted alkyl, $R^{14}$-substituted or unsubstituted heteroalkyl (e.g. $R^{14}$-substituted or unsubstituted alkylthio or $R^{14}$-substituted or unsubstituted alkoxy such as $R^{14}$-substituted or unsubstituted haloalkoxy or $R^{14}$-substituted or unsubstituted alkoxycarbonyl), $R^{14}$-substituted or unsubstituted cycloalkyl, $R^{14}$-substituted or unsubstituted heterocycloalkyl, $R^{14}$-substituted or unsubstituted aryl, $R^{14}$-substituted or unsubstituted heteroaryl. In some embodiments, $R^{13}$, $R^{13A}$ and $R^{13B}$ are independently hydrogen, halogen, —CN, —OH, —SH, —$NH_2$, —COOH, or —$CF_3$. In some embodiments, $R^{13}$, $R^{13A}$ and $R^{13B}$ are independently $R^{14}$-substituted or unsubstituted alkyl, or $R^{14}$-substituted or unsubstituted heteroalkyl. In some embodiments, $R^{13}$, $R^{13A}$ and $R^{13B}$ are independently $R^{14}$-substituted or unsubstituted cycloalkyl, or $R^{14}$-substituted or unsubstituted heterocycloalkyl. In some embodiments, $R^{13}$, $R^{13A}$ and $R^{13B}$ are independently $R^{14}$-substituted or unsubstituted aryl, or $R^{14}$-substituted or unsubstituted heteroaryl. In some embodiments, $R^{13}$, $R^{13A}$ and $R^{13B}$ are independently $R^{14}$-substituted or unsubstituted heteroaryl. In certain embodiments, where $R^{13}$ is -$L^{13}$-$R^{13B}$, $R^{14}$ is not -$L^{11}$-$R^{15A}$.

$R^{14}$ is independently hydrogen, halogen, —CN, —OH, —SH, —$NH_2$, —COOH, —$CONH_2$, —$NO_2$, —$CF_3$, $R^{15}$-substituted or unsubstituted alkyl, $R^{15}$-substituted or unsubstituted heteroalkyl (e.g. $R^{15}$-substituted or unsubstituted alkylthio or $R^{15}$-substituted or unsubstituted alkoxy such as $R^{15}$-substituted or unsubstituted haloalkoxy or $R^{15}$-substituted or unsubstituted alkoxycarbonyl), $R^{15}$-substituted or unsubstituted cycloalkyl, $R^{15}$-substituted or unsubstituted heterocycloalkyl, $R^{15}$-substituted or unsubstituted aryl, $R^{15}$-substituted or unsubstituted heteroaryl or -$L^{11}$-$R^{15A}$. In some embodiments, $R^{14}$ is independently hydrogen, halogen, —CN, —OH, —SH, —$NH_2$, —COOH, or —$CF_3$. In some embodiments, $R^{14}$ is independently $R^{15}$-substituted or unsubstituted alkyl, or $R^{15}$-substituted or unsubstituted heteroalkyl. In some embodiments, $R^{14}$ is independently $R^{15}$-substituted or unsubstituted cycloalkyl, or $R^{15}$-substituted or unsubstituted heterocycloalkyl. In some embodiments, $R^{14}$ is independently $R^{15}$-substituted or unsubstituted aryl, or $R^{15}$-substituted or unsubstituted heteroaryl. In some embodiments, $R^{14}$ is independently $R^{15}$-substituted or unsubstituted heteroaryl. $L^{11}$ is —O—, —$NR^{15C}$—, —C(O)—, —C(O)O—, —C(O)$NR^{15C}$—, —$NR^{15C}$C(O), —S(O)$_{y'}$—, —$NR^{15C}$S(O)$_2$—, or —S(O)$_2$$NR^{15C}$— or —$NR^{15C}$C(O)$NR^{15D}$—, $R^{15C}$-substituted or unsubstituted alkylene, $R^{15C}$-substituted or unsubstituted heteroalkylene, $R^{15C}$-substituted or unsubstituted cycloalkylene, $R^{15C}$-substituted or unsubstituted heterocycloalkylene, $R^{15C}$-substituted or unsubstituted arylene, or $R^{15C}$-substituted or unsubstituted heteroarylene. The symbol y' is 0, 1 or 2. $R^{15C}$—, and $R^{15D}$ are independently hydrogen, unsubstituted alkyl, unsubstituted heteroalkyl, unsubstituted cycloalkyl, unsubstituted heterocycloalkyl, unsubstituted aryl or unsubstituted heteroaryl.

$R^{15}$ and $R^{15A}$ are independently hydrogen, halogen, —CN, —OH, —SH, —$NH_2$, —COOH, —$NO_2$, —$CONH_2$, —$CF_3$, $R^{23}$-substituted or unsubstituted alkyl, $R^{23}$-substituted or unsubstituted heteroalkyl (e.g. $R^{23}$-substituted or unsubstituted alkylthio or $R^{23}$-substituted or unsubstituted alkoxy such as $R^{23}$-substituted or unsubstituted haloalkoxy or $R^{23}$-substituted or unsubstituted alkoxycarbonyl), $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl. In some embodiments, $R^{15}$ and $R^{15A}$ are independently hydrogen, halogen, —CN, —OH, —SH, —$NH_2$, —COOH, or —$CF_3$. In some embodiments, $R^{15}$ and $R^{15A}$ are independently $R^{23}$-substituted or unsubstituted alkyl, or $R^{23}$-substituted or unsubstituted heteroalkyl. In some embodiments, $R^{15}$ and $R^{15A}$ are independently $R^{23}$-substituted or unsubstituted cycloalkyl, or $R^{23}$-substituted or unsubstituted heterocycloalkyl. In some embodiments, $R^{15}$ and $R^{15A}$ are independently $R^{23}$-substituted or unsubstituted aryl, or $R^{23}$-substituted or unsubstituted heteroaryl. In some embodiments, $R^{15}$ and $R^{15A}$ are independently $R^{23}$-substituted or unsubstituted heteroaryl. In some embodiments, $R^{15}$ and $R^{15A}$ are independently $R^{23}$-substituted or unsubstituted aryl. In some embodiments, $R^{15}$ and $R^{15A}$ are independently unsubstituted alkyl or unsubstituted heteroalkyl. In some embodiments, $R^{15}$ and $R^{15A}$ are independently unsubstituted cycloalkyl or unsubstituted heterocycloalkyl. In some embodiments, $R^{15}$ and $R^{15A}$ are independently unsubstituted aryl or unsubstituted heteroaryl. In some embodiments, $R^{15}$ and $R^{15A}$ are independently unsubstituted heteroaryl. In some embodiments, $R^{15}$ and $R^{15A}$ are independently unsubstituted aryl.

$R^{23}$ is independently halogen, —CN, —OH, —SH, —$NH_2$, —COOH, —$CONH_2$, —$NO_2$, —$CF_3$, $R^{25}$-substituted or unsubstituted alkyl, $R^{25}$-substituted or unsubstituted heteroalkyl (e.g. $R^{25}$-substituted or unsubstituted alkylthio or $R^{25}$-substituted or unsubstituted alkoxy such as $R^{25}$-substituted or unsubstituted haloalkoxy or $R^{25}$-substituted or unsubstituted alkoxycarbonyl), $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl, or -$L^{12}$-$R^{24}$. In some embodiments, $R^{23}$ is independently hydrogen, halogen, —CN, —OH, —SH, —$NH_2$, —COOH, or —$CF_3$. $R^{24}$ is independently halogen, —CN, —OH, —SH, —$NH_2$, —COOH, —$CONH_2$, —$CF_3$, $R^{25}$-substituted or unsubstituted alkyl, $R^{25}$-substituted or unsubstituted heteroalkyl (e.g. $R^{25}$-substituted or unsubstituted alkylthio or $R^{25}$-substituted or unsubstituted alkoxy such as $R^{25}$-substituted or unsubstituted haloalkoxy or $R^{25}$-substituted or unsubstituted alkoxycarbonyl), $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl. $L^{12}$ is —O—, —$NR^{26}$—, —C(O)—, —C(O)O—, —C(O)$NR^{26}$—, —$NR^{26}$C(O), —S(O)$_{j'}$—, —$NR^{26}$S(O)$_2$—, or —S(O)$_2$$NR^{26}$— or —$NR^{26}$C(O)$NR^{27}$—, $R^{26}$-substituted or unsubstituted alkylene, $R^{26}$-substituted or unsubstituted heteroalkylene, $R^{26}$-substituted or unsubstituted cycloalkylene, $R^{26}$-substituted or unsubstituted heterocycloalkylene, $R^{26}$-substituted or unsubstituted arylene, or $R^{26}$-substituted or unsubstituted heteroarylene. The symbol j' is 0, 1 or 2. $R^{25}$, $R^{26}$ and $R^{27}$ are independently hydrogen, hydrogen, halogen, —CN, —OH, —SH, —$NH_2$, —COOH, —$CONH_2$, —$NO_2$, —$CF_3$, unsubstituted alkyl, unsubstituted heteroalkyl, unsubstituted cycloalkyl, unsubstituted heterocycloalkyl, unsubstituted aryl or unsubstituted heteroaryl.

In some embodiments, $R^5$ is hydrogen, $R^{30}$-substituted or unsubstituted alkyl, $R^{30}$-substituted or unsubstituted heteroalkyl (e.g. $R^{30}$-substituted or unsubstituted alkylthio or $R^{30}$-substituted or unsubstituted alkoxy such as $R^{30}$-substituted or unsubstituted haloalkoxy or $R^{30}$-substituted or unsubstituted alkoxycarbonyl), $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl, $R^{30}$ is independently halogen, —CN, —OH, —SH, —$NH_2$, —COOH, —$NO_2$, —$CONH_2$, —$CF_3$, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^1$ is $R^7$-substituted or unsubstituted 6,5 fused ring heteroaryl, $R^7$-substituted or unsubstituted 5,6 fused ring heteroaryl, $R^7$-substituted or unsubstituted 5,5 fused ring heteroaryl, $R^7$-substituted or unsubstituted 6,6 fused ring heteroaryl, or $R^7$-substituted or unsubstituted 5 or 6 membered heteroaryl having at least 2 (e.g. 2 to 4) ring nitrogens. In certain embodiments, $R^1$ is $R^7$-substituted phenyl, $R^7$-substituted piperidinyl, $R^7$-substituted 6-membered heterocycloalkyl, $R^7$-substituted 6,5 fused ring heteroaryl, $R^7$-substituted or unsubstituted 5,6 fused ring heteroaryl. $R^7$ may be halogen, —CN, —OH, —SH, —$NH_2$, —COOH, $R^{12}$-substituted or unsubstituted alkyl, $R^{12}$-substituted or unsubstituted heteroalkyl, $R^{12}$-substituted or unsubstituted cycloalkyl, $R^{12}$- substituted or unsubstituted heterocycloalkyl, $R^{12}$-substituted or unsubstituted aryl, or $R^{12}$-substituted or unsubstituted heteroaryl or -$L^4$-$R^{7B}$. $R^{7B}$ may be $R^{12}$-substituted or unsubstituted cycloalkyl, $R^{12}$-substituted or unsubstituted heterocycloalkyl, $R^{12}$-substituted or unsubstituted aryl, or $R^{12}$-substituted or unsubstituted heteroaryl. In some embodiments, $L^4$ is substituted or unsubstituted alkylene, or substituted or unsubstituted heteroalkylene. In some embodiments, $L^4$ is substituted or unsubstituted $C_1$-$C_{10}$ alkylene. In some embodiments $L^4$ is a bond. $L^4$ may be —O—, —NH—, —C(O)—, —C(O)NH—, —S(O)$_m$—, or —S(O)$_m$NH—. $R^{12}$ may be —OH, or $R^{13}$-substituted or unsubstituted alkyl.

In some related embodiments, $R^7$, $R^{7A}$ and $R^{7B}$ are independently $R^{12}$-substituted or unsubstituted cycloalkyl, $R^{12}$-substituted or unsubstituted heterocycloalkyl, $R^{12}$-substituted or unsubstituted aryl, $R^{12}$-substituted or unsubstituted heteroaryl, or -$L^4$-$R^{7AB}$. In other related embodiments, $R^7$ is $R^{12}$-substituted or unsubstituted heteroaryl, or -$L^4$-$R^{7B}$. $L^4$ may be —C(O). $R^{7B}$ may be $R^{12}$-substituted or unsubstituted heteroaryl.

In some embodiments, $R^1$ is a substituted or unsubstituted heteroaryl, such as an $R^7$-substituted or unsubstituted heteroaryl. The heteroaryl may be a substituted (e.g. $R^7$-substituted) or unsubstituted pyrrolopyrimidinyl, substituted (e.g. $R^7$-substituted) or unsubstituted indolyl, substituted (e.g. $R^7$-substituted) or unsubstituted pyrazolyl, substituted (e.g. $R^7$-substituted) or unsubstituted indazolyl, substituted (e.g. $R^7$-substituted) or unsubstituted imidazolyl, substituted (e.g. $R^7$-substituted) or unsubstituted thiazolyl, substituted (e.g. $R^7$-substituted) or unsubstituted benzothiazolyl, substituted (e.g. $R^7$-substituted) or unsubstituted oxazolyl, substituted (e.g. $R^7$-substituted) or unsubstituted benzimidazolyl, substituted (e.g. $R^7$-substituted) or unsubstituted benzoxazolyl, substituted (e.g. $R^7$-substituted) or unsubstituted isoxazolyl, substituted (e.g. $R^7$-substituted) or unsubstituted benzisoxazolyl, substituted (e.g. $R^7$-substituted) or unsubstituted triazolyl, substituted (e.g. $R^7$-substituted) or unsubstituted benzotriazolyl, substituted (e.g. $R^7$-substituted) or unsubstituted quinolinyl, substituted (e.g. $R^7$-substituted) or unsubstituted isoquinolinyl, substituted (e.g. $R^7$-substituted) or unsubstituted quinazolinyl, substituted (e.g. $R^7$-substituted) or unsubstituted pyrimidinyl, substituted (e.g. $R^7$-substituted) or unsubstituted pyridinyl N-oxide, substituted (e.g. $R^7$-substituted) or unsubstituted furanyl, substituted (e.g. $R^7$-substituted) or unsubstituted thiophenyl, substituted (e.g. $R^7$-substituted) or unsubstituted benzofuranyl, substituted (e.g. $R^7$-substituted) or unsubstituted benzothiophenyl, substituted or unsubstituted imidazo[1,2b]pyridazinyl. In some embodiments, $R^1$ is a substituted (e.g. $R^7$-substituted) or unsubstituted triazolyl, substituted (e.g. $R^7$-substituted) or unsubstituted imidazolyl, or substituted (e.g. $R^7$-substituted) or unsubstituted pyrazolyl. In some embodiments, $R^1$ is a substituted (e.g. $R^7$-substituted) or unsubstituted benzotriazolyl, substituted (e.g. $R^7$-substituted) or unsubstituted quinolinyl, substituted (e.g. $R^7$-substituted) or unsubstituted isoquinolinyl, substituted (e.g. $R^7$-substituted) or unsubstituted quinazolinyl, or substituted (e.g. $R^7$-substituted) or unsubstituted pyrimidinyl. In some embodiments, $R^1$ is a substituted or unsubstituted 6,5 fused ring heteroaryl, a substituted or unsubstituted 5,6 fused ring heteroaryl, a substituted or unsubstituted 5,5 fused ring heteroaryl, or a substituted or unsubstituted 6,6 fused ring heteroaryl. In other embodiments, $R^1$ is a substituted or unsubstituted 5 or 6 membered heteroaryl having at least 2 (e.g. 2 to 4) ring nitrogens. As discussed above any $R^1$ substituent may be $R^7$-substituted, including the substituents recited in this paragraph.

In some embodiments, $R^7$ is substituted (e.g. $R^{12}$-substituted) or unsubstituted purinyl, substituted (e.g. $R^{12}$-substituted) or unsubstituted pyrimidinyl, substituted (e.g. $R^{12}$-substituted) or unsubstituted imidazolyl, substituted (e.g. $R^{12}$-substituted) or unsubstituted 1H-pyrrolo[2,3-b]pyridinyl, substituted (e.g. $R^{12}$-substituted) or unsubstituted pyrimidinyl, substituted (e.g. $R^{12}$-substituted) or unsubstituted 1H-indazolyl, or substituted (e.g. $R^{12}$-substituted) or unsubstituted 7H-pyrrolo[2,3-d]pyrimidinyl. $R^7$ may also be substituted (e.g. $R^{12}$-substituted) or unsubstituted pyrrolopyrimidinyl, substituted (e.g. $R^{12}$-substituted) or unsubstituted indolyl, substituted (e.g. $R^{12}$-substituted) or unsubstituted pyrazolyl, substituted (e.g. $R^{12}$-substituted) or unsubstituted indazolyl, substituted (e.g. $R^{12}$-substituted) or unsubstituted imidazolyl, substituted (e.g. $R^{12}$-substituted) or unsubstituted thiazolyl, substituted (e.g. $R^{12}$-substituted) or unsubstituted benzothiazolyl, substituted (e.g. $R^{12}$-substituted) or unsubstituted oxazolyl, substituted (e.g. $R^{12}$-substituted) or unsubstituted benzimidazolyl, substituted (e.g. $R^{12}$-substituted) or unsubstituted benzoxazolyl, substituted (e.g. $R^{12}$-substituted) or unsubstituted isoxazolyl, substituted (e.g. $R^{12}$-substituted) or unsubstituted benzisoxazolyl, substituted (e.g. $R^{12}$-substituted) or unsubstituted triazolyl, substituted (e.g. $R^{12}$-substituted) or unsubstituted benzotriazolyl, substituted (e.g. $R^{12}$-substituted) or unsubstituted quinolinyl, substituted (e.g. $R^{12}$-substituted) or unsubstituted isoquinolinyl, substituted (e.g. $R^{12}$-substituted) or unsubstituted quinazolinyl, substituted (e.g. $R^{12}$-substituted) or unsubstituted pyrimidinyl, substituted (e.g. $R^{12}$-substituted) or unsubstituted pyridinyl N-oxide, substituted (e.g. $R^{12}$-substituted) or unsubstituted furanyl, substituted (e.g. $R^{12}$-substituted) or unsubstituted thiophenyl, substituted (e.g. $R^{12}$-substituted) or unsubstituted benzofuranyl, substituted (e.g. $R^{12}$-substituted) or unsubstituted benzothiophenyl, substituted (e.g. $R^{12}$-substituted) or unsubstituted imidazo[1,2b]pyridazinyl. In some embodiments, $R^7$ is a substituted (e.g. $R^{12}$-substituted) or unsubstituted triazolyl, substituted (e.g. $R^{12}$-substituted) or unsubstituted imidazolyl, or substituted (e.g. $R^{12}$-substituted) or unsubstituted pyrazolyl. In some embodiments, $R^7$ is a substituted (e.g. $R^{12}$-substituted) or unsubstituted benzotriazolyl, substituted (e.g. $R^{12}$-substituted) or unsubstituted quinolinyl, substituted (e.g. $R^{12}$-substituted) or unsubstituted isoquinolinyl, substituted (e.g. $R^{12}$-substituted) or unsubstituted quinazolinyl, or substituted (e.g. $R^{12}$-substituted) or unsubstituted pyrimidinyl. In some embodiments, $R^7$ is $R^{12}$-substituted or unsubstituted 6,5 fused ring heteroaryl, $R^{12}$-substituted or unsubstituted 5,6 fused ring heteroaryl, $R^{12}$-substituted or unsubstituted 5,5 fused ring heteroaryl, or $R^{12}$-substituted or unsubstituted 6,6 fused ring heteroaryl. In other embodiments, $R^7$ is a $R^{12}$-substituted or unsubstituted 5 or 6 membered heteroaryl having at least 2 (e.g. 2 to 4) ring nitrogens.

In some embodiments, $R^7$ is a substituted or unsubstituted phenyl, substituted or unsubstituted pyrimidinyl, substituted or unsubstituted piperidinyl, substituted or unsubstituted pyrrolidinyl, substituted or unsubstituted quinolinyl, or substituted or unsubstituted quinazolinyl. In some embodiments, $R^7$ is a $R^{12}$-substituted or unsubstituted phenyl, $R^{12}$-substituted or unsubstituted pyrimidinyl, $R^{12}$-substituted or unsubstituted piperidinyl, $R^{12}$-substituted or unsubstituted pyrrolidinyl, $R^{12}$-substituted or unsubstituted quinolinyl, or $R^{12}$-substituted or unsubstituted quinazolinyl.

In some embodiments, $R^7$ is

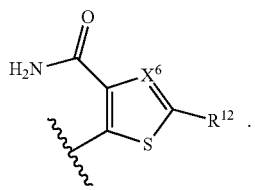

$X^6$ can be nitrogen or $C(-L^{10}-R^{13A})$. $R^{13A}$ may independently be hydrogen, halogen, —CN, —OH, —SH, —NH$_2$, —COOH, —CF$_3$, unsubstituted alkyl, unsubstituted heteroalkyl, unsubstituted cycloalkyl, unsubstituted heterocycloalkyl, unsubstituted aryl, or unsubstituted heteroaryl. $L^{10}$ may be —O—, —NH—, —C(O)—, —C(O)NH—, —S(O)$_m$—, or —S(O)$_2$NH—.

In some embodiments, $L^1$ is a bond, —C(O)—, —N(L$^2$R$^5$)C(O)—, —OC(O)—, —S(O)$_n$—, —(OL$^2$R$^5$)OP(O)—, —N(L$^2$R$^5$)SO$_2$—, —(N(L$^2$R$^5$))NP(O)—, $R^{16}$-substituted or unsubstituted alkylene, $R^{16}$-substituted or unsubstituted heteroalkylene, $R^{16}$-substituted or unsubstituted cycloalkylene, $R^{16}$-substituted or unsubstituted heterocycloalkylene, $R^{16}$-substituted or unsubstituted arylene, or $R^{16}$-substituted or unsubstituted heteroarylene. The symbol n is 0, 1 or 2. In some embodiments, $L^1$ is a bond. In some embodiments, $L^1$ is —N(L$^2$R$^5$)C(O)—. In some embodiments, $L^1$ is —NHC(O)—.

$L^1$ may also be a bond, $R^{16}$-substituted or unsubstituted alkylene, $R^{16}$-substituted or unsubstituted heteroalkylene, $R^{16}$-substituted or unsubstituted cycloalkylene, $R^{16}$-substituted or unsubstituted heterocycloalkylene, $R^{16}$-substituted or unsubstituted arylene, or $R^{16}$-substituted or unsubstituted heteroarylene.

$R^{16}$ is independently hydrogen, halogen, —CN, —OH, —SH, —NH$_2$, —COOH, —NO$_2$, —CONH$_2$, —CF$_3$, $R^{31}$-substituted or unsubstituted alkyl, $R^{31}$-substituted or unsubstituted heteroalkyl (e.g. $R^{31}$-substituted or unsubstituted alkylthio or $R^{31}$-substituted or unsubstituted alkoxy such as $R^{31}$-substituted or unsubstituted haloalkoxy or $R^{31}$-substituted or unsubstituted alkoxycarbonyl), $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

$R^{31}$ is independently halogen, —CN, —OH, —SH, —NH$_2$, —COOH, —NO$_2$, —CONH$_2$, —CF$_3$, unsubstituted alkyl, unsubstituted heteroalkyl, unsubstituted cycloalkyl, unsubstituted heterocycloalkyl, unsubstituted aryl, or unsubstituted heteroaryl.

In some embodiments, $L^2$ is independently a bond, $R^{28}$-substituted or unsubstituted alkylene, $R^{28}$-substituted or unsubstituted heteroalkylene, $R^{28}$-substituted or unsubstituted cycloalkylene, $R^{28}$-substituted or unsubstituted heterocycloalkylene, $R^{28}$-substituted or unsubstituted arylene, or $R^{28}$-substituted or unsubstituted heteroarylene. $R^{28}$ is halogen, —CN, —OH, —SH, —NH$_2$, —COOH, —CF$_3$, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^2$ is independently $R^{2A}$-substituted or unsubstituted alkyl, $R^{2A}$-substituted or unsubstituted heteroalkyl (e.g. $R^{2A}$-substituted or unsubstituted alkylthio or $R^{2A}$-substituted or unsubstituted alkoxy such as $R^{2A}$-substituted or unsubstituted haloalkoxy or $R^{2A}$-substituted or unsubstituted alkoxycarbonyl), $R^{2A}$-substituted or unsubstituted cycloalkyl, $R^{2A}$-substituted or unsubstituted heterocycloalkyl, $R^{2A}$-substituted or unsubstituted aryl, or $R^{2A}$-substituted or unsubstituted heteroaryl. In some embodiments, $R^3$ is independently $R^{3A}$-substituted or unsubstituted alkyl, $R^{3A}$-substituted or unsubstituted heteroalkyl (e.g. $R^{3A}$-substituted or unsubstituted alkylthio or $R^{3A}$-substituted or unsubstituted alkoxy such as $R^{3A}$-substituted or unsubstituted haloalkoxy or $R^{3A}$-substituted or unsubstituted alkoxycarbonyl), $R^{3A}$-substituted or unsubstituted cycloalkyl, $R^{3A}$-substituted or unsubstituted heterocycloalkyl, $R^{3A}$-substituted or unsubstituted aryl, or $R^{3A}$-substituted or unsubstituted heteroaryl.

$R^{2A}$ and $R^{3A}$ are independently halogen, —CN, —OH, —SH, —NH$_2$, —COOH, —NO$_2$, —CONH$_2$, —CF$_3$, unsubstituted alkyl, unsubstituted heteroalkyl, unsubstituted cycloalkyl, unsubstituted heterocycloalkyl, unsubstituted aryl, or unsubstituted heteroaryl. In some embodiments, $R^{2A}$ and $R^{3A}$ are independently unsubstituted alkyl or unsubstituted heteroalkyl.

In certain embodiments, $R^2$ and $R^3$ are optionally joined together to form a substituted or unsubstituted cycloalkyl, substituted or unsubstituted heterocycloalkyl, substituted or unsubstituted aryl, or substituted or unsubstituted heteroaryl. In some embodiments, $R^2$ and $R^3$ are optionally joined together to form a $R^{17}$-substituted or unsubstituted cycloalkyl, $R^{17}$-substituted or unsubstituted heterocycloalkyl, $R^{17}$-substituted or unsubstituted aryl, or $R^{17}$-substituted or unsubstituted heteroaryl. In some embodiments, $R^2$ and $R^3$ are optionally joined together to form a substituted or unsubstituted cycloalkyl. In some embodiments, $R^2$ and $R^3$ are optionally joined together to form a $R^{17}$-substituted or unsubstituted cycloalkyl. In some embodiments, $R^2$ and $R^3$ are optionally joined together to form a substituted or unsubstituted cyclopropyl. In some embodiments, $R^2$ and $R^3$ are optionally joined together to form a $R^{17}$-substituted or unsubstituted cyclopropyl. In some embodiments, $R^2$ and $R^3$ are optionally joined together to form an unsubstituted cyclopropyl.

$R^{17}$ is independently hydrogen, halogen, —CN, —OH, —SH, —NH$_2$, —COOH, —NO$_2$, —CONH$_2$, —CF$_3$, $R^{32}$-substituted or unsubstituted alkyl, $R^{32}$-substituted or unsubstituted heteroalkyl (e.g. $R^{32}$-substituted or unsubstituted alkylthio or $R^{32}$-substituted or unsubstituted alkoxy such as $R^{32}$-substituted or unsubstituted haloalkoxy or $R^{32}$-substituted or unsubstituted alkoxycarbonyl), $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl, $R^{32}$ is independently halogen, —CN, —OH, —SH, —NH$_2$, —COOH, —NO$_2$, —CONH$_2$, —CF$_3$, unsubstituted alkyl, unsubstituted heteroalkyl, unsubstituted cycloalkyl, unsubstituted heterocycloalkyl, unsubstituted aryl, or unsubstituted heteroaryl.

In some embodiments, $R^4$ is independently hydrogen, —NR$^{4A}$R$^{4B}$, —OR$^{4A}$, —SR$^{4A}$, cyano, $R^{18}$-substituted or unsubstituted alkyl, $R^{18}$-substituted or unsubstituted heteroalkyl (e.g. $R^{18}$-substituted or unsubstituted alkylthio or $R^{18}$-substituted or unsubstituted alkoxy such as $R^{18}$-substituted or unsubstituted haloalkoxy or $R^{18}$-substituted or unsubstituted alkoxycarbonyl), $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl. $R^{4A}$ and $R^{4B}$ are independently hydrogen, $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl.

In some embodiments, $R^4$ is hydrogen. In some embodiments, $R^4$ is $-NR^{4A}R^{4B}$. In some embodiments, $R^4$ is substituted or unsubstituted alkyl. In some embodiments, $R^4$ is $R^{18}$-substituted or unsubstituted alkyl. In some embodiments, $R^4$ is $R^{18}$-substituted unsubstituted $C_1$-$C_{10}$ alkyl. In some embodiments, $R^4$ is $R^{18}$-substituted or unsubstituted cycloalkyl. In some embodiments, $R^4$ is $R^{18}$-substituted or unsubstituted $C_3$-$C_6$ cycloalkyl. $R^{4A}$ and $R^{4B}$ are independently hydrogen or unsubstituted alkyl. In some embodiments, $R^{4A}$ and $R^{4B}$ are independently methyl, propyl, butyl, pentyl or hexyl. In some embodiments, $R^4$ is $-NMe_2$. In some embodiments, $R^2$ is unsubstituted cycloalkyl, $R^3$ is hydrogen, and $R^4$ is $-NMe_2$. In some embodiments, $R^2$ and $R^3$ are optionally joined together to form a substituted or unsubstituted cyclopropyl, and $R^4$ is $-NMe_2$.

$R^{18}$ is independently halogen, $-CN$, $-OH$, $-SH$, $-NH_2$, $-COOH$, $-NO_2$, $-CONH_2$, $-CF_3$, unsubstituted alkyl, unsubstituted heteroalkyl, unsubstituted cycloalkyl, unsubstituted heterocycloalkyl, unsubstituted aryl, or unsubstituted heteroaryl.

In some embodiments, $L^4$ is independently a bond, $-C(O)-$, $-C(O)N(L^6R^8)-$, $-N(L^6R^8)C(O)-$, $-C(O)O-$, $-S(O)_w-$, $-O-$, $-N(L^6R^8)-$, $-P(O)(OL^6R^8)O-$, $-SO_2N(L^6R^8)-$, $-N(L^6R^8)SO_2-$, $-N(L^6R^8)C(O)N(L^7R^9)-$, $-P(O)(N(L^6R^8))N-$, $R^{19}$-substituted or unsubstituted alkylene, $R^{19}$-substituted or unsubstituted heteroalkylene, $R^{19}$-substituted or unsubstituted cycloalkylene, $R^{19}$-substituted or unsubstituted heterocycloalkylene, $R^{19}$-substituted or unsubstituted arylene, or $R^{19}$-substituted or unsubstituted heteroarylene. The symbol w is 0, 1 or 2.

$L^6$ and $L^7$ can be independently a bond, $R^{19}$-substituted or unsubstituted alkylene, $R^{19}$-substituted or unsubstituted heteroalkylene, $R^{19}$-substituted or unsubstituted cycloalkylene, $R^{19}$-substituted or unsubstituted heterocycloalkylene, $R^{19}$-substituted or unsubstituted arylene, or $R^{19}$-substituted or unsubstituted heteroarylene.

$R^{19}$ is independently hydrogen, halogen, $-CN$, $-OH$, $-SH$, $-NH_2$, $-COOH$, $-CONH_2$, $-CF_3$, $R^{19A}$-substituted or unsubstituted alkyl, $R^{19A}$-substituted or unsubstituted heteroalkyl (e.g. $R^{19A}$-substituted or unsubstituted alkylthio or $R^{19A}$-substituted or unsubstituted alkoxy such as $R^{19A}$-substituted or unsubstituted haloalkoxy or $R^{19A}$-substituted or unsubstituted alkoxycarbonyl), $R^{19A}$-substituted or unsubstituted cycloalkyl, $R^{19A}$-substituted or unsubstituted heterocycloalkyl, $R^{19A}$-substituted or unsubstituted aryl, or $R^{19A}$-substituted or unsubstituted heteroaryl, $R^{19A}$ is independently halogen, $-CN$, $-OH$, $-SH$, $-NH_2$, $-COOH$, $-NO_2$, $-CONH_2$, $-CF_3$, unsubstituted alkyl, unsubstituted heteroalkyl, unsubstituted cycloalkyl, unsubstituted heterocycloalkyl, unsubstituted aryl, or unsubstituted heteroaryl.

$R^8$ and $R^9$ can be independently hydrogen, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

$R^{20}$ is independently halogen, $-CN$, $-OH$, $-SH$, $-NH_2$, $-COOH$, $-NO_2$, $-CONH_2$, $-CF_3$, unsubstituted alkyl, unsubstituted heteroalkyl, unsubstituted cycloalkyl, unsubstituted heterocycloalkyl, unsubstituted aryl, or unsubstituted heteroaryl.

$L^5$ can be independently a bond, $-C(O)-$, $-C(O)N(L^8R^{10})-$, $-N(L^8R^{10})C(O)-$, $-C(O)O-$, $-S(O)_v-$, $-O-$, $-N(L^8R^{10})-$, $-P(O)(OL^8R^{10})O-$, $-SO_2N(L^8R^{10})-$, $-N(L^8R^{10})SO_2-$, $-N(L^8R^{10})C(O)N(L^9R^{11})-$, $-P(O)(N(L^8R^{10}))N-$, $R^{21}$-substituted or unsubstituted alkylene, $R^{21}$-substituted or unsubstituted heteroalkylene, $R^{21}$-substituted or unsubstituted cycloalkylene, $R^{21}$-substituted or unsubstituted heterocycloalkylene, $R^{21}$-substituted or unsubstituted arylene, or $R^{21}$-substituted or unsubstituted heteroarylene. The symbol v is 0, 1 or 2.

$R^{21}$ is independently halogen, $-CN$, $-OH$, $-SH$, $-NH_2$, $-COOH$, $-NO_2$, $-CONH_2$, $-CF_3$, unsubstituted alkyl, unsubstituted heteroalkyl, unsubstituted cycloalkyl, unsubstituted heterocycloalkyl, unsubstituted aryl, or unsubstituted heteroaryl.

$L^8$ and $L^9$ can independently be a bond, $R^{12}$-substituted or unsubstituted alkylene, $R^{12}$-substituted or unsubstituted heteroalkylene, $R^{12}$-substituted or unsubstituted cycloalkylene, $R^{12}$-substituted or unsubstituted heterocycloalkylene, $R^{12}$-substituted or unsubstituted arylene, or $R^{12}$-substituted or unsubstituted heteroarylene.

In some embodiments, $R^{10}$ and $R^{11}$ are independently hydrogen, $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

$R^{22}$ is independently halogen, $-CN$, $-OH$, $-SH$, $-NH_2$, $-COOH$, $-NO_2$, $-CONH_2$, $-CF_3$, unsubstituted alkyl, unsubstituted heteroalkyl, unsubstituted cycloalkyl, unsubstituted heterocycloalkyl, unsubstituted aryl, or unsubstituted heteroaryl.

Reference to embodiments set forth herein is meant to include all combinations of the embodiments unless stated otherwise.

In some embodiments, the compound of Formula (I) has the structure:

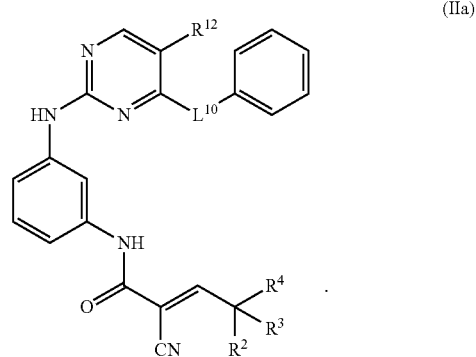

(IIa)

In Formula IIa, $R^2$, $R^3$, $R^4$, $R^{12}$ and $L^{10}$ are as defined above. In some embodiments, $R^2$ and $R^3$ are joined together to form cyclopropyl. In some embodiments, $R^4$ is hydrogen or $NMe_2$.

In some embodiments, the compound of Formula (I) has the structure:

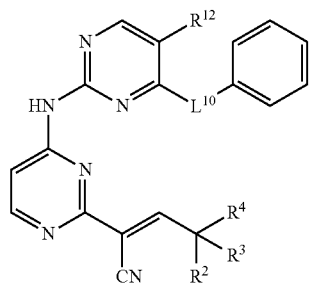

(IIb)

In Formula IIb, $R^2$, $R^3$, $R^4$, $R^{12}$ and $L^{10}$ are as defined above. In some embodiments, $R^2$ and $R^3$ are joined together to form cyclopropyl. In some embodiments, $R^4$ is hydrogen or $NMe_2$.

In some embodiments, the compound of Formula (I) has the structure:

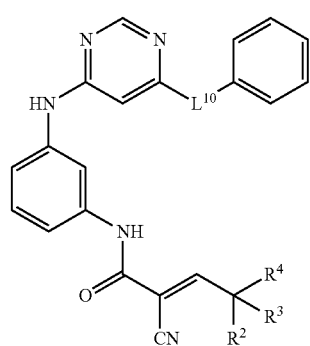

(IIc)

In Formula IIc, $R^2$, $R^3$, $R^4$, and $L^{10}$ are as defined above. In some embodiments, $R^2$ and $R^3$ are joined together to form cyclopropyl. In some embodiments, $R^4$ is hydrogen or $NMe_2$.

In some embodiments, the kinase inhibitor has the structure:

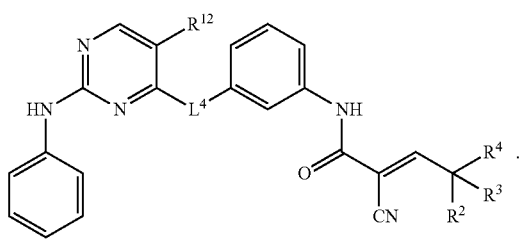

(IIIa)

In Formula IIIa, $R^2$, $R^3$, $R^4$, $R^{12}$ and $L^4$ as defined above. $R^1$, -$L^1$-Z—$R^1$ and/or -$L^1$-$R^1$ may be designed to be a kinase ATP binding site moiety. A "kinase ATP binding site moiety," as used herein, is a moiety capable of fitting within a kinase ATP binding site and/or binding to amino acids within the kinase ATP binding site. Kinase ATP binding sites are well known for wide variety of kinases, and may be easily determined from the primary amino acid structure of a kinase using computer modeling techniques commonly employed in the art. In certain embodiments, -$L^1$-Z—$R^1$ is a kinase ATP binding site moiety and the electron deficient olefin carbon binds to a sulfhydryl of a kinase active site cysteine. Thus, in some embodiments the kinase inhibitors provided herein bind to at least two points of the protein kinase: at least one residue within the ATP binding site moiety and a sulfhydryl of a kinase active site cysteine. In some embodiments, $R^4$ can be a kinase ATP binding site moiety. In some embodiments, $R^4$ is not a kinase ATP binding site moiety. In some embodiments, none of $R^2$, $R^3$ or $R^4$ is a kinase ATP binding site moiety. In some embodiments, none of $R^2$, $R^3$ or $R^4$ are an electron withdrawing group. The term "electron withdrawing group" ("EWD") refers to a chemical substituent that modifies the electron density acting on a nearby chemical reaction center by allowing pi electron delocalization. With regard to Formula I, an EWD allows electron delocalizations in such a way that greater electron density is present on the α-carbon (which has a partial negative charge) unless less electron density is present on the β-carbon (which has a partial positive charge). The α-carbon and β-carbon, as used herein, is indicated below:

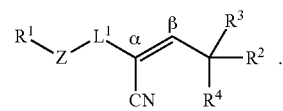

In some embodiments, the kinase inhibitors provided herein (e.g. compounds of Formula I above or embodiments thereof) are reversible kinase inhibitors, and may measurably dissociate from the protein kinase when the protein kinase is not denatured, partially denatured, or fully denatured. In some embodiments, the reversible kinase inhibitor measurably dissociates from the protein kinase only when the protein kinase is fully denatured or partially denatured, but does not measurably dissociate from the protein kinase when the protein kinase is intact, or dissociates at least 10, $1\times10^2$, $1\times10^3$, $1\times10^4$, $1\times10^5$, $1\times10^6$, $1\times10^7$, $1\times10^8$, $1\times10^9$, $1\times10^{10}$ fold slower when the protein kinase is intact relative to the dissociation when the protein kinase is fully or partially denatured (referred to herein as a "cysteine dependent reversible kinase inhibitor"). In some embodiments, the protein kinase is denatured or fully denatured (i.e. not intact) when placed in denaturing solution, such as 6 N guanidine, 1% SDS, 50% MeCN, or similar protein denaturant, for seconds or minutes (e.g. 30 to 120 seconds, such as 60 seconds). In some embodiments, the reversible kinase inhibitors described herein, after binding to the kinase active site cysteine residue, are capable of dissociating from the kinase within seconds or minutes after denaturing/unfolding the kinase with 6 N guanidine, 1% SDS, 50% MeCN, or similar protein denaturant. In other embodiments, the reversible kinase inhibitors described herein, after covalently binding to the kinase active site cysteine residue, are capable of dissociating from the kinase within seconds or minutes after the kinase has been subject to a protease (e.g. trypsin). In some embodiments, the reversible kinase inhibitors described herein bind to a cysteine residue. In some embodiments, the reversible kinase inhibitors described herein bind to a cysteine residue in a catalytic site for a protein kinase. In some embodiments, the reversible kinase inhibitors described herein are a cysteine dependent reversible kinase inhibitor. In some embodiments, the reversible kinase inhibitor has a slow off rate (a slow off-rate inhibitor).

In some embodiments, the compound of Formula (I) has the structure:

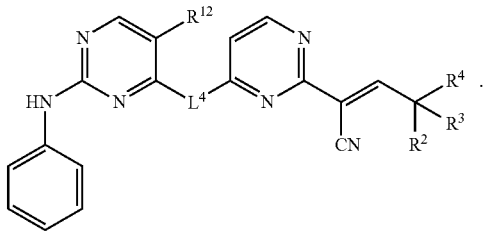
(IIIb)

In Formula IIIb, $R^2$, $R^3$, $R^4$, $R^{12}$ and $L^4$ as defined above. In some embodiments, $R^2$ and $R^3$ are joined together to form cyclopropyl. In some embodiments, $R^4$ is hydrogen or NMe$_2$.

In some embodiments, the compound of Formula (I) has the structure:

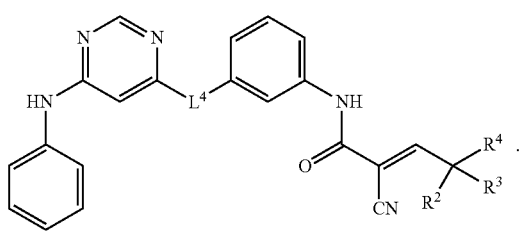
(IIIc)

In Formula IIIc, $R^2$, $R^3$, $R^4$ and $L^5$ are as defined above. In some embodiments, $R^2$ and $R^3$ are joined together to form cyclopropyl. In some embodiments, $R^4$ is hydrogen or NMe$_2$.

In some embodiments, the compound of Formula (I) has the structure:

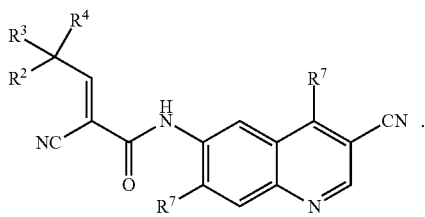
(IVa)

In Formula IVa, $R^2$, $R^3$, $R^4$ and $R^7$ are as defined above. In some embodiments, $R^4$ is —$N^{4A}R^{4B}$ as defined above. In some embodiments, $R^7$ at the 8-position on the quinolinyl ring is $L^4R^{7A}$, and $L^4$ is —O— and $R^{7A}$ is as defined above. In some embodiments, $R^7$ at the 4-position on the quinolinyl ring is $L^4R^{7A}$, and $L^4$ is —NH— and $R^{7A}$ is as defined above. In some embodiments, $R^{7A}$ is $R^{12}$-substituted or unsubstituted aryl, or $R^{12}$-substituted or unsubstituted heteroaryl, as defined above.

In some embodiments, the compound of Formula (I) has the structure:

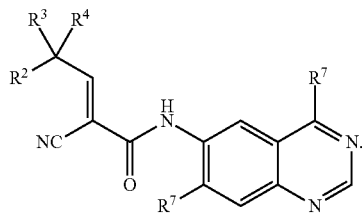
(IVb)

In Formula IVb, $R^2$, $R^3$, $R^4$ and $R^7$ are as defined above. In some embodiments, $R^4$ is —$N^{4A}R^{4B}$ as defined above. In some embodiments, $R^7$ at the 7-position on the quinazolinyl ring is $L^4R^{7A}$, and $L^4$ is —O— and $R^{7A}$ is as defined above. In some embodiments, $R^7$ at the 4-position on the quinazolinyl ring is $L^4R^{7A}$, and $L^4$ is —NH— and $R^{7A}$ is as defined above. In some embodiments, $R^{7A}$ is $R^{12}$-substituted or unsubstituted aryl, or $R^{12}$-substituted or unsubstituted heteroaryl, as defined above.

In some embodiments, the compound of Formula (I) has the structure:

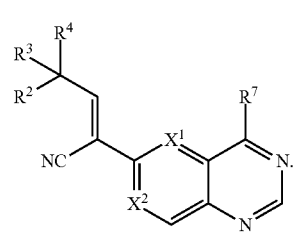
(IVc)

In Formula IVc, $R^2$, $R^3$, $R^4$, $R^7$, $X^1$ and $X^2$ are as defined above. In some embodiments, $R^7$ is $L^4R^{7A}$, and $L^4$ is —NH— and $R^{7A}$ is as defined above. In some embodiments, $R^{7A}$ is $R^{12}$-substituted or unsubstituted aryl, or $R^{12}$-substituted or unsubstituted heteroaryl, as defined above.

In some embodiments, the compound of Formula (I) has the structure:

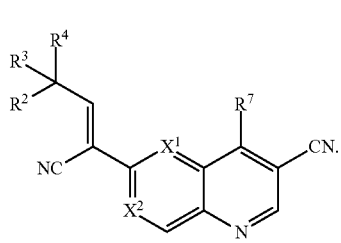
(IVd)

In Formula IVd, $R^2$, $R^3$, $R^4$, $R^7$, $X^1$ and $X^2$ are as defined above. In some embodiments, $R^7$ is $L^4R^{7A}$, and $L^4$ is —NH— and $R^{7A}$ is as defined above. In some embodiments, $R^{7A}$ is $R^{12}$-substituted or unsubstituted aryl, or $R^{12}$-substituted or unsubstituted heteroaryl, as defined above.

In some embodiments, the compound of Formula (I) has the structure:

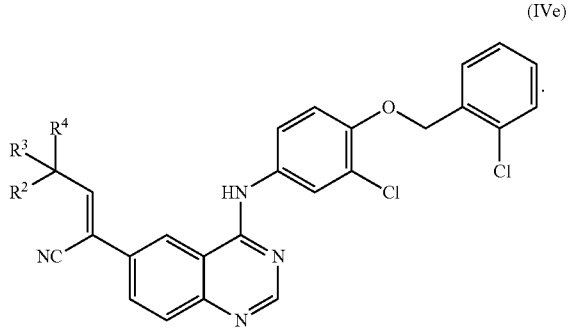

(IVe)

In Formula IVe, $R^2$, $R^3$ and $R^4$ are as defined above. In some embodiments, $R^2$ and $R^3$ are joined together to form cyclopropyl. In some embodiments, $R^4$ is hydrogen or $NMe_2$.

In some embodiments, the compound of Formula (I) has the structure:

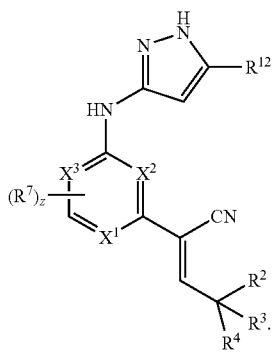

(Va)

In Formula Va, $R^2$, $R^3$, $R^4$, $R^7$, $R^{12}$, $X^1$, $X^2$, and $X^3$ are as defined above. In some embodiments, $R^4$ is —$N^{4A}R^{4B}$ as defined above. In some embodiments, $R^2$ and $R^3$ are joined together to form cyclopropyl. In some embodiments, $R^4$ is hydrogen or $NMe_2$.

In some embodiments, the compound of Formula (I) has the structure:

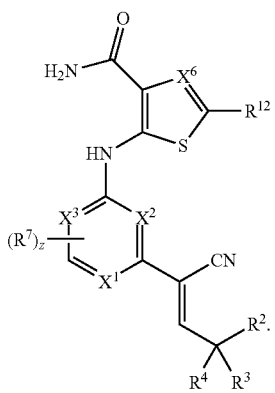

(Vb)

In Formula Vb, $R^2$, $R^3$, $R^4$, R, $R^{12}$, $X^1$, $X^2$, $X^3$ and $X^4$ are as defined above. In some embodiments, $R^4$ is —$N^{4A}R^{4B}$ as defined above. In some embodiments, $R^{12}$ is $R^{13}$-substituted or unsubstituted aryl or $R^{13}$-substituted or unsubstituted heteroaryl as defined above.

In some embodiments, the compound of Formula (I) has the structure:

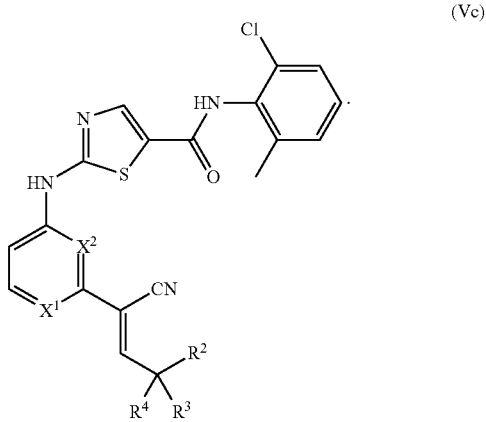

(Vc)

In Formula Vc, $R^2$, $R^3$, $R^4$, $X^1$ and $X^2$ are as defined above. In some embodiments, $X^1$ and $X^2$ are nitrogen. In some embodiments, $R^2$ and $R^3$ are joined together to form cyclopropyl. In some embodiments, $R^4$ is hydrogen or $NMe_2$.

In some embodiments, the compound of Formula (I) has the structure:

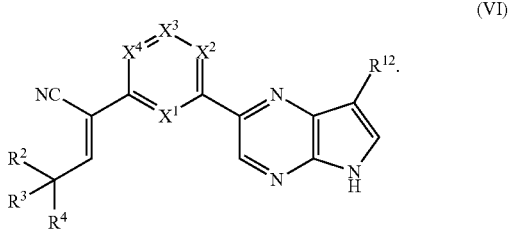

(VI)

In Formula VI, $R^2$, $R^3$, $R^4$, $R^{12}$, $X^1$, $X^2$, $X^3$, $X^4$ are as defined above. In some embodiments, $R^{12}$ is $L^{10}$-$R^{13A}$. In some embodiments, $L^{10}$ is —C(O)— and $R^{13A}$ is as defined above. In some embodiments, $R^2$ and $R^3$ are joined together to form cyclopropyl. In some embodiments, $R^4$ is hydrogen or $NMe_2$. In some embodiments, $R^{12}$ can be hydrogen. In some embodiments, $X^1$ and $X^2$ are nitrogen. In some embodiments, $X^1$, $X^2$ and $X^3$ are nitrogen. In some embodiments, $X^1$, $X^2$ and $X^4$ are nitrogen.

In some embodiments, the compound of Formula (I) has the structure:

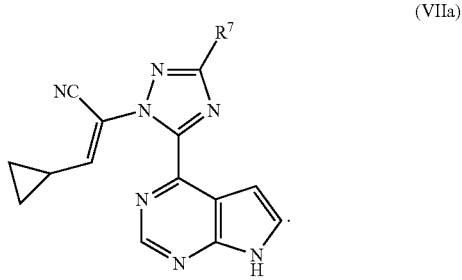

(VIIa)

In formula VIIA, $R^7$ is as defined above.

In some embodiments, the compound of Formula (I) has the structure:

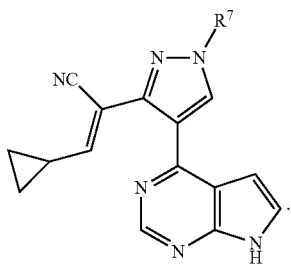
(VIIb)

In Formula VIIb, $R^7$ is as defined above.

In some embodiments, the compound of Formula (I) has the structure:

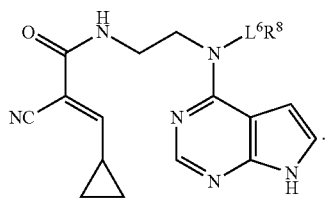
(VIIc)

In Formula (VIIc), $L^6$ and R are as defined above.

In some embodiments, the compound of Formula (I) has the structure:

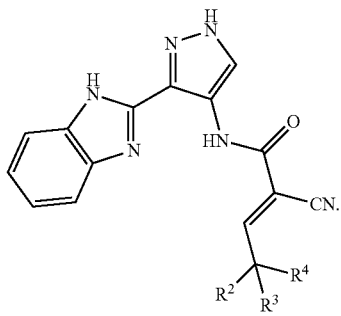
(VIII)

In Formula VIII, $R^2$, $R^3$ and $R^4$ are as defined above.

In some embodiments, -$L^1$-Z—$R^1$ is not $H_2NC(O)$—. In some embodiments, -$L^1$-Z—$R^1$ is not —$C(O)NH_2$. In other embodiments, -$L^1$-Z—$R^1$ is not —$C(O)OH$, or —$C(O)OR''$, wherein R'' is an unsubstituted $C_1$-$C_{10}$ alkyl (e.g. unsubstituted $C_1$-$C_5$ alkyl such as methyl). In some embodiments, -$L^1$-Z—$R^1$ is not —$C(O)N(CH_3)_2$ or —$C(O)NH(CH_3)$. In some embodiments, the selected compound combination of $R^2$, $R^3$ and $R^4$ does not have the formula:

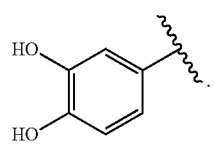

In other embodiments, the selected compound combination of $R^2$, $R^3$ and $R^4$ is not a phenyl substituted with hydroxyl.

The kinase inhibitor may be a reversible kinase inhibitor (as discussed herein). In some embodiments, the kinase inhibitor is a reversible denatured kinase inhibitor (as discussed herein). In some embodiments, the kinase inhibitor is a cysteine reversible kinase inhibitor (as discussed herein). In other embodiments, the kinase inhibitor is a cysteine reversible denatured kinase inhibitor (as discussed herein).

In some embodiments, the compounds of the Formulae provided herein, and embodiments thereof, are stable at pH 7.5 (e.g. in phosphate-buffered saline at 37° C.). In some embodiments, where the compound of Formula I, and embodiments thereof, are stable at pH 7.5, the compound has a half life of greater than 6 hours, 12 hours, 24 hours, or 48 hours. In some embodiments, where the compounds of the Formulae provided herein, and embodiments thereof, are stable at pH 7.5, the compound has a half life of greater than 12 hours. In some embodiments, where the compounds of the Formulae provided herein, and embodiments thereof, are stable at pH 7.5, the compound has a half life of greater than 24 hours. In some embodiments, where the compounds of the Formulae provided herein, and embodiments thereof, are stable at pH 7.5, the compound has a half life of greater than 48 hours. In certain embodiments, the compounds of the Formulae provided herein, and embodiments thereof, exhibit kinase inhibition within a cell. In some embodiments, the cell is a prokaryote or eukaryote. The cell may be a eukaryote (e.g. protozoan cell, fungal cell, plant cell or an animal cell). In some embodiments, the cell is a mammalian cell such as a human cell, cow cell, pig cell, horse cell, dog cell and cat cell, mouse cell, or rat cell. In some embodiments, the cell is a human cell. The cell may form part of an organ or an organism. In certain embodiments, the cell does not form part of an organ or an organism.

In some embodiments, each substituted group described above in the compounds of the Formulae provided herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted or unsubstituted cycloalkylene, substituted or unsubstituted heterocycloalkylene, substituted or unsubstituted arylene, or substituted or unsubstituted heteroarylene described above in the compounds of the Formulae provided herein is substituted with at least one substituent group. In other embodiments, at least one or all of these groups are substituted with at least one size-limited substituent group. Alternatively, at least one or all of these groups are substituted with at least one lower substituent group.

In other embodiments of the compounds of the Formulae provided herein, each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, each substituted or unsubstituted heterocycloalkyl is a substituted or unsubstituted 4 to 8 membered heterocycloalkyl, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene substituted or unsubstituted $C_4$-$C_8$ cycloalkylene, and each substituted or unsubstituted heterocycloalkylene is a substituted or unsubstituted 4 to 8 membered heterocycloalkylene.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene substituted or unsubstituted $C_5$-$C_6$ cycloalkylene, and each substituted or unsubstituted heterocycloalkylene is a substituted or unsubstituted 5 to 7 membered heterocycloalkylene.

In some embodiments, Z is $R^a$-substituted or unsubstituted heterocycloalkylene. In some embodiments, Z is $R^{a1}$-substituted or unsubstituted piperidinylene. In some embodiments, Z is unsubstituted piperidinylene. In some related embodiments, $L^1$ is —C(O)—. Thus, in some embodiments, the compound has the formula:

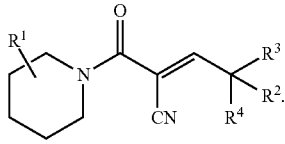
(IA)

In other embodiments, the compound has the formula:

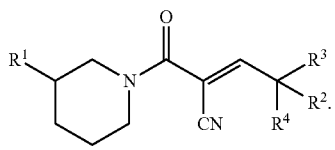
(IB)

In some embodiments of Formula (I), (IA) or (IB), $R^1$ is:

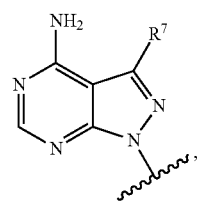
(IC)

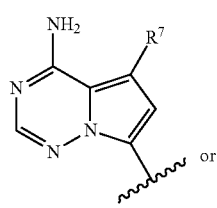
(ID)

or

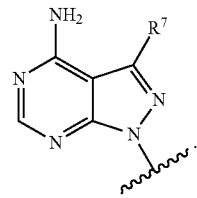
(IE)

In some embodiments of the compounds provided herein (e.g. Formula (IC), (ID) or (IE)), $R^7$ is independently a substituted or unsubstituted aryl (e.g. phenyl) or substituted or unsubstituted heteroaryl. In other embodiments of the compounds provided herein (e.g. Formula (IC), (ID) or IE)), $R^7$ is independently a $R^{12}$-substituted or unsubstituted aryl (e.g. phenyl) or $R^{12}$-substituted or unsubstituted heteroaryl.

In other embodiments of the compounds provided herein (e.g. Formula (I), (IA) or (IB)), $R^1$ is:

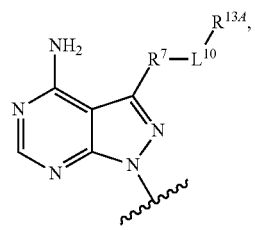
(IF)

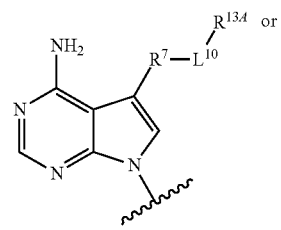
(IG)

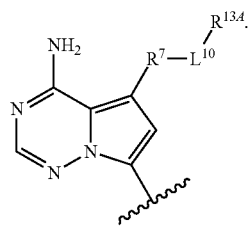
(IH)

In some embodiments of the compounds provided herein (e.g. Formula (IF), (IG) or (IH)), $R^7$ is a substituted or unsubstituted aryl (e.g. phenyl) or substituted or unsubstituted heteroaryl. In other embodiments of the compounds provided herein (e.g. Formula (IF), (IG) or (IH)), $L^{10}$ is —C(O)NR$^{13C}$—, —NR$^{13C}$C(O)— or —NR$^{13C}$C(O)NR$^{13D}$—. In some embodiments of the compounds provided herein (e.g. Formula (IF), (IG) or (IH)), $R^{13C}$ and $R^{13D}$ are hydrogen. In some embodiments of the compounds provided herein (e.g. Formula (IF), (IG) or (IH)), $R^{13A}$ is $R^{14}$-substituted or unsubstituted aryl or $R^{14}$-substituted or unsubstituted heteroaryl (e.g. isoxazolyl or indazolyl). In some embodiments of the compounds provided herein (e.g. Formula (IF), (IG) or (IH)), $R^{14}$ is independently halogen, —OH, —CF$_3$ or $R^{15}$-substituted or unsubstituted alkyl (e.g. $R^{15}$-substituted or unsubstituted $C_1$-$C_{10}$ alkyl). In some embodiments of the compounds provided herein (e.g. Formula (IF), (IG) or (IH)), $R^{14}$ is independently halogen, —OH, —CF$_3$, or $R^{15}$-substituted or unsubstituted C$_1$-C$_6$ alkyl. In some embodiments of the compounds provided herein (e.g. Formula (IF), (IG) or (IH)), $R^{14}$ is independently halogen, —OH, —CF$_3$, or $R^{15}$-substituted or unsubstituted C$_1$-C$_4$ alkyl. In some embodiments of the compounds provided herein (e.g. Formula (IF), (IG) or (IH)), $R^{14}$ is independently halogen, —OH, —CF$_3$, methyl, ethyl, propyl or butyl (e.g. t-butyl).

In some of the compounds provided herein (e.g. Formula (I), (IA), (IB) (IC), (ID), (IE), (IF), (IG) or (IH)), $R^2$, $R^3$ and $R^4$ are independently unsubstituted C$_1$-C$_{10}$ alkyl (e.g. unsubstituted C$_1$-C$_6$ alkyl such as unsubstituted C$_1$-C$_4$ alkyl), wherein $R^2$ and $R^3$ are optionally joined together to form an unsubstituted cycloalkyl (e.g. cyclopropyl or cyclobutyl). In some embodiments, $R^2$, $R^3$ and $R^4$ are hydrogen. In some embodiments, $R^2$ and $R^3$ are joined together to form an unsubstituted cyclopropyl and $R^4$ is hydrogen.

In some embodiments of the compounds provided herein (e.g. Formula (I), (IA), (IB) (IC), (ID), (IE), (IF), (IG) or (IH)), $R^{13.4}$ is:

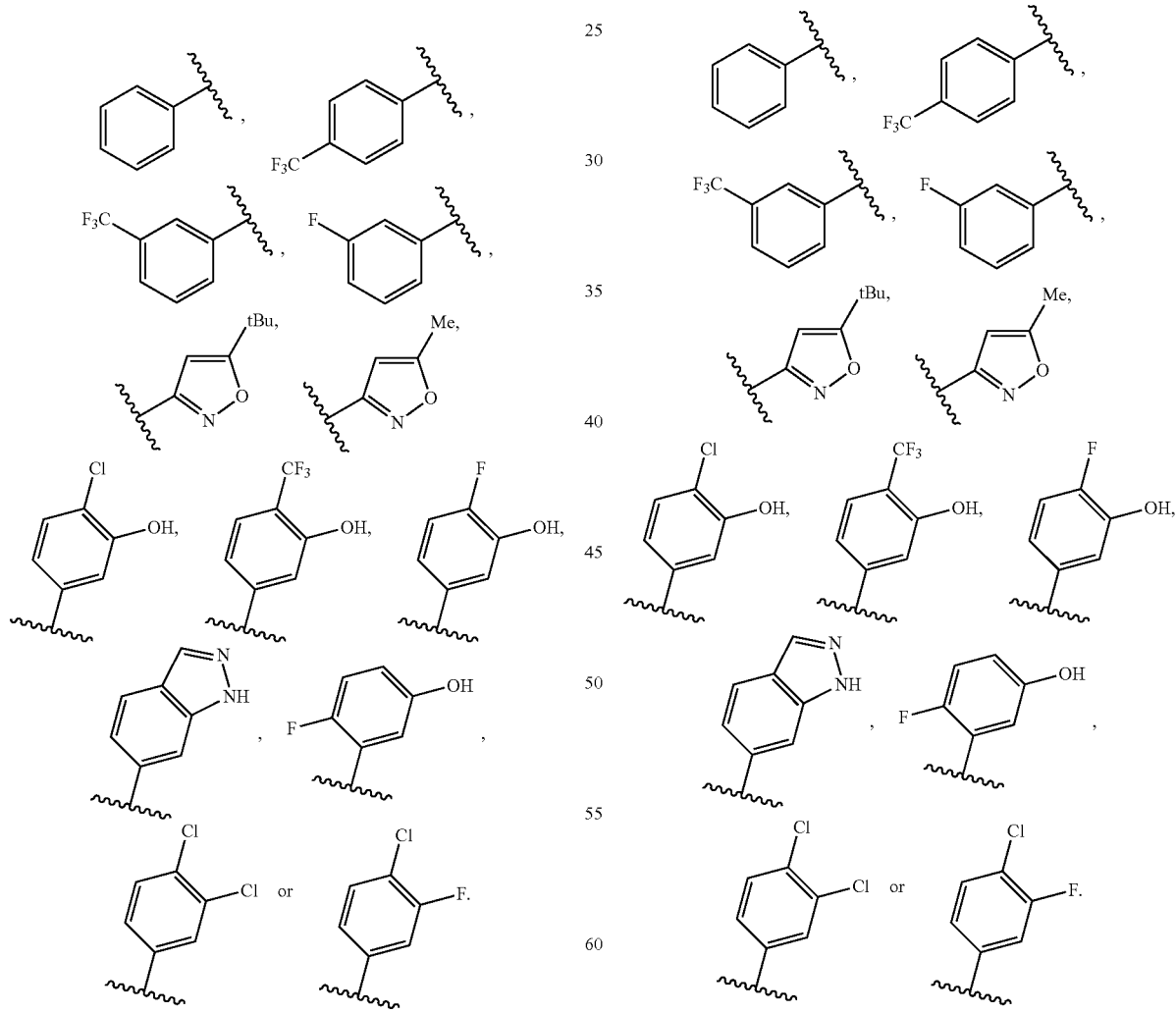

In some embodiments of the compounds provided herein (e.g. Formula (I), (IA), (IB) (IC), (ID), (IE), (IF), (IG) or (IH)), $R^7$ is:

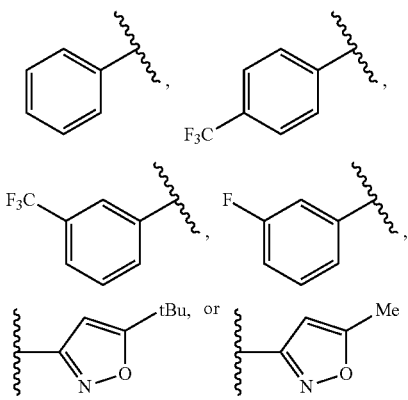

In some embodiments of the compounds provided herein (e.g. Formula (I), (IA), (IB) (IC), (ID), (IE), (IF), (IG) or (IH)), $R^{13.4}$ is:

In some embodiments of the compounds provided herein (e.g. Formula (I), (IA), (IB) (IC), (ID), (IE), (IF), (IG) or (IH)), $R^7$ is:

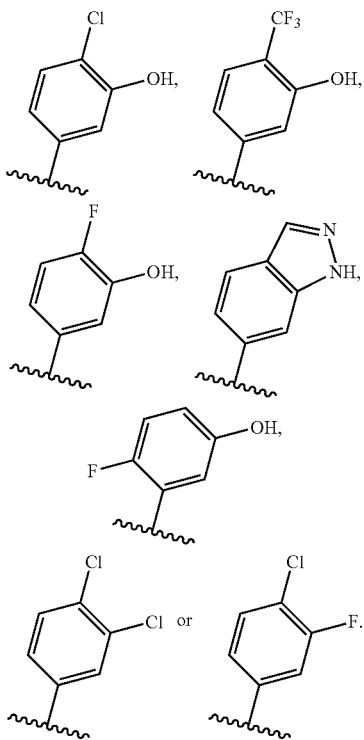

In some embodiments, the compound of Formula (I) has the structure:

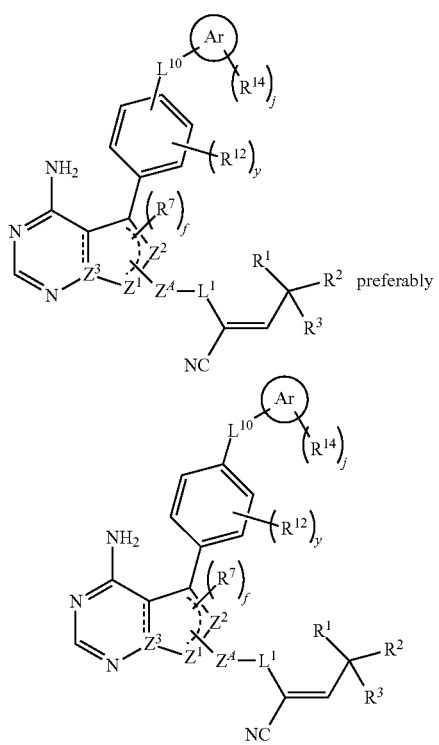

In Formula (IX), the dashed lines are optionally a bond. Thus the dashed line indicates the presence of a double bond or a single bond at the designated location. The compound of Formula (IX) includes pharmaceutically acceptable salts thereof.

The symbol y is an integer from 0 to 2. The symbol j is an integer from 0 to 3. The symbol f is 0 or 1. $Z^1$, $Z^2$, and $Z^3$ are N or C (according to the normal chemical valency rules), provided that at least one and not more than two of $Z^1$, $Z^2$, and $Z^3$ are simultaneously N. As stated above $Z^1$, $Z^2$, and $Z^3$ are N or C and obey the normal rules of valency. The valency of N or C for $Z^1$, $Z^2$, and $Z^3$ is filled with a single of double bond to a neighboring ring atom, a bond to $Z^4$, a bond to $R^7$ and/or a bond to hydrogen.

Ar is aryl, heteroaryl, cycloalkyl or heterocycloalkyl. Ar is $R^{14}$-substituted or unsubstituted as indicated in Formula (IX). In one embodiment, Ar is a monocyclic or fused bicyclic ($C_6$-$C_{10}$)aryl, monocyclic or fused bicyclic 5-10 membered heteroaryl containing 1-4 heteroatoms selected from N, O or S, monocyclic ($C_3$-$C_{10}$) cycloalkyl or 4 to 8 membered heterocycloalkyl containing 1-4 heteroatoms selected from N, O or S and is optionally fused to monocyclic aryl or monocyclic heteroaryl as defined above and can contain one to two —CO— groups in the ring.

$R^7$ is as defined above in the description of Formula I. In some embodiments, $R^7$ is hydrogen, halogen, —OH, —CN, $R^{12}$-substituted or unsubstituted alkyl or $R^{12}$-substituted or unsubstituted heteroalkyl (e.g. $R^{12}$-substituted or unsubstituted alkoxy). $R^{12}$ is as defined above in the description of Formula I. In some embodiments, $R^{12}$ is —OH or halogen (e.g. fluoro). In some embodiments, $R^7$ is hydrogen, halogen, —OH, —CN, $R^{12}$-substituted or unsubstituted alkyl or $R^{12}$-substituted or unsubstituted heteroalkyl (e.g. $R^{12}$-substituted or unsubstituted alkoxy), wherein $R^{12}$ is —OH or halogen. In some embodiments, $R^7$ is hydrogen, halogen, —OH, —CN, $R^{12}$-substituted or unsubstituted $C_1$ or $C_6$ saturated alkyl or $R^{12}$-substituted or unsubstituted heteroalkyl (e.g. $R^{12}$-substituted or unsubstituted alkoxy), wherein $R^{12}$ is —OH or halogen.

$R^{12}$ is as defined above in the description of Formula I. In some embodiments, $R^{12}$ is independently hydrogen, halogen —OH, —CN, $R^{13}$-substituted or unsubstituted alkyl, $R^{13}$-substituted or unsubstituted heteroalkyl (e.g. $R^{13}$-substituted or unsubstituted alkoxy). $R^{13}$ is as defined above in the description of Formula I. In some embodiments, $R^{13}$ is —OH or halogen (e.g. fluoro). In some embodiments, $R^{12}$ is independently hydrogen, halogen —OH, —CN, $R^{13}$-substituted or unsubstituted alkyl, $R^{13}$-substituted or unsubstituted heteroalkyl (e.g. $R^{13}$-substituted or unsubstituted alkoxy), wherein $R^{12}$ is —OH or halogen. In some embodiments, $R^{12}$ is independently hydrogen, halogen —OH, —CN, $R^{13}$-substituted or unsubstituted saturated alkyl, $R^{13}$-substituted or unsubstituted heteroalkyl (e.g. $R^{13}$-substituted or unsubstituted alkoxy), wherein $R^{12}$ is —OH or halogen. In one embodiment, $R^7$ and $R^{12}$ are independently hydrogen, ($C_1$-$C_6$) unsubstituted saturated alkyl, hydroxyl, unsubstituted saturated ($C_1$-$C_6$) alkoxy, halogen, unsubstituted saturated ($C_1$-$C_6$) haloalkyl or unsubstituted saturated ($C_1$-$C_6$) haloalkoxy.

$R^{14}$ is as defined above in the description of Formula I. In some embodiments, $R^{14}$ is hydrogen, halogen, —OH, —NH$_2$, —CN, —COOH, —CONH$_2$, $R^{15}$-substituted or unsubstituted alkyl, $R^{15}$-substituted or unsubstituted heteroalkyl (e.g. $R^{15}$-substituted or unsubstituted alkoxycarbonyl, $R^{15}$-substituted or unsubstituted alkoxy or $R^{15}$-substituted or unsubstituted haloalkoxy), or -$L^{11}$-$R^{15A}$. $L^{11}$ is as defined above in the description of Formula I. In some embodiments, $L^{11}$ is —NR$^{15C}$— or —C(O)O—. $R^{15C}$ is as defined above. In some embodiments, $R^{15C}$ is hydrogen. In other embodiments, $R^{15C}$ independently unsubstituted alkyl, unsubstituted heteroalkyl, unsubstituted cycloalkyl, unsubstituted heterocycloalkyl, unsubstituted aryl or unsubstituted heteroaryl. $R^{15A}$ is as defined above. In some embodiments, $R^{14}$ is hydrogen, halogen, —OH, —NH$_2$, —CN, —COOH, —CONH$_2$, $R^{15}$-substituted or unsubstituted alkyl, $R^{15}$-substituted or unsubstituted heteroalkyl (e.g. $R^{15}$-substituted or unsubstituted alkoxycarbonyl, $R^{15}$-substituted or unsubstituted alkoxy or $R^{15}$-substituted or unsubstituted haloalkoxy), or -L$^{11}$-R$^{15A}$, wherein $R^{15}$ is independently unsubstituted alkyl, unsubstituted heteroalkyl, unsubstituted cycloalkyl, unsubstituted heterocycloalkyl, unsubstituted aryl or unsubstituted heteroaryl. In some embodiments, $R^{14}$ is hydrogen, halogen, —OH, —NH$_2$, —CN, —COOH, —CONH$_2$, $R^{15}$-substituted or unsubstituted saturated alkyl, $R^{15}$-substituted or unsubstituted heteroalkyl (e.g. $R^{15}$-substituted or unsubstituted alkoxycarbonyl, $R^{15}$-substituted or unsubstituted alkoxy or $R^{15}$-substituted or unsubstituted haloalkoxy), or -L$^{11}$-R$^{15A}$, wherein $R^{15}$ is independently unsubstituted saturated alkyl, unsubstituted heteroalkyl, unsubstituted cycloalkyl, unsubstituted heterocycloalkyl, unsubstituted aryl or unsubstituted heteroaryl. In one embodiment, $R^{14}$ is hydrogen, (C$_1$-C$_6$) unsubstituted saturated alkyl, hydroxyl, unsubstituted saturated (C$_1$-C$_6$) alkoxy, halo, unsubstituted saturated (C$_1$-C$_6$) haloalkyl or unsubstituted saturated (C$_1$-C$_6$) haloalkoxy, carboxyl, —C(O)O—(C$_1$-C$_6$) unsubstituted saturated alkyl, cyano, —CONH$_2$, or —NR$^x$R$^y$ where R$^x$ is hydrogen or —(C$_1$-C$_6$) unsubstituted saturated alkyl, and R$^y$ is hydrogen, (C$_1$-C$_6$) unsubstituted saturated alkyl, unsubstituted saturated (C$_3$-C$_6$) cycloalkyl, unsubstituted saturated (C$_3$-C$_6$) cycloalkyl-(C$_1$-C$_6$) unsubstituted saturated alkyl-, —COR wherein R is —(C$_1$-C$_6$) unsubstituted saturated alkyl, or —SO$_2$—(C$_1$-C$_6$) unsubstituted saturated alkyl.

L$^{10}$ is as defined above in the description of Formula I. In some embodiments, L$^{10}$ is —O—, —NR$^{13}$—, —C(O)—, —C(O)NR$^{13}$—, —NR$^{13}$C(O), —S(O)$_{m'}$—, —NR$^{13C}$S(O)$_2$—, or —S(O)$_2$NR$^{13C}$— or —NR$^{13C}$(O)NR$^{13D}$— or unsubstituted alkylene (e.g. C$_1$ to C$_4$ alkylene such as methylene). R$^{13C}$ and R$^{13D}$ are as defined above. In some embodiment, R$^{13C}$ and R$^{13D}$ are independently hydrogen or unsubstituted alkyl (e.g. C$_1$ to C$_6$ alkyl). In some embodiments, L$^{10}$ is —O—, —NR$^{13C}$—, —C(O)—, —C(O)NR$^{13C}$—, —NR$^{13C}$C(O), —S(O)$_{m'}$—, —NR$^{13C}$S(O)$_2$—, or —S(O)$_2$NR$^{13C}$— or —NR$^{13C}$C(O)NR$^{13D}$— or unsubstituted alkylene (e.g. C$_1$ to C$_4$ alkylene such as methylene), wherein R$^{13C}$ and R$^{13D}$ are independently hydrogen or unsubstituted saturated alkyl (e.g. C$_1$ to C$_6$ saturated alkyl).

In one embodiment, L$^{10}$ is O, CO, CH$_2$, S, SO, SO$_2$, NR$^{13C}$, NR$^{13C}$CO, CONR$^{13C}$, NR$^{13C}$SO$_2$, SO$_2$NR$^{13C}$, or NR$^{13C}$SCONR$^{13D}$, where (each R$^{13C}$ and R$^{13D}$ is independently hydrogen or C$_1$ to C$_6$ unsubstituted saturated alkyl). Z$^A$ is bond, —NR$^a$— (where R$^a$ is hydrogen or (C$_1$-C$_6$) unsubstituted saturated alkyl), —O—, —S—, —SO—, —SO$_2$—, (C$_1$-C$_6$) unsubstituted saturated alkylene, (C$_3$-C$_6$) unsubstituted saturated cycloalkylene, (C$_1$-C$_6$) unsubstituted saturated alkylene where one, two or three carbons in the alkylene chain is replaced by —O—, N(H, alkyl, or —(C$_1$-C$_6$) saturated alkyl substituted with one, two, or three substituents independently selected from hydroxyl, unsubstituted saturated (C$_1$-C$_6$) alkoxy, carboxy, cyano, —COO—(C$_1$-C$_6$) unsubstituted saturated alkyl, —S—(C$_1$-C$_6$) unsubstituted saturated alkyl, —SO$_2$—(C$_1$-C$_6$) unsubstituted saturated alkyl, halo, —CONRR' or —NRR' (where each R is hydrogen, —(C$_1$-C$_6$) unsubstituted saturated alkyl, (C$_3$-C$_6$) unsubstituted saturated cycloalkyl, —(C$_1$-C$_6$) saturated alkyl substituted with one, two, or three hydroxy or 1-3 unsubstituted saturated (C$_1$-C$_6$) alkoxy and R' is hydrogen, —(C$_1$-C$_6$) unsubstituted saturated alkyl, or unsubstituted saturated (C$_3$-C$_6$) cycloalkyl) or 4 to 8 membered heterocycloalkyl containing 1-4 heteroatoms selected from N, O or S (preferably heterocycloamino) wherein the heterocycloalkyl ring is optionally substituted with one or two substituents independently selected from —(C$_1$-C$_6$) unsubstituted saturated alkyl, hydroxyl, unsubstituted saturated (C$_1$-C$_6$) alkoxy, —S—(C$_1$-C$_6$) unsubstituted saturated alkyl, —SO$_2$—(C$_1$-C$_6$) unsubstituted saturated alkyl, or halo), —S—, —SO—, —SO$_2$—, or —CO— (also referred to herein as heteroalkylene), or —(Z$^b$)$_{n1}$-aryl, or —(Z$^b$)$_{n1}$-heteroaryl [wherein n$_1$ is 0 or 1, Z$^b$ is NR$^b$ (where R$^b$ is hydrogen or (C$_1$-C$_6$) unsubstituted saturated alkyl), —O—, —S—, —SO—, —SO$_2$—, (C$_1$-C$_6$) unsubstituted saturated alkylene, or (C$_1$-C$_6$) unsubstituted saturated alkylene where one, two or three carbons in the alkylene chain is replaced by —O—, N(H, alkyl, or —(C$_1$-C$_6$) saturated alkyl substituted with one, two, or three substituents independently selected from hydroxyl, unsubstituted saturated (C$_1$-C$_6$) alkoxy, carboxy, cyano, —COO—(C$_1$-C$_6$) unsubstituted saturated alkyl, —S—(C$_1$-C$_6$) unsubstituted saturated alkyl, —SO$_2$—(C$_1$-C$_6$) unsubstituted saturated alkyl, halo, —CONRR' or —NRR' (where each R is hydrogen, —(C$_1$-C$_6$) unsubstituted saturated alkyl, (C$_3$-C$_6$) unsubstituted saturated cycloalkyl, —(C$_1$-C$_6$) saturated alkyl substituted with one, two, or three hydroxy or 1-3 unsubstituted saturated (C$_1$-C$_6$) alkoxy and R' is hydrogen, —(C$_1$-C$_6$) unsubstituted saturated alkyl, or unsubstituted saturated (C$_3$-C$_6$) cycloalkyl or 4 to 8 membered heterocycloalkyl containing 1-4 heteroatoms selected from N, O or S (preferably heterocycloamino) wherein the heterocycloalkyl ring is optionally substituted with one or two substituents independently selected from —(C$_1$-C$_6$) unsubstituted saturated alkyl, hydroxyl, unsubstituted saturated (C$_1$-C$_6$) alkoxy, —S—(C$_1$-C$_6$) unsubstituted saturated alkyl, —SO$_2$—(C$_1$-C$_6$) unsubstituted saturated alkyl, or halo), —S—, —SO—, —SO$_2$—, or —CO— (also referred to herein as heteroalkylene), and aryl or heteroaryl is optionally substituted with one or two substituents independently selected from hydrogen, unsubstituted saturated (C$_1$-C$_6$) haloalkyl, unsubstituted saturated (C$_1$-C$_6$) alkoxy, —S(C$_1$-C$_6$) unsubstituted saturated, halo substituted (C$_1$-C$_6$) saturated alkyl, or unsubstituted saturated (C$_1$-C$_6$) haloalkoxy, where aryl is a monocyclic or fused bicyclic (C$_6$-C$_{10}$)aryl, and heteroaryl is monocyclic or fused bicyclic 5-10 membered ring containing 1-4 heteroatoms selected from N, O or S].

L$^1$ is as defined above in the description of Formula I. In some embodiments, L$^1$ is a bond, —C(O)—, —N(L$^2$R$^5$)C(O)—, —OC(O)—, —S(O)$_n$—, —(OL$^2$R$^5$)OP(O)—, —N(L$^2$R$^5$)SO$_2$—, —(N(L$^2$R$^5$))NP(O)—, R$^{16}$-substituted or unsubstituted alkylene (e.g. R$^{16}$-substituted or unsubstituted methylene or R$^{16}$-substituted or unsubstituted ethylene), R$^{16}$-substituted or unsubstituted heteroalkylene, R$^{16}$-substituted or unsubstituted arylene, or R$^{16}$-substituted or unsubstituted heteroarylene. In some embodiments, L$^1$ is a bond, —C(O)—, —S(O)$_n$—, —N(L$^2$R$^5$)C(O)—, —N(L$^2$R$^5$)SO$_2$—, R$^{16}$-substituted or unsubstituted alkylene (e.g. R$^{16}$-substituted or unsubstituted methylene or R$^{16}$-substituted or unsubstituted ethylene), R$^{16}$-substituted or unsubstituted arylene, or R$^{16}$-substituted or unsubstituted heteroarylene. The symbol n is as defined above. In some embodiments, n is 1 or 2.

R$^{16}$ is as defined above in the description of Formula I. In some embodiments, R$^{16}$ is R$^{31}$-substituted or unsubstituted alkyl. R$^{31}$ is as defined above. In some embodiments, R$^{31}$ is halogen. In some embodiments, L$^1$ is R$^{16}$-substituted or unsubstituted arylene, or $R^{16}$-substituted or unsubstituted heteroarylene and $R^{16}$ is hydrogen, halogen, $R^{31}$-substituted or unsubstituted alkyl, $R^{31}$-substituted or unsubstituted heteroalkyl (e.g. $R^{31}$-substituted or unsubstituted alkoxy, $R^{31}$-substituted or unsubstituted alkylthio, $R^{31}$-substituted or unsubstituted haloalkoxy). In some embodiments, $R^{16}$ is $R^{31}$-substituted or unsubstituted alkyl and $R^{31}$ is halogen.

$L^2$ is as defined above in the description of Formula I. In some embodiments $L^2$ is a bond, $R^{28}$-substituted or unsubstituted alkylene, or $R^{28}$-substituted or unsubstituted cycloalkylene. In one embodiment, $L^2$ is a bond. $R^5$ is as defined above in the description of Formula I. In some embodiments, $R^5$ is hydrogen, $R^{30}$-substituted or unsubstituted alkyl or $R^{30}$-substituted or unsubstituted cycloalkyl.

In some embodiments, $L^1$ is a bond, —C(O)—, —N(L$^2$R$^5$)C(O)—, —OC(O)—, —S(O)$_n$—, —(OL$^2$R$^5$)OP(O)—, —N(L$^2$R$^5$)SO$_2$—, —(N(L$^2$R$^5$))NP(O)—, $R^{16}$-substituted or unsubstituted saturated alkylene (e.g. $R^{16}$-substituted or unsubstituted methylene or $R^{16}$-substituted or unsubstituted ethylene), $R^{16}$-substituted or unsubstituted heteroalkylene, $R^{16}$-substituted or unsubstituted arylene, or $R^{16}$-substituted or unsubstituted heteroarylene, wherein $R^{16}$ is $R^{31}$-substituted or unsubstituted saturated alkyl, $R^{31}$ is halogen, $L^2$ is a bond, $R^{28}$-substituted or unsubstituted saturated alkylene, or $R^{28}$-substituted or unsubstituted cycloalkylene. In one embodiment, $R^5$ is hydrogen, $R^{30}$-substituted or unsubstituted alkyl or $R^{30}$-substituted or unsubstituted cycloalkyl.

In one embodiment, $L^1$ is —CH(halo substituted saturated alkyl)-, —S(O$_2$)—, —S(O)—, —CO—, —NR$^5$CO—, —NR$^5$SO$_2$—, —(OR$^5$)OP(O)—,

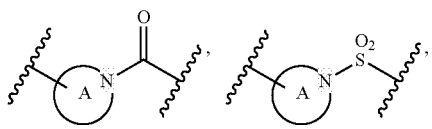

heteroarylene, or arylene; wherein each $R^5$ is independently hydrogen, (C$_1$-C$_6$) unsubstituted saturated alkyl, substituted alkyl, or (C$_3$-C$_6$) unsubstituted saturated cycloalkyl; ring A is heterocycloamino where the carbonyl and sulfonyl groups are attached to —C(CN)=CH(R$^2$)(R$^3$)(R$^4$); and heterocycloamino, arylene and heteroarylene are substituted with one, two or three substituents independently selected from hydrogen, —(C$_1$-C$_6$) unsubstituted saturated alkyl, unsubstituted saturated (C$_1$-C$_6$) alkoxy, hydroxyl, cyano, nitro, halo, unsubstituted saturated (C$_1$-C$_6$) haloalkyl, unsubstituted saturated (C$_1$-C$_6$) haloalkoxy, —S(C$_1$-C$_6$) saturated alkyl, —SO$_2$(C$_1$-C$_6$) unsubstituted saturated alkyl, carboxy, or —COO—(C$_1$-C$_6$) unsubstituted saturated alkyl and where arylene is monocyclic or fused bicyclic (C$_6$-C$_{10}$)aryl, and heteroarylene is a monocyclic or fused bicyclic 5-10 membered heteroaryl containing 1-4 heteroatoms selected from N, O or S.

$R^2$ and $R^3$ are as defined above in the description of Formula I. In some embodiments, $R^2$ is $R^{2A}$-substituted or unsubstituted alkyl and $R^3$ is $R^{3A}$-substituted or unsubstituted alkyl. In some embodiments, $R^2$ is $R^{2A}$-substituted or unsubstituted saturated alkyl and $R^3$ is $R^{3A}$-substituted or unsubstituted saturated alkyl. In other embodiments, $R^2$ and $R^3$ are joined together to form a $R^{17}$-substituted or unsubstituted cycloalkyl.

In one embodiment, $R^2$ and $R^3$ are independently (C$_1$-C$_6$) unsubstituted saturated alkyl, unsubstituted saturated (C$_1$-C$_6$) haloalkoxy, —(C$_1$-C$_6$) saturated alkyl which is substituted with one, two, or three substituents independently selected from hydroxyl, unsubstituted saturated (C$_1$-C$_6$) alkoxy, carboxy, cyano, —COO—(C$_1$-C$_6$) unsubstituted saturated alkyl, —S—(C$_1$-C$_6$) unsubstituted saturated alkyl, —SO$_2$—(C$_1$-C$_6$) unsubstituted saturated alkyl, halo, —CONRR' or —NRR' (where each R is hydrogen, —(C$_1$-C$_6$) unsubstituted saturated alkyl, (C$_3$-C$_6$) unsubstituted saturated cycloalkyl, —(C$_1$-C$_6$) saturated alkyl substituted with one, two or three hydroxy or one to three unsubstituted saturated (C$_1$-C$_6$) alkoxy and R' is hydrogen, —(C$_1$-C$_6$) unsubstituted saturated alkyl, or unsubstituted saturated (C$_3$-C$_6$) cycloalkyl or 4 to 8 membered heterocycloalkyl containing 1-4 heteroatoms selected from N, O or S (preferably heterocycloamino) and which is optionally substituted with one or two groups independently selected from —(C$_1$-C$_6$) unsubstituted saturated alkyl, hydroxyl, unsubstituted saturated (C$_1$-C$_6$) alkoxy, —S—(C$_1$-C$_6$) unsubstituted saturated alkyl, —SO$_2$—(C$_1$-C$_6$) unsubstituted saturated alkyl, or halo, or $R^2$ and $R^3$ together with the carbon atom to which they are attached form (C$_3$-C$_6$) unsubstituted saturated cycloalkyl).

$R^4$ is as defined above in the description of Formula I. In some embodiments, $R^4$ is independently hydrogen, —NR$^{4A}$R$^{4B}$, $R^{18}$-substituted or unsubstituted alkyl, $R^{18}$-substituted or unsubstituted heteroalkyl (e.g. $R^{18}$-substituted or unsubstituted haloalkoxy). $R^{4A}$ and $R^{4B}$ are as defined above in the description of Formula I. In some embodiments, $R^{4A}$ is hydrogen, $R^8$-substituted or unsubstituted alkyl, of $R^{18}$-substituted or unsubstituted cycloalkyl. $R^{4B}$ may be hydrogen or $R^{18}$-substituted or unsubstituted alkyl. In some embodiments, $R^4$ is independently hydrogen, —NR$^{4A}$R$^{4B}$, $R^{18}$-substituted or unsubstituted saturated alkyl, $R^{18}$-substituted or unsubstituted heteroalkyl (e.g. $R^{18}$-substituted or unsubstituted haloalkoxy), and $R^{4A}$ is hydrogen, $R^{18}$-substituted or unsubstituted saturated alkyl, of $R^{18}$-substituted or unsubstituted cycloalkyl. In one embodiment, $R^4$ is hydrogen, (C$_1$-C$_6$) unsubstituted saturated alkyl, or —NR$^{4A}$R$^{4B}$ where $R^{4A}$ and $R^{4B}$ are independently hydrogen, (C$_1$-C$_6$) unsubstituted saturated alkyl, or (C$_3$-C$_6$) unsubstituted saturated cycloalkyl In some embodiments, the compound of Formula (I) has the structure:

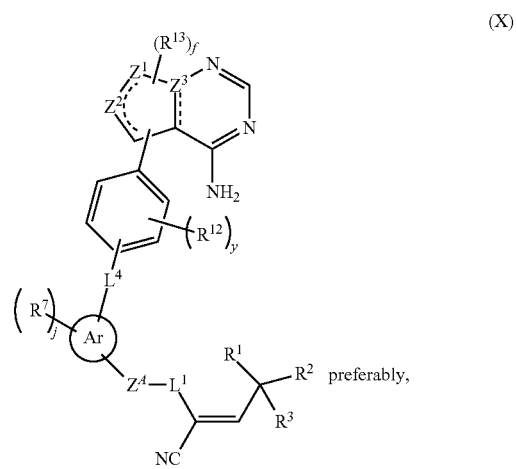

preferably,

-continued

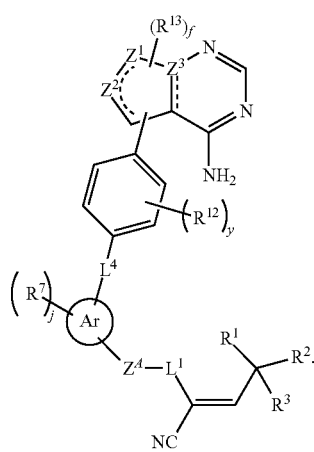

In Formula (X), the dashed lines are optionally a bond. Thus the dashed line indicates the presence of a double bond or a single bond at the designated location. The compound of Formula (X) includes pharmaceutically acceptable salts thereof.

The symbol f is 0-2; j is 0-2 and Ar, $Z^3$, $R^2$, $R^3$, $R^4$, $R^{12}$, $L^1$, $Z^A$ and the symbol y are as defined above in Formula (IX). The symbol y may an integer from 0 to 2. $Z^1$ and $Z^2$ are independently —N=, —NH—, —CH=, —CH$_2$—, —N($R^{13}$)—, —C($R^{13}$)=, —CH($R^{13}$)—, —N(-)—, —C(-)=, —CH(-)—, wherein (-) designated the point of attachment to the phenylene moiety.

$R^{13}$ is as defined above in the description of Formula I. In some embodiments, $R^{13}$ is hydrogen, halogen, —OH, —CN, $R^{14}$-substituted or unsubstituted alkyl or $R^{14}$-substituted or unsubstituted heteroalkyl (e.g. $R^{14}$-substituted or unsubstituted alkoxy). $R^{14}$ is as defined above in the description of Formula I. In some embodiments, $R^{14}$ is —OH or halogen (e.g. fluoro). In some embodiments, $R^{13}$ is hydrogen, halogen, —OH, —CN, $R^{14}$-substituted or unsubstituted saturated alkyl or $R^{14}$-substituted or unsubstituted heteroalkyl (e.g. $R^{14}$-substituted or unsubstituted alkoxy), and $R^{14}$ is —OH or halogen (e.g. fluoro). In one embodiment, $R^{13}$ is hydrogen, $(C_1-C_6)$ unsubstituted saturated alkyl, hydroxy, unsubstituted saturated $(C_1-C_6)$ alkoxy, halogen, unsubstituted saturated $(C_1-C_6)$ haloalkyl, or unsubstituted saturated $(C_1-C_6)$ haloalkoxy.

$R^7$ is as defined above in the description of Formula I. In some embodiments, $R^7$ is hydrogen, halogen, —OH, —NH$_2$, —CN, —COOH, —CONH$_2$, $R^{12}$-substituted or unsubstituted alkyl, $R^{12}$-substituted or unsubstituted heteroalkyl (e.g. $R^{12}$-substituted or unsubstituted alkoxycarbonyl) or —N($L^6R^8$)—$R^{7B}$. $L^{7B}$ is as defined above. $L^6$ and $R^8$ are as defined above in the description of Formula I. In some embodiments, $L^6$ is a bond and $R^8$ is hydrogen. In other embodiments, $L^6$ is a bond and $R^8$ is independently $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl or $R^{20}$-substituted or unsubstituted heteroaryl. $R^{7B}$ is as defined above. In some embodiments, $R^7$ is hydrogen, halogen, —OH, —NH$_2$, —CN, —COOH, —CONH$_2$, $R^{12}$-substituted or unsubstituted saturated alkyl, $R^{12}$-substituted or unsubstituted heteroalkyl (e.g. $R^{12}$-substituted or unsubstituted alkoxycarbonyl) or —N($L^6R^8$)—$R^{7B}$, $L^6$ is a bond and $R^8$ is hydrogen or independently $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl or $R^{20}$-substituted or unsubstituted heteroaryl. In one embodiment, $R^7$ is hydrogen, $(C_1-C_6)$ unsubstituted saturated alkyl, hydroxy, unsubstituted saturated $(C_1-C_6)$ alkoxy, halo, halo substituted $(C_1-C_6)$ saturated alkyl, unsubstituted saturated $(C_1-C_6)$ haloalkoxy, carboxy, —COO—$(C_1-C_6)$ unsubstituted saturated alkyl, cyano, —CONH$_2$, or —NR$^x$R$^y$ where R$^x$ is hydrogen or —$(C_1-C_6)$ unsubstituted saturated alkyl, and R$^y$ is hydrogen, $(C_1-C_6)$ unsubstituted saturated alkyl, unsubstituted saturated $(C_3-C_6)$ cycloalkyl, unsubstituted saturated $(C_3-C_6)$ cycloalkyl-$(C_1-C_6)$unsubstituted saturated alkyl-, —COR wherein R is —$(C_1-C_6)$ unsubstituted saturated alkyl, or —SO$_2$—$(C_1-C_6)$ unsubstituted saturated alkyl.

$L^4$ is as defined above in the description of Formula I. In some embodiments, $L^4$ is —O—, —N($L^6R^8$)—, —C(O)—, —C(O)N($L^6R^8$)—, —N($L^6R^8$)C(O), —S(O)$_w$—, —N($L^6R^8$)S(O)$_2$—, or —S(O)$_2$N($L^6R^8$)— or —N($L^6R^8$)C(O)N($L^7R^9$)—, or unsubstituted alkylene (e.g. $C_1$ to $C_4$ alkylene such as methylene). $L^6$, $L^7$, $R^8$ and $R^9$ are as defined above in the description of Formula I. In some embodiment, $L^6$ and $L^7$ are bonds and $R^8$ and $R^9$ are independently hydrogen or unsubstituted alkyl (e.g. $C_1$ to $C_6$ alkyl). In some embodiments, $L^4$ is —O—, —N($L^6R^8$)—, —C(O)—, —C(O)N($L^6R^8$)—, —N($L^6R^8$)C(O), —S(O)$_w$—, —N($L^6R^8$)S(O)$_2$—, or —S(O)$_2$N($L^6R^8$)— or —N($L^6R^8$)C(O)N($L^7R^9$)—, or unsubstituted saturated alkylene (e.g. $C_1$ to $C_4$ alkylene such as methylene), $L^6$ and $L^7$ are bonds and $R^8$ and $R^9$ are independently hydrogen or unsubstituted saturated alkyl (e.g. $C_1$ to $C_6$ alkyl). In one embodiment, $L^4$ is —O—, —CO—, —CH$_2$—, —S—, —SO—, —SO$_2$—, —NR$^8$—, —NR$^8$CO—, —CONR$^8$—, —NR$^8$SO$_2$—, —SO$_2$NR$^8$—, or —NR$^8$CONR$^9$—, where each $R^8$ and $R^9$ is independently hydrogen or $C_1$ to $C_6$ unsubstituted saturated alkyl.

In some embodiments, the compound of Formula (I) has the structure:

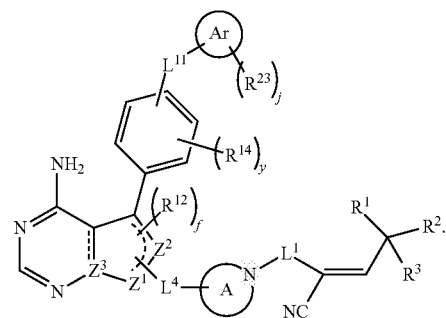

(XI)

In Formula (X), the dashed line is optionally a double bond. Thus the dashed line indicates the presence of a double bond or a single bond at the designated location. The compound of Formula (X) includes pharmaceutically acceptable salts thereof.

Ar, $Z^3$, $R^2$, $R^3$, $R^4$, and the symbols f, y and j are as defined above in Formula (IX). $Z^1$ and $Z^2$ are independently —N=, —NH—, —CH=, —CH$_2$—, —N($R^{12}$)—, —C($R^{12}$)=, —CH($R^{12}$)—, —N($L^4$-)—, —C($L^4$-)=, —CH($L^4$-)-.

$R^{12}$ is as defined above in the description of Formula I. In some embodiments, $R^{12}$ is hydrogen, halogen, —OH, —CN, $R^{13}$-substituted or unsubstituted alkyl or $R^{13}$-substituted or unsubstituted heteroalkyl (e.g. $R^{13}$-substituted or unsubstituted alkoxy). $R^{13}$ is as defined above. In some embodiments, $R^{13}$ is —OH or halogen (e.g. fluoro). In some embodiments, $R^{12}$ is hydrogen, halogen, —OH, —CN, $R^{13}$-substituted or unsubstituted saturated alkyl or $R^{13}$-substituted or unsubstituted heteroalkyl (e.g. $R^{13}$-substituted or unsubstituted alkoxy) and $R^{13}$ is —OH or halogen (e.g. fluoro). In one embodiment, $R^{12}$ is hydrogen, ($C_1$-$C_6$) unsubstituted saturated alkyl, hydroxy, unsubstituted saturated ($C_1$-$C_6$) alkoxy, halogen, halo substituted ($C_1$-$C_6$) saturated alkyl, or unsubstituted saturated ($C_1$-$C_6$) haloalkoxy.

$R^{14}$ is as defined above in the description of Formula I. In some embodiments, $R^{14}$ is hydrogen, halogen, —OH, —CN, $R^{15}$-substituted or unsubstituted alkyl or $R^{15}$-substituted or unsubstituted heteroalkyl (e.g. $R^{15}$-substituted or unsubstituted alkoxy). $R^{15}$ is as defined above in the description of Formula I. In some embodiments, $R^{15}$ is —OH or halogen (e.g. fluoro). In some embodiments, $R^{14}$ is hydrogen, halogen, —OH, —CN, $R^{15}$-substituted or unsubstituted saturated alkyl or $R^{15}$-substituted or unsubstituted heteroalkyl (e.g. $R^{15}$-substituted or unsubstituted alkoxy) and $R^{15}$ is —OH or halogen (e.g. fluoro). In one embodiment, $R^{14}$ is hydrogen, ($C_1$-$C_6$) unsubstituted saturated alkyl, hydroxy, unsubstituted saturated ($C_1$-$C_6$) alkoxy, halogen, unsubstituted saturated ($C_1$-$C_6$) haloalkyl, or unsubstituted saturated ($C_1$-$C_6$) haloalkoxy.

$L^1$ is as defined above in the description of Formula I. In some embodiments, $L^1$ is —C(O)— or —$SO_2$—.

$L^4$ is as defined above. In some embodiments, $L^4$ is a bond, —O—, —C(O)—, —N($L^6R^8$)—, —S(O)$_w$—, —N($L^6R^8$)C(O)—, —N($L^6R^8$)$SO_2$—, —P(O)(O$L^6R^8$)O—, $R^{19}$-substituted or unsubstituted alkylene (e.g. $R^{19}$-substituted or unsubstituted methylene or $R^{19}$-substituted or unsubstituted ethylene), $R^{19}$-substituted or unsubstituted heteroalkylene, $R^{19}$-substituted or unsubstituted arylene, or $R^{19}$-substituted or unsubstituted heteroarylene. In some embodiments, $L^4$ is a bond, —C(O)—, —N($L^6R^8$)—, —S(O)$_w$—, —N($L^6R^8$)C(O)—, —N($L^6R^8$)$SO_2$—, —P(O)(O$L^6R^8$)O—, $R^{19}$-substituted or unsubstituted alkylene (e.g. $R^{19}$-substituted or unsubstituted methylene or $R^{19}$-substituted or unsubstituted ethylene), $R^{19}$-substituted or unsubstituted arylene, or $R^{19}$-substituted or unsubstituted heteroarylene. The symbol w is as defined above in the description of Formula I. In some embodiments, w is 1 or 2.

$R^{19}$ is as defined above in the description of Formula I. In some embodiments, $R^{19}$ is $R^{19A}$-substituted or unsubstituted alkyl. $R^{19A}$ is as defined above. In some embodiments, $R^{19A}$ is halogen. In some embodiments, $L^4$ is $R^{19}$-substituted or unsubstituted arylene, or $R^{19}$-substituted or unsubstituted heteroarylene and $R^{19}$ is hydrogen, halogen, $R^{19A}$-substituted or unsubstituted alkyl, $R^{19A}$-substituted or unsubstituted heteroalkyl (e.g. $R^{19A}$-substituted or unsubstituted alkoxy, $R^{19A}$-substituted or unsubstituted alkylthio or $R^{19A}$-substituted or unsubstituted haloalkoxy). In some embodiments, $R^{19}$ is $R^{19A}$-substituted or unsubstituted alkyl and $R^{19A}$ is halogen.

$L^6$ is as defined above in the description of Formula I. In some embodiments $L^6$ is a bond, $R^{19}$-substituted or unsubstituted alkylene, or $R^{19}$-substituted or unsubstituted cycloalkylene. In one embodiment, $L^2$ is a bond. $R^8$ is as defined above in the description of Formula I. In some embodiment, $R^8$ is hydrogen, $R^{20}$-substituted or unsubstituted alkyl or $R^{20}$-substituted or unsubstituted cycloalkyl. In some embodiments, $L^4$ is a bond, —C(O)—, —N($L^6R^8$)—, —S(O)$_w$—, —N($L^6R^8$)C(O)—, —N($L^6R^8$)$SO_2$—, —P(O)(O$L^6R^8$)O—, $R^{19}$-substituted or unsubstituted saturated alkylene (e.g. $R^{19}$-substituted or unsubstituted methylene or $R^{19}$-substituted or unsubstituted ethylene), $R^{19}$-substituted or unsubstituted heteroalkylene, $R^{19}$-substituted or unsubstituted arylene, or $R^{19}$-substituted or unsubstituted heteroarylene, $R^{19}$ is $R^{19A}$-substituted or unsubstituted saturated alkyl, $R^{19A}$ is halogen. In a further embodiment, $L^6$ is a bond, $R^{19}$-substituted or unsubstituted saturated alkylene, or $R^{19}$-substituted or unsubstituted cycloalkylene and $R^8$ is hydrogen, $R^{20}$-substituted or unsubstituted saturated alkyl or $R^{20}$-substituted or unsubstituted cycloalkyl. In some embodiments, $L^4$ is a bond, —NH—, —O—, or methylene.

Ring A is a $R^7$-substituted or unsubstituted heterocycloamino. There may be one, two or three $R^7$ substituents where Ring A is a $R^7$-substituted heterocycloamino. In some embodiments, ring A is an unsubstituted heterocycloamino. $R^7$ is as defined above in the description of Formula I. In some embodiments, $R^7$ is —OH, —COOH, —CN, —$NO_2$, -halogen, $R^{12'}$-substituted or unsubstituted alkyl, $R^{12'}$-substituted or unsubstituted heteroalkyl (e.g. $R^{12'}$-substituted or unsubstituted alkylthio, $R^{12'}$-substituted or unsubstituted alkoxy, $R^{12'}$-substituted or unsubstituted alkoxycarbonyl, $R^{12'}$-substituted or unsubstituted haloalkoxy) or -$L^{4'}$-$R^{7B}$. $R^{12'}$, as used herein, is defined as $R^{12}$ in the description of Formula I. Each recitation of $R^{12'}$ is independent, and $R^{12'}$ is independent from $R^{12}$ as set forth in Formula XI. Likewise, $L^{4'}$, as used herein, is defined as $L^4$ in the description of Formula I. Each recitation of $R^{4'}$ is independent, and $R^{4'}$ is independent from $L^4$ as set forth in Formula XI. In some embodiments, $L^{4'}$ is —S(O)$_2$—, —C(O)N($L^{6'}R^{8'}$)—, —S(O)$_2$N($L^{6'}R^{8'}$)—. $L^{6'}$, as used herein, is defined as $L^6$ in the description of Formula I. Each recitation of $L^{6'}$ is independent, and $L^{6'}$ is independent from $L^6$ as set forth in the description of Formula XI. In some embodiments, $L^{6'}$ is a bond. $R^{8'}$ as used herein, is defined as $R^8$ in the description of Formula I. Each recitation of $R^{8'}$ is independent, and $R^{8'}$ is independent from $R^8$ as set forth in the description of Formula XI. In some embodiments, $R^{8'}$ is hydrogen, $R^{20'}$-substituted or unsubstituted alkyl, $R^{20'}$-substituted or unsubstituted heteroalkyl, $R^{20'}$-substituted or unsubstituted cycloalkyl, $R^{20'}$-substituted or unsubstituted heterocycloalkyl, $R^{20'}$-substituted or unsubstituted aryl or $R^{20'}$-substituted or unsubstituted heteroaryl. $R^{20'}$ as used herein, is defined as $R^{20}$ in the description of Formula I. Each recitation of $R^{20'}$ is independent, and $R^{20'}$ is independent from $R^{20}$ as set forth in the description of Formula XI. $R^{7B}$ is as defined above in the description of Formula I. In some embodiments, $R^{7B}$ is halogen or $R^{12'}$-substituted or unsubstituted alkyl. In some embodiments Ring A is a $R^7$-substituted or unsubstituted heterocycloamino, $R^7$ is —OH, —COOH, —CN, —$NO_2$, -halogen, $R^{12'}$-substituted or unsubstituted saturated alkyl, $R^{12'}$-substituted or unsubstituted heteroalkyl (e.g. $R^{12'}$-substituted or unsubstituted alkylthio, $R^{12'}$-substituted or unsubstituted alkoxy, $R^{12'}$-substituted or unsubstituted alkoxycarbonyl, $R^{12'}$-substituted or unsubstituted haloalkoxy) or -$L^{4'}$-$R^{7B}$, $L^{4'}$ is —S(O)$_2$—, —C(O)N($L^{6'}R^{8'}$)—, —S(O)$_2$N($L^{6'}R^{8'}$)—, $L^{6'}$, is a bond, $R^{8'}$ is hydrogen, $R^{20'}$-substituted or unsubstituted saturated alkyl, $R^{20'}$-substituted or unsubstituted heteroalkyl, $R^{20'}$-substituted or unsubstituted cycloalkyl, $R^{20'}$-substituted or unsubstituted heterocycloalkyl, $R^{20'}$-substituted or unsubstituted aryl or $R^{20'}$-substituted or unsubstituted heteroaryl, and $R^{7B}$ is halogen or $R^{12'}$-substituted or unsubstituted alkyl. In some embodiments, ring A is azetidin-1-yl, piperazin-1-yl, pyrrolidin-1-yl or piperidin-1-yl.

$L^{11}$ is as defined above in the description of Formula I. In some embodiments, $L^{11}$ is —O—, —NR$^{15C}$—, —C(O)—, —C(O)NR$^{15C}$—, —NR$^{15C}$C(O), —S(O)$_y$—, —NR$^{15C}$S(O)$_2$—, or —S(O)$_2$NR$^{15C}$— or —NR$^{15C}$C(O)NR$^{15D}$— or unsubstituted alkylene (e.g. $C_1$ to $C_4$ alkylene such as methylene). R$^{15C}$—, and R$^{15D}$ are as defined above. In some embodiment, R$^{15C}$ and R$^{15D}$ are independently hydrogen or unsubstituted alkyl (e.g. $C_1$ to $C_6$ alkyl). In some embodiments, $L^{11}$ is —O—, —NR$^{15C}$—, —C(O)—, —C(O)NR$^{15C}$—, —NR$^{15C}$C(O), —S(O)$_y$—, —NR$^{15C}$S(O)$_2$—, or —S(O)$_2$NR$^{15C}$— or —NR$^{15C}$C(O)NR$^{15D}$— or unsubstituted saturated alkylene (e.g. $C_1$ to $C_4$ alkylene such as methylene), and R$^{15C}$—, and R$^{15D}$ are independently hydrogen or unsubstituted saturated alkyl (e.g. $C_1$ to $C_6$ alkyl).

In one embodiment, $L^{11}$ is O, CO, CH$_2$, S, SO, SO$_2$, NR$^{15C}$, NR$^{15C}$CO, CONR$^{15C}$, NR$^{15C}$SO$_2$, SO$_2$NR$^{15C}$, or NR$^{15C}$CONR$^{15D}$, where (each R$^{15C}$—, and R$^{15D}$ is independently hydrogen or $C_1$ to $C_6$ unsubstituted saturated alkyl). R$^{23}$ is as defined above in the description of Formula I. In some embodiments, R$^{23}$ is hydrogen, halogen, —OH, —NH$_2$, —CN, —COOH, —CONH$_2$, R$^{25}$-substituted or unsubstituted alkyl, R$^{25}$-substituted or unsubstituted heteroalkyl (e.g. R$^{25}$-substituted or unsubstituted alkoxycarbonyl, R$^{25}$-substituted or unsubstituted alkoxy or R$^{25}$-substituted or unsubstituted haloalkoxy), or -L$^{13}$-R$^{24}$. $L^{12}$ is as defined above in the description of Formula I. In some embodiments, $L^{12}$ is —NR$^{26}$— or —C(O)O—. R$^{26}$ is as defined above. In some embodiments, R$^{26}$ is hydrogen. In other embodiments, R$^{26}$ independently unsubstituted alkyl, unsubstituted heteroalkyl, unsubstituted cycloalkyl, unsubstituted heterocycloalkyl, unsubstituted aryl or unsubstituted heteroaryl. R$^{24}$ is as defined above. In some embodiments, R$^{23}$ is hydrogen, halogen, —OH, —NH$_2$, —CN, —COOH, —CONH$_2$, R$^{25}$-substituted or unsubstituted saturated alkyl, R$^{25}$-substituted or unsubstituted heteroalkyl (e.g. R$^{25}$-substituted or unsubstituted alkoxycarbonyl, R$^{25}$-substituted or unsubstituted alkoxy or R$^{25}$-substituted or unsubstituted haloalkoxy), or -L$^{12}$-R$^{24}$, $L^{12}$ is —NR$^{26}$— or —C(O)O—, R$^{26}$ is hydrogen, unsubstituted saturated alkyl, unsubstituted heteroalkyl, unsubstituted cycloalkyl, unsubstituted heterocycloalkyl, unsubstituted aryl or unsubstituted heteroaryl. In one embodiment, R$^{14}$ is hydrogen, ($C_1$-$C_6$) unsubstituted saturated alkyl, hydroxy, unsubstituted saturated ($C_1$-$C_6$) alkoxy, halo, unsubstituted saturated ($C_1$-$C_6$) haloalkyl, unsubstituted saturated ($C_1$-$C_6$) haloalkoxy, carboxy, —COO—($C_1$-$C_6$) unsubstituted saturated alkyl, cyano, —CONH$_2$, or —NR$^x$R$^y$ where R$^x$ is hydrogen or —($C_1$-$C_6$) unsubstituted saturated alkyl, and R$^y$ is hydrogen, ($C_1$-$C_6$) unsubstituted saturated alkyl, ($C_3$-$C_6$) cycloalkyl, ($C_3$-$C_6$) cycloalkyl-($C_1$-$C_6$) unsubstituted saturated alkyl, —COR wherein R is —($C_1$-$C_6$) unsubstituted saturated alkyl, or —SO$_2$—($C_1$-$C_6$) unsubstituted saturated alkyl.

R$^2$ and R$^3$ are as defined above in the description of Formula I. In some embodiments, R$^2$ is R$^{2A}$-substituted or unsubstituted alkyl and R$^3$ is R$^{3A}$-substituted or unsubstituted alkyl. In some embodiments, R$^2$ is R$^{2A}$-substituted or unsubstituted saturated alkyl and R$^3$ is R$^{3A}$-substituted or unsubstituted saturated alkyl. In other embodiments, R$^2$ and R$^3$ are joined together to form a R$^{17}$-substituted or unsubstituted cycloalkyl.

In one embodiment, R$^2$ and R$^3$ are independently ($C_1$-$C_6$) unsubstituted saturated alkyl, unsubstituted saturated ($C_1$-$C_6$) haloalkoxy, —($C_1$-$C_6$) saturated alkyl substituted with one, two, or three substituents independently selected from hydroxyl, unsubstituted saturated ($C_1$-$C_6$) alkoxy, carboxy, cyano, —COO—($C_1$-$C_6$) unsubstituted saturated alkyl, —S—($C_1$-$C_6$) unsubstituted saturated alkyl, —SO$_2$—($C_1$-$C_6$) unsubstituted saturated alkyl, halo, —CONRR' or —NRR' (where each R is hydrogen, —($C_1$-$C_6$) unsubstituted saturated alkyl, ($C_3$-$C_6$) unsubstituted saturated cycloalkyl, —($C_1$-$C_6$) saturated alkyl substituted with one, two, or three hydroxy or 1-3 unsubstituted saturated ($C_1$-$C_6$) alkoxy and R' is hydrogen, —($C_1$-$C_6$) unsubstituted saturated alkyl, or unsubstituted saturated ($C_3$-$C_6$) cycloalkyl or 4 to 8 membered heterocycloalkyl containing 1-4 heteroatoms selected from N, O or S (preferably heterocycloamino) and is optionally substituted with one or two groups independently selected from —($C_1$-$C_6$) unsubstituted saturated alkyl, hydroxyl, unsubstituted saturated ($C_1$-$C_6$) alkoxy, —S—($C_1$-$C_6$) unsubstituted saturated alkyl, —SO$_2$—($C_1$-$C_6$) unsubstituted saturated alkyl, or halo), or R$^2$ and R$^3$ together with the carbon atom to which they are attached form ($C_3$-$C_6$) unsubstituted saturated cycloalkyl).

R$^4$ is as defined above in the description of Formula I. In some embodiments, R$^4$ is independently hydrogen, —NR$^{4A}$R$^{4B}$, R$^{18}$-substituted or unsubstituted alkyl, R$^{18}$-substituted or unsubstituted heteroalkyl (e.g. R$^{18}$-substituted or unsubstituted haloalkoxy). R$^{4A}$ and R$^{4B}$ are as defined above in the description of Formula I. In some embodiments, R$^{4A}$ is hydrogen, R$^{18}$-substituted or unsubstituted alkyl, of R$^{18}$-substituted or unsubstituted cycloalkyl. R$^{4B}$ may be hydrogen or R$^{18}$-substituted or unsubstituted alkyl. In some embodiments, R$^4$ is independently hydrogen, —NR$^{4A}$R$^{4B}$, R$^{18}$-substituted or unsubstituted saturated alkyl, R$^{18}$-substituted or unsubstituted heteroalkyl (e.g. R$^{18}$-substituted or unsubstituted haloalkoxy), and R$^{4A}$ is hydrogen, R$^{18}$-substituted or unsubstituted saturated alkyl, of R$^{18}$-substituted or unsubstituted cycloalkyl. In one embodiment, R$^4$ is hydrogen, ($C_1$-$C_6$) unsubstituted saturated alkyl, or —NR$^{4A}$R$^{4B}$ where R$^{4A}$ and R$^{4B}$ are independently hydrogen, ($C_1$-$C_6$) unsubstituted saturated alkyl, or ($C_3$-$C_6$) unsubstituted saturated cycloalkyl In some embodiments of Formulae (IX) to (XI), provided is an embodiment (A) wherein the ring

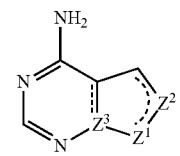

may have the following structure, where Y is R$^7$, R$^{12}$, R$^{13}$ or R$^{23}$ in Formulae (IX), (X), (XI) and (XII), respectively:

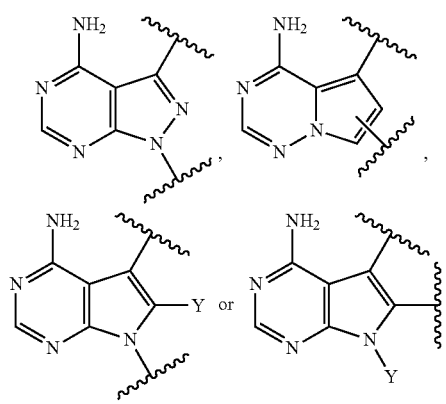

In some embodiments, the ring is

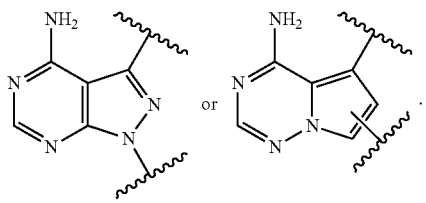

In some embodiments, the ring is

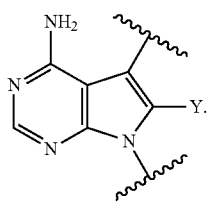

In some embodiments, the ring is

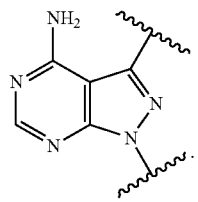 [SMILES: *c1nn(*)c2ncnc(N)c12]

In another embodiment (referred to herein as embodiment (B)), within the compound of Formula (IX)-(XI) and embodiment (A) above, $L^{10}$ (compound IX), $L^{11}$ (compound XI) and $L^4$ (compound X) are independently —O—, —S—, —SO—, —SO$_2$, —N(R$^5$)— or NHCONH. In some embodiments, $L^{10}$ (compound IX), $L^{11}$ (compound XI) and $L^4$ (compound X) are independently O—, —S—, —SO—, —SO$_2$, —N(H)—, —N(—CH$_3$)— or NCONH. In certain embodiments, $L^{10}$ (compound IX), $L^{11}$ (compound XI) and $L^4$ (compound X) are independently —O— or —NHCONH—. Within this embodiment (B), in one group of compounds $L^{10}$ (compound IX), $L^{11}$ (compound XI) and $L^4$ (compound X) are independently —O—. Within this embodiment (B), in one group of compounds $L^{10}$ (compound IX), $L^{11}$ (compound XI) and $L^4$ (compound X) are independently —NHCONH—, —NHCO—, or —CONH—, preferably —NHCONH—.

Within this embodiment (B) and groups contained therein, in one group of compounds $R^7$, $R^{12}$, or $R^{13}$ in Formulae (IX), (XI), and (X), respectively are absent, methyl, fluoro, or trifluoromethyl, preferably absent.

In another embodiment (referred to herein as embodiment (C)), within the compound of Formula (IX)-(XI) and embodiments (A) and (B) and groups contained therein, in one group of compounds $R^{12}$ in Formula (IX) and (X) and $R^{14}$ in Formula (XI) are independently absent, unsubstituted saturated (C$_1$-C$_6$) alkyl, unsubstituted saturated (C$_1$-C$_6$) alkoxy, cyano, halo, unsubstituted saturated (C$_1$-C$_6$) haloalkyl or unsubstituted saturated (C$_1$-C$_6$) haloalkoxy; preferably $R^{12}$ and $R^{14}$ are independently absent, methyl, fluoro, methoxy, chloro, trifluoromethyl, or trifluoromethoxy. Preferably, $R^{12}$ and $R^{14}$ are independently absent, methoxy or fluoro.

In another embodiment (referred to herein as embodiment (D)), within the compound of Formula (IX)-(XI) and embodiments (A), (B) and (C) and groups contained therein, in one group of compounds $R^{14}$ of Formula (IX), $R^7$ of Formula (X), and $R^{23}$ of Formula (XI) are independently absent, unsubstituted saturated (C$_1$-C$_6$) alkyl, unsubstituted saturated (C$_1$-C$_6$) alkoxy, halo, unsubstituted saturated (C$_1$-C$_6$) haloalkyl, unsubstituted saturated (C$_1$-C$_6$) haloalkoxy, or cyano. Preferably, $R^{14}$ of Formula (IX), $R^7$ of Formula (X), and $R^{23}$ of Formula (XI) are independently absent, methyl, methoxy, fluoro, chloro, trifluoromethyl, trifluoromethoxy, or cyano.

In another embodiment (referred to herein as embodiment (E)), within the compound of Formulae (IX), (X) and (XI) and embodiments (A), (B), (C) and (D) and groups contained therein, in one group of compounds $Z^A$ in a compound of Formula (IX) and (X) and $L^4$ (XI) is a bond, —NR$^a$—, —O—, or methylene, preferably bond, —O—, —NH— or methylene.

Within embodiment (E), in one embodiment (referred to herein as embodiment (Ea)), in compounds of Formula (IX) and (X), in one group of compounds $L^1$ is C$_6$ aryl or 5 or 6-membered ring containing 1-3 heteroatoms selected from N, O or S (heteroaryl), preferably, $L^1$ is selected from:

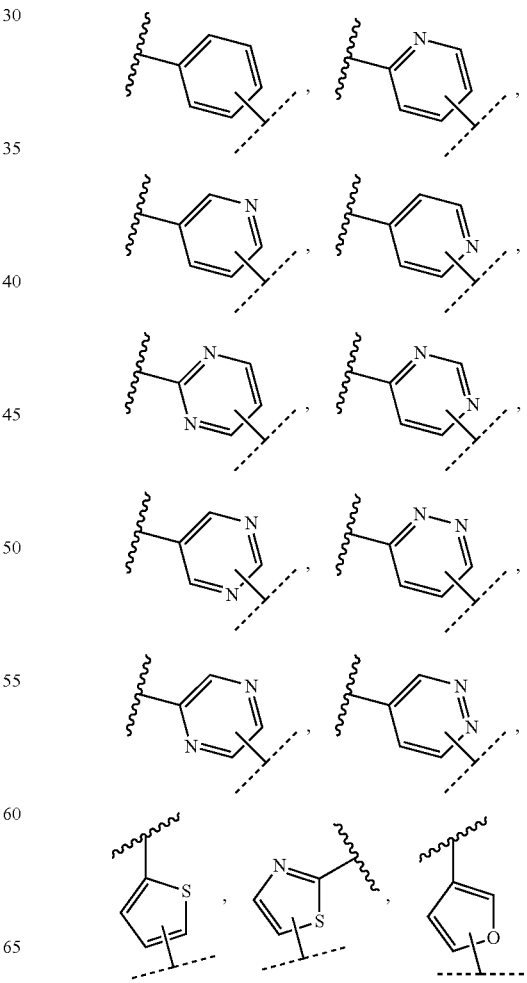

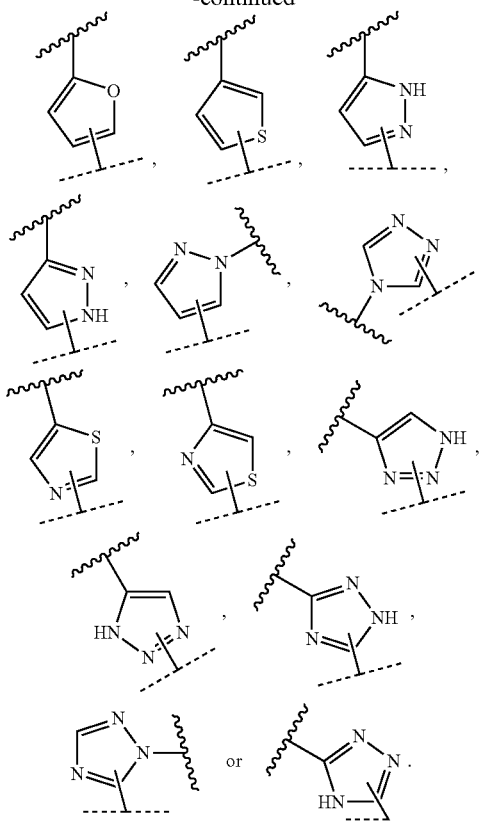

or pyrazol-4-yl, wherein each is substituted with one, two or three substituents independently selected from hydrogen, unsubstituted saturated $(C_1-C_6)$ alkyl, unsubstituted saturated $(C_1-C_6)$ alkoxy, hydroxyl, cyano, nitro, halo, unsubstituted saturated $(C_1-C_6)$ haloalkyl, unsubstituted saturated $(C_1-C_6)$ haloalkoxy, unsubstituted saturated $(C_1-C_6)$ alkylthio, unsubstituted saturated $(C_1-C_6)$ alkylsulfonyl, —COOH, or unsubstituted saturated $(C_1-C_6)$ alkoxycarbonyl. Preferably when $L^1$ is phenyl or heteroaryl wherein heteroaryl ring is six membered ring shown above, then $Z^A$ is a bond, O, or $NR^a$, preferably a bond.

symbol denotes point of attachment of the ring to —Z— when Z is other than bond and directly to the rest of the molecule when $Z^A$ is a bond and is bond attaching the ring to —C(CN)=CHCR$^2$R$^3$R$^4$.

Within embodiment (E), in another embodiment (referred to herein as embodiment (E)(b)), in compounds of Formula (IX) and (X), in another group of compounds —$Z^A$-$L^1$- is selected from:

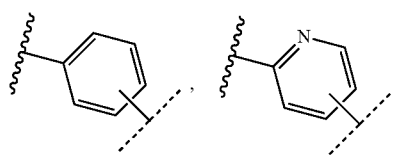
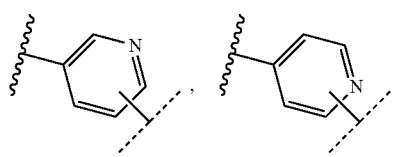
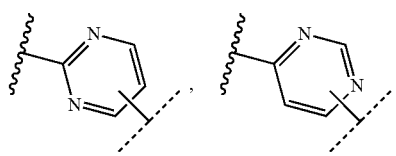
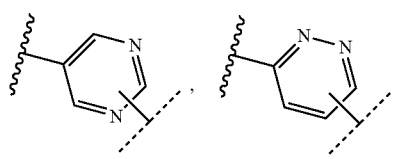
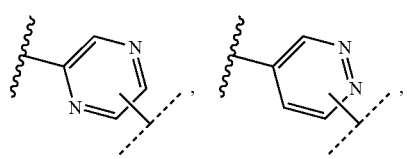
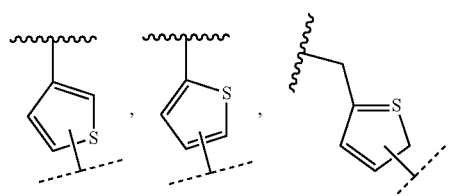
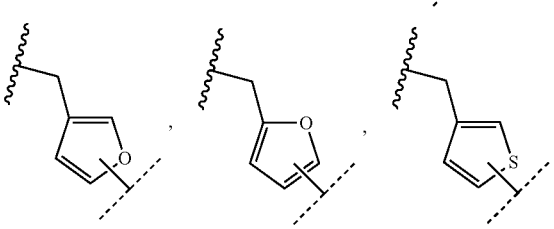
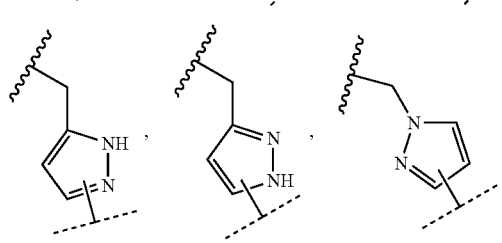
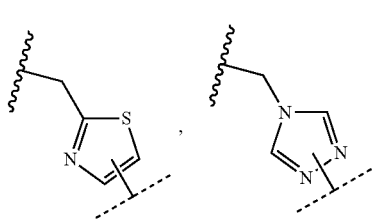

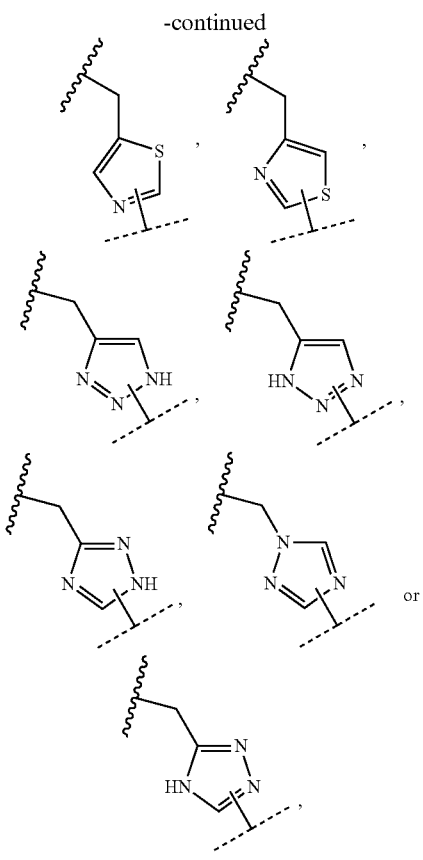

wherein each ring substituted with one or two substituents independently selected from hydrogen, unsubstituted saturated ($C_1$-$C_6$) alkyl, unsubstituted saturated ($C_1$-$C_6$) alkoxy, hydroxyl, cyano, nitro, halo, unsubstituted saturated ($C_1$-$C_6$) haloalkyl, unsubstituted saturated ($C_1$-$C_6$) haloalkoxy, unsubstituted saturated ($C_1$-$C_6$) alkylthio, unsubstituted saturated ($C_1$-$C_6$) alkylsulfonyl, —COOH, or unsubstituted saturated ($C_1$-$C_6$) alkoxycarbonyl. Preferably, —$Z^A$-$L^1$- is selected from: phenyl, 2-, 3-, or 4-pyridyl substituted as defined above.

(i) Within groups in embodiment (E)(a) and (E)(b) and groups contained therein, in one group of compounds when $L^1$ is a six membered ring, then the —C(CN)=CHCR²R³R⁴ group is attached to the carbon atom in the six membered ring that is preferably meta to the carbon atom that attaches the six membered ring to —$Z^A$.

(ii) Within groups in embodiment (E)(a) and (E)(b) and groups contained therein, in one group of compounds when $L^1$ is a five membered ring, then the —C(CN)=CHCR²R³R⁴ group is attached to the atom in the five membered ring that is preferably ortho to the atom that attaches the five membered ring to —$Z^A$—.

(iii) Within embodiment (E), in another embodiment (referred to herein as embodiment (E)(c)), in compounds of Formula (XI), in one group of compounds $L^4$ is bond, —NR$^a$—, —O—, or methylene and $L^1$ is —C(O)— or —SO$_2$—, where ring A substituted with one or two substituents independently selected from hydrogen, unsubstituted saturated alkyl, unsubstituted saturated ($C_1$-$C_6$) alkoxy, hydroxyl, cyano, halo, unsubstituted saturated ($C_1$-$C_6$) haloalkyl, unsubstituted saturated ($C_1$-$C_6$) haloalkoxy, unsubstituted saturated ($C_1$-$C_6$) alkylthio, unsubstituted saturated ($C_1$-$C_6$) alkylsulfonyl, or unsubstituted saturated ($C_1$-$C_6$) alkoxycarbonyl. Preferably, ring A is azetidinyl, pyrrolidinyl, piperidinyl, or piperazinyl optionally substituted with hydrogen, methyl, or fluoro. Within embodiment (E)(c) and groups contained therein in one group of compounds $L^4$ is a bond or methylene and azetidinyl, pyrrolidinyl, or piperidinyl is attached at the 2 or 3-position of the ring, the nitrogen ring atom being position 1. Preferably, ring A is pyrrolidinyl attached at C-2 position and $L^4$ is methylene.

(iv) Within embodiment (E), in another embodiment (referred to herein as embodiment (E)(d)), in compounds of Formula (X) in one group of compounds —$Z^A$-$L^1$- is a bond when Ar has electron deficient π system. Preferably Ar² is pyridyl optionally substituted with R⁷ or phenyl substituted with R⁷ that is electron withdrawing in nature.

(v) Within embodiment (E), in another embodiment (referred to herein as embodiment (E)(e)), in compounds of Formula (IX) and (X), in one group of compounds $Z^A$ is bond, or unsubstituted saturated alkylene and $L^1$-N($L^2$R⁵)CO— or —N($L^2$R⁵)SO$_2$—, preferably —NHCO—.

(vi) Within embodiment (E), in another embodiment (referred to herein as embodiment (E)(f)), in compounds of Formula (IX) and (X), in one group of compounds $Z^A$ is bond and $L^1$-CO—.

In another embodiment (referred to herein as embodiment (F)), within the embodiments (A)-(E) and groups contained therein, in one group of compounds R² and R³ are independently unsubstituted saturated $C_1$-$C_6$ alkyl or together form saturated unsubstituted cycloalkyl, preferably R² is methyl, R³ is methyl, or R² and R³ together form unsubstituted saturated cyclopropyl; and R⁴ is hydrogen, methyl, hydroxymethyl, hydroxyethyl, methylamino, dimethylamino, 2-methylaminoethyl, or 2,2-dimethylaminoethyl.

In another embodiment (referred to herein as embodiment (G)), within the compound of Formula (IX), (X) and (XI), embodiments (A), (B), (C), (D), (E), and (F), and groups contained therein, Ar is phenyl not substituted with R¹⁴, R⁷ and R²³.

In another embodiment (referred to herein as embodiment (H)), within the compound of Formula (IX), (X) and (XI), embodiments (A), (B), (C), (D), (E), (F) and (G), and groups contained therein Ar is phenyl substituted at meta and/or para, preferably meta position(s) with one or two R¹⁴, R⁷ and R²³ respectively, which are independently selected from fluoro, methyl, trifluoromethoxy, trifluoromethyl, or methoxy.

In another embodiment (referred to herein as embodiment (I)), within the compound of Formula (IX), (X) and (XI), embodiments (A), (B), (C), (D), (E), (F), (G) and (H), and groups contained therein, Ar is heteroaryl, pyridinyl or thienyl optionally substituted with one or R¹⁴, R⁷ and R²³ independently selected from fluoro, methyl or methoxy.

In another embodiment (referred to herein as embodiment (J)), within the compound of Formula (IX), (X) and (XI), embodiments (A), (B), (C), (D), (E), (F), (G), (H) and (I), and groups contained therein, Ar is heterocycloalkyl, preferably piperidinyl, pyrrolidinyl or 2,3-dihydroindolyl optionally substituted with one or two R¹⁴, R⁷ and R²³ respectively and are independently selected from fluoro, methyl or methoxy.

Other compounds of Formula (I) include:
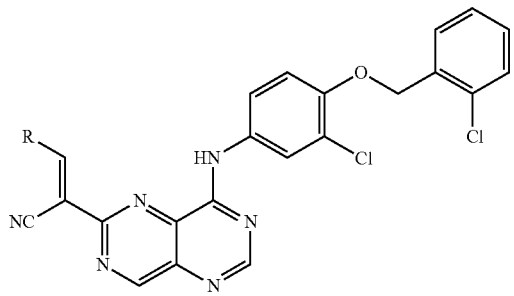
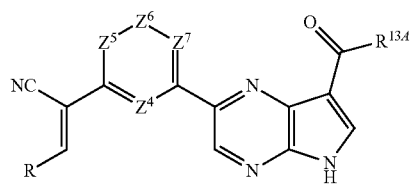
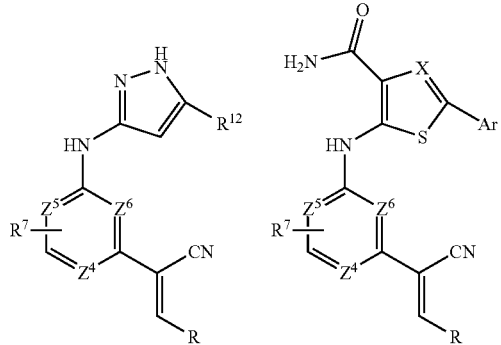
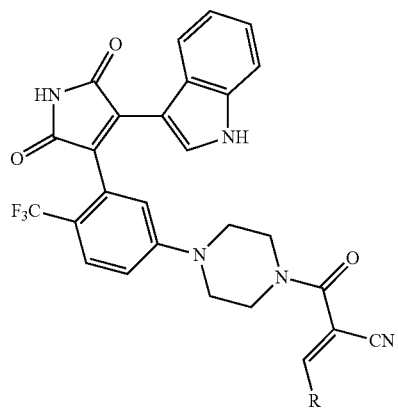
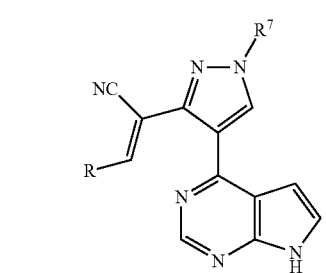
-continued
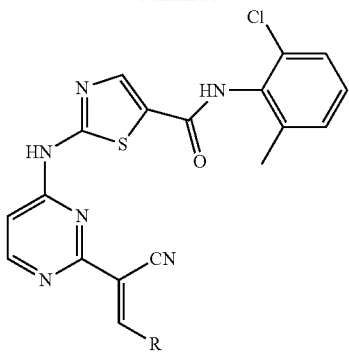
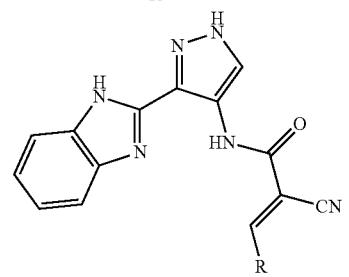
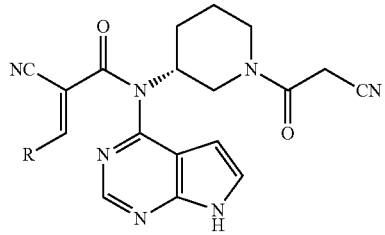
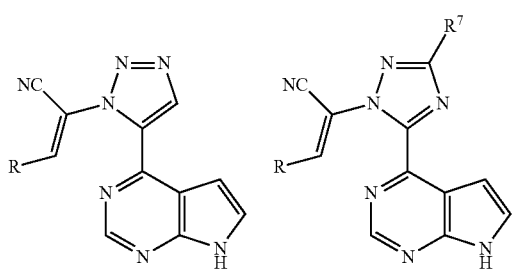
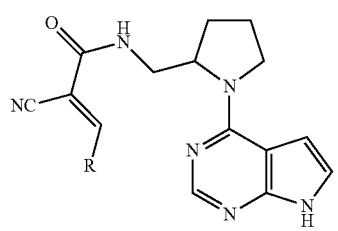
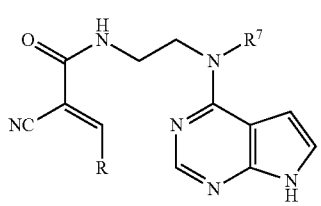

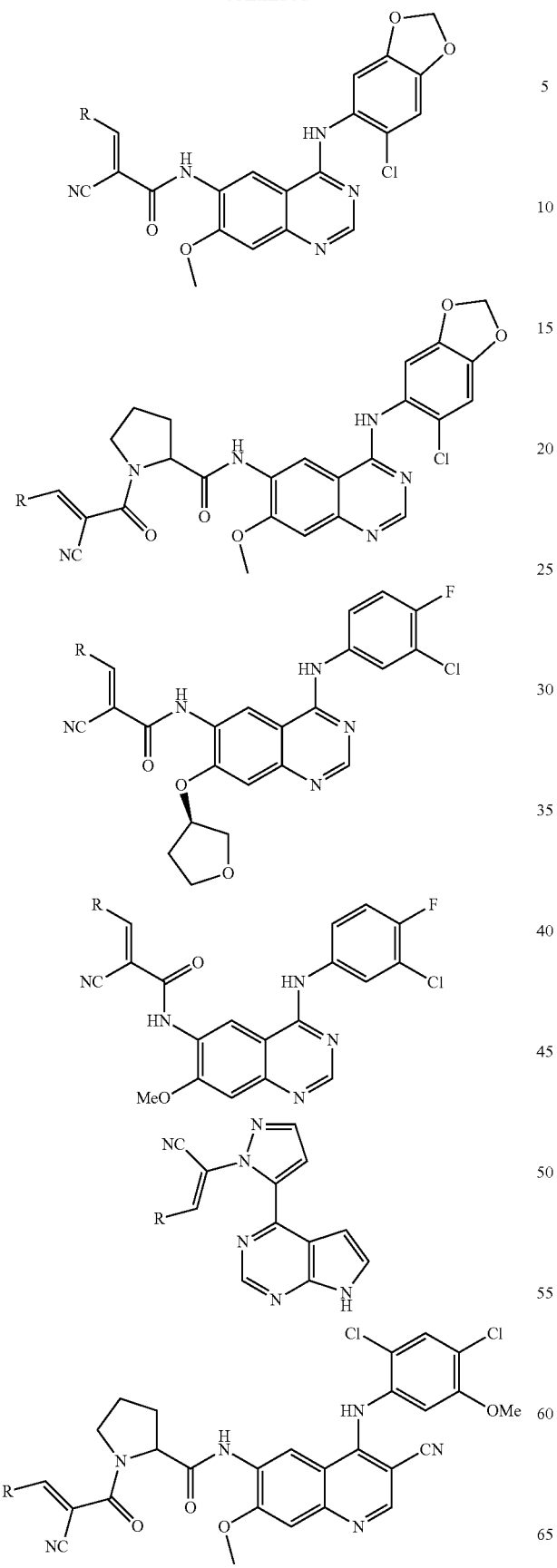
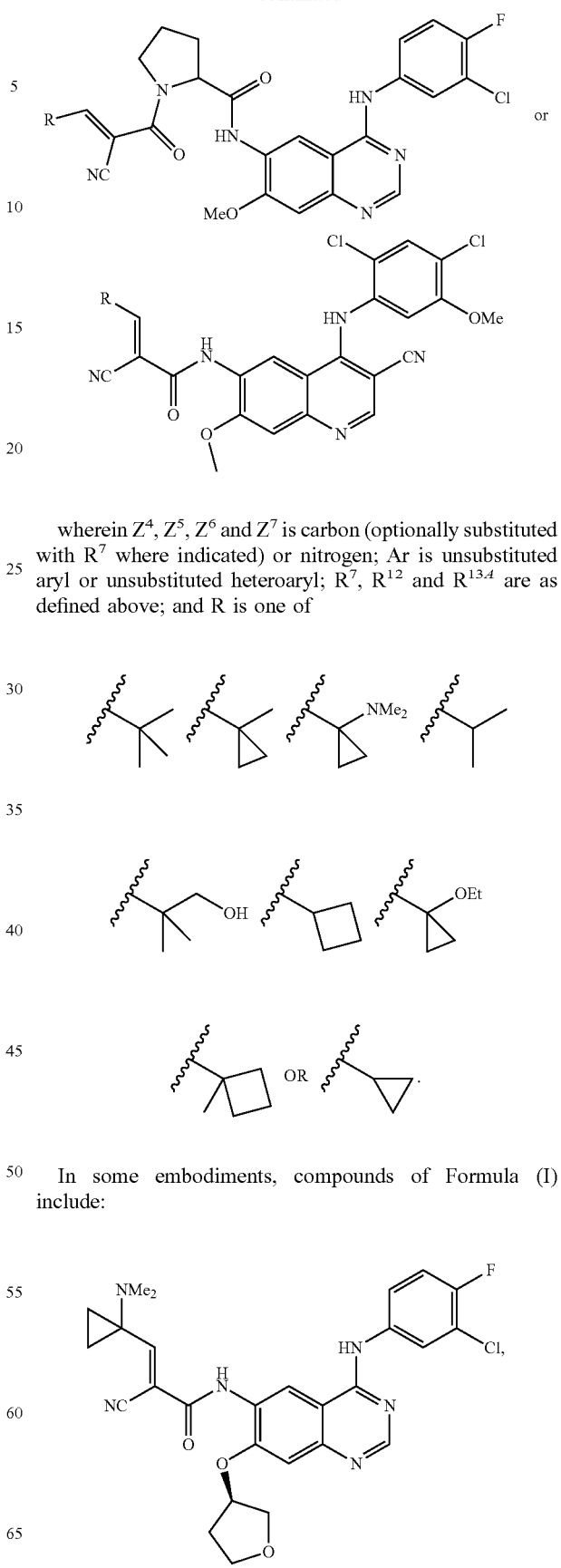
wherein $Z^4$, $Z^5$, $Z^6$ and $Z^7$ is carbon (optionally substituted with $R^7$ where indicated) or nitrogen; Ar is unsubstituted aryl or unsubstituted heteroaryl; $R^7$, $R^{12}$ and $R^{13.4}$ are as defined above; and R is one of
In some embodiments, compounds of Formula (I) include:

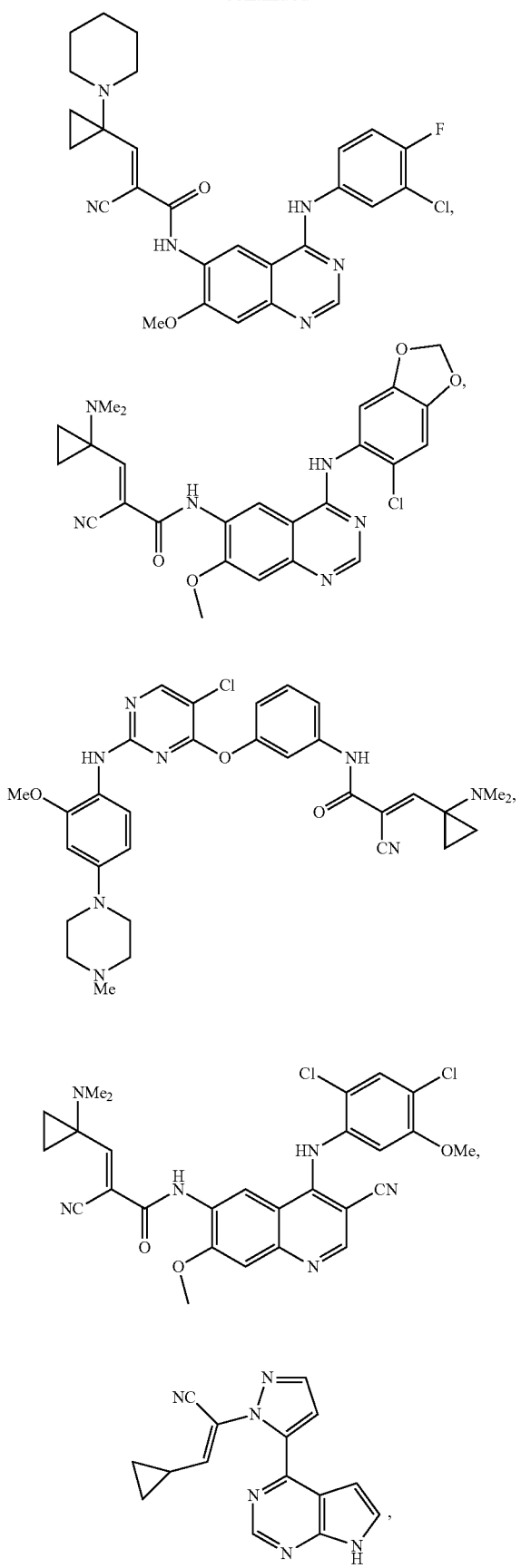
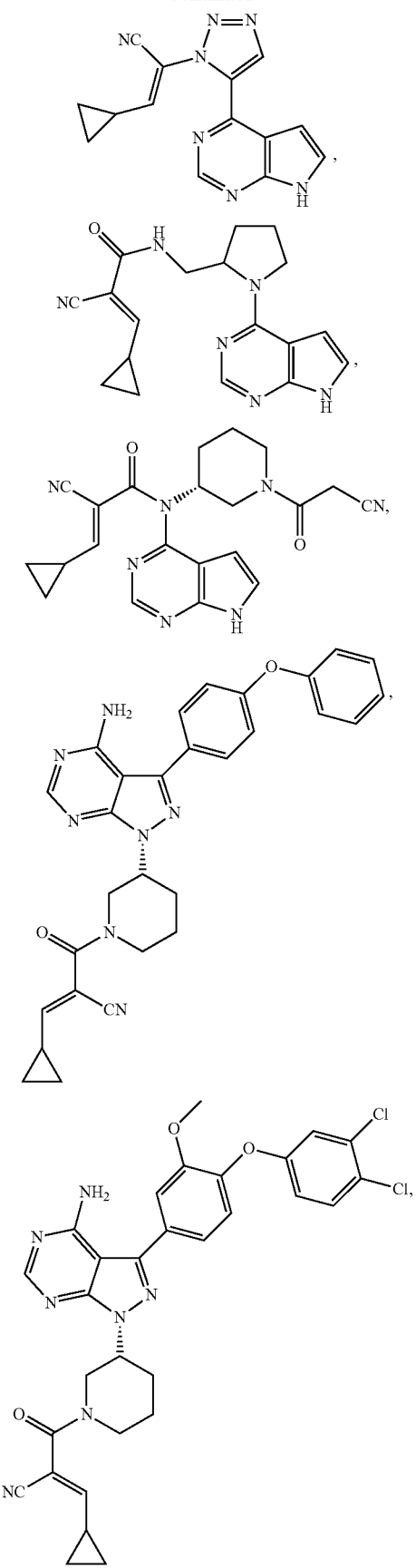

77
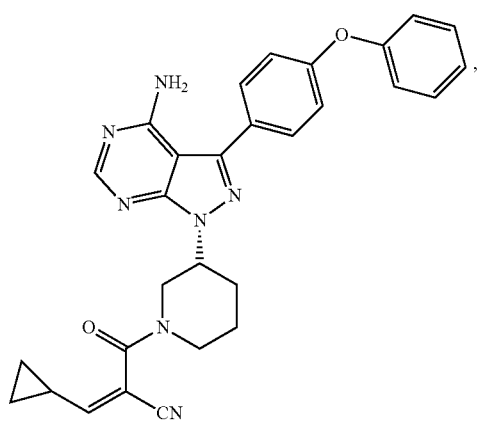
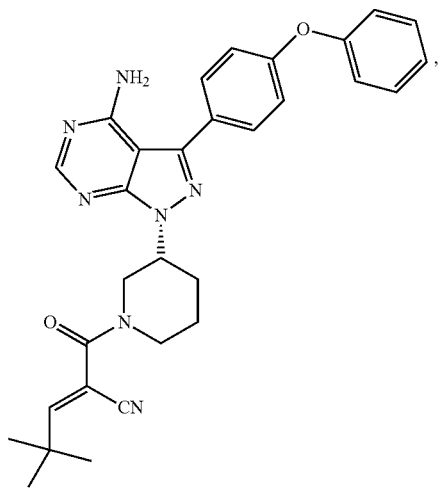
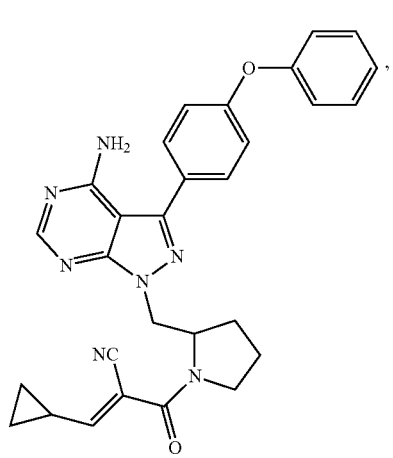
78
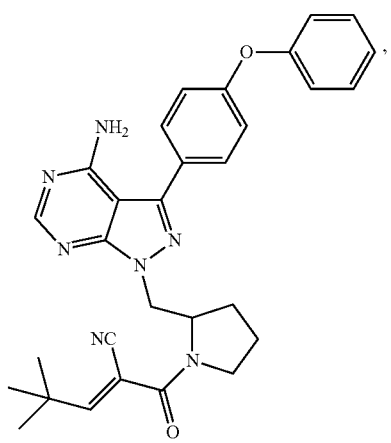
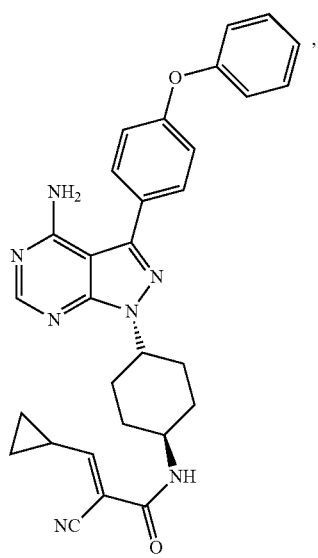
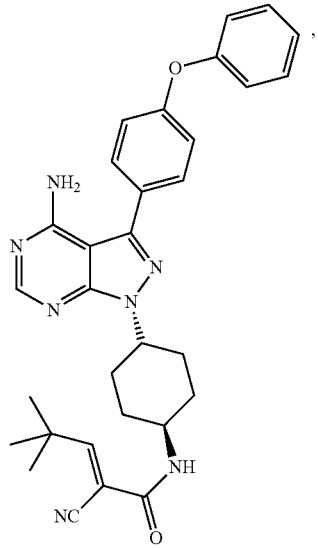

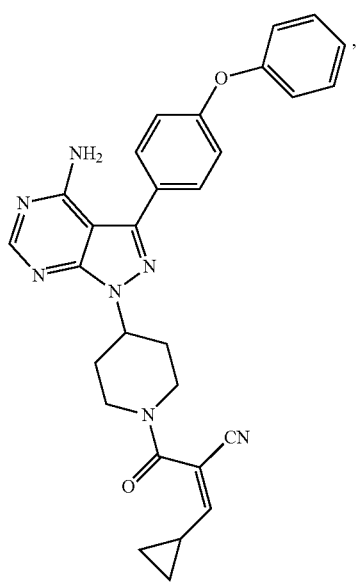
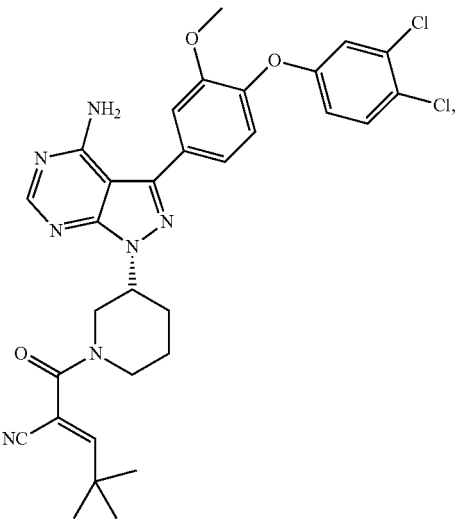
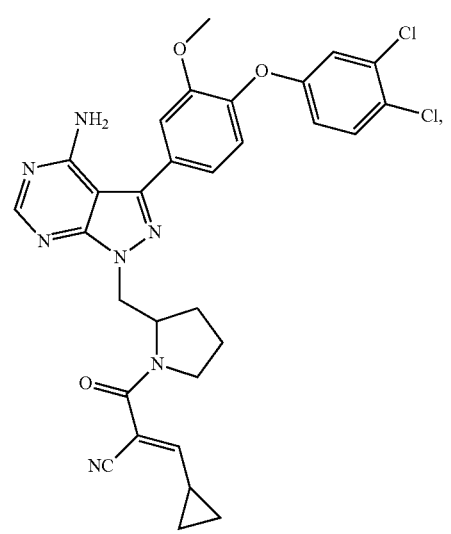
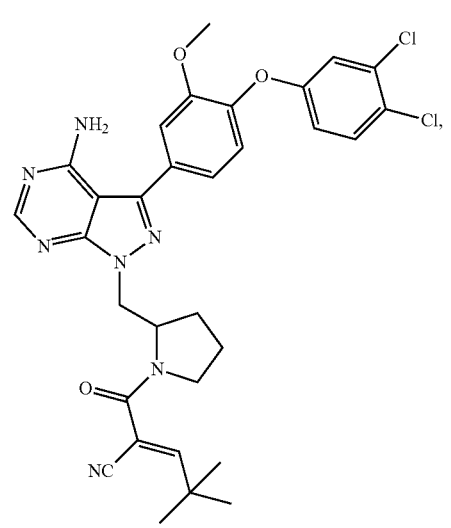

81
-continued
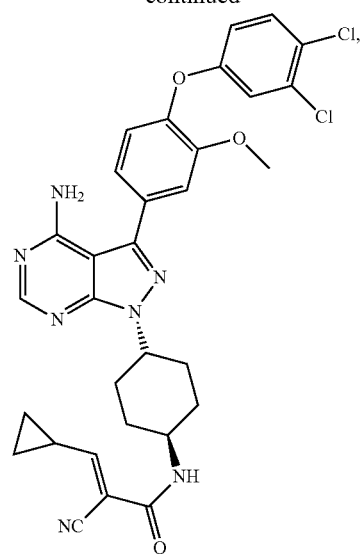
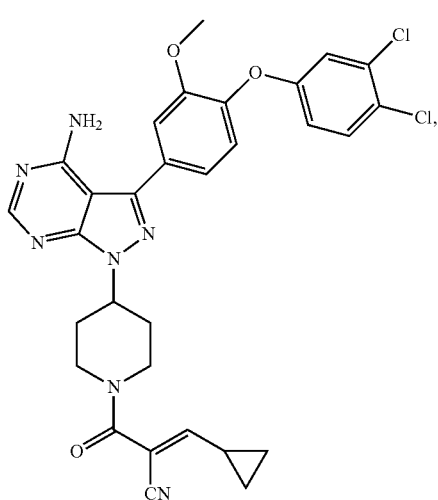
82
-continued
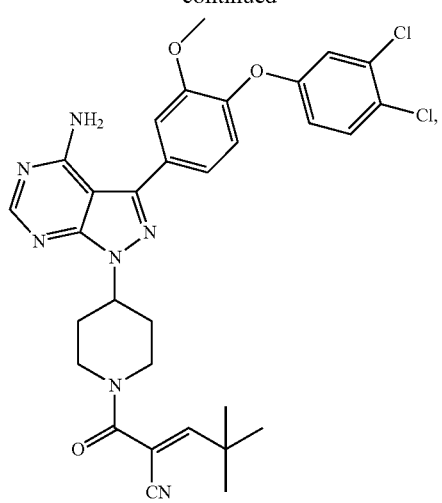
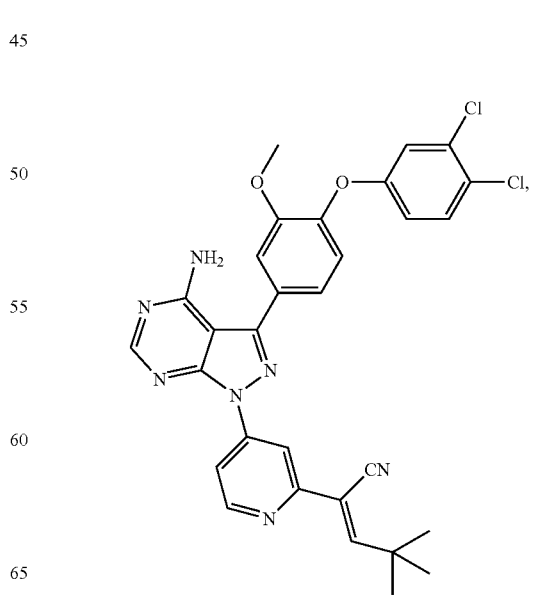

-continued
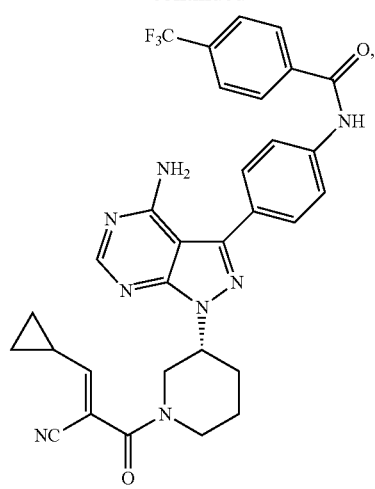
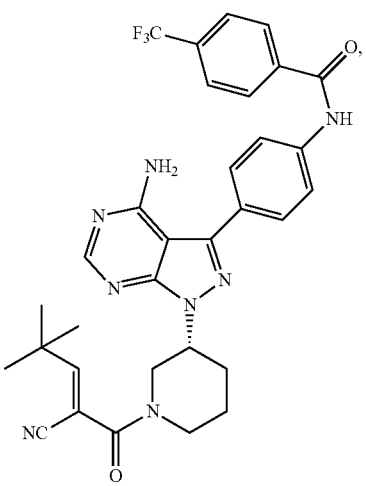
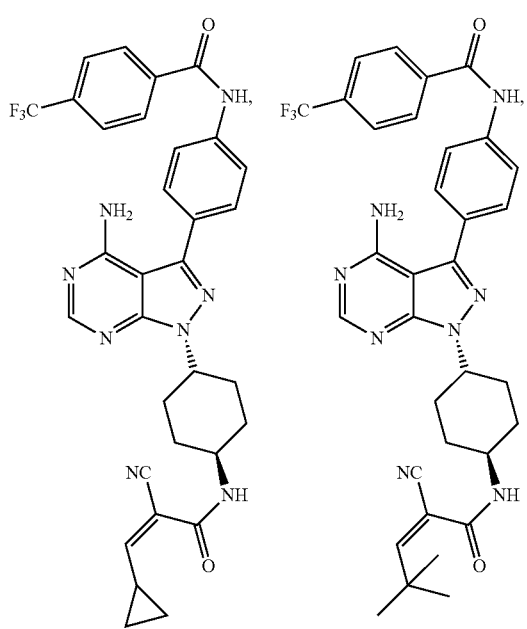
-continued
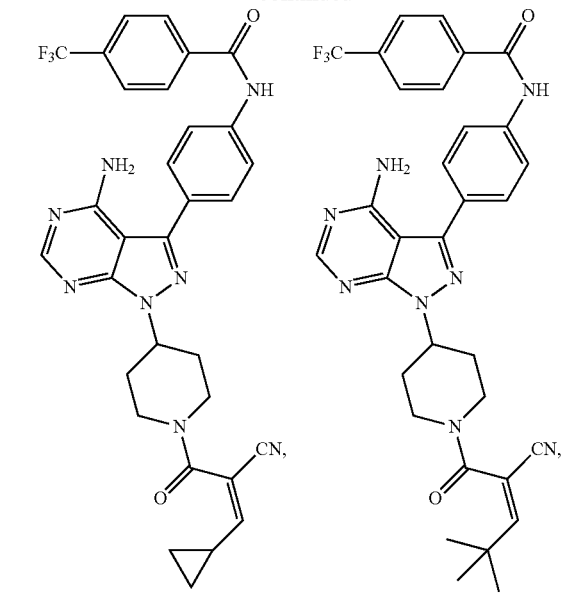
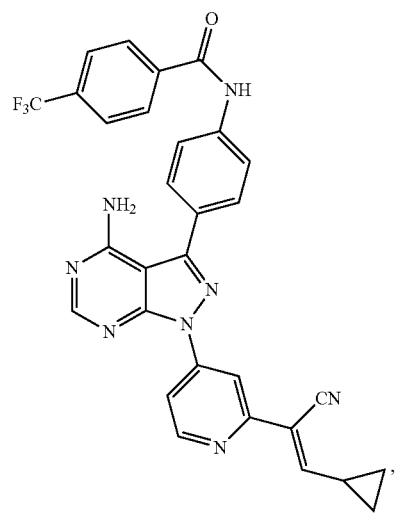
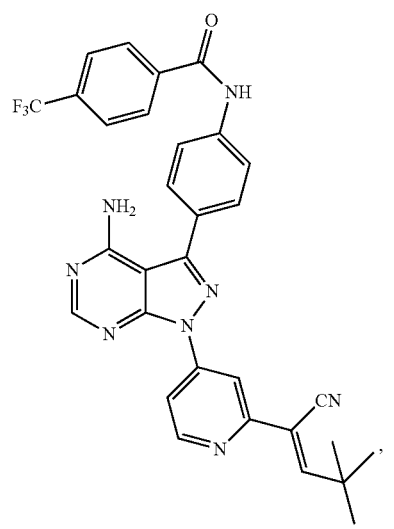

85
-continued
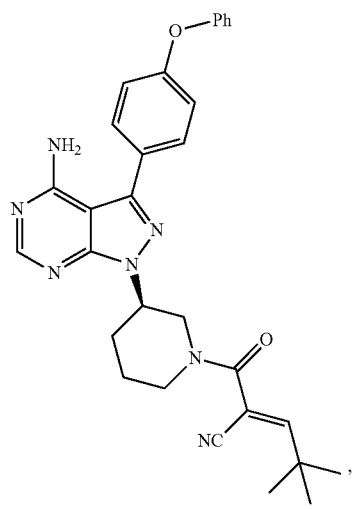
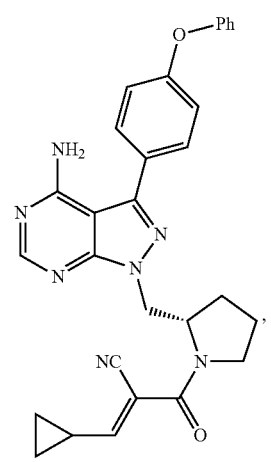
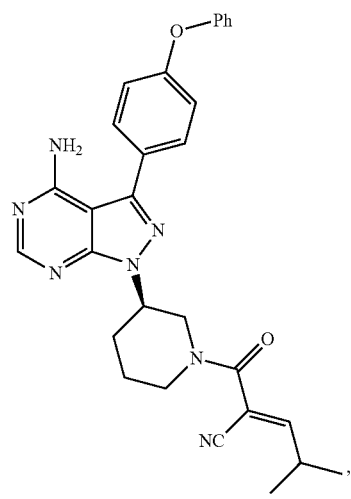
86
-continued
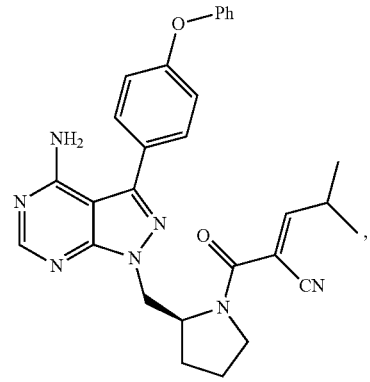
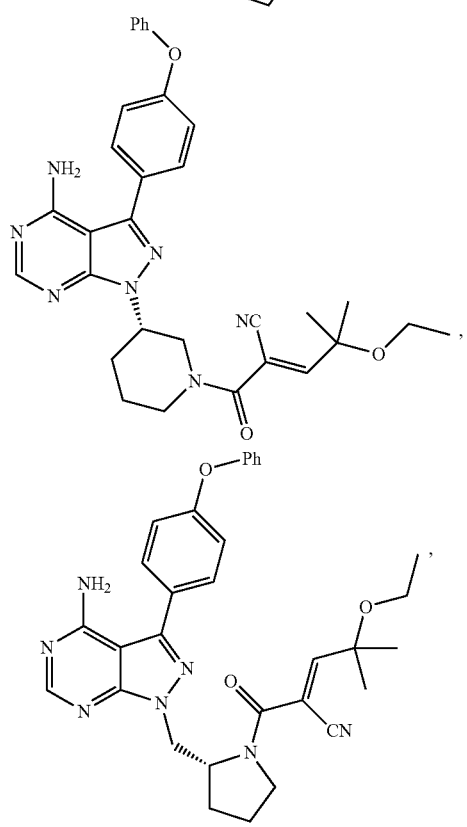
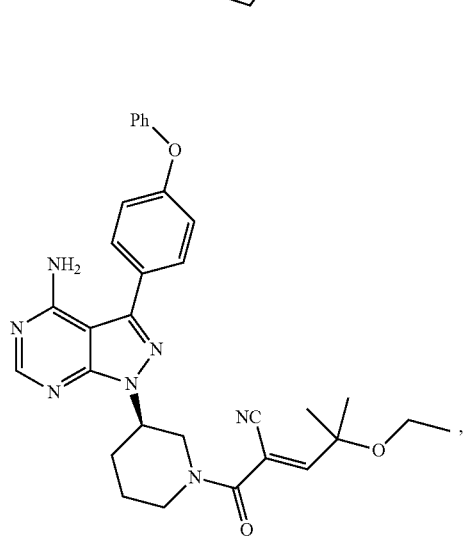

87
-continued
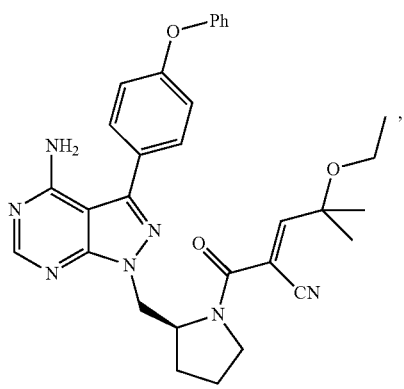
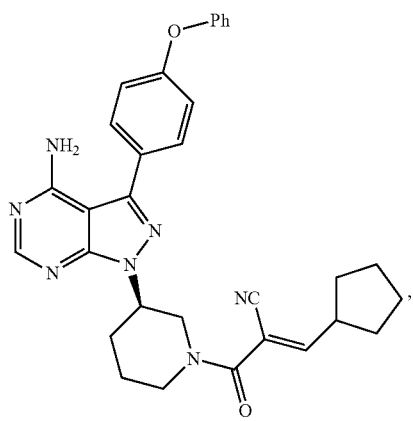
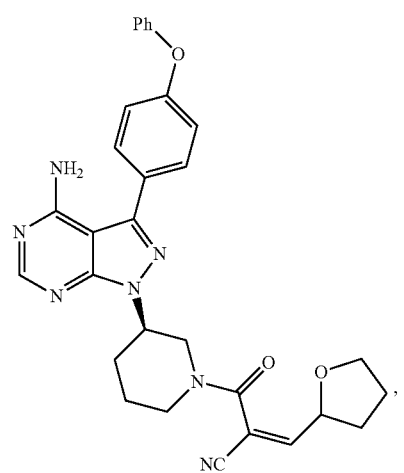
88
-continued
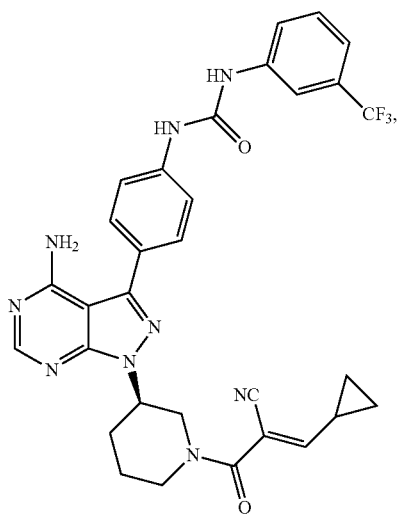
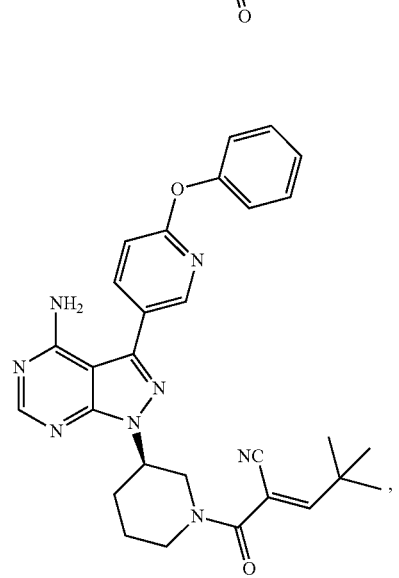

89
-continued
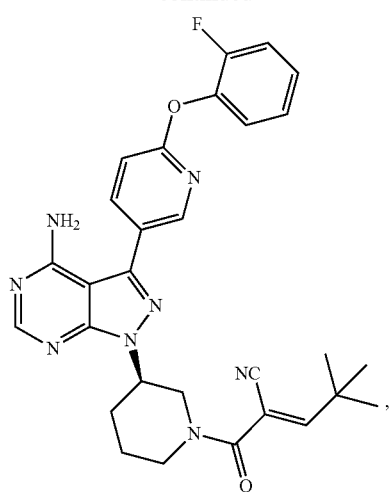
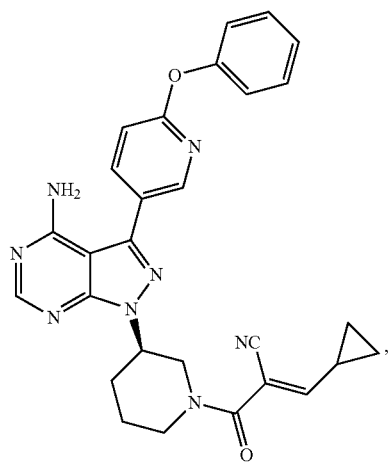
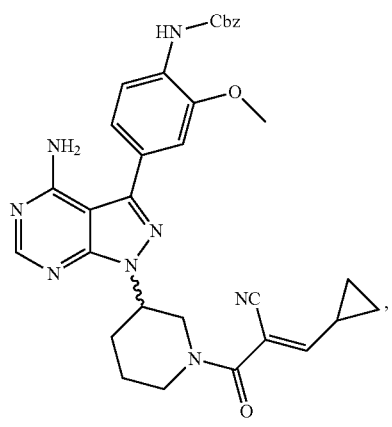
90
-continued
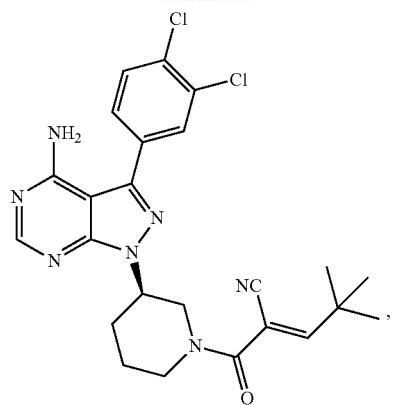
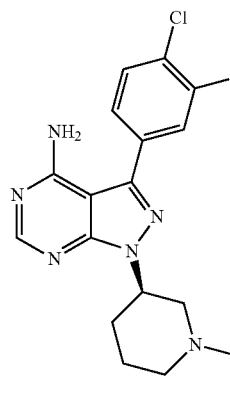
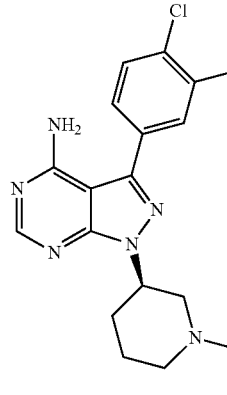
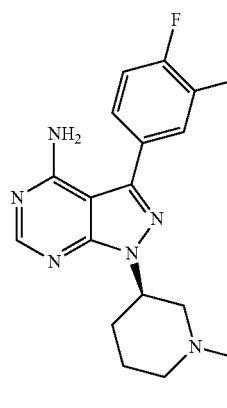

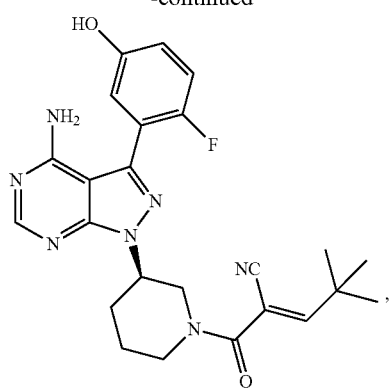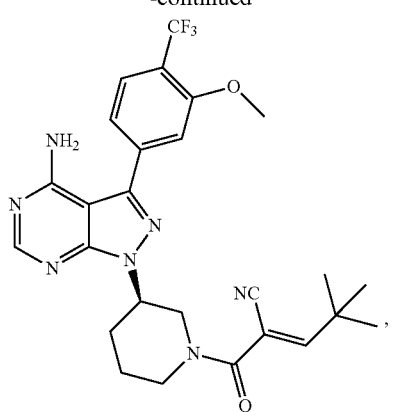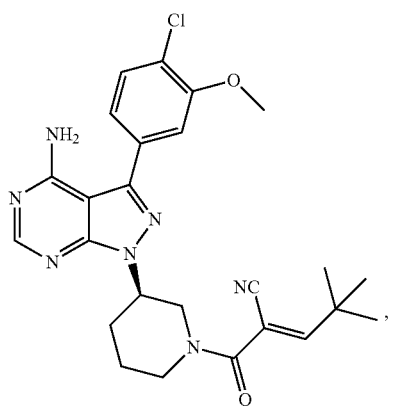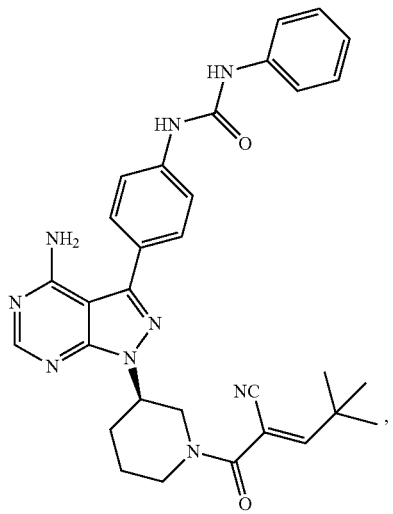

-continued
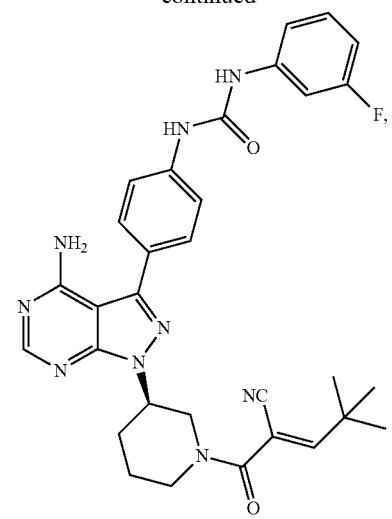
-continued
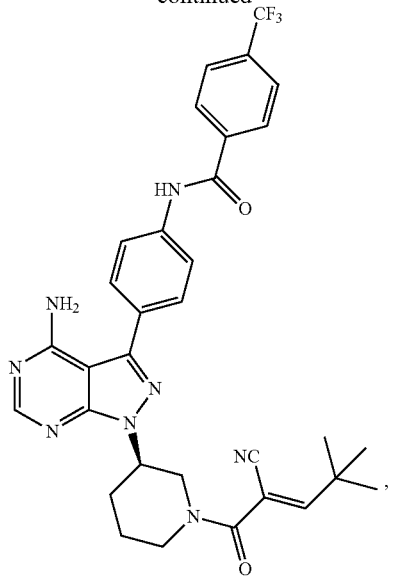
or a pharmaceutically acceptable salt thereof.
III. General Synthetic Schemes
The compound of Formula (I) can be prepared using chemical synthesis techniques generally known in the art. In this regard, some guidance in preparing a representative number of compounds of Formula (I) is provided in the Schemes and the Examples section. The Schemes and Examples disclosed in this application are merely illustrative and is not meant to be an exhaustive or restrictive teaching on how to prepare the compounds of this invention, Various modifications to these schemes can be made and will be suggested to one skilled in the art having referred to this disclosure and what is known in the art. One of ordinary skill in the art will also appreciate the Formulae provided herein are not limited to any particular stereochemistry.

The starting materials and reagents used in preparing the compound of Formula (I) are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

I. Compounds of Formula (IX) where $Z^1$ is nitrogen, $Z^2$ is carbon or nitrogen and $Z^3$ is carbon Ar, $R^2$, $R^3$, $R^4$, $R^7$, $R^{12}$, $R^{14}$, and $L^{10}$ are as defined in this application can be prepared as illustrated and described in Scheme A below.

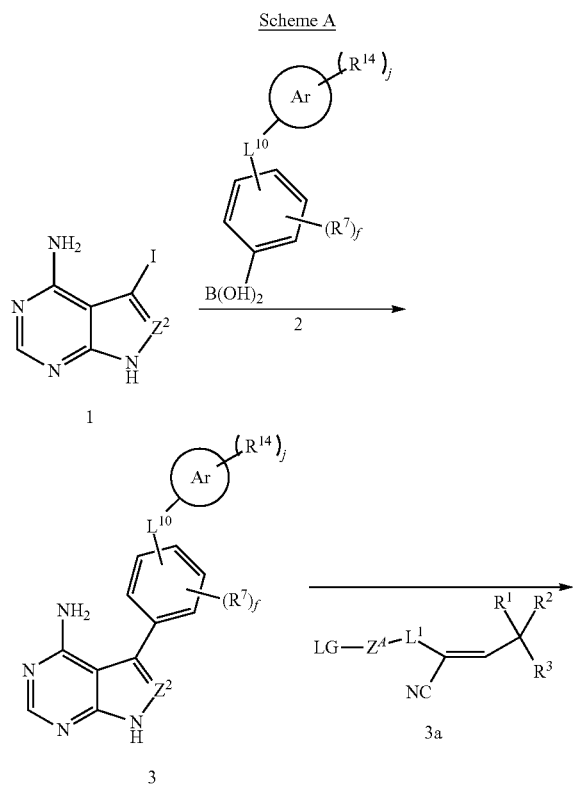

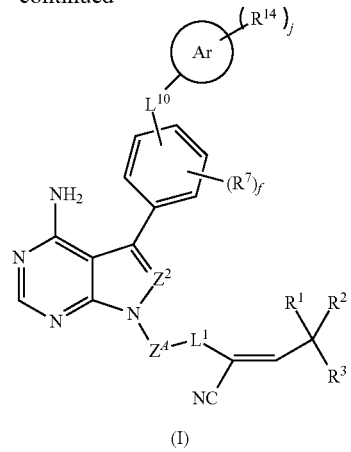

Coupling of an iodo compound of formula 1 where with a boronic acid compound of formula 2 or boronate esters thereofr, $R^1$, $R^2$, $R^3$, $R^7$, $R^{12}$, $R^{14}$, and $L^{10}$ are as defined in this application under Suzuki coupling reaction conditions provides a compound of formula 3. The Suzuki coupling reaction can be carried out in organic solvents (such as toluene, benzene, N,N-dimethylformamide (DMF), tetrahydrofuran, methanol, ethanol, acetonitrile, dimethoxythane, acetone and the like) or water in the presence of base (such as sodium ethylate, sodium hydroxide, potassium hydroxide, sodium bicarbonate, potassium bicarbonate, potassium carbonate, sodium carbonate, triethylamine, and the like) and a palladium catalyst (such as tetrakis(triphenylphosphine)palladium, dichlorobis(triphenylphosphine)-palladium, palladium acetate, and the like). The reaction is carried out at room temperature to 120° C. Compounds of formula 1 are either commercially available or can be readily prepared by methods well known in the art.

Treatment of a compound of formula 3 with a compound of formula 3a where LG is a suitable leaving group such as halo, tosylate, mesylate, triflate, and the like provides a compound of Formula (I). The alkylation or arylation reaction is typically carried out in the presence of a base such as sodium hydride or potassium tert-butoxide, potassium carbonate, and the like, and a catalyst such as 18-crown-6 in a suitable solvent such as N-methylpyrolidone, dimethylformamide, tetrahydrofuran, toluene, and the like.

It will be recognized by a person skilled in the art that precursors to the cyano substituted alkene group i.e., —$Z^4$-$L^1$-C(CN)=CHR$^2$R$^3$R$^4$ in the compound of Formula (IX) can be substituted at any step in the synthetic procedure illustrated in Scheme A above and converted to the cyano substituted alkyene group as defined in this application at alternate stages in the synthetic process based on feasibility of the transformations.

For example, substitution of precursors —$Z^4$-$L^1$-C(CN)=CHR$^2$R$^3$R$^4$ in the synthesis of compounds of Formula (IX) when —$Z^4$-$L^1$-C(CN)=CHR$^2$R$^3$R$^4$ where $Z^4$ is a bond and $L^{10}$ is heterocycloaminocarbonyl is illustrated and described below.

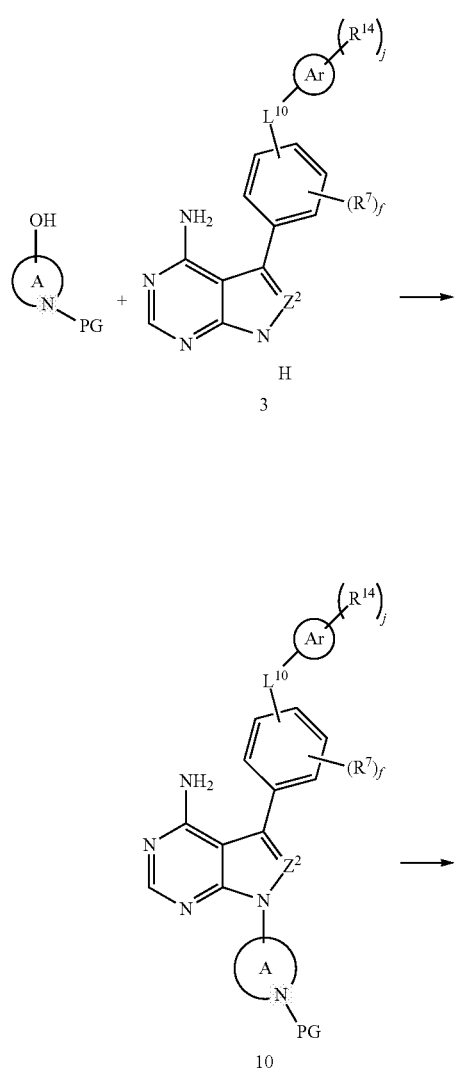

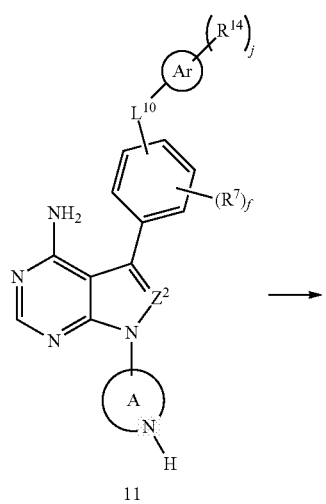

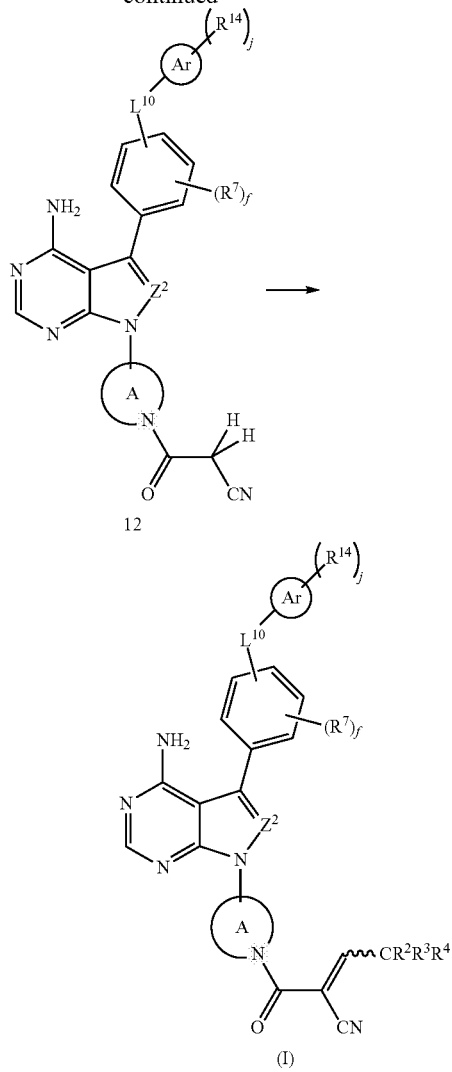

Treatment of a N-protected heterocycloamino precursor compound substituted alcohol with a compound of formula 3 under Mitsunobu reaction conditions provides a compound of formula 10 where Ar, $R^4$, $R^2$, $R^3$, $R^7$, $R^{12}$, $R^{14}$, and $L^{10}$ and $Z^2$ are as defined in this application. Removal of the amino protecting group provides a compound of formula 11. Coupling of compound of formula 11 with $CNCH_2CO_2H$ under standard amide coupling conditions such as carbon diimidazole (CDI) and the like or an acid derivative thereof provides a compound of formula 12. Subsequent condensation of a compound of formula 12 with aldehydes of formula $R^2R^3R^4CHO$ where $R^2$, $R^3$, $R^4$ are as defined in this application e.g., t-butyl or cyclopropyl aldehyde, in an organic solvent such as ethanol, and the like at temperatures ranging from 0° C. to reflux provides a compound of Formula (IX). It will recognized by a person of ordinary skill in the art that the $L^1$ moiety can be assembled at multiple points throughout the synthetic scheme and standard protecting group (PG) strategies can be employed as required.

Compounds of Formula (IX) where $Z^1$ and $Z^3$ are nitrogen and $Z^2$ is carbon, and Ar, $R^4$, $R^2$, $R^3$, $R^7$, $R^{12}$, $R^{14}$, and $L^{10}$ are as defined in this application can be prepared as illustrated and described in Scheme B below.

Scheme B

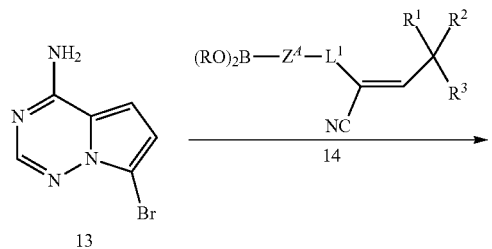

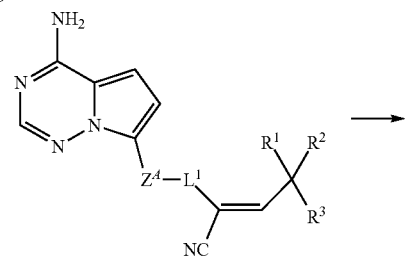

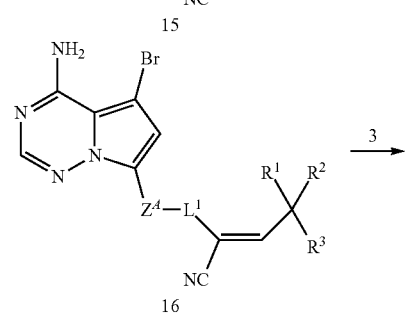

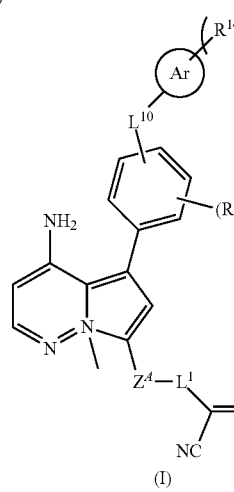

Cross coupling (Suzuki) of a compound of formula 13 (available commercially) with an appropriately substituted boronic acid or boronate esters of formula 14 (as described in Scheme A) provides a compound of formula 15. Halogenation of compound 15 with a suitable halogenating agent such as N-bromosuccinamide, bromine, and the like, in an organic solvent (such as DMF, dichloromethane, tetrahydrofuran, toluene, acetic acid, water and the like) at temperatures ranging from −78° C. to reflux temperature provides a compound of formula 16. Compound 16 is then coupled with a compound of formula 3 under Suzuki coupling reaction conditions as described in Scheme A to provide a compound of Formula (IX).

It will be recognized by a person skilled in the art that precursors to cyano substituted alkene moiety can be substituted at any step in Scheme B and converted to the desired cyano substituted alkene moiety at alternate stages in the synthetic process based on feasibility of the transformations. For example, substitution of precursors to cyano substituted alkene moiety in the synthesis of compounds of Formula (IX) when Z is a bond and $L^1$ is heterocycloaminocarbonyl is illustrated and described below. The $L^1$ moiety can be assembled at multiple points in the synthetic scheme. Standard protecting group (PG) strategies employed by those skilled in the art can be employed as required.

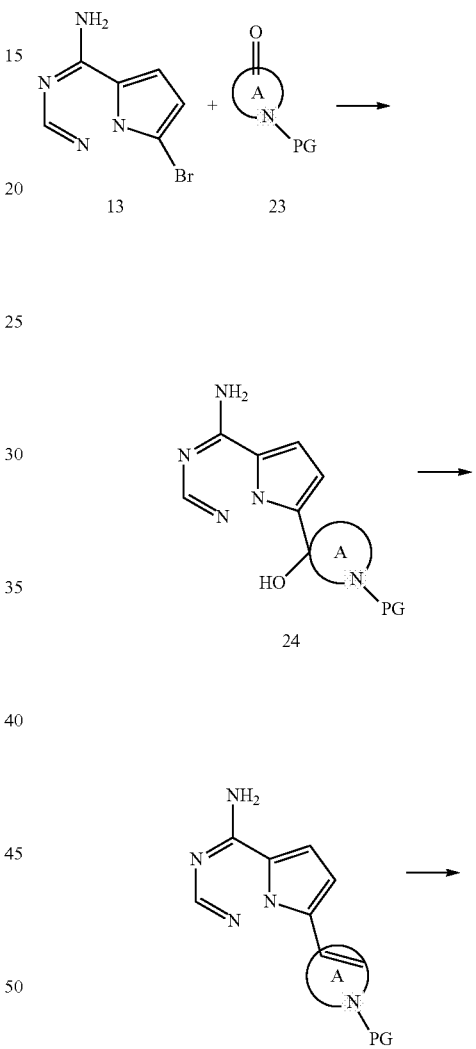

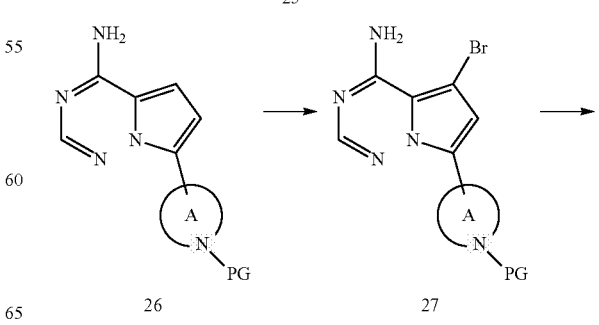

-continued

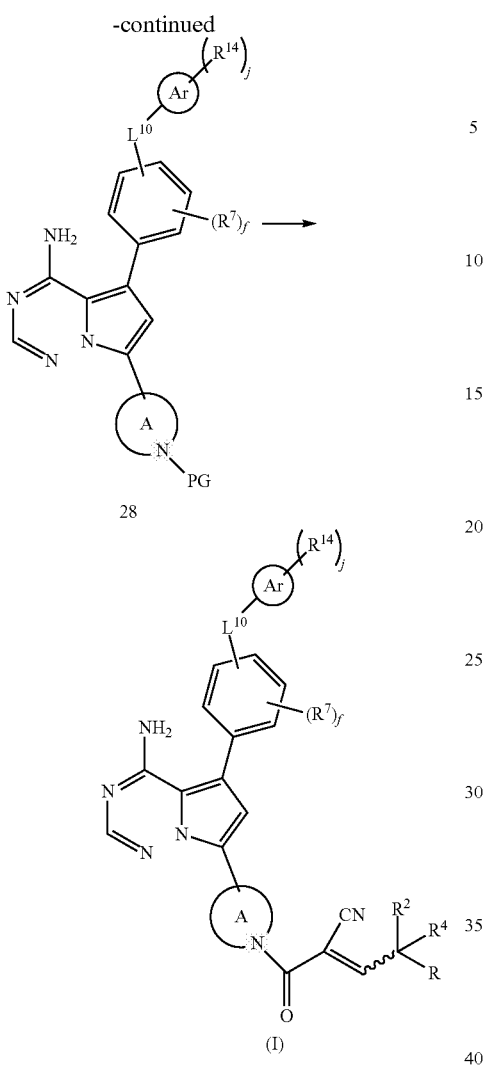

Treatment of compound 13 with trimethylsilyl chloride in solvents such as tetrahydrofuran (THF) at temperatures ranging from 0° C. to room temperature prior to treatment by a Grignard reaction (for example by treatment with isopropyl magnesium chloride in THF at temperatures ranging from 0° C. to room temperature) and subsequent addition of alkene precursor compound of formula 23 bearing a ketone moiety where PG is a suitable protecting group such as benzyloxycarbonyl (Boc), benzyl (Bn) or 2-trimethylsilylethoxymethyl (SEM)), provides a compound of formula 24 which is converted to a compound of formula 25 under dehydration reaction conditions e.g., treatment of compound 24 with acids such as trifluoroacetic anhydride or trifluoroacetic acid, and the like, in solvents such as pyridine, toluene, methanol, and the like and temperatures ranging from −20° C. to reflux. Reduction of the double bond in the compound of formula 25 with a suitable hydrogenation reaction conditions e.g., with platinum oxide or palladium hydroxide or palladium on carbon in alcoholic solvents such as methanol or ethanol, and the like in the presence or absence of acetic acid and under a hydrogen atmosphere provides a compound of formula 26.

Halogenation of a compound of formula 26 with a suitable halogenating agent as described in Scheme B above provides a compound of formula 27 which can then be converted to a compound of Formula (IX) as described in Scheme A above.

Compounds of Formula (IX) where $Z^1$ and $Z^2$ are nitrogen and $Z^3$ is carbon and Ar, $R^4$, $R^2$, $R^3$, $R^7$, $R^{12}$, $R^{14}$, and $L^{10}$ are as defined in this application can be prepared as illustrated and described in Scheme C below.

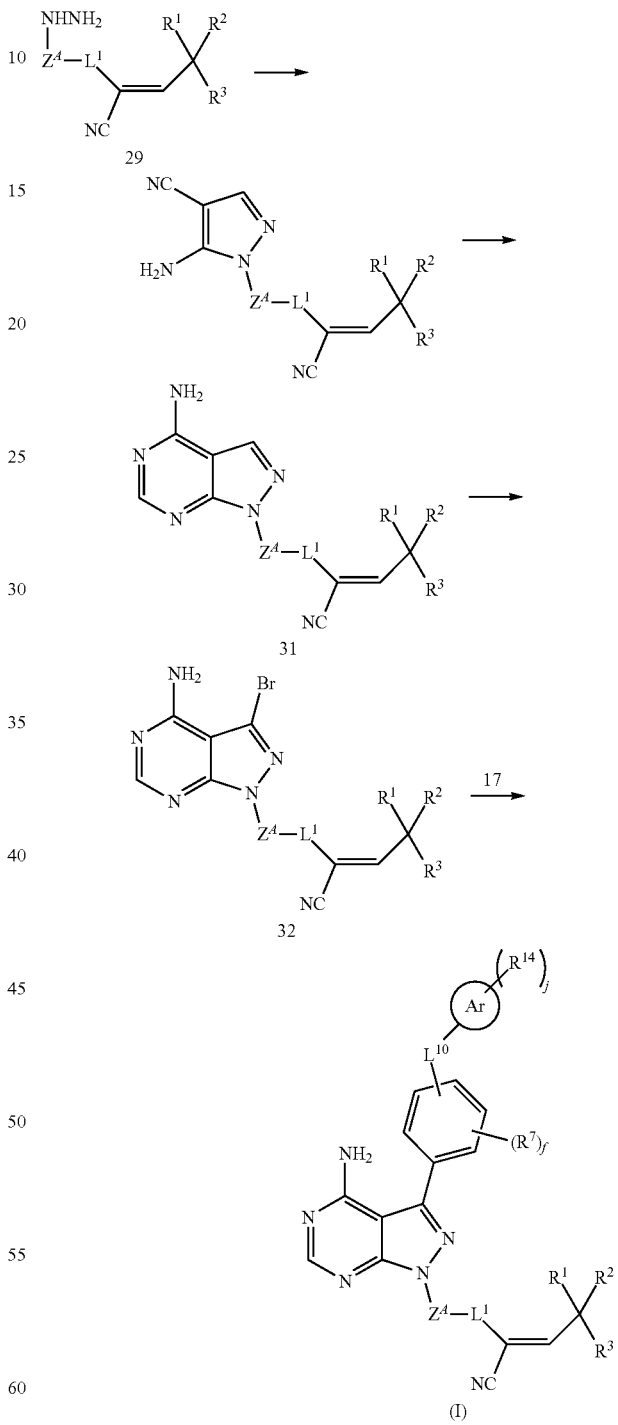

Reaction of a hydrazine compound of formula 28 with ethoxymethylene malonitrile in a suitable organic solvent such as ethanol and the like and at temperatures from 0° C. to reflux provide a compound of formula 30. Compound of formula 29 that are either commercially available or readily synthesized by methods that are well known in the art.

Treatment of compound 30 with formamide or formamidine in the absence of solvent or in solvents such as ethanol and the like at temperatures from room temperature to 200° C. provides a compound of formula 31. Halogenation of 31 under halogenating conditions described above provides the compound of formula 32 which can then be converted to a compound of Formula (I) as described in Scheme A above.

It will be recognized by a person skilled in the art that precursors to the cyano substituted alkene group can be substituted at any step in Scheme C above and then converted to the cyano substituted alkene group at alternate stages in the synthetic process based on feasibility of the transformations. For example substitution of precursors to cyano substituted alkene group in the synthesis of compounds of Formula (I) when $R^1$ is $-Z^4L^1$-C(CN)=CHCR$^2$R$^3$R$^4$ where Z is a bond and $L^1$ is heterocycloaminocarbonyl is illustrated and described below. The $L^1$ moiety can be assembled at multiple points in the synthetic scheme. Standard protecting group (PG) strategies employed by those skilled in the art can be employed as required.

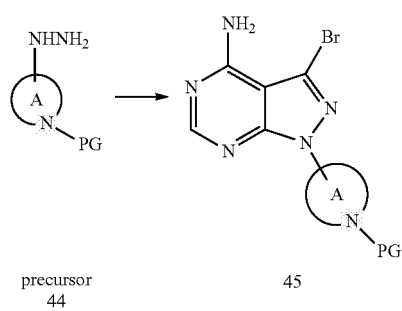

precursor 44

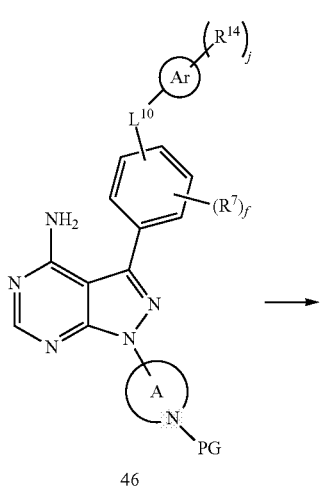

46

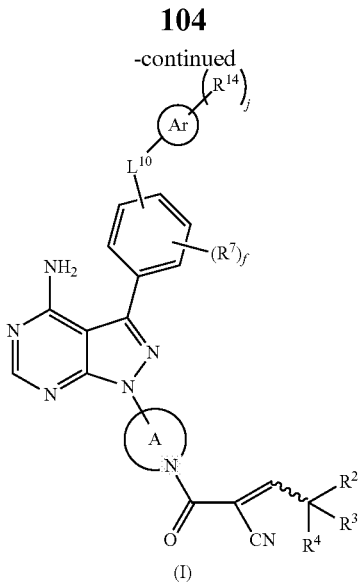

(I)

Substituting compound of formula 33 with a compound of formula 44 followed by steps 2-5 in Method (d) above provides a compound of formula 46. Compound 46 can then be converted to a compound of Formula (I) by methods described above.

Accordingly, in one aspect provided herein is a process of making a compound of Formula (I):

$$R^1\text{-}Z\text{-}L^1\text{-}C(CN)=CHCR^2R^3R^4 \quad (I)$$

In Formula (I) $R^1$ is substituted saturated ($C_3$-$C_6$) cycloalkyl, substituted saturated 4 to 8 membered saturated heterocycloalkyl containing one or two heteroatoms independently selected from N, O, S, SO or $SO_2$, substituted monocyclic or fused bicyclic ($C_6$-$C_{10}$) aromatic aryl, or substituted monocyclic or fused bicyclic 5-10 membered aromatic heteroaryl; Z is a bond or unsubstituted saturated ($C_1$-$C_6$) alkylene; $L^1$ is —C(O)—, —N($L^2R^5$)$SO_2$—, —N($L^2R^5$)C(O)—,

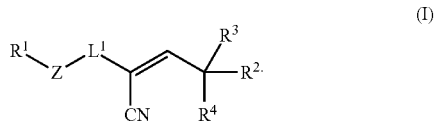

wherein $L^2$ is a bond or substituted or unsubstituted saturated ($C_1$-$C_6$) alkylene; and $R^5$ is hydrogen; Ring A in

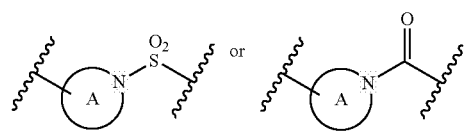

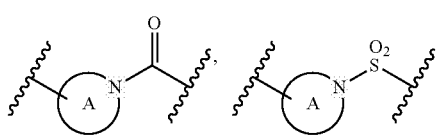

is heterocycloamino where the —CO— and —$SO_2$— groups are attached to —C(CN)=CHC($R^2$)($R^3$)($R^4$); and the heterocycloamino is substituted with one, two, or three substituents independently selected from hydrogen, unsubstituted saturated ($C_1$-$C_6$) alkyl, unsubstituted saturated ($C_1$-$C_6$) alkoxy, hydroxyl, cyano, nitro, halo, unsubstituted saturated ($C_1$-$C_6$) haloalkyl, unsubstituted saturated ($C_1$-$C_6$) haloalkoxy, —S($C_1$-$C_6$) unsubstituted saturated alkyl, —$SO_2$($C_1$-$C_6$) unsubstituted saturated alkyl, carboxy, or —COO—($C_1$-$C_6$) unsubstituted saturated alkyl; $R^2$ and $R^3$ are independently substituted or unsubstituted saturated ($C_1$-$C_8$) alkyl, or $R^2$ and $R^3$ are optionally joined together to form a substituted or unsubstituted ($C_3$-$C_6$) cycloalkyl, or substituted or unsubstituted 4 to 8 membered heterocycloalkyl containing one or two heteroatoms independently selected from N, O, S, SO or $SO_2$; $R^4$ is hydrogen, —$NR^{4A}R^{4B}$, —$OR^{4A}$, —$SR^{4A}$, substituted or unsubstituted alkyl or substituted or unsubstituted 4 to 8 membered heterocycloalkyl containing one or two heteroatoms independently selected from N, O, S, SO or $SO_2$ where $R^{4A}$ and $R^{4B}$ are independently hydrogen, substituted or unsubstituted ($C_1$-$C_6$) alkyl, or substituted or unsubstituted 4 to 8 membered heterocycloalkyl containing one or two heteroatoms independently selected from N, O, S, SO or $SO_2$ provided that alkyl and heterocycloalkyl in $R^2$, $R^3$ and $R^4$ are not substituted with substituted or unsubstituted aryl, substituted or unsubstituted heteroaryl, substituted or unsubstituted cycloalkyl or substituted or unsubstituted heterocycloalkyl; comprising: (i) reacting a compound of formula (a):

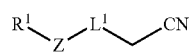

(a)

where $R^1$, Z and $L^1$ are as defined above, with an aldehyde of formula (b) under condensation reaction conditions:

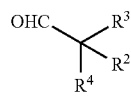

(b)

where $R^2$, $R^3$ and $R^4$ are as defined above; or (ii) reacting a compound of formula (c):

(c)

where $R^1$ and Z are as defined above and X is —NH($L^2R^5$) where $L^2$ and $R^5$ are as defined above or

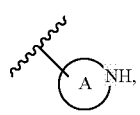

preferably X is —$NH_2$,

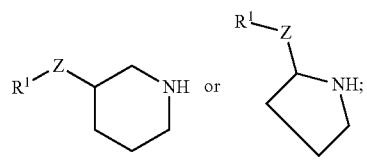

with a cyanoalkene of formula (d):

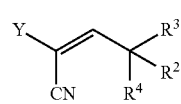

(d)

where $R^2$, $R^3$ and $R^4$ are as defined above, and Y is —$SO_2$LG or —COLG where LG is a leaving group under sulfonylating where Y is —$SO_2$LG or acylating conditions where Y is —COLG; preferably halo; (iii) optionally modifying any of the substituents in compound obtained from step (i) or (ii) to give a compound of Formula (I); (iv) optionally converting the compound from step (i), (ii) or (iii) to an acid addition salt; (v) optionally converting the compound from step (i), (ii), (iii) or (iv) to a free base.

In one embodiment (embodiment (a)), in the process above, the compound of Formula (I) does not contain:
(i) a substituted or unsubstituted heteroaryl ring (e.g. unsubstituted heteroaryl ring) of formula

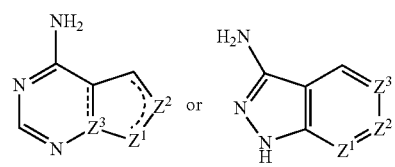

where the dashed lines are an optional bond; and $Z^1$, $Z^2$, and $Z^3$ are N or C, provided that one or two of $Z^1$, $Z^2$, and $Z^3$ are N; or (ii) a substituted or unsubstituted ring (e.g. unsubstituted heteroaryl ring) of formula

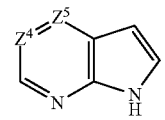

where $Z^4$ and $Z^5$ are independently N or C provided that at least one of $Z^4$ and $Z^5$ is N and further provided that both $Z^4$ and $Z^5$ are not N. $Z^1$, $Z^2$, and $Z^3$ are N or C (according to the normal chemical valency rules), provided that at least one and not more than two of $Z^1$, $Z^2$, and $Z^3$ are simultaneously N. As stated above $Z^1$, $Z^2$, and $Z^3$ are N or C and obey the normal rules of valency. The valency of N or C for $Z^1$, $Z^2$, and $Z^3$ is filled with a single of double bond to a neighboring ring atom, a bond to $Z^4$, a bond to $R^7$ and/or a bond to hydrogen or to a substituent within the scope of the invention.

In another embodiment (embodiment (b)), in the process in embodiment (a) above, $R^{4A}$ and $R^{4B}$ are independently hydrogen, unsubstituted saturated ($C_1$-$C_6$) alkyl, or saturated ($C_1$-$C_6$) alkyl substituted with one to three substituents independently selected from —OR' or —NR'R" where R' and R" are independently hydrogen or unsubstituted saturated ($C_1$-$C_6$) alkyl.

In another embodiment (embodiment (c)), in the processing embodiment (a) and/or (b) above, $R^2$ and $R^3$ are independently unsubstituted saturated ($C_1$-$C_6$) alkyl and $R^4$ is hydrogen, unsubstituted saturated ($C_1$-$C_6$) alkyl, saturated ($C_1$-$C_6$) alkyl substituted with one to three substituents independently selected from —OR' or —NR'R" (where R' and R" are independently hydrogen or unsubstituted saturated ($C_1$-$C_6$) alkyl), —$NR^{4A}R^{4B}$, —$OR^{4A}$ [where $R^{4A}$ and $R^{4B}$ are independently hydrogen, unsubstituted saturated ($C_1$-$C_6$) alkyl, or saturated ($C_1$-$C_6$) alkyl substituted with one to three substituents independently selected from —OR' or —NR'R" (where R' and R" are independently hydrogen or unsubstituted saturated ($C_1$-$C_6$) alkyl)], unsubstituted saturated 4-7-membered heterocycloalkyl containing one to two heteroatoms selected from N, O, S, SO or $SO_2$, saturated 4-7-membered heterocycloalkyl containing one to two heteroatoms selected from N, O, S, SO or $SO_2$ and substituted with one or two unsubstituted saturated ($C_1$-$C_6$) alkyl, hydroxy, unsubstituted —O($C_1$-$C_6$) alkyl, or fluoro, saturated ($C_1$-$C_6$) alkyl substituted with one saturated 4-7-membered heterocycloalkyl containing one to two heteroatoms selected from N, O, S, SO or $SO_2$, or saturated ($C_1$-$C_6$) alkyl substituted with one saturated 4-7-membered heterocycloalkyl containing one to two heteroatoms selected from N, O, S, SO or $SO_2$ and substituted with one or two unsubstituted saturated ($C_1$-$C_6$) alkyl, hydroxy, unsubstituted saturated —O($C_1$-$C_6$) alkyl, or fluoro.

In another embodiment (embodiment (d)), in the process in embodiment (a) and/or (b) above, $R^2$ and $R^3$ are independently unsubstituted saturated ($C_1$-$C_6$) alkyl and $R^4$ is hydrogen or unsubstituted saturated ($C_1$-$C_6$) alkyl.

In another embodiment (embodiment (e)), in the process in embodiment (a) and/or (b) above, $R^2$ and $R^3$ are independently unsubstituted saturated ($C_1$-$C_6$) alkyl and $R^4$ is saturated ($C_1$-$C_6$) alkyl substituted with one to three substituents independently selected from —OR' or —NR'R" where R' and R" are independently hydrogen or unsubstituted saturated ($C_1$-$C_6$) alkyl.

In another embodiment (embodiment (f)), in the process in embodiment (a) and/or (b) above, $R^2$ and $R^3$ are independently unsubstituted saturated ($C_1$-$C_6$) alkyl and $R^4$ is —$NR^{4A}R^{4B}$ or —$OR^{4A}$ where $R^{4A}$ and $R^{4B}$ are independently hydrogen, unsubstituted saturated ($C_1$-$C_6$) alkyl, or saturated ($C_1$-$C_6$) alkyl substituted with one to three substituents independently selected from —OR' or —NR'R" where R' and R" are independently hydrogen or unsubstituted saturated ($C_1$-$C_6$) alkyl.

In another embodiment (embodiment (g)), in the process in embodiment, $R^2$ and $R^3$ are independently unsubstituted saturated ($C_1$-$C_6$) alkyl and $R^4$ is unsubstituted saturated 4-7-membered heterocycloalkyl containing one to two heteroatoms selected from N, O, S, SO or $SO_2$ or saturated 4-7-membered heterocycloalkyl containing one to two heteroatoms selected from N, O, S, SO or $SO_2$ and substituted with one or two unsubstituted saturated ($C_1$-$C_6$) alkyl, hydroxy, unsubstituted saturated —O($C_1$-$C_6$) alkyl, or fluoro.

In another embodiment (embodiment (h)), in the process in embodiment process in embodiment (a) and/or (b) above, $R^2$ and $R^3$ are joined together to form a unsubstituted saturated ($C_3$-$C_6$) cycloalkyl or saturated ($C_3$-$C_6$) cycloalkyl substituted with one or two substituents independently selected from unsubstituted saturated ($C_1$-$C_6$) alkyl, hydroxy, unsubstituted saturated —O($C_1$-$C_6$) alkyl, or halo.

In another embodiment (embodiment (i)), in the process in embodiment (a) and/or (b) above, $R^2$ and $R^3$ are joined together to form a unsubstituted saturated ($C_3$-$C_6$) cycloalkyl.

In another embodiment (embodiment (j)), in the process in embodiment (a) and/or (b) above, $R^2$ and $R^3$ are joined together to form unsubstituted saturated 4 to 6 membered heterocycloalkyl containing one to two heteroatoms selected from N, O, S, SO or $SO_2$ or saturated 4 to 6 membered heterocycloalkyl containing one to two heteroatoms selected from N, O, S, SO or $SO_2$ substituted with one to three substituents independently selected from unsubstituted saturated ($C_1$-$C_6$) alkyl, hydroxy, unsubstituted saturated O($C_1$-$C_6$) alkyl, or halo.

In another embodiment (embodiment (k)), in the process in embodiment (i), and/or (j) above, $R^4$ is hydrogen or unsubstituted saturated ($C_1$-$C_6$) alkyl. In another embodiment (embodiment (l)), in the process in embodiment (a) and/or (b) above, $R^2$ and $R^3$ are methyl or ethyl and $R^4$ is hydrogen, methyl, ethyl, amino, methylamino, dimethylamino, diethylamino, methylethylamino, isopropylamino, butylamino, hydroxy, methoxy, ethoxy, propoxy, methoxymethyl, 2-methoxyethyl, ethoxymethyl, 2-ethoxyethyl, pyrrolidinyl, piperidinyl, piperazinyl, morpholinyl, thiomorpholinyl, tetrahydropyranyl, tetrahydrofuranyl, oxetanyl, or azetidinyl wherein each of the aforementioned ring is optionally substituted with one or two substituents independently selected from methyl, ethyl, propyl, hydroxy, methoxy, ethoxy, chloro, or fluoro.

In another embodiment (embodiment (m)), in the process in embodiment (a) and/or (b) above, $R^2$ and $R^3$ are joined together to form a cyclopropyl, cyclobutyl, cyclohexyl, pyrrolidinyl, piperidinyl, piperazinyl, tetrahydropyranyl, tetrahydrofuranyl, azetidinyl, or oxetanyl where pyrrolidinyl, piperidinyl, piperazinyl, or azetidinyl is optionally substituted with one or two substituents independently selected from methyl, ethyl, propyl, hydroxy, methoxy, ethoxy, chloro or fluoro and $R^4$ is hydrogen or methyl or ethyl.

In another embodiment (embodiment (n)), in the process in embodiment any of the embodiment (a)-(k) or (a)-(m) above or combinations thereof, $L^1$ is CO and $R^1$ is substituted saturated 4 to 8 membered saturated heterocycloalkyl containing one or two heteroatoms independently selected from N, O, S, SO or $SO_2$.

In another embodiment (embodiment (o)), in the process in embodiment (a)-(k) or (a)-(n) above or combinations thereof, $L^1$ is —CO— and $R^1$ is a pyrrolidinyl, piperidinyl, or azetidinyl, each of aforementioned ring is attached to $L^1$ via nitrogen ring atom and is substituted with one or two substituents independently selected from hydrogen, halogen, or —OR' (where R' is hydrogen or unsubstituted saturated ($C_1$-$C_6$) alkyl) and is substituted with a third substituent selected from —OR', —NR'R", or R' where R" is hydrogen or unsubstituted saturated ($C_1$-$C_6$) alkyl and R' is -(unsubstituted saturated ($C_1$-$C_6$) alkylene)-monocyclic or fused bicyclic ($C_6$-$C_{10}$) aromatic aryl, -(unsubstituted saturated ($C_1$-$C_6$) alkylene)-monocyclic or fused bicyclic 5 to 10 membered aromatic heteroaryl, monocyclic or fused bicyclic ($C_6$-$C_{10}$) aromatic aryl or monocyclic or fused bicyclic 5 to 10 membered aromatic heteroaryl wherein the aryl and heteroaryl rings in -(unsubstituted saturated ($C_1$-$C_6$) alkylene)-monocyclic or fused bicyclic ($C_6$-$C_{10}$) aromatic aryl, -(unsubstituted saturated ($C_1$-$C_6$) alkylene)-monocyclic or fused bicyclic 5 to 10 membered aromatic heteroaryl, monocyclic or fused bicyclic ($C_6$-$C_{10}$) aromatic aryl or monocyclic or fused bicyclic 5 to 10 membered aromatic heteroaryl are: (i) substituted with one to three substituents independently selected from hydrogen, halogen, —OR', —NR'R", —SR', —OC(O)R', —C(O)R', —$CO_2$R', —CONR'R", —OC(O)NR'R", —NR"C(O)R', —NR'—C(O)NR'R", —NR"C(O)$_2$R', —S(O)$_2$R', —S(O)$_2$NR'R", —NR'SO$_2$R', R', —CN, —$NO_2$, unsubstituted saturated fluoro($C_1$-$C_4$) alkoxy, and unsubstituted saturated fluoro($C_1$-$C_4$) alkyl where R" is hydrogen or unsubstituted saturated ($C_1$-$C_6$) alkyl and R' is hydrogen, unsubstituted saturated ($C_1$-$C_6$) alkyl), saturated ($C_1$-$C_6$) alkyl substituted with one or two halogen, —OR', or —NR'R" (where R' and R" are independently hydrogen or unsubstituted saturated ($C_1$-$C_6$) alkyl; or R' and R" are attached to the same nitrogen atom, they can be combined with the nitrogen atom to form 4-7 membered ring), unsubstituted saturated ($C_3$-$C_6$) cycloalkyl, 4 to 8 membered saturated heterocycloalkyl containing one or two heteroatoms independently selected from N, O, S, SO or $SO_2$, monocyclic or fused bicyclic ($C_6$-$C_{10}$) aromatic aryl or monocyclic or fused bicyclic 5 to 10 membered aromatic heteroaryl wherein the heterocycloalkyl, aryl or heteroaryl in (i), whether attached directly or indirectly, are: (ii) substituted with one to three substituents independently selected from hydrogen, halogen, —OR', —NR'R", —SR', —OC(O)R', —C(O)R', —$CO_2$R', —CONR'R", —OC(O)NR'R", —NR"C(O)R', —NR'—C(O)NR'R", —NR"C(O)$_2$R', —S(O)$_2$R', —S(O)$_2$NR'R", —NR'SO$_2$R', R', —CN, —$NO_2$, unsubstituted saturated fluoro($C_1$-$C_4$) alkoxy, and unsubstituted saturated fluoro($C_1$-$C_4$) alkyl where R" is hydrogen or unsubstituted saturated ($C_1$-$C_6$) alkyl) and R' is hydrogen, unsubstituted saturated ($C_1$-$C_6$) alkyl), saturated ($C_1$-$C_6$) alkyl substituted with one or two halogen, —OR', or —NR'R" (where R' and R" are independently hydrogen, unsubstituted saturated ($C_1$-$C_6$) alkyl, or R' and R" are attached to the same nitrogen atom, they can be combined with the nitrogen atom to form 4-7 membered ring), unsubstituted saturated ($C_3$-$C_6$) cycloalkyl, 4 to 8 membered saturated heterocycloalkyl containing one or two heteroatoms independently selected from N, O, S, SO or $SO_2$, monocyclic or fused bicyclic ($C_6$-$C_{10}$) aromatic aryl or monocyclic or fused bicyclic 5 to 10 membered aromatic heteroaryl wherein heterocycloalkyl, aryl or heteroaryl, whether attached directly or indirectly, are substituted with one to three substituents independently selected from hydrogen, halogen, unsubstituted saturated ($C_1$-$C_6$) alkyl, —OR', —NR'R", —C(O)R', —$CO_2$R', —S(O)$_2$R', —CN, unsubstituted saturated fluoro($C_1$-$C_4$) alkoxy, and unsubstituted saturated fluoro($C_1$-$C_4$) alkyl wherein R' is hydrogen or unsubstituted saturated ($C_1$-$C_6$) alkyl.

In another embodiment (embodiment (p)), in the process in embodiment (o) above, —OR', —NR'R", or R' attached to $R^1$ are attached at the 3 position of piperidinyl and at the 2 position of pyrrolidinyl and R' is -(unsubstituted saturated ($C_1$-$C_6$) alkylene)-5 to 10 membered aromatic heteroaryl or 5 to 10 membered aromatic heteroaryl where the monocyclic or fused bicyclic heteroaryl ring is indazolyl, quinolinyl, isoquinolinyl, quinazolinyl, benzimidazolyl, pyrimidinyl, pyridinyl, indolyl, 7-azaindolyl, or purinyl.

In another embodiment (embodiment (q)), in the process in any of the embodiments (a)-(k) or (a)-(p) above or combinations thereof, $L^1$ is —NHCO— or —NHSO$_2$— and $R^1$ is monocyclic or fused bicyclic ($C_6$-$C_{10}$) aromatic aryl or monocyclic or fused bicyclic 5 to 10 membered aromatic heteroaryl substituted with: (i) one to three substituents independently selected from hydrogen, halogen, —OR', —NR'R", —SR', —OC(O)R', —C(O)R', —$CO_2$R', —CONR'R", —OC(O)NR'R", —NR"C(O)R', —NR'—C(O)NR'R", —NR"C(O)$_2$R', —S(O)$_2$R', —S(O)$_2$NR'R", —NR'SO$_2$R', R', —CN, —$NO_2$, saturated fluoro($C_1$-$C_4$) alkoxy, and saturated fluoro($C_1$-$C_4$) alkyl where R" is hydrogen or unsubstituted saturated ($C_1$-$C_6$) alkyl and R' is hydrogen, unsubstituted saturated ($C_1$-$C_6$) alkyl, saturated ($C_1$-$C_6$) alkyl substituted with one or two halogen, —OR', or —NR'R" (where R' and R" are independently hydrogen, unsubstituted saturated ($C_1$-$C_6$) alkyl, or R' and R" are attached to the same nitrogen atom, they can be combined with the nitrogen atom to form 4-7 membered saturated ring), unsubstituted saturated ($C_3$-$C_6$) cycloalkyl, 4 to 8 membered saturated heterocycloalkyl containing one or two heteroatoms independently selected from N, O, S, SO or $SO_2$, monocyclic or fused bicyclic ($C_6$-$C_{10}$) aromatic aryl, or monocyclic or fused bicyclic 5 to 10 membered aromatic heteroaryl provided at least one of the three substituent is not hydrogen and wherein heterocycloalkyl, aryl or heteroaryl in (i), whether attached directly or indirectly to $R^1$, is: (ii) substituted with one to three substituents independently selected from hydrogen, halogen, —OR', —NR'R", —SR', —OC(O)R', —C(O)R', —$CO_2$R', —CONR'R", —OC(O)NR'R", —NR"C(O)R', —NR'—C(O)NR'R", —NR"C(O)$_2$R', —S(O)$_2$R', —S(O)$_2$NR'R", —NR'SO$_2$R', R', —CN, —$NO_2$, unsubstituted saturated fluoro($C_1$-$C_4$) alkoxy, and unsubstituted saturated fluoro($C_1$-$C_4$) alkyl where R" is hydrogen or unsubstituted saturated ($C_1$-$C_6$) alkyl) and R' is hydrogen, unsubstituted saturated ($C_1$-$C_6$) alkyl, saturated ($C_1$-$C_6$) alkyl substituted with one or two halogen, —OR', or —NR'R" (where R' and R" are independently hydrogen, unsubstituted saturated ($C_1$-$C_6$) alkyl, or R' and R" are attached to the same nitrogen atom, they can be combined with the nitrogen atom to form 4-7 membered ring), unsubstituted saturated ($C_3$-$C_6$) cycloalkyl, 4 to 8 membered saturated heterocycloalkyl containing one or two heteroatoms independently selected from N, O, S, SO or $SO_2$, monocyclic or fused bicyclic ($C_6$-$C_{10}$) aromatic aryl or monocyclic or fused bicyclic 5 to 10 membered aromatic heteroaryl wherein heterocycloalkyl, aryl or heteroaryl, whether attached directly or indirectly, is substituted with one to three substituents independently selected from hydrogen, halogen, unsubstituted saturated ($C_1$-$C_6$) alkyl, —OR', —NR'R", —C(O)R', —$CO_2$R', —S(O)$_2$R', —CN, unsubstituted saturated fluoro($C_1$-$C_4$) alkoxy, and unsubstituted saturated fluoro($C_1$-$C_4$) alkyl wherein R' is hydrogen or unsubstituted saturated ($C_1$-$C_6$) alkyl.

In another embodiment (embodiment (r)), in the process in embodiment The process of embodiment(s) (q) above, $R^1$ is phenyl or monocyclic or fused bicyclic heteroaryl selected from indazolyl, quinolinyl, isoquinolinyl, benzimidazolyl, pyrimidinyl, pyridinyl, indolyl, quinazolinyl, purinyl, or 7-azaindolyl.

In another aspect, there is provided a protein adduct comprising a protein bound to a kinase inhibitor provided herein. In some embodiments, the adduct has the formula:

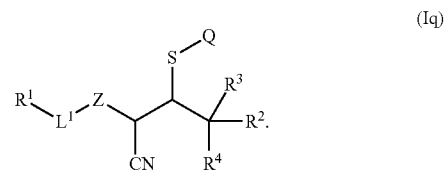

(Iq)

The symbols in the protein adduct above are as defined above wherein the symbol Q represents a protein (e.g. peptide). The sulfur attached to the Q typically forms part of a cysteine amino acid. In some embodiments, the cysteine linked to the inhibitor compounds is Cys-481 of BTK, Cys-909 of JAK3, or Cys-436 of RSK2. A person of ordinary skill in the art will immediately recognize, based on the Formula Iq above, that similar adduct formulae corresponding to the embodiments of Formula I are within the description provided herein (i.e. wherein the β-carbon is attached to —S-Q).

IV. Methods of Inhibiting Protein Kinases

In another aspect, methods of inhibiting protein kinases are provided. The methods include contacting a protein kinase with an effective amount of a kinase inhibitor provided herein. The kinase inhibitor may have the structure of the Formulae provided herein (or any of the embodiments thereof described above). In some embodiments, the methods of inhibiting a protein kinase are conducted within a cell. Thus, in certain embodiments, methods of inhibiting a protein kinase within a cell are provided. The method includes contacting a cell with an effective amount of a kinase inhibitor provided herein. The kinase inhibitor may have the structure of the Formulae provided herein (or any of the embodiments thereof described above). In some embodiments, the cell is a prokaryote or eukaryote. The cell may be a eukaryote (e.g. protozoan cell, fungal cell, plant cell or an animal cell). In some embodiments, the cell is a mammalian cell such as a human cell, cow cell, pig cell, horse cell, dog cell and cat cell, mouse cell, or rat cell. In some embodiments, the cell is a human cell. The cell may form part of an organ or an organism. In certain embodiments, the cell does not form part of an organ or an organism.

The kinase inhibitor may be a reversible kinase inhibitor. A reversible kinase inhibitor is a kinase inhibitor, as disclosed herein (e.g. the compounds of the Formulae provided herein and embodiments thereof), is capable of measurably dissociating from the protein kinase when the protein kinase is intact (i.e. not denatured) or denatured (e.g. partially denatured or fully denatured). A "denatured" kinase is a kinase without sufficient tertiary or secondary structure sufficient to retain kinase activity. An "intact" kinase is a kinase with sufficient tertiary or secondary structure sufficient to retain kinase activity. Therefore, in some embodiments, the method of inhibiting a protein kinase includes contacting a protein kinase with a reversible kinase inhibitor and allowing the reversible kinase inhibitor to reversibly bind to an active site cysteine residue, thereby inhibiting the protein kinase.

In some embodiments, the reversible kinase inhibitor measurably dissociates from the protein kinase only when the protein kinase is denatured, but does not measurably dissociate from the protein kinase when the protein kinase is intact (or dissociates at least 1, $1\times10^2$, $1\times10^3$, $1\times10^4$, $1\times10^5$, $1\times10^6$, $1\times10^7$, $1\times10^8$, $1\times10^9$, $1\times10^{10}$ fold slower relative to the dissociation when the protein kinase is denatured). A reversible kinase inhibitor that measurably dissociates (or dissociates at least 1, $1\times10^2$, $1\times10^3$, $1\times10^4$, $1\times10^5$, $1\times10^6$, $1\times10^7$, $1\times10^8$, $1\times10^9$, $1\times10^{10}$ fold slower relative to the dissociation when the protein kinase is denatured) from the protein kinase only when the protein kinase is denatured, but does not measurably dissociate from the protein kinase when the protein kinase is intact is referred to herein as a "reversible denatured kinase inhibitor." After dissociating from the kinase, the reversible denatured kinase inhibitor can bind to the same or another kinase.

In certain embodiments, the method of inhibiting the protein kinase includes contacting the protein kinase with a kinase inhibitor wherein the kinase inhibitor inhibits the protein kinase with an inhibition constant of less than 100 nM. And where the protein kinase inhibitor is a reversible protein kinase inhibitor, the method of inhibiting the protein kinase includes contacting the protein kinase with a reversible kinase inhibitor wherein the reversible kinase inhibitor inhibits the protein kinase with an inhibition constant of less than 100 nM.

Where a kinase (also referred to herein as a protein kinase) is inhibited using a kinase inhibitor described herein, it is meant that kinase activity (i.e. phosphorylation of a substrate molecule (e.g. a protein substrate)) is decreased when contacted with the kinase inhibitor relative to the activity of the kinase in the absence of the kinase inhibitor. In some embodiments, the kinase inhibitor decreases the kinase activity 1, 2, 3, 4, 5, 6, 7, 8, 9, 10, 25, 50, 100, 250, 500, 1000, 5000, 10,000, 100,000, 500,000, 1,000,000, or more fold. In some embodiments, the kinase inhibitor inhibits the activity of the kinase with an inhibition constant ($K_i$) of less than 100 µM, 10 µM, 5 µM, 1 µM, 500 nM, 250 nM, 100 nM, 75 nM, 50 nM, 25 nM, 10 nM, 1 nM, 500 pM, 250 pM, 100 pM, 75 pM, 50 pM, 25 pM, 10 pM, or 1 pM. In some embodiments, the kinase inhibitor inhibits the activity of the kinase with an $IC_{50}$ of less than 100 µM, 10 µM, 5 µM, 1 µM, 500 nM, 250 nM, 100 nM, 75 nM, 50 nM, 25 nM, 10 nM, 1 nM, 500 pM, 250 pM, 100 pM, 75 pM, 50 pM, 25 pM, 10 pM, or 1 pM, when measured under the conditions set forth in the examples section.

Where a reversible kinase inhibitor provided herein reversibly binds to an active site cysteine residue, a reversible bond is formed between the active site cysteine residue and the reversible kinase inhibitor. The reversible bond is typically a covalent bond. A "cysteine reversible kinase inhibitor," as used herein, refers to a reversible kinase inhibitor that forms a bond with the kinase active site cysteine residue. In some embodiments, the cysteine reversible kinase inhibitor measurably dissociates from the protein kinase only when the protein kinase is denatured, but does not measurably dissociate (or dissociates at least 1, $1\times10^2$, $1\times10^3$, $1\times10^4$, $1\times10^5$, $1\times10^6$, $1\times10^7$, $1\times10^8$, $1\times10^9$, $1\times10^{10}$ fold slower relative to the dissociation when the protein kinase is fully or partially denatured) from the protein kinase when the protein kinase is intact (referred to herein as a "cysteine reversible denatured kinase inhibitor"). In some embodiments, the protein kinase is denatured (i.e. not intact) when placed in denaturing solution, such as 6 N guanidine, 1% SDS, 50% MeCN, or similar protein denaturant, for second or minutes (e.g. 30 to 120 seconds, such as 60 seconds).

In some embodiments, the cysteine reversible kinase inhibitor forms a bond between the cysteine sulfhydryl groups and a carbon atom forming part of the carbon-carbon double bond (i.e. olefin) of the compound of the Formulae provided herein. Thus, in some embodiments, electrons of the sulfur atom of the active site cysteine sulfhydryl group attacks an electron deficient carbon atom of the carbon-carbon double bond (olefin). In some embodiments, the resulting thiol adduct is stable at about pH 2 to about pH 7 (e.g. about pH 3). In some embodiments, the reversible kinase inhibitors described herein, after covalently binding to the kinase active site cysteine residue as described herein, is capable of dissociating from the kinase within seconds or minutes after denaturing/unfolding the kinase with 6 N guanidine, 1% SDS, 50% MeCN, or similar protein denaturant.

In some embodiments, the reversible kinase inhibitors set forth herein is completely reversible. The term "completely reversible" means the reversible kinase inhibitor exhibits a measurable dissociation rate under conditions in which the kinase is not denatured. In some embodiments, the kinase inhibitors provided herein are not completely reversible (i.e. do not exhibit a measurable dissociation rate under conditions in which the kinase is intact). Dissociation may be measured using any appropriate means, including dialysis and mass spectrometry. Specific methods of measuring dissociation are set forth in the Examples section below.

In some embodiments, the reversible denatured kinase inhibitor binds reversibly to cellular components other than the protein kinase that the reversible denatured kinase inhibitor inhibits (or specifically inhibits). The cellular components may be GSH, proteins or protein fragments that are not targeted kinases (e.g. a kinase that does not include an active site cysteine or does not include an active site cysteine within sufficient proximity to an ATP binding site), protein fragments of targeted kinases (e.g. a kinase that has been digested such that the number of bonding points to the kinase reversible denatured kinase inhibitor has been decreased such that the reversible denatured kinase inhibitor dissociates from the kinase). Thus, in some embodiments, the reversible denatured kinase inhibitor measurably dissociates from the kinase where the kinase is partly or fully digested. The ability of a reversible denatured kinase inhibitor to measurably dissociate from cellular components other than the intact of full length protein kinase that the reversible denatured kinase inhibitor inhibits may provide decreased toxicity, including decreased immunogenic toxicity. In certain embodiments, the -$L^1$-Z—$R^1$ group of the reversible denatured kinase inhibitor is a kinase ATP binding site moiety and the electron deficient olefin carbon binds to a sulfhydryl of a kinase active site cysteine. Thus, in some embodiments the kinase inhibitors provided herein bind to at least two points of the protein kinase: at least one residue within the ATP binding site moiety and a sulfhydryl of a kinase active site cysteine.

In some embodiments, physiological concentrations of glutathione (e.g. 5 or 10 mM GSH) have little or no measurable effect on the ability of the reversible kinase inhibitors (e.g. provided herein to inhibit a protein kinase (e.g. eversible denatured kinase inhibitor only reversibly binds to GSH thereby enabling increased binding to the target kinase). In some embodiments, the IC50 or $K_i$ of the reversible kinase inhibitor is increased no more than 20%, 15%, 10%, 9%, 8%, 7%, 6%, 5%, 4%, 3%, 2%, 1%, 0.5%, 0.1%, 0.01% or 0.001% in the presence of physiological concentrations of glutathione (e.g. 5 or 10 mM GSH). In other embodiments, the IC50 or $K_i$ of the reversible kinase inhibitor is not measurably increased by the presence of physiological concentrations of glutathione (e.g. 5 or 10 mM GSH). In some embodiments, the physiological concentrations of glutathione (e.g. 5 or 10 mM GSH) have little or no measurable effect on the ability of the reversible kinase inhibitors provided herein to inhibit a protein kinase wherein the reversible kinase inhibitor is present at low concentrations (e.g. less than 100 nM, 75 nM, 50 nM, 25 nM, 10 nM, 5 nM, 3 nM, 1 nM, 500 pM, 250 pM, 100 pM, 75 pM, 50 pM, 25 pM, 10 pM, or 1 pM). In some embodiments, the physiological concentrations of glutathione (e.g. 5 or 10 mM GSH) have little or no measurable effect on the ability of the reversible kinase inhibitors provided herein to inhibit a protein kinase wherein the reversible kinase inhibitor is present at a concentration of less than 10 nM, 5 nM, 4 nM 3 nM, 2 nM or 1 nM. In certain embodiments, the physiological concentrations of glutathione (e.g. 5 or 10 mM GSH) have little or no measurable effect on the ability of the reversible kinase inhibitors provided herein to inhibit a protein In some embodiments, physiological concentrations of adenosine triphosphate (e.g. 1 mM ATP) have little or no measurable effect on the ability of the reversible kinase inhibitors provided herein to inhibit a protein kinase. In some embodiments, the IC50 or $K_i$ of the reversible kinase inhibitor is increased no more than 10%, 9%, 8%, 7%, 6%, 5%, 4%, 3%, 2%, 1%, 0.5%, 0.1%, 0.01% or 0.001% in the presence of physiological concentrations of adenosine triphosphate (e.g. 1 mM ATP). In other embodiments, the IC50 or $K_i$ of the reversible kinase inhibitor is not measurably increased by the presence of physiological concentrations of adenosine triphosphate (e.g. 1 mM ATP).

In certain embodiments, the reversible kinase inhibitors provided herein reacts reversibly with GSH. In certain embodiments, the reversible kinase inhibitors provided herein react rapidly and reversibly with GSH. Thus, in certain embodiments, the reversible kinase inhibitors provided herein react reversibly with GSH (e.g. rapidly and reversibly) while also reversibly binding to an active site cysteine residue (e.g. at a concentration of less than 10 nM, 5 nM, 4 nM 3 nM, 2 nM or 1 nM). The GSH may be at physiological concentration (e.g. 5-10 mM). Without being bound by any particular mechanistic theory, it is believed that the ability of reversible kinase inhibitors provided herein to react rapidly and reversibly with cellular glutathione protects most non-targeted cellular proteins from the electrophilic qualities of the reversible kinase inhibitor.

The protein kinase may be any appropriate kinase. In some embodiments, the protein kinase includes a cysteine residue in the active site. A protein kinase active site is a portion of the protein kinase in which the protein kinase substrate is phosphorylated. The kinase active site is typically a pocket or cleft containing amino acid residues that bind to a substrate (also referred to herein as kinase active site binding residues) and amino acid residues that participate in the catalytic phosphorylation reaction (also referred to herein as kinase active site catalytic residues). The reversible kinase inhibitors provided herein are capable of inhibiting the kinase catalytic action by fitting into the kinase active site and disrupting the ability of the kinase to phosphorylate the substrate. The active sites of many protein kinases are known in the art through structure determinations (e.g. X-ray crystallography or three dimensional NMR techniques). Where the three dimensional structure has not been determined, the structure of an active site of a protein kinase may be determined by the primary amino acid sequence using computer software modeling programs generally known in the art.

Protein kinases inhibited using the kinase inhibitors provided herein include, but are not limited to, serine/threonine-specific protein kinases, tyrosine-specific protein kinases, receptor tyrosine kinases, receptor-associated tyrosine kinases, histidine-specific protein kinases, and aspartic acid/glutamic acid-specific protein kinases, as known in the art. In some embodiments, the kinase is a tyrosine protein kinase or serine/threonine protein kinases. Examples of kinases include SRC, YES, FGR, CHK2, FGFR1-4, BTK, EGFR, HER2, HER4, HER3, JAK3, PLK1-3, MPS1, RON, MEK1/2, ERK1/2, VEGFR, KIT, KDR, PDGFR, FLT3, CDK8, MEK7, ROR1, RSK1-4, MSK1/2, MEKK1, NEK2, MEK5, MNK1/2, MEK4, TGFbR2, ZAP70, WNK1-4, BMX, TEC, TXK, ITK, BLK, MK2/3, LIMK1, TNK1, CDK11, p70S6Kb, EphB3, ZAK, and NOK.

In another aspect, a method of making a reversible kinase inhibitor is provided. The method includes the step of modifying a non-reversible or irreversible kinase inhibitor to include a substituent having the formula:

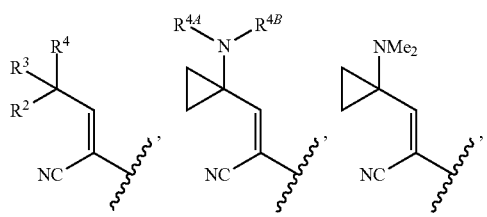

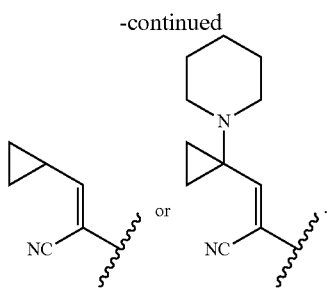

$R^2$, $R^3$, $R^4$, $R^{4A}$ and $R^{4B}$ are as defined above. The symbol ⸹ represents the point of attachment of the substituent to the remainder of the compound.

In yet another aspect, a method of making a reversible covalent kinase inhibitor is provided. The method includes the step of converting a compound that binds to the ATP binding domain of a kinase to a compound that is substituted with a group of formula —Z-$L^1$C(CN)=CHC($R^2$)($R^3$)($R^4$) such that the double bond in —Z-$L^1$-C(CN)=CHC($R^2$)($R^3$)($R^4$) forms a reversible covalent bond with a cysteine residue of said kinase, preferably the reversible covalent bond is form with the cysteine residue at the active/catalytic site of the kinase.

In some embodiments, the kinase inhibitors thus formed may measurably dissociate from the protein kinase when the protein kinase is not denatured, partially denatured, or fully denatured. In some embodiments, the reversible kinase inhibitor measurably dissociates from the protein kinase only when the protein kinase is fully denatured or partially denatured, but does not measurably dissociate from the protein kinase when the protein kinase is intact, or dissociates at least 10, $1\times10^2$, $1\times10^3$, $1\times10^4$, $1\times10^5$, $1\times10^6$, $1\times10^7$, $1\times10^8$, $1\times10^9$, $1\times10^{10}$ fold slower when the protein kinase is intact relative to the dissociation when the protein kinase is fully or partially denatured. In some embodiments, the protein kinase is denatured or fully denatured (i.e. not intact) when placed in denaturing solution, such as 6 N guanidine, 1% SDS, 50% MeCN, or similar protein denaturant, for seconds or minutes (e.g. 30 to 120 seconds, such as 60 seconds). In some embodiments, the reversible kinase inhibitors described herein, after binding to the kinase active site cysteine residue, are capable of dissociating from the kinase within seconds or minutes after denaturing/unfolding the kinase with 6 N guanidine, 1% SDS, 50% MeCN, or similar protein denaturant. In other embodiments, the reversible kinase inhibitors described herein, after covalently binding to the kinase active site cysteine residue, are capable of dissociating from the kinase within seconds or minutes after the kinase has been subject to a protease (e.g. trypsin). In some embodiments, the reversible kinase inhibitor has a slow off rate (i.e., is a reversible slow off-rate inhibitor). Thus the non-covalent reversible inhibitors differs from the reversible slow off-rate or reversible covalent inhibitor in that the former interacts with and inhibits the kinase only via non-covalent interactions and the reversible slow off-rate inhibitor interacts with and inhibits the kinase via non-covalent and cysteine-mediated interactions. The result of such a combination of interactions provides an inhibitor with a slow off-rate and protracted duration of action, in some instances comparable to an irreversible covalent inhibitor without forming permanent irreversible protein adducts.

Accordingly, in another aspect, provided herein is a process comprising converting a compound that binds to the ATP binding domain of a kinase to a compound that is substituted with a group of formula —Z-$L^1$C(CN)=CHC($R^2$)($R^3$)($R^4$) where: Z is a bond or unsubstituted saturated ($C_1$-$C_6$) alkyl, preferably bond or methylene; $L^1$ is —C(O)—, —N($L^2R^5$)C(O)—, —OC(O)—, —S(O)$_n$—, —N($L^2R^5$)SO$_2$—,

where $L^2$ is a bond or substituted or unsubstituted saturated alkylene, $R^5$ is hydrogen, and Ring A in

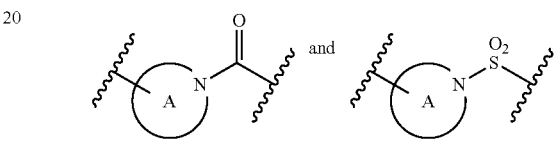

is heterocycloamino where: the —CO— and —SO$_2$— groups are attached to —C(CN)=CHC($R^2$)($R^3$)($R^4$); and the heterocycloamino is substituted with one, two, or three substituents independently selected from hydrogen, unsubstituted saturated ($C_1$-$C_6$) alkyl, unsubstituted saturated ($C_1$-$C_6$) alkoxy, hydroxyl, cyano, nitro, halo, unsubstituted saturated ($C_1$-$C_6$) haloalkyl, unsubstituted saturated ($C_1$-$C_6$) haloalkoxy, —S($C_1$-$C_6$) unsubstituted saturated alkyl, —SO$_2$($C_1$-$C_6$) unsubstituted saturated alkyl, carboxy, or —COO—($C_1$-$C_6$) unsubstituted saturated alkyl; preferably $L^1$ is —C(O)—, —N(H)C(O)—, —N(H)SO$_2$—, piperidin-1-ylcarbonyl, or pyrrolidinylcarbonyl; $R^2$ and $R^3$ are independently substituted or unsubstituted saturated ($C_1$-$C_8$) alkyl, or $R^2$ and $R^3$ are optionally joined together to form a substituted or unsubstituted saturated ($C_3$-$C_6$) cycloalkyl, or substituted or unsubstituted 4 to 8 membered saturated heterocycloalkyl containing one or two heteroatoms independently selected from N, O, S, SO or SO$_2$; and $R^4$ is hydrogen, —NR$^{4A}$R$^{4B}$, —OR$^{4A}$, —SR$^{4A}$, substituted or unsubstituted saturated ($C_1$-$C_6$) alkyl or substituted or unsubstituted saturated 4 to 8 membered heterocycloalkyl containing one or two heteroatoms independently selected from N, O, S, SO or SO$_2$ where $R^{4A}$ and $R^{4B}$ are independently hydrogen, substituted or unsubstituted ($C_1$-$C_6$) alkyl, or substituted or unsubstituted 4 to 8 membered heterocycloalkyl containing one or two heteroatoms independently selected from N, O, S, SO or SO$_2$; provided that alkyl and heterocycloalkyl in $R^2$, $R^3$ and $R^4$ are not substituted with substituted or unsubstituted aryl, substituted or unsubstituted heteroaryl, substituted or unsubstituted cycloalkyl or substituted or unsubstituted heterocycloalkyl; provided that the double bond in —Z-$L^1$-C(CN)=CHC($R^2$)($R^3$)($R^4$) forms a reversible covalent bond with a cysteine residue of said kinase; and further provided that the compound does not contain: (i) a substituted or unsubstituted heteroaryl ring of formula

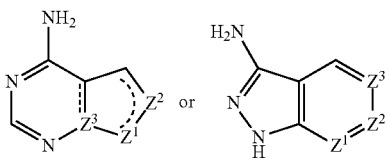

where the dashed lines are an optional bond; and $Z^1$, $Z^2$, and $Z^3$ are N or C, provided that one or two of $Z^1$, $Z^2$, and $Z^3$ are N; or (ii) a substituted or unsubstituted heteroaryl ring of formula

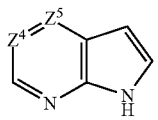

where $Z^4$ that both $Z^4$ and $Z^5$ are not N.

In one embodiment, the cysteine residue that forms the reversible covalent bond with the double bond in —Z-$L^1$-C(CN)=CHR$^c$ is selected from the group CYS1, CYS2, CYS3, CYS5, CYS6, CYS7, CYS8, CYS9, CYS10, CYS11, CYS12, CYS13, CYS14, CYS15, CYS16, CYS17, CYS18, CYS19, CYS10, CYS21, CYS22, or CYS23.

In some embodiments, the reversible covalent inhibitor is prepared by: (i) the compound that binds to the ATP binding domain of the kinase is first converted to a compound that is substituted with —Z-$L^1$-CH$_2$CN where Z and $L^1$ are as defined above; and (ii) the compound obtained from Step (i) is reacted with a group of formula $R^4R^3R^2$CHO to give a compound that is substituted with —Z-$L^1$-C(CN)=CHCR$^2$R$^3$R$^4$; (iii) optionally converting the compound from step (i) or (ii) to an acid addition salt; (iv) optionally converting the compound from step (i), (ii), or (iii) to a free base.

In the processes above in one embodiment, $R^{4A}$ and $R^{4B}$ are independently hydrogen, unsubstituted saturated (C$_1$-C$_6$) alkyl, or saturated (C$_1$-C$_6$) alkyl substituted with one to three substituents independently selected from —OR' or —NR'R" where R' and R" are independently hydrogen or unsubstituted saturated (C$_1$-C$_6$) alkyl.

In the processes above in another embodiment, $R^2$ and $R^3$ are independently unsubstituted saturated (C$_1$-C$_6$) alkyl and $R^4$ is hydrogen, unsubstituted saturated (C$_1$-C$_6$) alkyl, saturated (C$_1$-C$_6$) alkyl substituted with one to three substituents independently selected from —OR' or —NR'R" (where R' and R" are independently hydrogen or unsubstituted saturated (C$_1$-C$_6$) alkyl), —NR$^{4A}$R$^{4B}$, —OR$^{4A}$ [where $R^{4A}$ and $R^{4B}$ are independently hydrogen, unsubstituted saturated (C$_1$-C$_6$) alkyl, or saturated (C$_1$-C$_6$) alkyl substituted with one to three substituents independently selected from —OR' or —NR'R" (where R' and R" are independently hydrogen or unsubstituted saturated (C$_1$-C$_6$) alkyl)], unsubstituted saturated 4-7-membered heterocycloalkyl containing one to two heteroatoms selected from N, O, S, SO or SO$_2$, saturated 4-7-membered heterocycloalkyl containing one to two heteroatoms selected from N, O, S, SO or SO$_2$ and substituted with one or two unsubstituted saturated (C$_1$-C$_6$) alkyl, hydroxy, unsubstituted saturated —O(C$_1$-C$_6$) alkyl, or fluoro, saturated (C$_1$-C$_6$) alkyl substituted with one saturated 4-7-membered heterocycloalkyl containing one to two heteroatoms selected from N, O, S, SO or SO$_2$, or saturated (C$_1$-C$_6$) alkyl substituted with one saturated 4-7-membered heterocycloalkyl containing one to two heteroatoms selected from N, O, S, SO or SO$_2$ and substituted with one or two unsubstituted saturated (C$_1$-C$_6$) alkyl, hydroxy, unsubstituted saturated —O(C$_1$-C$_6$) alkyl, or fluoro.

In the processes above in yet another embodiment, $R^2$ and $R^3$ are independently unsubstituted saturated (C$_1$-C$_6$) alkyl and $R^4$ is hydrogen or unsubstituted saturated (C$_1$-C$_6$) alkyl.

In the processes above in yet another embodiment, $R^2$ and $R^3$ are independently unsubstituted saturated (C$_1$-C$_6$) alkyl and $R^4$ is saturated (C$_1$-C$_6$) alkyl substituted with one to three substituents independently selected from —OR' or —NR'R" where R' and R" are independently hydrogen or unsubstituted saturated (C$_1$-C$_6$) alkyl.

In the processes above in yet another embodiment, $R^2$ and $R^3$ are independently unsubstituted saturated (C$_1$-C$_6$) alkyl and $R^4$ is —NR$^{4A}$R$^{4B}$ or —OR$^{4A}$ where $R^{4A}$ and $R^{4B}$ are independently hydrogen, unsubstituted saturated (C$_1$-C$_6$) alkyl, or saturated (C$_1$-C$_6$) alkyl substituted with one to three substituents independently selected from —OR' or —NR'R" where R' and R" are independently hydrogen or unsubstituted saturated (C$_1$-C$_6$) alkyl.

In the processes above in yet another embodiment, $R^2$ and $R^3$ are independently unsubstituted saturated (C$_1$-C$_6$) alkyl and $R^4$ is unsubstituted saturated 4-7-membered heterocycloalkyl containing one to two heteroatoms selected from N, O, S, SO or SO$_2$ or saturated 4-7-membered heterocycloalkyl containing one to two heteroatoms selected from N, O, S, SO or SO$_2$ and substituted with one or two unsubstituted saturated (C$_1$-C$_6$) alkyl, hydroxy, unsubstituted saturated —O(C$_1$-C$_6$) alkyl, or fluoro.

In the processes above in yet another embodiment, $R^2$ and $R^3$ are joined together to form a unsubstituted saturated (C$_3$-C$_6$) cycloalkyl or saturated (C$_3$-C$_6$) cycloalkyl substituted with one or two substituents independently selected from unsubstituted saturated (C$_1$-C$_6$) alkyl, hydroxy, unsubstituted saturated —O(C$_1$-C$_6$) alkyl, or halo.

In the processes above in yet another embodiment, $R^2$ and $R^3$ are joined together to form a unsubstituted saturated (C$_3$-C$_6$) cycloalkyl.

In the processes above in yet another embodiment, $R^2$ and $R^3$ are joined together to form unsubstituted saturated 4 to 6 membered heterocycloalkyl containing one to two heteroatoms selected from N, O, S, SO or SO$_2$ or saturated 4 to 6 membered heterocycloalkyl containing one to two heteroatoms selected from N, O, S, SO or SO$_2$ substituted with one to three substituents independently selected from unsubstituted saturated (C$_1$-C$_6$) alkyl, hydroxy, unsubstituted saturated O(C$_1$-C$_6$) alkyl, or halo. Within this embodiment in one embodiment, $R^4$ is hydrogen or unsubstituted saturated (C$_1$-C$_6$) alkyl.

In the processes above in yet another embodiment, $R^2$ and $R^3$ are methyl or ethyl and $R^4$ is hydrogen, methyl, ethyl, amino, methylamino, dimethylamino, diethylamino, methylethylamino, isopropylamino, butylamino, hydroxy, methoxy, ethoxy, propoxy, methoxymethyl, 2-methoxyethyl, ethoxymethyl, 2-ethoxyethyl, pyrrolidinyl, piperidinyl, piperazinyl, morpholinyl, thiomorpholinyl, tetrahydropyranyl, tetrahydrofuranyl, oxetanyl, or azetidinyl wherein each of the aforementioned ring is optionally substituted with one or two substituents independently selected from methyl, ethyl, propyl, hydroxy, methoxy, ethoxy, chloro, or fluoro.

In the processes above in yet another embodiment, $R^2$ and $R^3$ are joined together to form a cyclopropyl, cyclobutyl, cyclohexyl, pyrrolidinyl, piperidinyl, piperazinyl, tetrahydropyranyl, tetrahydrofuranyl, azetidinyl, or oxetanyl where pyrrolidinyl, piperidinyl, piperazinyl, or azetidinyl is optionally substituted with one or two substituents independently selected from methyl, ethyl, propyl, hydroxy, methoxy, ethoxy, chloro or fluoro and $R^4$ is hydrogen or methyl or ethyl.

V. Methods of Treating Disease

In another aspect, a method of treating a disease associated with kinase activity in a subject in need of such treatment. The method includes administering to the subject an effective amount (e.g. a therapeutically effective amount) of a compound having the structure of the Formulae provided herein (or an embodiment thereof as described above).

In some embodiments, the disease associated with kinase activity is chronic disease. The disease may be cancer, epilepsy, HIV infection, autoimmune disease (e.g. arthritis), ischemic disease (e.g. heart attack or stroke), stroke, neurodegenerative diseases, metabolic or inflammation. In certain embodiments, the disease is cancer, including, for example, leukemia, carcinomas and sarcomas, such as cancer of the brain, breast, cervix, colon, pancreas, head & neck, liver, kidney, lung, non-small cell lung, prostate, melanoma, mesothelioma, ovary, sarcoma, stomach, uterus and medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas. In some embodiments, the disease is liver cancer, colon cancer, breast cancer, melanoma, acute myelogenous leukemia, chronic myelogenous leukemia, or nonsmall-cell lung cancer. In some embodiments, the disease is cancers which have metastasized. In some embodiments, the disease is acute lymphoblastic leukemia. In other embodiments, the disease is acute myeloid leukemia. In some embodiments, the disease is rheumatoid arthritis, systemic lupus erythematosus, multiple sclerosis, scleroderma or polymyositis. In some embodiments, the disease is diabetes, obesity, or lipid disorders. In other embodiments, the disease is fibrosis. In other embodiments, the disease is atherosclerosis. In some embodiments, the disease is a gastrointestinal stromal tumor (GIST). In some embodiments, the disease may be caused by an infectious agent such as caused by bacteria, parasite or virus. In some embodiments, the disease is acute such as myocardial infarction, stroke or asthma. In some embodiments the disease is Parkinson's disease or amyotrophic lateral sclerosis.

VI. Assays

Using techniques known in the art and the guidance provided herein, candidate kinase inhibitors may be easily assayed for their ability to inhibit any known protein kinase. For example, candidate kinase inhibitors having the structure of the Formulae provided herein or embodiments thereof may be first assayed using computer modeling techniques in order to assess potential binding contacts between kinase active site binding residues and/or kinase active site catalytic residues. Such computer modeling techniques may also be referred to as in silico techniques. As discussed above, the kinase active site binding residues and/or kinase active site catalytic residues are known or easily determined for any kinase in which the primary amino acid structure is known. In particular, computer modeling techniques may be employed to assess the ability of candidate kinase inhibitors to react with a kinase active site cysteine residue with the electron deficient olefin carbon to form a thiol adduct. For example, where the kinase inhibitor electron deficient olefin carbon is within 10 Å of the kinase active site cysteine sulfhydryl, the potency and/or selectivity of kinase inhibitor may be improved (e.g. by 1000-10,000-fold).

Likewise, computer modeling techniques may be used to assess the ability of candidate kinase inhibitors to fit into the kinase active site without creating stearic clashes. As described above, in some embodiments, $—R^1$ or $-L-R^1$ to fit within the kinase ATP binding site and/or make contacts with amino acid residues within the kinase ATP binding site. Therefore, computer modeling techniques may be used to assess the ability of $—R^1$ or $-L-R^1$ to fit within the kinase ATP binding site and/or make contacts with amino acid residues within the kinase ATP binding site. The computer modeling assays described above may be used to assess the kinase inhibition ability of candidate kinase inhibitors having different general chemical scaffolds within the structure of the Formulae provided herein or embodiments thereof. In this way, new classes of chemical scaffolds may be assessed using computer modeling prior to performing in vitro activity assays.

In vitro assays may also be used to assess the kinase inhibiting properties of candidate kinase inhibitors having the structure of the Formulae provided herein or embodiments thereof. In vitro kinase assays are well known in the art. High throughput techniques are known and useful for quickly assessing large numbers of kinase inhibitor candidates using binding assays for a large number of kinase panels. See, for example, Karaman et al., *Nat Biotechnol.* 2008 January; 26(1):127-32.

Compounds that decrease kinase catalytic activity may also be identified and tested using biologically active protein kinases, either recombinant or naturally occurring. Protein kinases can be found in native cells, isolated in vitro, or co-expressed or expressed in a cell. Certain protein kinases specifically phosphorylate particular substrates. Where specific substrates are known, the ability of a candidate kinase inhibitor to reduce phosphorylation of the specific substrate may be assayed. General, or non-specific, kinase substrates may also be employed.

The kinase inhibitors provided herein may also be tested in vitro for their ability to inhibit a mutant of a kinase that does not contain an active site cysteine. The ability of a kinase inhibitor to decrease the catalytic activity of a kinase having an active site cysteine while not having the ability (or having measurably decreased ability) to decrease the catalytic activity of a mutant of the kinase that does not contain an active site cysteine is indicative of a kinase inhibitor that inhibits the kinase by binding to the active cite cysteine. For example, the C436V mutant of RSK2 may be resistant to certain kinase inhibitors (IC50>10 uM) that show strong inhibitory activity against the wild type RSK2. This result supports the conclusion that RSK2 inhibition requires the formation of a covalent bond between Cys436 and the inhibitor.

The kinase inhibitors provided herein may also be tested in vitro for their ability to reversibly bind to the active site cysteine of a protein kinase by measuring association and dissociation of the kinase inhibitor from the protein kinase (e.g. partially or fully denatures) or from a thiol compound (e.g. 2-mercaptoethanol (BME)). The ability of the reaction center carbon of a kinase inhibitor provided herein to reversibly bind to the sulfhydryl of a kinase active cite cysteine may be measured using any appropriate means, including dialysis, mass spectrometry, NMR and UV detection (see Examples section for more details). For example, the kinase inhibitors may be assayed by detecting the binding of a thiol compound such as BME. The binding may be assessed using UV detection of compounds that typically become less UV active upon binding to a thiol compound or by detecting the binding using proton NMR. Typically, the assays are conducted by titering in the thiol compound and examining a change in the endpoint binding detection parameter (e.g. UV activity or proton NMR). Reversibility is assessed by dilution. Specific examples are provided below in the Examples section.

The kinase inhibitors provided herein may also be tested in vitro for their stability at pH 7.5. Any appropriate method may be used to determine the stability of a kinase inhibitor set forth herein at pH 7.5. Appropriate methods include, for example, LC-MS (e.g. HPLC-MS) as well as measuring changes in UV absorption where the kinase inhibitor includes a chromophore group. UV absorption may be measured using high-throughput techniques (e.g. multiwell plated for scanning large numbers of kinase inhibitors simultaneously). Stability may be assessed using phosphate-buffered saline at pH 7.5 at 37° C. Compounds having half-lives greater than 6 hours, 12 hours, 24 hours, or 48 hours may be may be selected.

Cellular assays may also be used to assess the kinase inhibiting properties of candidate kinase inhibitors having the structure of the Formulae provided herein or embodiments thereof. Cellular assays include cells from any appropriate source, including plant and animal cells (such as mammalian cells). The cellular assays may also be conducted in human cells. Cellular assays of kinase inhibition are well known in the art, and include methods in which a kinase inhibitor is delivered into the cell (e.g. by electroporation, passive diffusion, microinjection and the like) and a kinase activity endpoint is measured, such as the amount of phosphorylation of a cellular substrate, the amount of expression of a cellular protein, or some other change in the cellular phenotype known to be affected by the catalytic activity of the particular kinase being measured. For example, phosphorylation of a particular cellular substrate may be assessed using a detection antibody specific or the phosphorylated cellular substrate followed by western blotting techniques and visualization using any appropriate means (e.g. fluorescent detection of a fluorescently labeled antibody).

Measuring the reduction in the protein kinase catalytic activity in the presence of a kinase inhibitor disclosed herein relative to the activity in the absence of the inhibitor may be performed using a variety of methods known in the art, such as the assays described in the Examples section below. Other methods for assaying the activity of kinase activity are known in the art. The selection of appropriate assay methods is well within the capabilities of those having ordinary skill in the art.

Once kinase inhibitors are identified that are capable of reducing kinase catalytic activity in vitro and/or in a cell, the compounds may be further tested for their ability to selectively inhibit kinase activity in animal models (e.g. whole animals or animal organs). Thus, kinase inhibitors may be further tested in cell models or animal models for their ability to cause detectable changes in phenotype related to a particular kinase activity. In addition to cell cultures, animal models may be used to test inhibitors of kinases for their ability to treat, for example, cancer in an animal model.

VII. Pharmaceutical Formulations

In another aspect, the present invention provides pharmaceutical compositions comprising a kinase inhibitor compound of the invention or a kinase inhibitor compound in combination with a pharmaceutically acceptable excipient (e.g. carrier).

The pharmaceutical compositions include optical isomers, diastereomers, or pharmaceutically acceptable salts of the inhibitors disclosed herein. For example, in some embodiments, the pharmaceutical compositions include a compound of the present invention and citrate as a pharmaceutically acceptable salt. The kinase inhibitor included in the pharmaceutical composition may be covalently attached to a carrier moiety, as described above. Alternatively, the kinase inhibitor included in the pharmaceutical composition is not covalently linked to a carrier moiety.

A "pharmaceutically suitable carrier," as used herein refers to pharmaceutical excipients, for example, pharmaceutically, physiologically, acceptable organic, or inorganic carrier substances suitable for enteral or parenteral application which do not deleteriously react with the extract. Suitable pharmaceutically acceptable carriers include water, salt solutions (such as Ringer's solution), alcohols, oils, gelatins and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like which do not deleteriously react with the compounds of the invention.

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

A. Formulations

The kinase inhibitors of the present invention can be prepared and administered in a wide variety of oral, parenteral and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

B. Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g. decreasing the number of cancer cells in a subject).

The dosage and frequency (single or multiple doses) of administered to a mammal can vary depending upon a variety of factors, including a disease that results in increased activity of kinase, whether the mammal suffers from another disease, and the route of administration; size, age, sex, health, body weight, body mass index, and diet of the recipient; nature and extent of symptoms of the disease being treated (e.g., cancer), type of concurrent treatment, complications from the disease being treated or other health-related problems. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of reducing the level of kinase catalytic activity, as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring kinase inhibition and adjusting the dosage upwards or downwards, as described above.

Dosages may be varied depending upon the requirements of the patient and the compound being employed. The dose administered to a patient, in the context of the present invention, should be sufficient to affect a beneficial therapeutic response in the patient over time. The size of the dose also will be determined by the existence, nature, and extent of any adverse side-effects. Generally, treatment is initiated with smaller dosages which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

D. Additional Agents and Therapeutic Modalities

In some embodiments, the kinase inhibitors provided herein may be used in combination with other therapeutic agents or therapeutic modalities. In some embodiments, the additional therapeutic agent is an anticancer agent. The therapeutic agent may be a chemotherapeutic agents, a biologic agent, hormonal therapy agent, or a kinase inhibitor that is not a kinase inhibitor of the Formulae provided herein (or embodiments thereof). The additional therapeutic agent may additionally be an alkylating agent, an anthracylcines, a monoclonal antibody, a cytokine, a nucleoside analog, prednisone, a taxane, estrogen, progesterone, hormone antagonists, a vinca alkaloid, an anti-metabolites or the like.

In some embodiments, the kinase inhibitors provided herein may be used in combination with other therapeutic modalities such as radiation therapy and surgery.

VIII. Examples

The following preparations of compounds of Formula (I) and intermediates (References) are given to enable those skilled in the art to more clearly understand and to practice the present invention. They should not be considered as limiting the scope of the invention, but merely as being illustrative and representative thereof.

Synthetic Examples

Reference A

Synthesis of 4-amino-3-(4-phenoxyphenyl)-1H-pyrazolo[3,4-d]pyrimidine

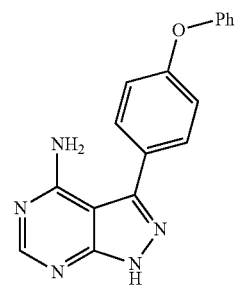

1

4-Amino-3-(4-phenoxyphenyl)-1H-pyrazolo[3,4-d]pyrimidine (1) was prepared from 4-phenoxybenzoic acid following the procedure reported in US 2008/0076921.

Reference B

Synthesis of 4-amino-3-(4-chlorophenyl)-1H-pyrazolo[3,4-d]pyrimidine

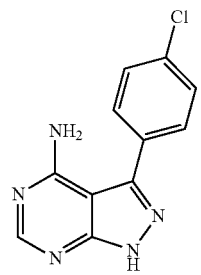

2

4-Amino-3-(4-chlorophenyl)-1H-pyrazolo[3,4-d]pyrimidine (2) was prepared from 4-chlorobenzoic acid following an analogous procedure.

127

Reference C

Synthesis of (3S)-1-pyrrolidinecarboxylic acid, 3-hydroxy-, 2-propen-1-yl ester

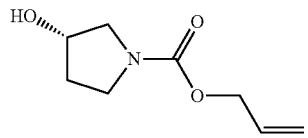

3

(3S)-1-Pyrrolidinecarboxylic acid, 3-hydroxy-, 2-propen-1-yl ester (3) was prepared as reported in EP0433759.

Example 1

Synthesis of (R)-2-(3-(4-amino-3-(4-chlorophenyl)-1H-pyrazolo[3,4-d]pyrimidin-1-yl)pyrrolidine-1-carbonyl)-3-cyclopropylacrylonitrile

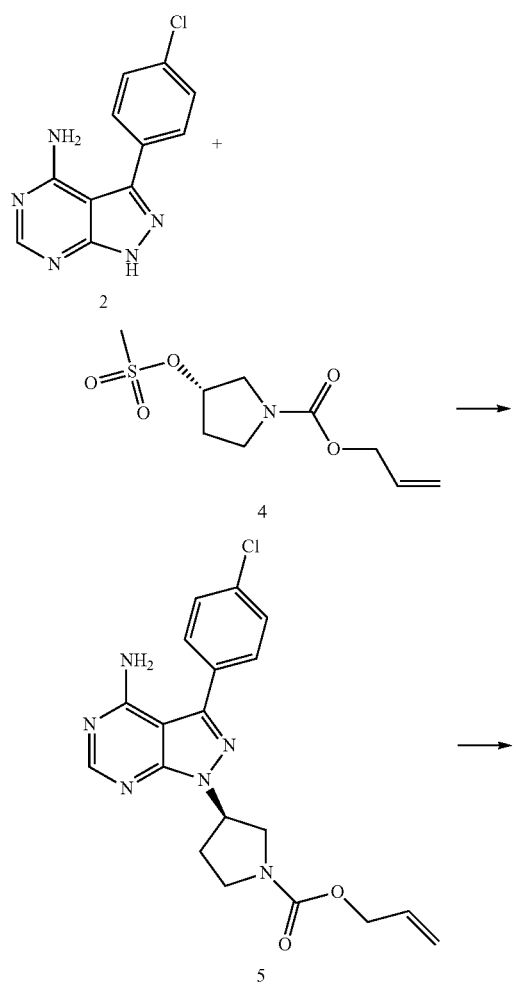

128

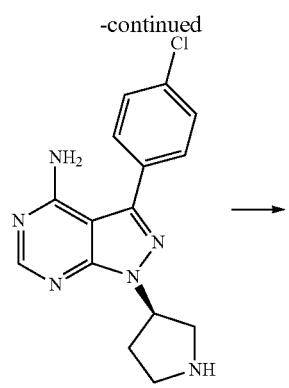

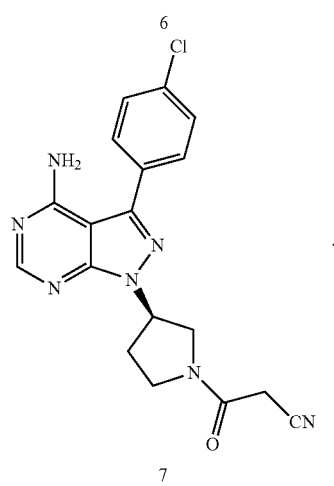

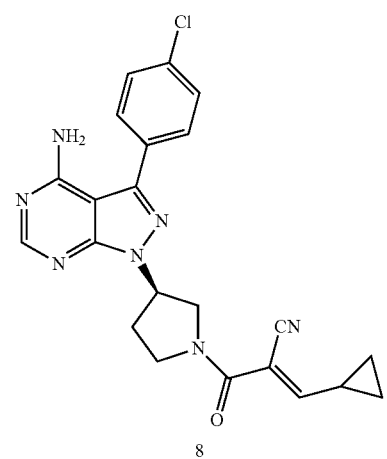 [SMILES: N#C/C(=C\C1CC1)C(=O)N1CC[C@@H](n2nc(-c3ccc(Cl)cc3)c3c(N)ncnc32)C1]

Step 1

A round bottom flask fitted with a magnetic stir bar was charged with alcohol 3 (343 mg), DCM (4 mL), and methanesulfonyl chloride (0.16 mL). The reaction mixture was cooled to 0° C. and DIPEA (0.4 mL) was added. The solution was stirred for 2 h at 0° C. and then diluted with DCM and extracted with 1 M HCl (2×10 mL), followed by 5% NaHCO$_3$ (2×10 mL). The organic layer was dried over Na$_2$SO$_4$, filtered, and concentrated under reduced pressure. The resulting residue was purified by Si-gel chromatography (elute with 1:1 EtOAc:Hex) to give (S)-allyl-3-(methylsulofnyloxy)pyrrolidine-1-carboxylate 4, 418 mg product (84% yield).

Step 2

A round bottom flask fitted with a magnetic stir bar was charged with pyrimidine 2 (120 mg), mesylate 4 (130 mg), cesium carbonate (195 mg), and DMF (2 mL). The reaction mixture was heated to 45° C. and stirred overnight. Approximately 40% of the starting material remained by TLC, so the reaction mixture was heated to 60° C. and stirred for an additional 4 h. The reaction mixture was diluted with water (20 mL) and extracted with EtOAc (3×20 mL). The organic layers were combined and dried over $Na_2SO_4$, filtered, and concentrated under reduced pressure. The resulting residue was purified by Si-gel chromatography (elute with 3:1 EtOAc:Hex increasing to 100% EtOAc) to give (R)-Allyl 3-(4-amino-3-(4-chlorophenyl)-1H-pyrazolo[3,4-d]pyrimidin-1-yl)pyrrolidine-1-carboxylate 175 mg (90% yield).

Step 3

A 20 mL vial fitted with a magnetic stir bar was charged with allyl carbamate 5 (150 mg), phenylsilane (0.46 mL), tetrakis(triphenylphosphine)palladium (10 mg), and degassed DMF (2 mL). The reaction mixture was stirred for 3 h at room temperature. A second portion of tetrakis(triphenylphosphine)palladium (10 mg) was added and the reaction mixture was stirred for an additional 2 h. The reaction mixture was acidified with 1 M HCl (5 mL) and washed with EtOAc (3×5 mL). The aqueous layer was neutralized with 1 M NaOH extracted with EtOAc (3×5 mL). The organic layers were combined and dried over $Na_2SO_4$, filtered, concentrated under reduced pressure, and dried in vacuo to give (R)-3-(4-Chlorophenyl)-1-(pyrrolidin-3-yl)-1H-pyrazolo[3,4-d]pyrimidin-4-amine (6) 97 mg (82% yield).

Step 4

A 20 mL vial fitted with a magnetic stir bar was charged with amine 6 (97 mg), cyanoacetic acid (40 mg), 1-hydroxy-7-azabenzotriazole (HOAt) (60 mg), N-(3-dimethylaminopropyl)-N'-ethylcarbodiimide hydrochloride (EDC) (85 mg), DIPEA (0.08 mL), and DCM (3 mL). The reaction mixture was stirred for 16 h at room temperature. The reaction mixture was diluted with DCM (5 mL) and washed with 1 M HCl (3×5 mL), 1 M NaOH (3×5 mL). The organic layer was dried over $Na_2SO_4$, filtered, concentrated under reduced pressure, and dried in vacuo to give (R)-3-(3-(4-Amino-3-(4-chlorophenyl)-1H-pyrazolo[3,4-d]pyrimidin-1-yl)pyrrolidin-1-yl)-3-oxopropanenitrile (7). 18 mg (16% yield).

Step 5

A 4 mL vial fitted with a magnetic stir bar was charged with cyanacetamide 7 (4.8 mg), cyclopropanecarboxaldehyde (2 μL), DBU (2 μL), and DMF (0.4 mL). The reaction mixture was heated to 60° C. and stirred for 16 h. The reaction mixture was purified by reverse-phase HPLC (5-80% MeCN/water) to give (R)-2-(3-(4-Amino-3-(4-chlorophenyl)-1H-pyrazolo[3,4-d]pyrimidin-1-yl)pyrrolidine-1-carbonyl)-3-cyclopropylacrylonitrile (8) 2.3 mg (42% yield). Calculated $[MH]^+$ 434.1. observed 434.1 by ESI-LCMS.

Example 2

Synthesis of 2-(3-(4-amino-3-(4-phenoxyphenyl)-1H-pyrazolo[3,4-d]pyrimidin-1-yl)piperidine-1-carbonyl)-3-phenylacrylonitrile

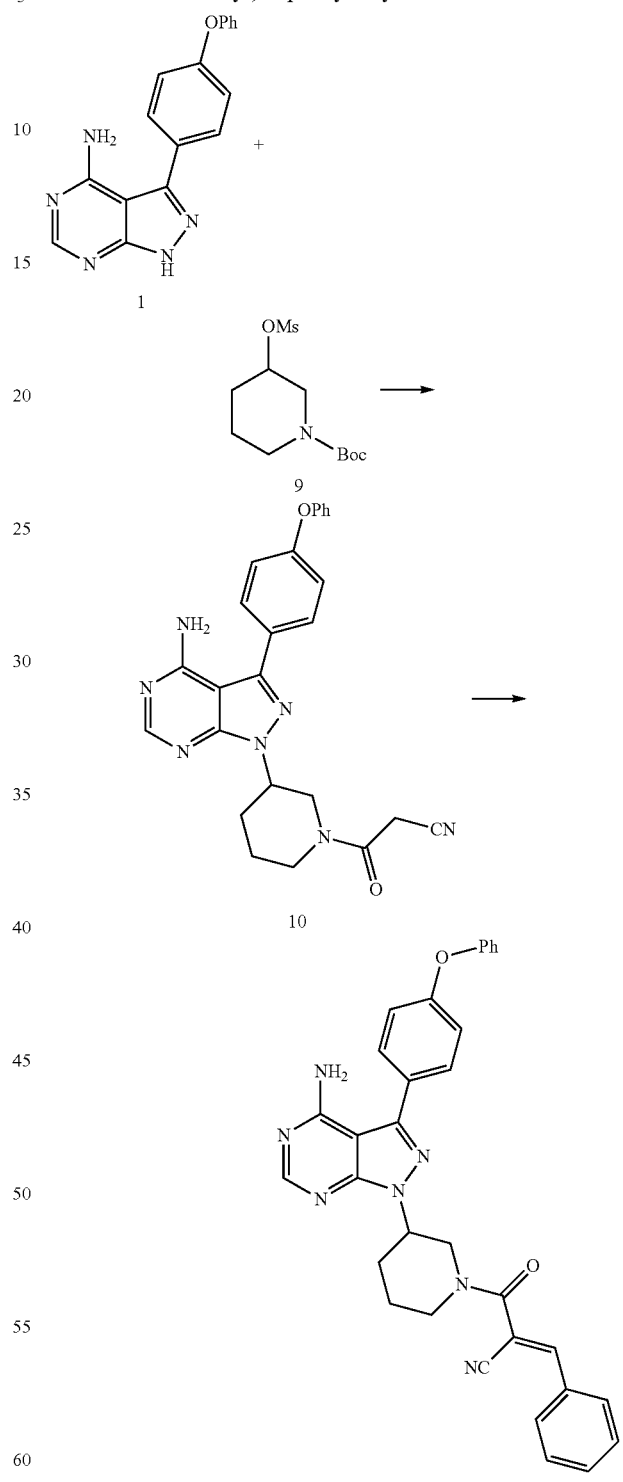

Step 1

A 20 mL vial fitted with a magnetic stir bar was charged with pyrimidine 1 (303 mg), mesylate 9 (300 mg) (tert-Butyl 3-(methylsulfonyloxy)piperidine-1-carboxylate (9) was prepared according to Costa, et al, *J. Med. Chem.* 1992, 35, 4334-4343), cesium carbonate (450 mg), and DMF (2 mL). The reaction mixture was heated to 50° C. and stirred for 3 d. The reaction mixture was diluted with water (20 mL) and extracted with EtOAc (3×20 mL). The organic layers were combined, washed with water (3×20 mL) and brine (1×20 mL). The organic layer was dried over Na$_2$SO$_4$, filtered, and concentrated under reduced pressure. The resulting residue was redissolved in DCM (3 mL), and treated with TFA (1 mL) and water (0.5 mL). The reaction mixture was stirred for 5 minutes at room temperature and the solution concentrated under reduced pressure. The residue was treated with TFA (1 mL) and stirred for 5 minutes and concentrated twice more. The residue was then diluted with EtOAc and washed with 5% NaHCO$_3$. The organic layer was then extracted with 1 M HCl. The acid washes were neutralized with NaOH and extracted with EtOAc. The resulting organic layer was dried over Na$_2$SO$_4$, filtered, and concentrated under reduced pressure. The resulting residue was redissolved in DCM (5 mL) and combined with cyanoacetic acid (170 mg), HOBt (130 mg), DIPEA (0.2 mL), and EDC (250 mg). The reaction mixture was stirred overnight at room temperature. The reaction mixture was diluted with EtOAc, washed with 5% citric acid, followed by 5% NaHCO$_3$, and then brine. The organic layer dried over Na$_2$SO$_4$, filtered, and concentrated under reduced pressure. The resulting residue was partially purified by Si-gel chromatography to give 3-(3-(4-amino-3-(4-phenoxyphenyl)-1H-pyrazolo[3,4-d]pyrimidin-1-yl)piperidin-1-yl)-3-oxopropanenitrile (10) 156 mg (34% yield over 3 steps).

Step 2

A 20 mL vial fitted with a magnetic stir bar was charged with pyrimidine 10 (13 mg), benzaldehyde (10 µL), DBU (5 µL), and DMF (1 mL). The reaction mixture was heated to 60° C. and stirred for 18 h. The reaction mixture was purified by reversed phase HPLC to give 2-(3-(4-amino-3-(4-phenoxyphenyl)-1H-pyrazolo[3,4-d]pyrimidin-1-yl)piperidine-1-carbonyl)-3-phenylacrylonitrile 4.8 mg (31% yield). Calculated [MH]$^+$ 542.2. observed 542.5 by ESI-LCMS.

Example 3

Synthesis of 2-(3-(4-amino-3-(4-phenoxyphenyl)-1H-pyrazolo[3,4-d]pyrimidin-1-yl)piperidine-1-carbonyl)-3-(2-chlorophenyl)acrylonitrile

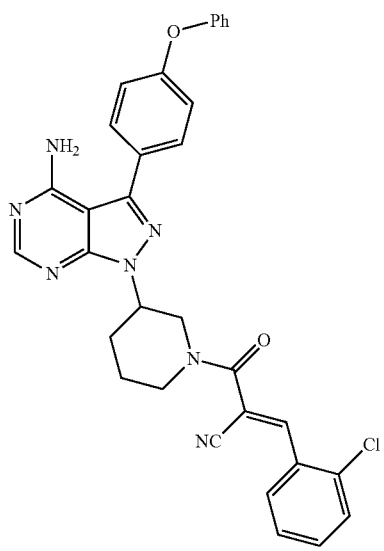 [SMILES: N#C/C(=C\c1ccccc1Cl)C(=O)N1CCCC(n2nc(-c3ccc(Oc4ccccc4)cc3)c3c(N)ncnc32)C1]

A 20 mL vial fitted with a magnetic stir bar was charged with pyrimidine 10 (14 mg), 2-chlorobenzaldehyde (10 µL), DBU (5 µL), and DMF (1 mL). The reaction mixture was heated to 60° C. and stirred for 18 h. The reaction mixture was purified by reversed phase HPLC to give 6.8 mg (38% yield) of title compound. Calculated [MH]$^+$ 576.2. observed 576.5 by ESI-LCMS.

Example 4

Synthesis of 2-(3-(4-smino-3-(4-phenoxyphenyl)-1H-pyrazolo[3,4-d]pyrimidin-1-yl)piperidine-1-carbonyl)-4,4-dimethylpent-2-enenitrile

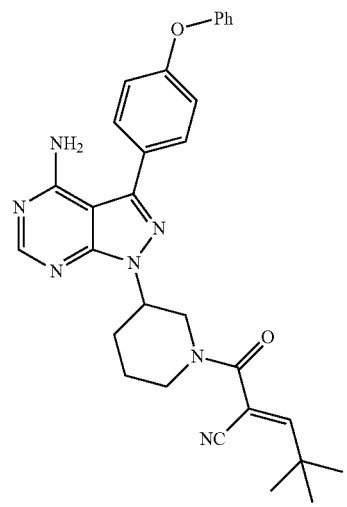 [SMILES: CC(C)(C)/C=C(\C#N)C(=O)N1CCCC(n2nc(-c3ccc(Oc4ccccc4)cc3)c3c(N)ncnc32)C1]

A 20 mL vial fitted with a magnetic stir bar was charged with pyrimidine 10 (20 mg), pivaldehyde (10 µL), DBU (10 µL), and DMF (1 mL). The reaction mixture was heated to 60° C. and stirred for 18 h. The reaction mixture was purified by reversed phase HPLC to give 2-(3-(4-smino-3-(4-phenoxyphenyl)-1H-pyrazolo[3,4-d]pyrimidin-1-yl)piperidine-1-carbonyl)-4,4-dimethylpent-2-enenitrile 2 mg (9% yield). Calculated [MH]$^+$ 522.2. observed 522.5 by ESI-LCMS.

Example 5

General Procedure A

Mitsunobu Reaction of Pyrimidine 1 with a Primary or Secondary Alcohol, Followed by Boc Deprotection and Acylation with 2-Cyanoacetic Acid

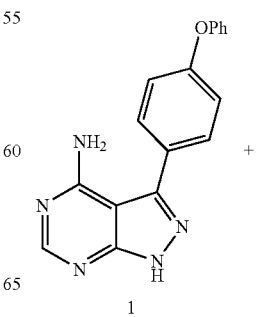

1

-continued

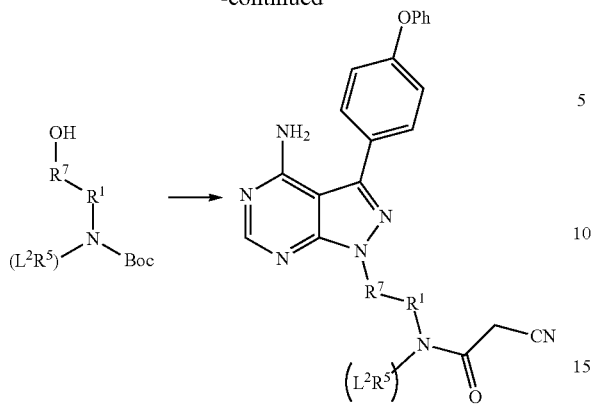

A 20 mL vial fitted with a magnetic stir bar was charged with pyrimidine 1 (303 mg), N-Boc-hydroxy-amine bifunctional alkane (1.5 mmol), triphenylphosphine (390 mg), and THF (5 mL). To the reaction mixture, DIAD (300 μL) was added dropwise. The reaction mixture was stirred for 1 h at room temperature. Concentrated hydrochloric acid (3 mL) was added to the reaction mixture and the resulting solution was stirred for 18 h at room temperature. The reaction mixture was washed with EtOAc (3×5 mL). The aqueous layer was neutralized with sodium hydroxide and extracted with EtOAc (3×5 mL). The organic layers were combined, dried over Na$_2$SO$_4$, filtered, and concentrated under reduced pressure. The resulting crude residue was redissolved in DCM (10 mL) and a magnetic stir bar was added to the flask. Subsequently, HOBt (135 mg), triethylamine (200 μL), cyanoacetic acid (130 mg), and EDC (200 mg) were added to the solution. The resulting mixture was stirred at room temperature for 2 h. The reaction mixture was diluted with EtOAc (5 mL), washed with 5% citric acid (3×5 mL), 5% NaHCO$_3$ (3×5 mL), and brine (1×5 mL). The organic layer was dried over Na$_2$SO$_4$, filtered, and concentrated under reduced pressure to yield the crude product, which was carried forward without further purification. $R^1$, $R^5$, $R^7$, and $L^2$ are as defined above.

Reference D

Synthesis of 3-(4-(4-amino-3-(4-phenoxyphenyl)-1H-pyrazolo[3,4-d]pyrimidin-1-yl)piperidin-1-yl)-3-oxopropanenitrile

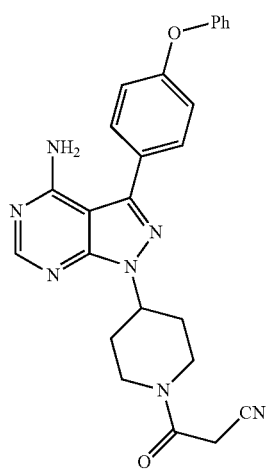 [SMILES: N#CCC(=O)N1CCC(n2nc(-c3ccc(Oc4ccccc4)cc3)c3c(N)ncnc32)CC1]

3-(4-(4-Amino-3-(4-phenoxyphenyl)-1H-pyrazolo[3,4-d]pyrimidin-1-yl)piperidin-1-yl)-3-oxopropanenitrile (14) was prepared by procedure A starting from 1 and N-Boc 4-hydroxypiperidine to give 277 mg of crude product.

Reference E

Synthesis of (R)-3-(3-(4-amino-3-(4-phenoxyphenyl)-1H-pyrazolo[3,4-d]pyrimidin-1-yl)piperidin-1-yl)-3-oxopropanenitrile

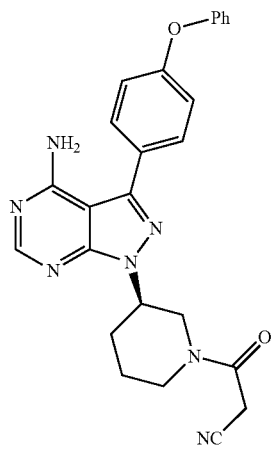 [SMILES: N#CCC(=O)N1CCC[C@@H](n2nc(-c3ccc(Oc4ccccc4)cc3)c3c(N)ncnc32)C1]

(R)-3-(3-(4-Amino-3-(4-phenoxyphenyl)-1H-pyrazolo[3,4-d]pyrimidin-1-yl)piperidin-1-yl)-3-oxopropanenitrile (15) was prepared by procedure A starting from 1 and (S)—N-Boc 3-hydroxypiperidine to give 339 mg of crude product.

Reference F

Synthesis of (S)-3-(3-(4-amino-3-(4-phenoxyphenyl)-1H-pyrazolo[3,4-d]pyrimidin-1-yl)piperidin-1-yl)-3-oxopropanenitrile

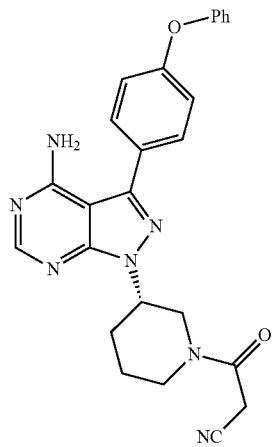 [SMILES: N#CCC(=O)N1CCC[C@H](n2nc(-c3ccc(Oc4ccccc4)cc3)c3c(N)ncnc32)C1]

(S)-3-(3-(4-Amino-3-(4-phenoxyphenyl)-1H-pyrazolo[3,4-d]pyrimidin-1-yl)piperidin-1-yl)-3-oxopropanenitrile (16) was prepared by procedure A starting from 1 and (R)—N-Boc 3-hydroxypiperidine to give 622 mg of crude product.

135

Reference G

Synthesis of 3-(4-((4-amino-3-(4-phenoxyphenyl)-1H-pyrazolo[3,4-d]pyrimidin-1-yl)methyl)piperidin-1-yl)-3-oxopropanenitrile

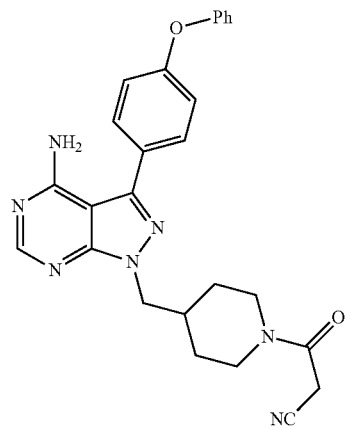 [SMILES: N#CCC(=O)N1CCC(Cn2nc(-c3ccc(Oc4ccccc4)cc3)c3c(N)ncnc32)CC1]

3-(4-((4-Amino-3-(4-phenoxyphenyl)-1H-pyrazolo[3,4-d]pyrimidin-1-yl)methyl)piperidin-1-yl)-3-oxopropanenitrile (17) was prepared by procedure A starting from 1 and N-Boc 4-hydroxymethylpiperidine to give 338 mg of crude product.

Reference H

Synthesis of 3-(3-((4-Amino-3-(4-phenoxyphenyl)-1H-pyrazolo[3,4-d]pyrimidin-1-yl)methyl)piperidin-1-yl)-3-oxopropanenitrile

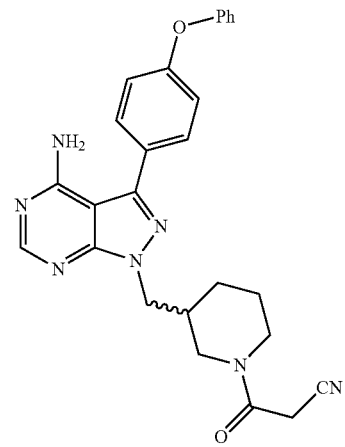 [SMILES: N#CCC(=O)N1CCCC(Cn2nc(-c3ccc(Oc4ccccc4)cc3)c3c(N)ncnc32)C1]

3-(3-((4-Amino-3-(4-phenoxyphenyl)-1H-pyrazolo[3,4-d]pyrimidin-1-yl)methyl)piperidin-1-yl)-3-oxopropanenitrile (18) was prepared by procedure A starting from 1 and N-Boc 3-hydroxymethylpiperidine to give 0.34 g of crude product.

136

Reference I

Synthesis of (S)-3-(3-(4-amino-3-(4-phenoxyphenyl)-1H-pyrazolo[3,4-d]pyrimidin-1-yl)pyrrolidin-1-yl)-3-oxopropanenitrile

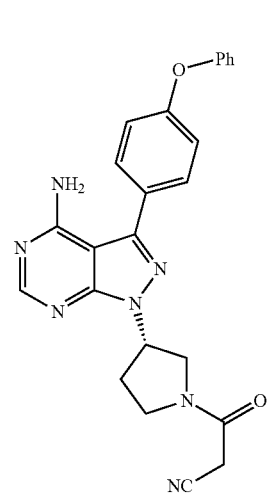 [SMILES: N#CCC(=O)N1CC[C@H](n2nc(-c3ccc(Oc4ccccc4)cc3)c3c(N)ncnc32)C1]

(S)-3-(3-(4-Amino-3-(4-phenoxyphenyl)-1H-pyrazolo[3,4-d]pyrimidin-1-yl)pyrrolidin-1-yl)-3-oxopropanenitrile (19) was prepared by procedure A starting from 1 and (R)—N-Boc 3-hydroxypyrrolidine to give 273 mg of crude product.

Reference J

Synthesis of (R)-3-(2-((4-amino-3-(4-phenoxyphenyl)-1H-pyrazolo[3,4-d]pyrimidin-1-yl)methyl)pyrrolidin-1-yl)-3-oxopropanenitrile

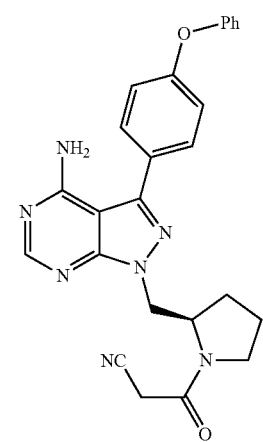 [SMILES: N#CCC(=O)N1CCC[C@@H]1Cn1nc(-c2ccc(Oc3ccccc3)cc2)c2c(N)ncnc21]

(R)-3-(2-((4-Amino-3-(4-phenoxyphenyl)-1H-pyrazolo[3,4-d]pyrimidin-1-yl)methyl)pyrrolidin-1-yl)-3-oxopropanenitrile (20) was prepared by procedure A starting from 1 and (S)—N-Boc 2-hydroxymethylpyrrolidine to give 317 mg of crude product.

Reference K

Synthesis of N-((1S,4S)-4-(4-amino-3-(4-phenoxyphenyl)-1H-pyrazolo[3,4-d]pyrimidin-1-yl)cyclohexyl)-2-cyanoacetamide

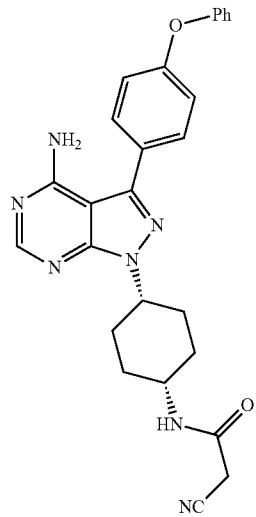 [SMILES: N#CCC(=O)N[C@H]1CC[C@@H](n2nc(-c3ccc(Oc4ccccc4)cc3)c3c(N)ncnc32)CC1]

N-((1s,4s)-4-(4-amino-3-(4-phenoxyphenyl)-1H-pyrazolo[3,4-d]pyrimidin-1-yl)cyclohexyl)-2-cyanoacetamide (21) was prepared by procedure A starting from 1 and (trans)-N-Boc 4-hydroxycyclohexylamine to give 306 mg of crude product.

Example 6

General Procedure B

Condensation of Cyanoacetamide with Cyclopropanecarboxaldehyde

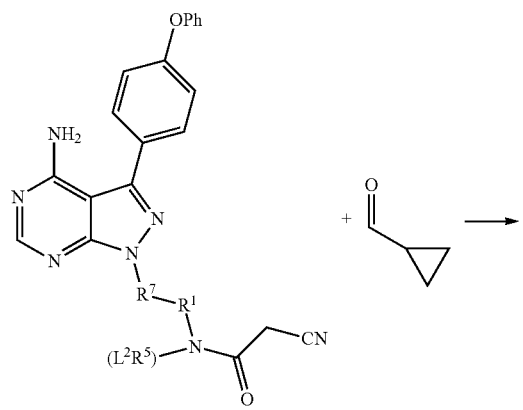

A 20 mL vial fitted with a magnetic stir bar was charged with cyanacetamide (0.05-0.1 mmol), cyclopropanecarboxaldehyde (10 μL), piperdinium acetate (5 mg), and 2-propanol (1 mL). The reaction mixture was stirred at room temperature for 18 h (alternatively stirred at 50-60° C. for 3-18 h). The reaction mixture was concentrated under reduced pressure and the resulting residue was purified by either Si-gel chromatography or by reversed phase HPLC. $R^1$, $R^5$, $R^7$, and $L^2$ are as defined above.

Example 7

Synthesis of 2-(4-(4-amino-3-(4-phenoxyphenyl)-1H-pyrazolo[3,4-d]pyrimidin-1-yl)piperidine-1-carbonyl)-3-cyclopropylacrylonitrile

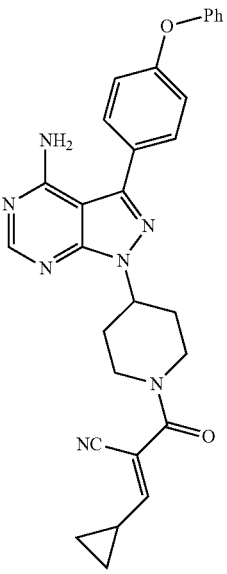 [SMILES: N#C/C(=C\C1CC1)C(=O)N1CCC(n2nc(-c3ccc(Oc4ccccc4)cc3)c3c(N)ncnc32)CC1]

2-(4-(4-Amino-3-(4-phenoxyphenyl)-1H-pyrazolo[3,4-d]pyrimidin-1-yl)piperidine-1-carbonyl)-3-cyclopropylacrylonitrile was prepared by procedure B using compound 14. Collected 20 mg product (54% yield). Calculated [MH]+ 506.2. observed 506.3 by ESI-LCMS.

Example 8

Synthesis of (R)-2-(3-(4-amino-3-(4-phenoxyphenyl)-1H-pyrazolo[3,4-d]pyrimidin-1-yl)piperidine-1-carbonyl)-3-cyclopropylacrylonitrile

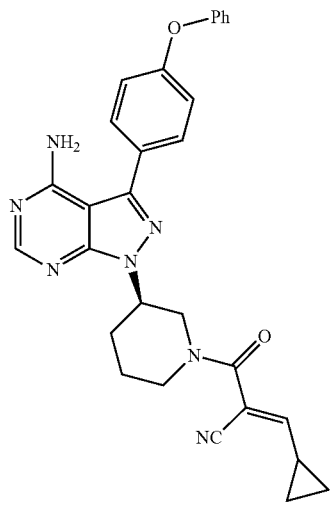 [SMILES: N#C/C(=C\C1CC1)C(=O)N1CCC[C@@H](n2nc(-c3ccc(Oc4ccccc4)cc3)c3c(N)ncnc32)C1]

(R)-2-(3-(4-amino-3-(4-phenoxyphenyl)-1H-pyrazolo[3,4-d]pyrimidin-1-yl)piperidine-1-carbonyl)-3-cyclopropylacrylonitrile was prepared by procedure B from compound 15. Collected 27 mg product (69% yield). Calculated [MH]$^+$ 506.2. observed 506.1 by ESI-LCMS.

Example 9

Synthesis of (S)-2-(3-(4-amino-3-(4-phenoxyphenyl)-1H-pyrazolo[3,4-d]pyrimidin-1-yl)piperidine-1-carbonyl)-3-cyclopropylacrylonitrile

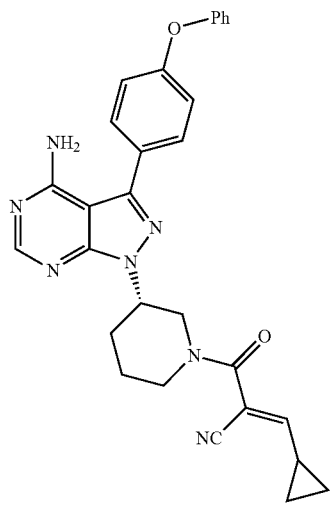 [SMILES: N#C/C(=C\C1CC1)C(=O)N1CCC[C@H](n2nc(-c3ccc(Oc4ccccc4)cc3)c3c(N)ncnc32)C1]

(S)-2-(3-(4-amino-3-(4-phenoxyphenyl)-1H-pyrazolo[3,4-d]pyrimidin-1-yl)piperidine-1-carbonyl)-3-cyclopropylacrylonitrile was prepared by procedure B from compound 16. Collected 8 mg product (31% yield). Calculated [MH]$^+$ 506.2. observed 506.5 by ESI-LCMS.

Example 10

Synthesis of 2-(4-((4-amino-3-(4-phenoxyphenyl)-1H-pyrazolo[3,4-d]pyrimidin-1-yl)methyl)piperidine-1-carbonyl)-3-cyclopropylacrylonitrile

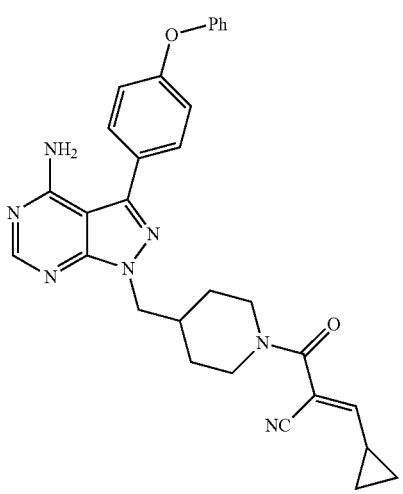 [SMILES: N#C/C(=C\C1CC1)C(=O)N1CCC(Cn2nc(-c3ccc(Oc4ccccc4)cc3)c3c(N)ncnc32)CC1]

2-(4-((4-Amino-3-(4-phenoxyphenyl)-1H-pyrazolo[3,4-d]pyrimidin-1-yl)methyl)piperidine-1-carbonyl)-3-cyclopropylacrylonitrile was prepared by procedure B from compound 17. Collected 23 mg product (67% yield). Calculated [MH]$^+$ 520.2. observed 520.2 by ESI-LCMS.

Example 11

Synthesis of 2-(3-((a-Amino-3-(4-phenoxyphenyl)-1H-pyrazolo[3,4-d]pyrimidin-1-yl)methyl)piperidine-1-carbonyl)-3-cyclopropylacrylonitrile

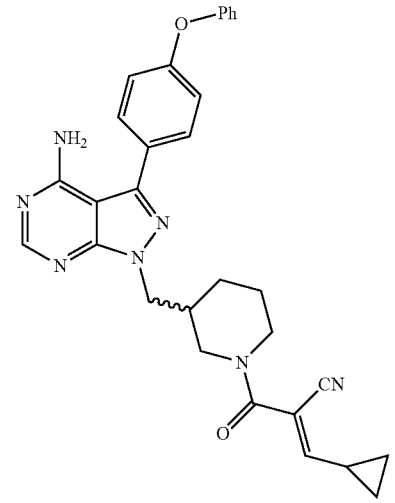 [SMILES: N#C/C(=C\C1CC1)C(=O)N1CCCC(Cn2nc(-c3ccc(Oc4ccccc4)cc3)c3c(N)ncnc32)C1]

2-(3-((4-Amino-3-(4-phenoxyphenyl)-1H-pyrazolo[3,4-d]pyrimidin-1-yl)methyl)piperidine-1-carbonyl)-3-cyclopropylacrylonitrile was prepared by procedure B from compound 18. Collect 18 mg product (40% yield). Calculated [MH]+ 520.2. observed 520.2 by ESI-LCMS.

Example 12

Synthesis of (S)-2-(3-(4-amino-3-(4-phenoxyphenyl)-1H-pyrazolo[3,4-d]pyrimidin-1-yl)pyrrolidine-1-carbonyl)-3-cyclopropylacrylonitrile

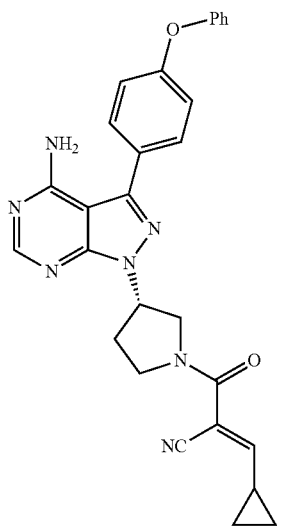 [SMILES: N#C/C(=C\C1CC1)C(=O)N1CC[C@H](n2nc(-c3ccc(Oc4ccccc4)cc3)c3c(N)ncnc32)C1]

(S)-2-(3-(4-Amino-3-(4-phenoxyphenyl)-1H-pyrazolo[3,4-d]pyrimidin-1-yl)pyrrolidine-1-carbonyl)-3-cyclopropylacrylonitrile was prepared by procedure B from compound 19. Collected 23 mg product (50% yield). Calculated [MH]+ 492.2. observed 492.2 by ESI-LCMS.

Example 13

Synthesis of (R)-2-(2-((a-amino-3-(4-phenoxyphenyl)-1H-pyrazolo[3,4-d]pyrimidin-1-yl)methyl)pyrrolidine-1-carbonyl)-3-cyclopropylacrylonitrile

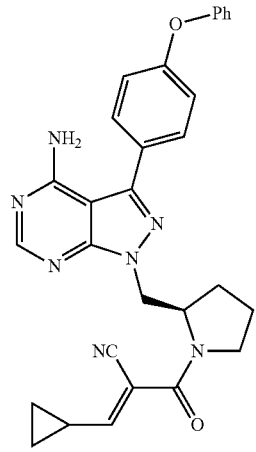 [SMILES: N#C/C(=C\C1CC1)C(=O)N1CCC[C@@H]1Cn1nc(-c2ccc(Oc3ccccc3)cc2)c2c(N)ncnc21]

(R)-2-(2-((4-amino-3-(4-phenoxyphenyl)-1H-pyrazolo[3,4-d]pyrimidin-1-yl)methyl)pyrrolidine-1-carbonyl)-3-cyclopropylacrylonitrile was prepared by procedure B from compound 20. Collected 18 mg product (50% yield). Calculated [MH]+ 506.2. observed 506.4 by ESI-LCMS.

Example 14

Synthesis of N-((1S,4S)-4-(4-amino-3-(4-phenoxyphenyl)-1H-pyrazolo[3,4-d]pyrimidin-1-yl)cyclohexyl)-2-cyano-3-cyclopropylacrylamide

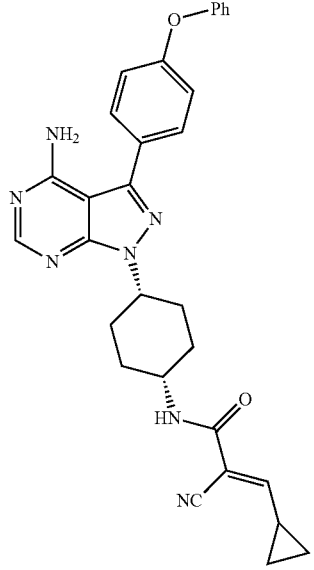 [SMILES: N#C/C(=C\C1CC1)C(=O)N[C@H]1CC[C@@H](n2nc(-c3ccc(Oc4ccccc4)cc3)c3c(N)ncnc32)CC1]

N-((1S,4S)-4-(4-amino-3-(4-phenoxyphenyl)-1H-pyrazolo[3,4-d]pyrimidin-1-yl)cyclohexyl)-2-cyano-3-cyclopropylacrylamide was prepared by procedure B from compound 21. Collected 23 mg product (65% yield). Calculated [MH]+ 520.2. observed 520.4 by ESI-LCMS.

Example 15

Synthesis of (R)-2-(3-(4-amino-3-(4-phenoxyphenyl)-1H-pyrazolo[3,4-d]pyrimidin-1-yl)piperidine-1-carbonyl)-4-(dimethylamino)-4-methylpent-2-enenitrile

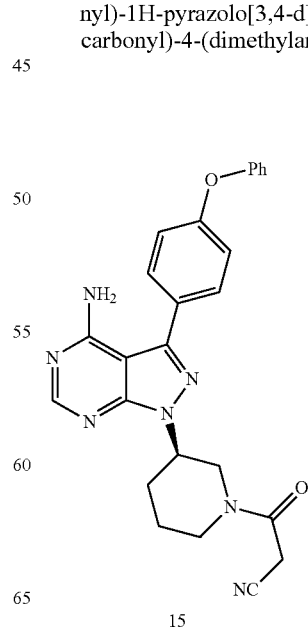

15

Step 1

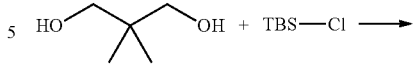

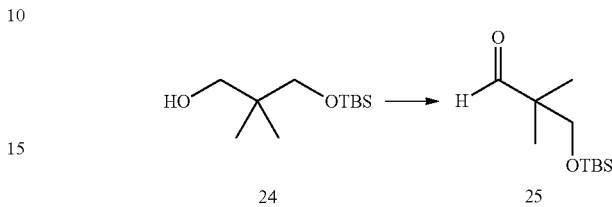

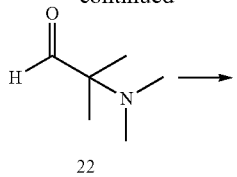

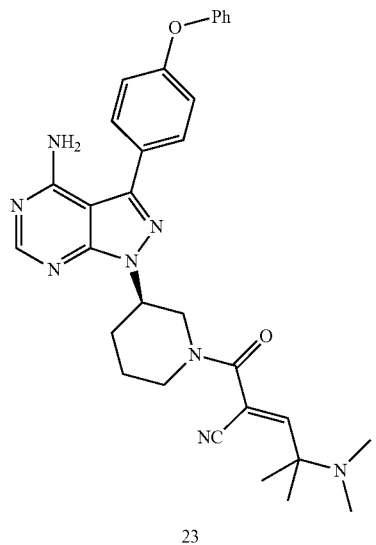

A 20 mL vial fitted with a magnetic stir bar was charged with cyanacetamide 15 (25 mg), aldehyde 22 (30 μL) (prepared according to Yang, et al, *Inorg. Chem.* 2009, 48, pp 7639-7644), piperdinium acetate (5 mg), and 2-propanol (1 mL). The reaction mixture was stirred at 100° C. for 18 h. The reaction mixture was concentrated under reduced pressure and the resulting residue was purified by reversed phase HPLC. Collected 9 mg of product (30% yield). Calculated [MH]$^+$ 551.3. observed 551.5 by ESI-LCMS.

Example 16

Synthesis of (R)-2-(3-(4-Amino-3-(4-phenoxyphenyl)-1H-pyrazolo[3,4-d]pyrimidin-1-yl)piperidine-1-carbonyl)-5-hydroxy-4,4-dimethylpent-2-enenitrile (a) A round bottom flask fitted with a magnetic stir bar was charged with neopentylglycol (1.90 g), TBS-Cl (3.08 g), imidazole (1.40 g) and DMF (40 mL). The solution was stirred for 18 h at room temperature. The reaction mixture was concentrated under reduced pressure and the resulting residue was purified by Si-gel chromatography (elute with 1:15 increasing to 1:7 of EtOAc:Hex) to give 3-(tert-butyldimethylsilyloxy)-2,2-dimethylpropan-1-ol (24). Collected 2.50 g product (63% yield).

(b) A round bottom flask fitted with a magnetic stir bar was charged with alcohol 24 (2.18 g), triethylamine (10 mL), and DCM (30 mL). Separately, sulfur trioxide pyridine complex (4.80 g) was dissolved in DMSO (10 mL). The DMSO solution was added to the reaction mixture and the resulting solution was stirred for 3 h at room temperature. The reaction mixture was quenched by the addition of 1 M HCl (30 mL). The resulting mixture was diluted with EtOAc and extracted with 1 M HCl (3×20 mL), 5% NaHCO$_3$ (3×20 mL), water (3×20 mL), and brine (1×20 mL). The organic layer was then dried over Na$_2$SO$_4$, filtered, concentrated under reduced pressure, and dried in vacuo to give 3-(tert-butyldimethylsilyloxy)-2,2-dimethylpropanal (25). Collected 1.28 g product (59% yield).

Step 2

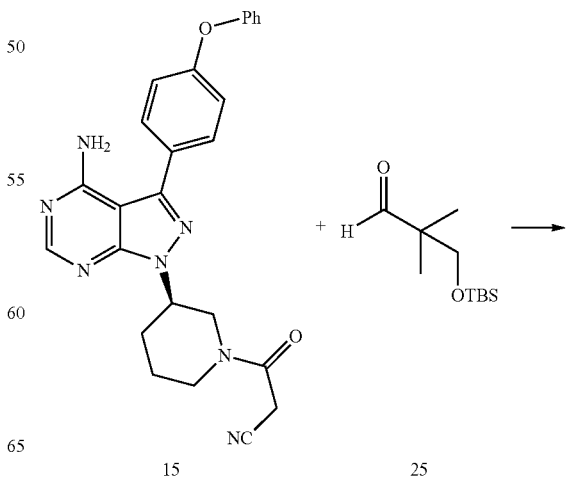

-continued

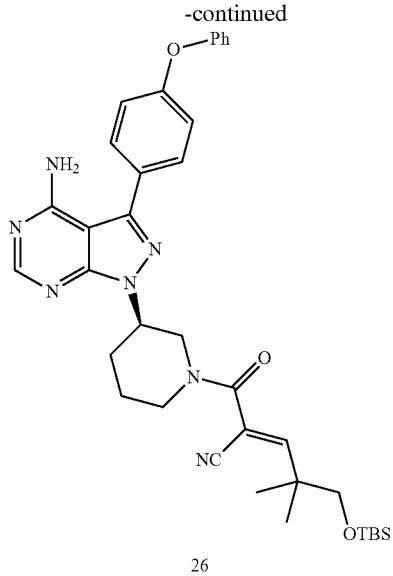

26

27

Example 17

Synthesis of 2-(3-(4-amino-3-(4-chlorophenyl)-1H-pyrazolo[3,4-d]pyrimidin-1-yl)piperidine-1-carbonyl)-3-cyclopropylacrylonitrile

2 + 9

28

29

(a) A 20 mL vial fitted with a magnetic stir bar was charged with cyanacetamide 15 (50 mg), aldehyde 25 (26 mg), piperdinium acetate (5 mg), and 2-propanol (1 mL). The reaction mixture was stirred at 100° C. for 18 h. The reaction mixture was concentrated under reduced pressure and the resulting residue was purified by Si-gel chromatography to give (R)-2-(3-(4-amino-3-(4-phenoxyphenyl)-1H-pyrazolo[3,4-d]pyrimidin-1-yl)piperidine-1-carbonyl)-5-(tert-butyldimethylsilyloxy)-4,4-dimethylpent-2-enenitrile (26). Collected 26 mg product (36% yield).

(b) A 20 mL vial fitted with a magnetic stir bar was charged with cyanoacrylamide 26 (18 mg), 1 M TBAF in THF (0.1 mL), and THF (1 mL). The reaction mixture was stirred at room temperature for 2 h. The reaction mixture was quenched by addition of 1 M HCl (1 mL) and extracted with EtOAc (3×3 mL). The combined organic layers were then dried over $Na_2SO_4$, filtered, concentrated under reduced pressure, and the resulting residue was purified by reversed phase HPLC. Collect 3 mg product (21% yield). Calculated $[MH]^+$ 538.3. observed 538.4 by ESI-LCMS.

147

-continued

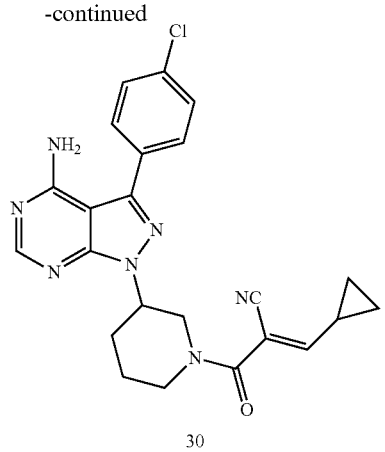

30

Step 1

A 20 mL vial fitted with a magnetic stir bar was charged with pyrimidine 2 (500 mg), mesylate 9 (428 mg), cesium carbonate (977 mg), and DMF (10 mL). The reaction mixture was heated to 60° C. and stirred for 3 d. The reaction mixture was diluted with EtOAc and washed with water (3×), 5% citric acid (3×), and 5% NaHCO$_3$ (3×). The organic layer was dried over Na$_2$SO$_4$, filtered, and concentrated under reduced pressure. The resulting residue was purified by Si-gel chromatography (elute with 1:1 EtOAc:Hex). Collected 0.17 g product 28 (19% yield).

Step 2

Pyrimidine 28 (170 mg) in a round bottom flask was treated with 95% TFA (1 mL) for 5 minutes at room temperature and the solution was concentrated under reduced pressure. The resulting residue was treated with 95% TFA for 5 minutes at room temperature and concentrated under reduced pressure twice more. The resulting residue redissolved in EtOAc and washed with 5% NaHCO$_3$ (3×). The organic layer was dried over Na$_2$SO$_4$, filtered, and concentrated under reduced pressure. The resulting residue was combined with cyanoacetic acid (45 mg), HOBt (72 mg), DIPEA (230 mg), EDC (102 mg), and DCM (5 mL) in a flask fitted with a magnetic stir bar. The reaction mixture was stirred for 2 h at room, at which time an additional portion of cyanoacetic acid (22 mg) and EDC (51 mg) were added. The reaction mixture was then stirred for an additional 2 h. The reaction mixture was diluted with EtOAc (50 mL) and washed with 5% citric acid (3×), 5% NaHCO$_3$ (3×), and brine (1×). The organic layer was dried over Na$_2$SO$_4$, filtered, and concentrated under reduced pressure. The resulting residue was purified by Si-gel chromatography (elute with 100% EtOAc increasing to 4% MeOH in EtOAc). Collected 81 mg product 29 (52% yield).

A vial fitted with a magnetic stir bar was charged with cyanacetamide 29 (50 mg), cyclopropanecarboxaldehyde (9 μL), DBU (17 μL), and DMF (2 mL). The reaction mixture was heated to 60° C. and stirred for 16 h. The reaction mixture was purified by reverse-phase HPLC to give 2-(3-(4-amino-3-(4-chlorophenyl)-1H-pyrazolo[3,4-d]pyrimidin-1-yl)piperidin-1-carbonyl)-3-cyclopropylacrylonitrile. Collect 6.4 mg product 30 (11% yield). Calculated [MH]$^+$ 448.2. observed 448.2 by ESI-LCMS.

148

Example 18

Synthesis of N-(4-(3-bromophenylamino)quinazolin-6-yl)-2-cyano-3-cyclopropylacrylamide

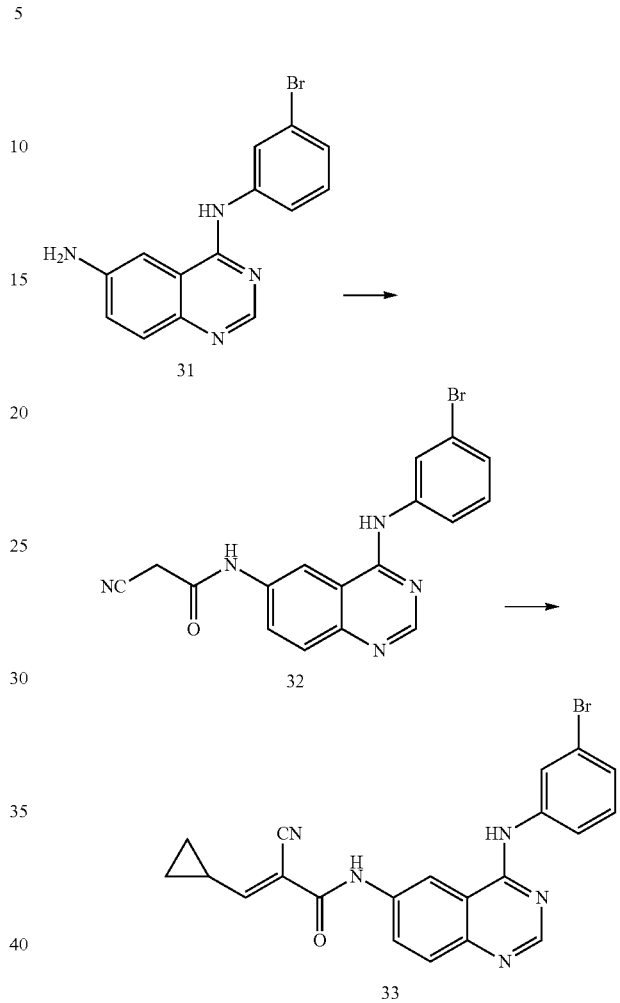

Step 1

N$^4$-(3-Bromophenyl)quinazoline-4,6-diamine (31) was prepared according to the procedure of Blair, et al, *Nat. Chem. Bio.*, 2007, 3, pp 229-238.

Step 2

A round bottom flask fitted with a magnetic stir bar was charged with pyrimidine 31 (550 mg), cyanoacetic acid (310 mg), DIPEA (0.61 mL), EDC (675 mg), and DMF (10 mL). The reaction mixture was stirred at room temperature for 3 h. The reaction mixture was diluted with water and filtered to collect the resulting precipitate. The solid was then washed with 1 M HCl, water, and EtOAc, and subsequently dried in vacuo to give N-(4-(3-bromophenylamino)-quinazolin-6-yl)-2-cyanoacetamide (32). Collected 664 mg of product (99% yield).

Step 3

A 20 mL vial fitted with a magnetic stir bar was charged with cyanacetamide 32 (40 mg), cyclopropanecarboxaldehyde (15 μL), piperdinium acetate (5 mg), and 2-propanol (1 mL). The reaction mixture was stirred at 60° C. for 18 h. The reaction mixture was diluted with water, stirred for 2 h at room temperature, and filtered to collect the resulting precipitate. The solid was then washed with water dried in vacuo to give N-(4-(3-bromophenylamino)quinazolin-6-yl)-2-cyano-3-cyclopropylacrylamide (33). Collected 26 mg of product (56% yield). Calculated [MH]$^+$ 434.1. observed 434.3 by ESI-LCMS.

Example 19

Synthesis of (R)-2-(3-(4-amino-3-(4-phenoxyphenyl)-1H-pyrazolo[3,4-d]pyrimidin-1-yl)piperidine-1-carbonyl)-3-cyclopropylacrylonitrile

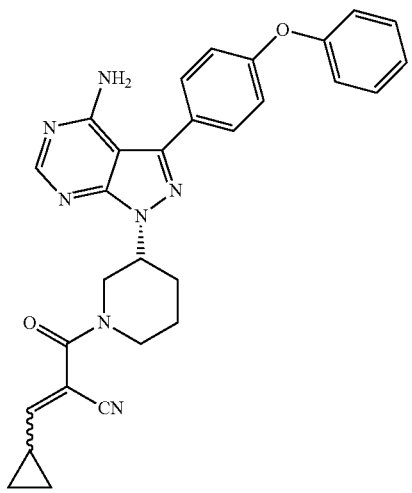

Step 1

A solution of 5-amino-1H-pyrazole-4-carbonitrile (10 g, 92.51 mmol, 1.00 equiv) in formamide (80 mL) was stirred under nitrogen at 165° C. for 5 h. The reaction mixture was cooled to room temperature and the solid was collected by filtration. The filter cake was washed first with 20 mL of water then 20 mL of methanol and dried to yield 9.5 g (76%) of 1H-pyrazolo[3,4-d]pyrimidin-4-amine as a white solid.

Step 2

A mixture of 1H-pyrazolo[3,4-d]pyrimidin-4-amine (150 g, 1.11 mol, 1.00 equiv) and N-iodo-succinimide (375 g, 1.67 mol, 1.58 equiv) in N,N-dimethylformamide (2.5 L) was stirred at 80° C. for 5 h. The reaction mixture was cooled to room temperature and then diluted with 10 L of water. The solid was collected by filtration, washed with 2×1 L of saturated aqueous sodium sulfite and dried under vacuum to give 150 g (52%) of 3-iodo-1H-pyrazolo[3,4-d]pyrimidin-4-amine as a yellow solid.

Step 3

To a stirred mixture of 3-iodo-1H-pyrazolo[3,4-d]pyrimidin-4-amine (5.9 g, 22.6 mmol, 1.00 equiv), (S)-tert-butyl 3-hydroxypiperidine-1-carboxylate (10 g, 50 mmol, 2.2 equiv) and triphenylphosphine (11.8 g, 45 mmol, 2.0 equiv) in tetrahydrofuran (300 mL) at 10° C. was added a solution of diisopropyl azodicarboxylate in tetrahydrofuran (30 mL) dropwise in 30 min. The resulting mixture was stirred at room temperature for 12 h and then concentrated under vacuum. The residue was purified on a silica gel column eluted with dichloromethane/methanol (100/1) to give 3 g (33%) of (R)-tert-butyl 3-(4-amino-3-iodo-1H-pyrazolo[3,4-d]pyrimidin-1-yl)piperidine-1-carboxylate as yellow solid.

Step 4

A mixture of tert-butyl 3-[4-amino-3-iodo-1H-pyrazolo[3,4-d]pyrimidin-1-yl]piperidine-1-carboxylate (1 g, 2.25 mmol, 1.00 equiv), (4-phenoxyphenyl)boronic acid (530 mg, 2.48 mmol, 1.10 equiv), sodium carbonate (480 mg, 4.53 mmol, 2.01 equiv) and tetrakis(triphenylphosphine) palladium (78 mg, 0.07 mmol, 0.03 equiv) in 1,4-dioxane (60 mL) and water (15 mL) was stirred under nitrogen at 90° C. for 24 h. The reaction mixture was cooled to room temperature and then concentrated under vacuum. The residue was dissolved in 500 mL of dichloromethane. The resulting solution was washed with 200 mL of water, dried over anhydrous sodium sulfate and concentrated under vacuum. The residue was purified on a silica gel column eluted with dichloromethane/methanol (100/1) to give 700 mg (64%) of tert-butyl 3-[4-amino-3-(4-phenoxyphenyl)-1H-pyrazolo[3,4-d]pyrimidin-1-yl]piperidine-1-carboxylate as a yellow solid.

Step 5

A mixture of tert-butyl 3-[4-amino-3-(4-phenoxyphenyl)-1H-pyrazolo[3,4-d]pyrimidin-1-yl]piperidine-1-carboxylate (700 mg, 1.44 mmol, 1.00 equiv) in dichloromethane (100 mL) and trifluoroacetic acid (20 mL) was stirred at room temperature for 12 h. The reaction mixture was concentrated under vacuum to yield 580 mg of crude 3-(4-phenoxyphenyl)-1-(piperidin-3-yl)-1H-pyrazolo[3,4-d]pyrimidin-4-amine as yellow oil.

Step 6

A mixture of 3-(4-phenoxyphenyl)-1-(piperidin-3-yl)-1H-pyrazolo[3,4-d]pyrimidin-4-amine (580 mg, 1.50 mmol, 1.00 equiv), carbonyldiimidazole (365 mg, 2.25 mmol, 1.50 equiv) and 2-cyanoacetic acid (190 mg, 2.24 mmol, 1.49 equiv) in dichloromethane (100 mL) was stirred at room temperature for 24 h. The reaction mixture was diluted with 100 mL of dichloromethane and washed with 3×100 mL of saturated aqueous ammonium chloride solution. The organic layer was dried over anhydrous sodium sulfate and concentrated under vacuum. The residue was purified on a silica gel column eluted with dichloromethane/methanol (100/1) to give 380 mg (56%) of 3-[3-[4-amino-3-(4-phenoxyphenyl)-1H-pyrazolo[3,4-d]pyrimidin-1-yl]piperidin-1-yl]-3-oxopropanenitrile as a white solid.

Step 7

A mixture of 3-[3-[4-amino-3-(4-phenoxyphenyl)-1H-pyrazolo[3,4-d]pyrimidin-1-yl]piperidin-1-yl]-3-oxopropanenitrile (120 mg, 0.26 mmol, 1.00 equiv), piperidine (27 mg, 0.28 mmol, 1.07 equiv) and cyclopropanecarbaldehyde (28 mg, 0.40 mmol, 1.51 equiv) in methanol (8 mL) was stirred in sealed tube at room temperature for 24 h. The resulting mixture was concentrated under vacuum and the residue was purified on a silica gel column eluted with dichloromethane/methanol (100/1) to give 85.4 mg (64%) of (2E)-2-[(E)-[3-[4-amino-3-(4-phenoxyphenyl)-1H-pyrazolo[3,4-d]pyrimidin-1-yl]piperidin-1-yl]carbonyl]-3-cyclopropylprop-2-enenitrile as a white solid. MS (ESI, pos. ion) m/z: 506 (M+H)$^+$.

Example 20

Synthesis of 2-((R)-3-(4-amino-3-(4-(3,4-dichlorophenoxy)-3-methoxyphenyl)-1H-pyrazolo[3,4-d]pyrimidin-1-yl)piperidine-1-carbonyl)-3-cyclopropylacrylonitrile

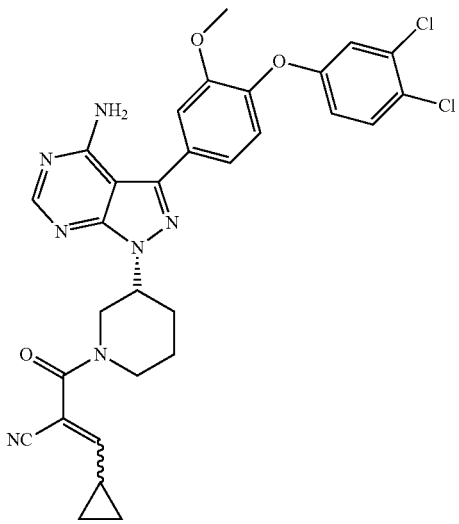

Step 1

A mixture of 3,4-dichlorophenol (38 g, 233.13 mmol, 1.00 equiv), 1-fluoro-2-methoxy-4-nitrobenzene (40 g, 233.75 mmol, 1.00 equiv) and potassium carbonate (64 g, 463.77 mmol, 1.99 equiv) in N,N-dimethylformamide (250 mL) was stirred overnight at 60° C. The resulting solution was diluted with 1000 mL of water, extracted with 3×200 mL of ethyl acetate and the organic layers combined. The resulting mixture was washed with 3×500 mL of brine. The mixture was dried over anhydrous sodium sulfate and concentrated under vacuum to yield 60 g (82%) of 1,2-dichloro-4-(2-methoxy-4-nitrophenoxy)benzene as a brown solid.

Step 2

A mixture of 1,2-dichloro-4-(2-methoxy-4-nitrophenoxy)benzene (60 g, 190.40 mmol, 1.00 equiv), Fe (53 g, 946.43 mmol, 4.97 equiv) and ammonium chloride (10 g, 188.68 mmol, 0.99 equiv) in tetrahydrofuran/water (1/2) (600 mL) was stirred overnight at 60° C. under an inert atmosphere of nitrogen. The mixture was filtered through Celite and the filtrate was concentrated under vacuum. The resulting solution was extracted with 3×500 mL of dichloromethane and the organic layers combined. The resulting mixture was washed with 3×500 mL of brine. The mixture was dried over anhydrous magnesium sulfate and concentrated under vacuum to give 40 g (74%) of 4-(3,4-dichlorophenoxy)-3-methoxyaniline as a light gray solid.

Step 3

A solution of sodium nitrite (14.4 g, 208.70 mmol, 1.98 equiv) in water (500 mL) was added dropwise into a solution of 4-(3,4-dichlorophenoxy)-3-methoxyaniline (30 g, 105.58 mmol, 1.00 equiv) in sulfuric acid (1000 mL) with stirring at 0° C. and the mixture was stirred for 30 min at 0° C. The above mixture was added dropwise to a solution of potassium iodide (1000 mL, 5%) in water with stirring at 50° C. The reaction was completed immediately. The reaction mixture was cooled to room temperature, extracted with 3×500 mL of ethyl acetate and the organic layers combined. The resulting mixture was washed with 3×500 mL of saturated aqueous sodium bicarbonate and 3×500 mL of brine. The mixture was dried over anhydrous sodium sulfate and concentrated under vacuum to give 24 g (crude) of 1,2-dichloro-4-(4-iodo-2-methoxyphenoxy)benzene as red oil.

Step 4

A mixture of 1,2-dichloro-4-(4-iodo-2-methoxyphenoxy)benzene (93 g, 235.43 mmol, 1.00 equiv) in 1,4-dioxane (500 mL), potassium acetate (46 g, 469.39 mmol, 1.99 equiv), 4,4,5,5-tetramethyl-2-(4,4,5,5-tetramethyl-1,3,2-dioxaborolan-2-yl)-1,3,2-dioxaborolane (89 g, 350.39 mmol, 1.49 equiv) and Pd(dppf)Cl$_2$ (4.65 g) was stirred overnight at 90° C. under an inert atmosphere of nitrogen. The reaction mixture was cooled to room temperature and concentrated under vacuum. The residue was dissolved in 500 mL of ethyl acetate and washed with mL of water and brine. The mixture was dried over anhydrous sodium sulfate and concentrated under vacuum. The residue was applied onto a silica gel column with ethyl acetate/petroleum ether (1/100) to yield 10 g (11%) of 2-[4-(3,4-dichlorophenoxy)-3-methoxyphenyl]-4,4,5,5-tetramethyl-1,3,2-dioxaborolane as light yellow oil.

2-[4-(3,4-Dichlorophenoxy)-3-methoxyphenyl]-4,4,5,5-tetramethyl-1,3,2-dioxaborolane was then covered to the title compound following the procedures described in Example 19, steps 4-7 above.

Example 21

Synthesis of (R)-2-(3-(4-amino-3-(4-phenoxyphenyl)-1H-pyrazolo[3,4-d]pyrimidin-1-yl) piperidine-1-carbonyl)-4,4-dimethylpent-2-enenitrile

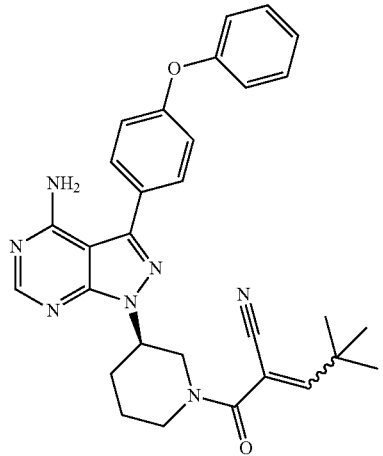 [SMILES: CC(C)(C)C=C(C#N)C(=O)N1CCC[C@@H](n2nc(-c3ccc(Oc4ccccc4)cc3)c3c(N)ncnc32)C1]

A mixture of 3-[3-[4-amino-3-(4-phenoxyphenyl)-1H-pyrazolo[3,4-d]pyrimidin-1-yl]piperidin-1-yl]-3-oxopropanenitrile (150 mg, 0.33 mmol, 1.00 equiv), methanol (15 mL), dichloromethane (5 mL), piperidine (56 mg, 0.66 mmol, 2 equiv) and pivalaldehyde (142 mg, 1.66 mmol, 5 equiv) was stirred for 48 h at 30° C. in a 25-mL sealed tube. The resulting mixture was concentrated under vacuum. The residue was applied onto a silica gel column with dichloromethane/methanol (100/1) to give 45 mg (26%) of (R)-2-(3-(4-amino-3-(4-phenoxyphenyl)-1H-pyrazolo[3,4-d]pyrimidin-1-yl)piperidine-1-carbonyl)-4,4-dimethylpent-2-enenitrile as a white solid. MS (ESI, pos. ion) m/z: 522 (M+1).

Example 22

Synthesis of 2-(2-((4-amino-3-(4-phenoxyphenyl)-1H-pyrazolo[3,4-d]pyrimidin-1-yl)methyl)pyrrolidine-1-carbonyl)-3-cyclopropylacrylonitrile

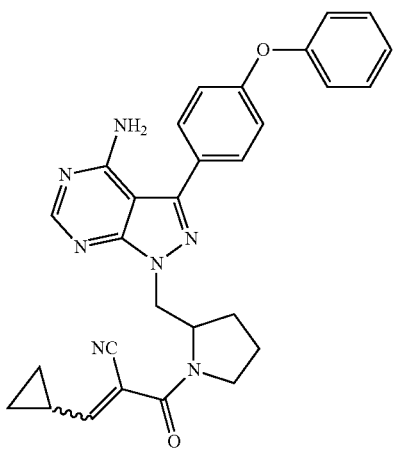 [SMILES: N#CC(=CC1CC1)C(=O)N1CCCC1Cn1nc(-c2ccc(Oc3ccccc3)cc2)c2c(N)ncnc21]

Synthesized as described in Examples 19 above, except using tert-butyl 2-(hydroxymethyl)pyrrolidine-1-carboxylate instead of (S)-tert-butyl 3-hydroxypiperidine-1-carboxylate.

Example 23

Synthesis of 2-(2-((4-amino-3-(4-phenoxyphenyl)-1H-pyrazolo[3,4-d]pyrimidin-1-yl)methyl)pyrrolidine-1-carbonyl)-4,4-dimethylpent-2-enenitrile

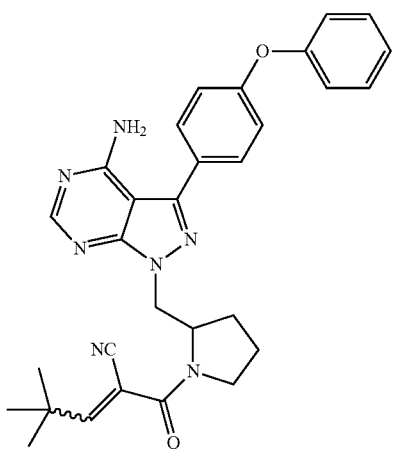 [SMILES: CC(C)(C)C=C(C#N)C(=O)N1CCCC1Cn1nc(-c2ccc(Oc3ccccc3)cc2)c2c(N)ncnc21]

Synthesized as Examples 19 and 21 above but using tert-butyl 2-(hydroxymethyl)-pyrrolidine-1-carboxylate instead of (S)-tert-butyl-3-hydroxypiperidine-1-carboxylate.

Example 24

Synthesis of (EZ)—N-((1r,4r)-4-(4-amino-3-(4-phenoxyphenyl)-1H-pyrazolo[3,4-d]pyrimidin-1-yl)cyclohexyl)-2-cyano-3-cyclopropylacrylamide

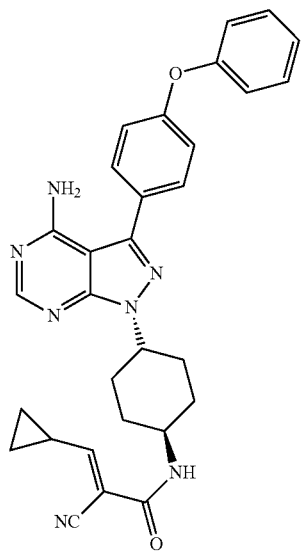

Synthesized as described in Example 19 above except using tert-butyl(1r,4r)-4hydroxycyclohexylcarbamate instead of (S)-tert-butyl 3-hydroxypiperidine-1-carboxylate.

Example 25

Synthesis of (EZ)—N-((1r,4r)-4-(4-amino-3-(4-phenoxyphenyl)-1H-pyrazolo[3,4-d]pyrimidin-1-yl)cyclohexyl)-2-cyano-3-cyclopropylacrylamide

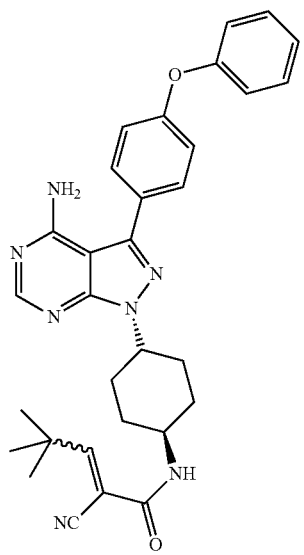

Synthesized as described in Examples 19 and 21 above except using tert-butyl(1r,4r)-4-hydroxycyclohexylcarbamate instead of (S)-tert-butyl 3-hydroxypiperidine-1-carboxylate.

Example 26

Synthesis of (EZ)-2-(4-(4-amino-3-(4-phenoxyphenyl)-1H-pyrazolo[3,4-d]pyrimidin-1-yl)piperidine-1-carbonyl)-3-cyclopropylacrylonitrile

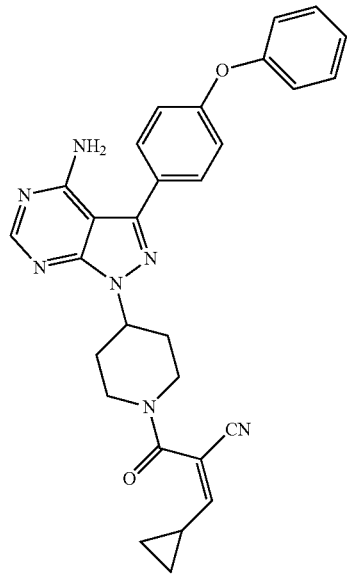 [SMILES: N#C/C(=C/C1CC1)C(=O)N1CCC(n2nc(-c3ccc(Oc4ccccc4)cc3)c3c(N)ncnc32)CC1]

Synthesized as described in Example 19 above except using, tert-butyl 4-hydroxypiperidine-1-carboxylate instead of (S)-tert-butyl 3-hydroxypiperidine-1-carboxylate.

Example 27

Synthesis of 2-(4-(4-amino-3-(4-phenoxyphenyl)-1H-pyrazolo[3,4-d]pyrimidin-1-yl)piperidine-1-carbonyl)-4,4-dimethylpent-2-enenitrile

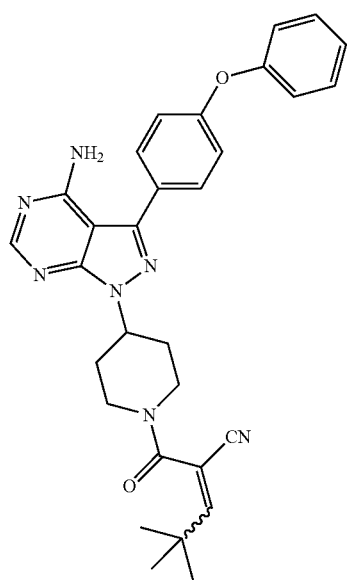 [SMILES: CC(C)(C)C=C(C#N)C(=O)N1CCC(n2nc(-c3ccc(Oc4ccccc4)cc3)c3c(N)ncnc32)CC1]

Synthesized as described in Examples 19 and 20 above except using, tert-butyl4-hydroxypiperidine-1-carboxylate instead of (S)-tert-butyl 3-hydroxypiperidine-1-carboxylate.

Example 28

Synthesis of (R,EZ)-2-(3-(4-amino-3-(4-(3,4-dichlorophenoxy)-3-methoxyphenyl)-1H-pyrazolo[3,4-d]pyrimidin-1-yl)piperidine-1-carbonyl)-4,4-dimethylpent-2-enenitrile

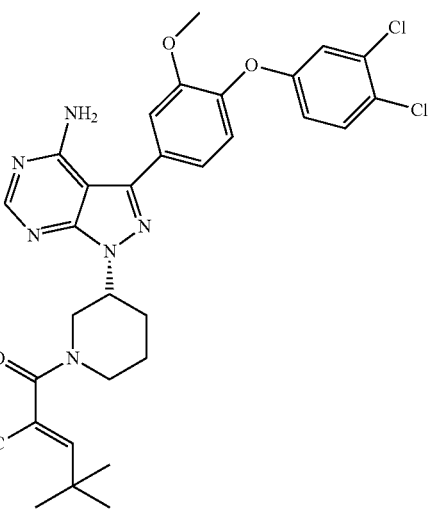

Synthesized as described in Examples 19 and 20 above using 2-(4-(3,4-dichlorophenoxy)-3-methoxyphenyl)-4,4,5,5-tetramethyl-1,3,2-dioxaborolane instead of 4-phenoxyphenylboronic acid.

Example 29

Synthesis of (R)—N-(4-(4-amino-1-(1-(2-cyano-3-cyclopropylacryloyl)piperidin-3-yl)-1H-pyrazolo[3,4-d]pyrimidin-3-yl)phenyl)-4-(trifluoromethyl)benzamide

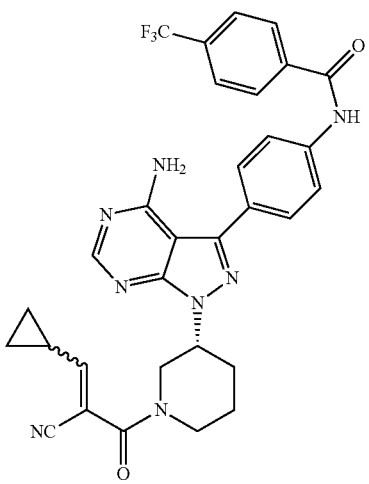 [SMILES: N#CC(=CC1CC1)C(=O)N1CCC[C@@H](n2nc(-c3ccc(NC(=O)c4ccc(C(F)(F)F)cc4)cc3)c3c(N)ncnc32)C1]

Step 1

A mixture of 3-iodo-1H-pyrazolo[3,4-d]pyrimidin-4-amine (5.9 g, 22.6 mmol, 1.00 equiv), (S)-tert-butyl 3-hydroxypiperidine-1-carboxylate (10 g, 50 mmol, 2.2 equiv), triphenylphosphine (11.8 g, 45 mmol, 2 equiv) in tetrahydrofuran (300 mL) was stirred at 10° C. Then Diisopropyl azodicarboxylate in tetrahydrofuran (30 mL) was dropped in the mixture slowly in 30 mins. The resulting mixture was stirred for 12 h at room temperature. The resulting mixture was concentrated under vacuum. The residue was applied onto a silica gel column with dichloromethane/methanol (100/1) to give 3 g (33%) of (R)-tert-butyl 3-(4-amino-3-iodo-1H-pyrazolo[3,4-d]pyrimidin-1-yl)piperidine-1-carboxylate as yellow solid. MS (ESI, pos. ion) m/z: 445 (M+1)

Step 2

Into a 250-mL 3-necked round-bottom flask purged and maintained with an inert atmosphere of nitrogen, was placed tert-butyl 4-[4-amino-3-iodo-1H-pyrazolo[3,4-d]pyrimidin-1-yl]piperidine-1-carboxylate (2 g, 4.50 mmol, 1.00 equiv), 4-boronobenzenaminium chloride (0.934 g), Pd(PPh3)4 (0.312 g), ethylene glycol dimethyl ether (100 mL), sodium carbonate (1.194 g), water (20 mL). The resulting solution was stirred for 12 h at 80° C. in an oil bath. The resulting mixture was concentrated under vacuum. The residue was applied onto a silica gel column with dichloromethane/methanol (50:1). This resulted in 1.5 g (81%) of tert-butyl 4-(4-amino-3-(4-aminophenyl)-1H-pyrazolo[3,4-d]pyrimidin-1-yl)piperidine-1-carboxylate as a brown solid.

Step 3

Into a 250-mL round-bottom flask, was placed tert-butyl 4-[4-amino-3-(4-aminophenyl)-1H-pyrazolo[3,4-d]pyrimidin-1-yl]piperidine-1-carboxylate (1.0 g, 2.44 mmol, 1.00 equiv), HATU (0.746 g), 4-(trifluoromethyl)benzoic acid (374 mg, 1.97 mmol, 0.81 equiv), triethylamine (500 mg, 4.94 mmol, 2.02 equiv), N,N-dimethylformamide (50 mL). The resulting solution was stirred for 5 h at 25° C. The resulting mixture was quenched with 200 mL of water The resulting solution was extracted with 3×200 mL of ethyl acetate and washed with 3×100 mL sodium chloride(sat). The organic layers dried over anhydrous magnesium sulfate and concentrated under vacuum. The residue was applied onto a silica gel column with dichloromethane/methanol (50:1). This resulted in 1.15 g (81%) of tert-butyl 4-[4-amino-3-(4-[[4-(trifluoromethyl)benzene]amido]phenyl)-1H-pyrazolo[3,4-d]pyrimidin-1-yl]piperidine-1-carboxylate as a brown solid.

Step 4

Into a 250-mL round-bottom flask, was placed tert-butyl 3-[4-amino-3-(4-[[4-(trifluoromethyl)benzene]amido]phenyl)-1H-pyrazolo[3,4-d]pyrimidin-1-yl]piperidine-1-carboxylate (1.1 g, 1.89 mmol, 1.00 equiv), dichloromethane (100 mL). This was followed by the addition of CF3COOH (20 mL) dropwise with stirring at 25° C. in 10 min. The resulting solution was stirred for 3 h at 25° C. The resulting mixture was concentrated under vacuum. This resulted in 0.829 g (91%) of N-[4-[4-amino-1-(piperidin-3-yl)-1H-pyrazolo[3,4-d]pyrimidin-3-yl]phenyl]-4-(trifluoromethyl)benzamide as brown oil.

Step 5

Into a 250-mL round-bottom flask, was placed N-[4-[4-amino-1-(piperidin-4-yl)- 1H-pyrazolo[3,4-d]pyrimidin-3-yl]phenyl]-4-(trifluoromethyl)benzamide (828 mg, 1.72 mmol, 1.00 equiv), 2-cyanoacetic acid (220 mg, 2.59 mmol, 1.50 equiv), CDI (420 mg, 2.59 mmol, 1.51 equiv), dichloromethane (80 mL). The resulting solution was stirred for 12 h at 25° C. The resulting mixture was washed with 2×50 mL of NH4Cl. The resulting mixture was concentrated under vacuum. The residue was applied onto a silica gel column with dichloromethane/methanol (50:1). This resulted in 300 mg (32%) of N-(4-[4-amino-1-[1-(2-cyanoacetyl)piperidin-4-yl]-1H-pyrazolo[3,4-d]pyrimidin-3-yl]phenyl)-4-(trifluoromethyl)benzamide as a yellow solid.

Step 6

Into a 10-mL round-bottom flask, was placed N-(4-[4-amino-1-[1-(2-cyanoacetyl)-piperidin-3-yl]-1H-pyrazolo[3,4-d]pyrimidin-3-yl]phenyl)-4-(trifluoromethyl)benzamide (65 mg, 0.12 mmol, 1.00 equiv), cyclopropanecarbaldehyde (16.6 mg, 0.24 mmol, 2.00 equiv), piperidine (10 mg, 0.12 mmol, 0.99 equiv), methanol (5 mL). The resulting solution was stirred for 12 h at 25° C. The resulting mixture was concentrated under vacuum. The residue was applied onto a silica gel column with dichloromethane/methanol (50:1). This resulted in 43 mg (60%) of N-[4-(4-amino-1-[1-[2-cyano-2-(cyclopropylmethylidene)acetyl]piperidin-3-yl]-1H-pyrazolo[3,4-d]pyrimidin-3-yl)phenyl]-4-(trifluoromethyl)benzamide as a white solid. MS (ESI, pos. ion) m/z: 601 (M+1).

Example 30

Preparation of (R)—N-(4-(4-amino-1-(1-(2-cyano-4,4-dimethylpent-2-enoyl)piperidin-3-yl)-1H-pyrazolo[3,4-d]pyrimidin-3-yl)phenyl)-4-(trifluoromethyl)benzamide

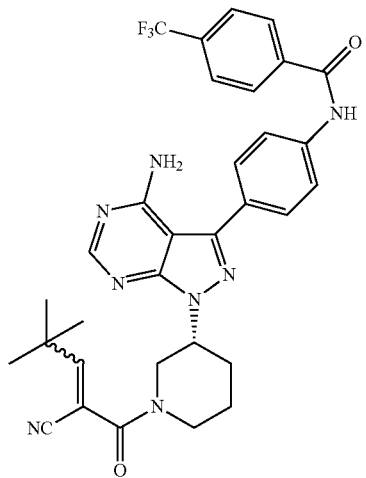 [SMILES: CC(C)(C)C=C(C#N)C(=O)N1CCC[C@@H](n2nc(-c3ccc(NC(=O)c4ccc(C(F)(F)F)cc4)cc3)c3c(N)ncnc32)C1]

Into a 50-mL round-bottom flask, was placed N-(4-[4-amino-1-[1-(2-cyanoacetyl-)piperidin-3-yl]-1H-pyrazolo[3,4-d]pyrimidin-3-yl]phenyl)-4-(trifluoromethyl)benzamide (130 mg, 0.24 mmol, 1.00 equiv), 2,2-dimethylpropanal (2 mL), piperidine (1 mL), methanol (30 mL). The resulting solution was stirred for 24 h at 30° C. in an oil bath. The resulting mixture was concentrated under vacuum. The residue was applied onto a silica gel column with dichloromethane/methanol (50/1). This resulted in 40 mg (27%) of N-[4-(4-amino-1- [1-[2-cyano-2-(2,2-dimethylpropylidene)

acetyl]piperidin-3-yl]-1H-pyrazol[3,4-d]pyrimidin-3-yl)phenyl]-4-(trifluoromethyl)benzamide as a white solid. MS (ESI, pos. ion) m/z: 617 (M+1).

Example 31

Synthesis of N-(3-((6-(2-chlorophenyl)-8-methyl-7-oxo-7,8-dihydropyrido[2,3-d]pyrimidin-2-yl)-amino)phenyl)-2-cyano-3-cyclopropylacrylamide

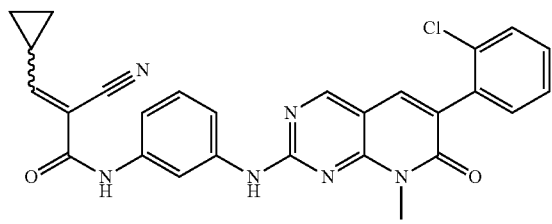 [SMILES: Cn1c(=O)c(-c2ccccc2Cl)cc2cnc(Nc3cccc(NC(=O)C(C#N)=CC4CC4)c3)nc21]

Step 1

To a solution of ethyl 4-chloro-2-(methylthio)pyrimidine-5-carboxylate (10 g, 42.98 mmol, 1.0 eq) in THF (100 mL) at 0° C. was added methylamine (43 mL, 86.0 mmol, 2 eq, 2M in THF). The resulted mixture was stirred at room temperature for 1 h. The solvent was removed and the residue dissolved in EtOAc and then washed with brine, dried and concentrated to afford ethyl 4-(methylamino)-2-(methylthio)pyrimidine-5-carboxylate as a brown solid (9.0 g, 92% in yield).

Step 2

LiAlH$_4$ (4.0 g, 106.0 mmol, 4.0 eq.) was added to anhydrous THF (100.0 mL) at −20° C. Ethyl 4-(methylamino)-2-(methylthio)pyrimidine-5-carboxylate (6.0 g, 26.4 mmol, 1 eq.) was dissolved in 20 mL of THF and added to the suspension of LiAlH$_4$ at the rate to maintain reaction temperature between −20 to 5° C. The mixture was then stirred at 0° C. for 1 h. The mixture was cooled to −15° C. and a solution of NaOH (2.0 g) in 20 ml of water was added at the rate to maintain temperature under 10° C. After completion of addition, the mixture was stirred for 12 h at room temperature. The precipitate was collected by filtration, washed with hot THF until TLC showed no compound in washings. Concentration of the filtrate afforded (4-(methylamino)-2-(methylthio)pyrimidin-5-yl)methanol as a white solid (4.0 g, 82% in yield).

Step 3

MnO$_2$ (13.0 g, 151.1 mmol, 7.0 eq.) was added to a solution of 4-(methylamino)-2-(methylthio)-pyrimidin-5-yl)-methanol (4.0 g, 21.6 mmol, 1.0 eq) in CH$_2$Cl$_2$ (200 mL). The resulted mixture was stirred for 12 h at room temperature, filtered and concentrated to afford 4-(methylamino)-2-(methylthio)pyrimidine-5-carbaldehyde (3.0 g, 76% in yield).

Step 4

DBU (4.1 g, 26.9 mmol, 1.2 eq) was added to a mixture of 4-(methylamino)-2-(methylthio)-pyrimidine-5-carbaldehyde (4.1 g, 22.4 mmol, 1.0 eq) and ethyl 2-(2-chlorophenyl) acetate (5.4 g, 26.9 mmol, 1.2 eq) at RT. The resulting mixture was then stirred at room temperature for 1 h, followed by addition of water and extraction with EtOAc. The combined organic layers were dried and concentrated to afford 6-(2-chlorophenyl)-8-methyl-2-(methylthio)pyrido[2,3-d]pyrimidin-7(8H)-one (5.0 g, 70% in yield).

Step 5

To a solution of 6-(2-chlorophenyl)-8-methyl-2-(methylthio)pyrido[2,3-d]pyrimidin-7(8H)-one (2.0 g, 6.29 mmol, 1.0 eq) in DCM (20 mL) at 0° C. was added m-CPBA (2.56 g, 12.59 mmol, 2.0 eq). The resulted mixture was then stirred at room temperature for 12 h. The reaction solution was washed with saturated NaHSO$_3$ and dried to afford 6-(2-chlorophenyl)-8-methyl-2-(methylsulfinyl)pyrido[2,3-d]pyrimidin-7(8H)-one (2.0 g, 95% in yield).

Step 6

A solution of 6-(2-chlorophenyl)-8-methyl-2-(methylsulfinyl)pyrido[2,3-d]pyrimidin-7(8H)-one (0.2 g) and benzene-1,3-diamine (0.2 g) in CH$_2$Cl$_2$ (5 mL) was concentrated to remove DCM, the resulted mixture was then stirred at 140° C. for 0.5 h. The residue was then purified by preparative TLC to afford 2-(3-aminophenylamino)-6-(2-chlorophenyl)-8-methylpyrido[2,3-d]pyrimidin-7(8H)-one (0.15 g, 66% in yield).

Step 7

To the solution of 2-(3-aminophenylamino)-6-(2-chlorophenyl)-8-methylpyrido[2,3-d]-pyrimidin-7(8H)-one (0.1 g, 0.26 mmol, 1.0 eq), 2-cyano-3-cyclopropylacrylic acid (0.043 g, 0.31 mmol, 1.2 eq) in CH$_2$Cl$_2$ (1 mL) was added HATU (0.13 g, 0.16 mmol, 1.3 eq) and DIEA (0.055 g, 0.24 mmol, 2.0 eq). The resulted mixture was stirred at room temperature for 2 h. Solvent was removed and the residue was purified by preparative TLC (10% MeOH in DCM) to afford the title compound as a white solid (0.015 g, 17% in yield). LCMS m/z 497.1 (M+H)$^+$.

Example 32

Synthesis of N-(3-(6-(2-chlorophenyl)-8-methyl-7-oxo-7,8-dihydropyrido[2,3-d]pyrimidin-2-ylamino)-benzyl)-2-cyano-3-cyclopropylacrylamide

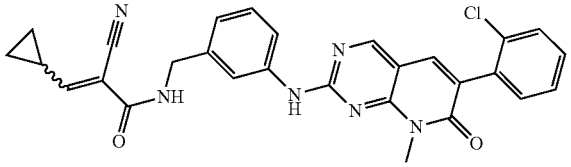 [SMILES: Cn1c(=O)c(-c2ccccc2Cl)cc2cnc(Nc3cccc(CNC(=O)C(C#N)=CC4CC4)c3)nc21]

Step 1

A solution of 6-(2-chlorophenyl)-8-methyl-2-(methylsulfinyl)pyrido[2,3-d]pyrimidin-7(8H)-one (0.2 g) and tert-butyl 3-aminobenzylcarbamate (0.1 g) in NMP (1 mL) was stirred at 140° C. for 1 h. LCMS showed completion of reaction and the reaction was purified by preparative TLC to afford tert-butyl 3-(6-(2-chlorophenyl)-8-methyl-7-oxo-7,8-dihydropyrido[2,3-d]pyrimidin-2-ylamino)benzylcarbamate (150 mg, 51% in yield).

Step 2

To a solution of tert-butyl 3-(6-(2-chlorophenyl)-8-methyl-7-oxo-7,8-dihydropyrido[2,3-d]-pyrimidin-2-yl-amino)benzylcarbamate (0.15 g) in DCM (1 mL) at room temperature was added TFA (1 mL) and stirring was continued for 0.5 h. The mixture was concentrated to remove TFA, $CH_2Cl_2$ (50 mL) was added and washed with saturated $NaHCO_3$. The organic layer was dried and concentrated to afford 2-(3-(aminomethyl)phenylamino)-6-(2-chlorophenyl)-8-methylpyrido[2,3-d]pyrimidin-7(8H)-one (120 mg, 100% in yield).

Step 3

To the solution of 2-(3-(aminomethyl)phenylamino)-6-(2-chlorophenyl)-8-methylpyrido-[2,3-d]pyrimidin-7(8H)-one (0.1 g, 0.26 mmol, 1.0 eq), 2-cyano-3-cyclopropylacrylic acid (0.041 g, 0.30 mmol, 1.2 eq) in DCM (2 mL) was added HATU (0.13 g, 0.33 mmol, 1.3 eq) and DIEA (0.053 g, 0.50 mmol, 2.0 eq). The resulted mixture was stirred at room temperature for 2 h. Solvent was removed and the residue was purified by preparative TLC (eluted with 10% MeOH in DCM) to afford 6-(2-chlorophenyl)-8-methyl-2-(methylsulfinyl)pyrido[2,3-d]pyrimidin-7(8H)-one (50 mg, 38% in yield). LCMS m/z 511.2 (M+H)+.

Example 33

Synthesis of N-(3-(6-(2-chlorophenyl)-8-methyl-7-oxo-7,8-dihydropyrido[2,3-d]pyrimidin-2-ylamino)-benzyl)-2-cyano-3-cyclopropyl-N-methylacrylamide

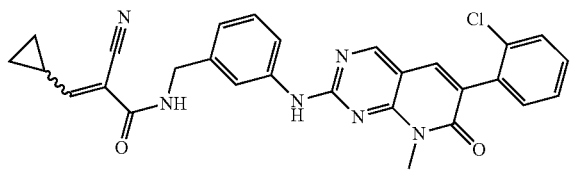 [SMILES: Cn1c(=O)c(-c2ccccc2Cl)cc2cnc(Nc3cccc(CNC(=O)C(C#N)=CC4CC4)c3)nc21]

Step 1

A solution of 6-(2-chlorophenyl)-8-methyl-2-(methylsulfinyl)pyrido[2,3-d]pyrimidin-7(8H)-one (0.1 g) and tert-butyl 3-aminobenzyl(methyl)carbamate (0.1 g) in DCM (5 mL) was concentrated to remove $CH_2Cl_2$. The resulted mixture was then stirred at 140° C. for 0.5 h. The mixture was purified by preparative TLC to afford tert-butyl 3-(6-(2-chlorophenyl)-8-methyl-7-oxo-7,8-dihydropyrido-[2,3-d]pyrimidin-2-ylamino)benzyl (methyl)carbamate (100 mg, 66% in yield).

Step 2

To a solution of tert-butyl 3-(6-(2-chlorophenyl)-8-methyl-7-oxo-7,8-dihydropyrido-[2,3-d]pyrimidin-2-ylamino)benzyl (methyl)carbamate (0.1 g) in DCM (1 mL) at room temperature, was added TFA (1 mL) and stirred for 0.5 h. LCMS showed completion of reaction. The mixture was concentrated to remove TFA, DCM (50 mL) was added and washed with saturated $NaHCO_3$. The organic layer was dried and concentrated to afford 6-(2-chlorophenyl)-8-methyl-2-(3-((methylamino)-methyl)phenylamino)pyrido[2,3-d]pyrimidin-7(8H)-one (50 mg, 61% in yield).

Step 3

To the solution of 6-(2-chlorophenyl)-8-methyl-2-(3-((methylamino)methyl)phenylamino) pyrido[2,3-d]pyrimidin-7(8H)-one (0.1 g, 0.25 mmol, 1.0 eq), 2-cyano-3-cyclopropyl acrylic acid (0.041 g, 0.30 mmol, 1.2 eq) in DCM (2 mL) was added HATU (0.13 g, 0.33 mmol, 1.3 eq) and DIEA (0.053 g, 0.50 mmol, 2.0 eq). The resulted mixture was stirred at room temperature for 2 h. Solvent was removed and the residue was purified by preparative TLC (eluted with 10% MeOH in DCM) affording the title product (17 mg, 13% in yield). LCMS m/z 525.2 (M+H)+.

Example 34

Synthesis of 2-(5-(6-(2-chlorophenyl)-8-methyl-7-oxo-7,8-dihydropyrido[2,3-d]-pyrimidin-2-ylamino)-1,2,3,4-tetrahydroisoquinoline-2-carbonyl)-3-cyclopropylacrylonitrile

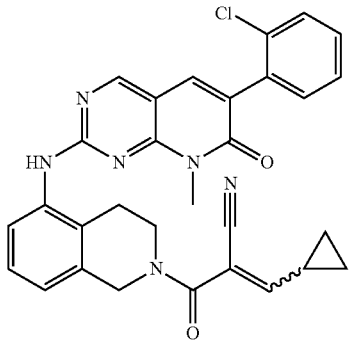 [SMILES: Cn1c(=O)c(-c2ccccc2Cl)cc2cnc(Nc3cccc4c3CCN(C(=O)C(C#N)=CC3CC3)C4)nc21]

Step 1

A solution of 6-(2-chlorophenyl)-8-methyl-2-(methylsulfinyl)pyrido[2,3-d]pyrimidin-7(8H)-one (0.2 g) and tert-butyl 5-amino-3,4-dihydroisoquinoline-2(1H)-carboxylate (0.2 g) in DCM (5 mL) was concentrated to remove DCM. The resulted mixture was then stirred at 140° C. for 0.5 h. LCMS showed completion of reaction and the mixture was purified by preparative TLC to afford tert-butyl 5-(6-(2-chlorophenyl)-8-methyl-7-oxo-7,8-dihydropyrido[2,3-d]pyrimidin-2-ylamino)-3,4-dihydroisoquinoline-2(1H)-carboxylate (150 mg, 48% in yield).

Step 2

To a solution of tert-butyl 5-(6-(2-chlorophenyl)-8-methyl-7-oxo-7,8-dihydropyrido[2,3-d]-pyrimidin-2-ylamino)-3,4-dihydroisoquinoline-2(1H)-carboxylate (0.1 g) in DCM (1 mL) at room temperature was added TFA (1 mL) and stirred for 0.5 h. The mixture was concentrated to remove TFA, DCM was added and washed with saturated $NaHCO_3$. The organic layer was dried and concentrated to afford 6-(2-chlorophenyl)-8-methyl-2-(1,2,3,4-tetrahydroisoquinolin-5-ylamino)pyrido[2,3-d]-pyrimidin-7(8H)-one (50 mg, 63% in yield).

Step 3

To the solution of 6-(2-chlorophenyl)-8-methyl-2-(1,2,3,4-tetrahydroisoquinolin-5-ylamino)pyrido-[2,3-d]pyrimidin-7(8H)-one (0.05 g, 0.12 mmol, 1.0 eq), 2-cyano-3-cyclopropylacrylic acid (0.02 g, 0.14 mmol, 1.2 eq) in DCM (1 mL) was added HATU (0.06 g, 0.16 mmol, 1.3 eq) and DIEA (0.025 g, 0.24 mmol, 2.0 eq). The resulted mixture was stirred at room temperature for 2 h. Solvent was removed and the residue was purified by preparative TLC (eluted with 10% MeOH in DCM) to afford the title compound as a white solid. LCMS m/z 537.3 (M+H)+.

Example 35

Synthesis of 2-cyano-3-cyclopropyl-N-(3-(2-(4-morpholinophenylamino)-pyrimidin-4-ylamino)phenyl)acrylamide

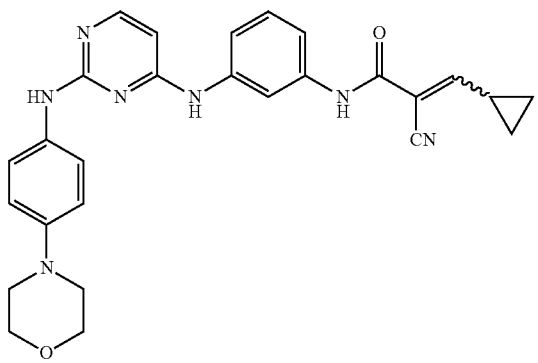 [SMILES: N#CC(=CC1CC1)C(=O)Nc1cccc(Nc2ccnc(Nc3ccc(N4CCOCC4)cc3)n2)c1]

Step 1

A mixture of 2,4-dichloropyrimidine (5.0 g, 33.56 mmol), 3-nitroaniline (4.65 g, 33.56 mmol) and EtN($^i$Pr)$_2$ (11.56 g, 100.68 mmol) in 100 ml of iPrOH was heated at reflux overnight. The mixture was diluted with H$_2$O, filtered to give a solid which was purified by silica gel column eluted with 25% EtOAc in petroleum ether to give 2-chloro-N-(3-nitrophenyl)pyrimidin-4-amine as a yellow solid (1 g, 12%).

Step 2

A mixture of 2-chloro-N-(3-nitrophenyl)pyrimidin-4-amine (500 mg, 1.99 mmol), 4-morpholinoaniline (356 mg, 1.99 mmol) in 10 mL of i-PrOH was added CF$_3$CO$_2$H (228 mg, 1.99 mmol) and the mixture was heated at reflux overnight. The mixture was cooled to RT and filtered, and the solid was washed with EtOAc to give N$^2$-(4-morpholinophenyl)-N$^4$-(3-nitrophenyl)pyrimidine-2,4-diamine (700 mg).

Step 3

A mixture of N$^2$-(4-morpholinophenyl)-N$^4$-(3-nitrophenyl)pyrimidine-2,4-diamine (700 mg, 1.78 mmol) and 10% Pd/C (200 mg) in 150 mL of methanol was hydrogenated under 1 atm overnight, the catalyst was removed, the filtrate was evaporated to give N$^4$-(3-aminophenyl)-N$^2$-(4-morpholinophenyl) pyrimidine-2,4-diamine (500 mg, 77%).

Step 4

To a solution of N$^4$-(3-aminophenyl)-N$^2$-(4-morpholinophenyl)pyrimidine-2,4-diamine (500 mg, 1.38 mmol) and Et$_3$N (279 mg, 2.76 mmol) in 20 ml of DCM at 0° C. was added 2-cyanoacetyl chloride (171 mg, 1.66 mmol) and then the mixture was stirred for 1 h at RT. The mixture was washed with water, evaporated to dryness and purified by silica gel column eluted with 50% EtOAc in petroleum ether to give 2-cyano-N-(3-(2-(4-morpholinophenylamino)pyrimidin-4-ylamino)phenyl)acetamide (400 mg, 68%).

Step 5

A mixture of 2-cyano-N-(3-(2-(4-morpholinophenylamino)pyrimidin-4-ylamino)phenyl)acetamide (100 mg, 0.23 mmol), cyclopropanecarbaldehyde (25 mg, 0.35 mmol) and piperidine acetic acid (7 mg, 0.046 mmol) in 5 ml of EtOH was heated at reflux for 2 h. The mixture was cooled to RT, evaporated, and dissolved in EtOAc, the solution was washed with water, dried over Na$_2$SO$_4$, evaporated and purified by silica gel column eluted with 50% EtOAc in petroleum ether to afford the title compound (47 mg. 42%). LCMS m/z 482 (M+H)+.

Example 36

Synthesis of 3-cyclopropyl-2-(3-(5-fluoro-2-(6-(4-methylpiperazin-1-yl)pyridin-3-ylamino) pyrimidin-4-ylamino)piperidine-1-carbonyl)acrylonitrile

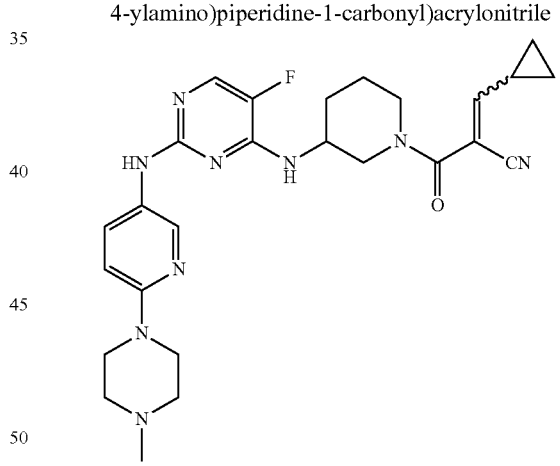

Step 1

A solution of 2,4-dichloro-5-fluoropyrimidine (2.70 g) and DIPEA (4.18 g) in THF (40 mL) at −78° C. was added tert-butyl 3-aminopiperidine-1-carboxylate (3.40 g). The resulted mixture was then stirred at RT overnight. The mixture was concentrated and purified on silica gel (eluting with 10% EtOAc in Petroleum ether) to afford tert-butyl 3-(2-chloro-5-fluoropyrimidin-4-ylamino)-piperidine-1-carboxylate as a clear oil (4.2 g, 78% in yield).

Step 2

To a solution of tert-butyl 3-(2-chloro-5-fluoropyrimidin-4-ylamino)piperidine-1-carboxylate (400 mg, 1.21 mmol)

and 6-(4-methylpiperazin-1-yl)pyridin-3-amine (235 mg, 1.21 mmol) in 12 mL of iPrOH was added TFA (50 mg, 0.09 mmol), the resulted mixture was heated to reflux overnight. The mixture was cooled to RT and evaporated to dryness to give tert-butyl 3-((5-fluoro-2-((6-(4-methylpiperazin-1-yl)-pyridin-3-yl)amino)pyrimidin-4-yl)amino)piperidine-1-carboxylate as a brown solid which was used directly for the next step.

Step 3

A solution of tert-butyl 3-((5-fluoro-2-((6-(4-methylpiperazin-1-yl)pyridin-3-yl)amino)-pyrimidin-4-yl)amino)piperidine-1-carboxylate (600 mg, 1.21 mmol) in 10 mL of HCl/MeOH was stirred at RT for 2 h. The reaction was concentrated to dryness to give 5-fluoro-N2-(6-(4-methyl-piperazin-1-yl)-pyridin-3-yl)-N4-(piperidin-3-yl)pyrimidine-2,4-diamine which was used for the next step directly.

Step 4

To a solution of 5-fluoro-N2-(6-(4-methylpiperazin-1-yl)pyridin-3-yl)-N4-(piperidin-3-yl)-pyrimidine-2,4-diamine (600 mg, 1.21 mmol) in 5 mL of ethyl 2-cyanoacetate was added 1 mL of DBU and the resulting reaction mixture was stirred at RT overnight. The mixture was purified by preparative TLC (eluting with 10% of MeOH in DCM) to give 3-(3-(5-fluoro-2-(6-(4-methyl-piperazin-1-yl)-pyridin-3-ylamino)pyrimidin-4-ylamino)piperidin-1-yl)-3-oxopropanenitrile (150 mg, yield: 28%) as an oil.

Step 5

To a solution of 3-(3-(5-fluoro-2-(6-(4-methylpiperazin-1-yl)pyridin-3-ylamino)-pyrimidin-4-yl-amino)piperidin-1-yl)-3-oxopropanenitrile (150 mg, 0.33 mmol) in 10 ml of EtOH was added cyclopropanecarbaldehyde (232 mg, 3.3 mmol) and the resulted mixture was heated to reflux for 4 h. The mixture was cooled to RT and evaporated to dryness and purified by preparative TLC (eluting with 10% of MeOH in DCM) to afforded 25 mg the title compound (15% yield). LCMS: m/z 506.0 (M+H)+.

Example 37

Synthesis of 3-cyclopropyl-2-[2-({5-fluoro-2-[6-(4-methyl-piperazin-1-yl)-pyridin-3-ylamino]-pyrimidin-4-ylamino}-methyl)-pyrrolidine-1-carbonyl]-acrylonitrile

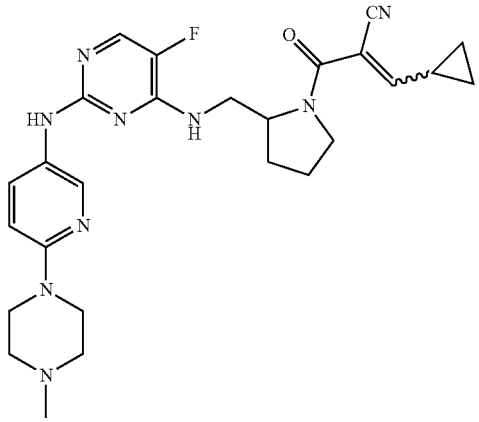 [SMILES: CN1CCN(c2ccc(Nc3ncc(F)c(NCC4CCCN4C(=O)C(C#N)=CC4CC4)n3)cn2)CC1]

Step 1

To a solution of tert-butyl 2-((2-chloro-5-fluoropyrimidin-4-ylamino)methyl)-pyrrolidine-1-carboxylate (600 mg, 1.81 mmol) and 6-(4-methylpiperazin-1-yl)pyridin-3-amine (419 mg, 0.36 mmol) in 5 ml of n-BuOH was added TFA (60 mg, 0.54 mmol) and the resulting mixture was heated to reflux overnight. The mixture was cooled to room temperature. The mixture was evaporated to dryness to give the crude product which was purified by prep TLC to give 2-({5-fluoro-2-[6-(4-methyl-piperazin-1-yl)-pyridin-3-ylamino]-pyrimidin-4-ylamino}-methyl)-pyrrolidine-1-carboxylic acid tert-butyl ester (330 mg, 37% in yield).

Step 2

A solution of 2-({5-fluoro-2-[6-(4-methyl-piperazin-1-yl)-pyridin-3-ylamino]-pyrimidin-4-ylamino}-methyl)-pyrrolidine-1-carboxylic acid tert-butyl ester (330 mg, 0.68 mmol) in HCl/MeOH (10 ml) was stirred for 30 min. The resulting mixture was concentrated to give a residue which was washed with saturated NaHCO3 solution, extracted with DCM, dried over Na2SO4, concentrated to give 5-fluoro-N2-(6-(4-methylpiperazin-1-yl)pyridin-3-yl)-N4-(pyrrolidin-2-ylmethyl)-pyrimidine-2,4-diamine (160 mg, 62% in yield).

Step 3

A solution of 5-fluoro-N2-(6-(4-methylpiperazin-1-yl)pyridin-3-yl)-N4-(pyrrolidin-2-ylmethyl)-pyrimidine-2,4-diamine (160 mg, 0.41 mmol), 2-cyanoacetic acid (42.5 mg, 0.5 mmol), HATU (234 mg, 0.615 mmol) and DIEA (106 mg, 0.82 mmol) in 5 mL of DCM was stirred for 2 h. The mixture was washed with H2O and extracted with DCM, dried over Na2SO4, concentrated to give the residue which was purified by TLC to give 3-[2-({5-fluoro-2-[6-(4-methyl-piperazin-1-yl)-pyridin-3-ylamino]-pyrimidin-4-ylamino}-methyl)-pyrrolidin-1-yl]-3-oxo-propionitrile (50 mg, 35.4% in yield).

Step 4

A solution of 3-[2-({5-fluoro-2-[6-(4-methyl-piperazin-1-yl)-pyridin-3-ylamino]-pyrimidin-4-ylamino}-methyl)-pyrrolidin-1-yl]-3-oxo-propionitrile (50 mg, 0.11 mmol), cyclopropanecarbaldehyde (9.25 mg, 0.13 mmol) and piperidine acetate (48 mg, 0.33 mmol) in EtOH (10 mL) was heated at reflux for 18 h. The mixture was concentrated and purified by prep-TLC to afford the title compound (13 mg, 23.3% in yield). LCMS: m/z 506.1 (M+H)+.

Example 38

Synthesis of 3-cyclopropyl-2-(3-(5-fluoro-2-(6-morpholinopyridin-3-ylamino)pyrimidin-4-ylamino)-piperidine-1-carbonyl)acrylonitrile

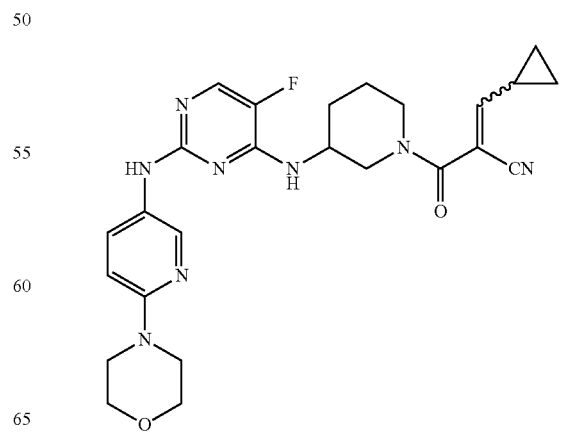

Step 1

To a solution of tert-butyl 3-(2-chloro-5-fluoropyrimidin-4-ylamino)piperidine-1-carboxylate (400 mg, 1.20 mmol) and 6-morpholinopyridin-3-amine (260 mg, 1.44 mmol) in 13 mL of isopropylamine was added TFA (100 mg, 0.09 mmol) and the resulted mixture was heated to reflux overnight. The mixture was cooled to RT. Then the mixture was evaporated to dryness to give 3-(5-fluoro-2-(6-morpholinopyridin-3-yl-amino)-pyrimidin-4-ylamino)piperidine-1-carboxylate as a brown solid which was used for the next step without further purification.

Step 2

A mixture of tert-butyl 3-(5-fluoro-2-(6-morpholinopyridin-3-ylamino)pyrimidin-4-ylamino)-piperidine-1-carboxylate (500 mg, 1.06 mmol) in 10 mL of 4M HCl/MeOH was stirred at room temperature for 3 h. The mixture was evaporated to dryness, the residue was dissolved in 10 ml of water, basified by addition of NaHCO$_3$, then extracted with 10% MeOH in DCM. The organic layer was evaporated to dryness to give 5-fluoro-N2-(6-morpholinopyridin-3-yl)-N4-(piperidin-3-yl)pyrimidine-2,4-diamine which was subjected to the next step without any further purification.

Step 3

To a mixture of 5-fluoro-N2-(6-morpholinopyridin-3-yl)-N4-(piperidin-3-yl)pyrimidine-2,4-diamine (100 mg, 0.27 mmol), 2-cyanoacetic acid (27 mg, 0.32 mmol) and DIPEA (104 mg, 0.80 mmol) in 15 mL DCM was added HATU (153 mg, 0.40 mmol), then the mixture was stirred for 5 h at RT under N$_2$. The mixture was evaporated to dryness and purified by preparative TLC to give 3-(3-(5-fluoro-2-(6-morpholinopyridin-3-ylamino)pyrimidin-4-ylamino)piperidin-1-yl)-3-oxopropanenitrile (40 mg, 34%).

Step 4

A mixture of 3-(3-(5-fluoro-2-(6-morpholinopyridin-3-ylamino)pyrimidin-4-ylamino)-piperidin-1-yl)-3-oxopropanenitrile (200 mg, 0.46 mmol), cyclopropanecarbaldehyde (64 mg, 0.92 mmol) and piperidine acetate (6 mg, 0.046 mmol) in 15 mL of THF was heated at reflux for 1 h. The mixture was cooled to RT and evaporated, the residue was purified by preparative TLC (eluted with EtOAc) to afford the title compound (65 mg, 29%). LCMS m/z 493.2 (M+H)$^+$.

Example 39

Synthesis of 3-cyclopropyl-2-(2-(((5-fluoro-2-((6-morpholinopyridin-3-yl)amino)pyrimidin-4-yl)-amino)methyl)pyrrolidine-1-carbonyl)acrylonitrile

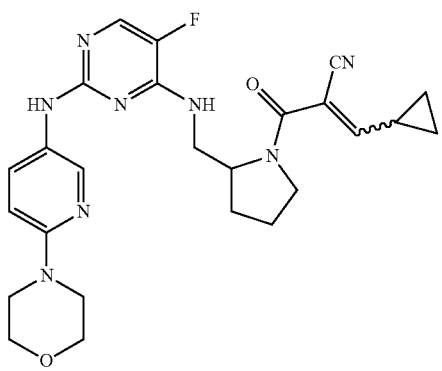 [SMILES: N#CC(=CC1CC1)C(=O)N1CCCC1CNc1nc(Nc2ccc(N3CCOCC3)nc2)ncc1F]

Step 1

A mixture of 2,4-dichloro-5-fluoropyrimidine (2500 mg, 14.9 mmol) and tert-butyl 2-(aminomethyl)-pyrrolidine-1-carboxylate (3244 mg, 16.2 mmol) in THF (50 mL) cooled to 0° C. was added DIPEA (2416 mg, 18.7 mmol) slowly. The mixture was stirred for 0.5 h at 0° C. and then warmed to room temperature and stirred for another 1 h. TLC showed completion of reaction. The reaction mixture was concentrated and the residue was taken up in CH$_2$Cl$_2$ and washed with saturated NH$_4$Cl solution. The separated organic layer was dried over anhydrous Na$_2$SO$_4$, filtered and concentrated to give crude tert-butyl 2-((2-chloro-5-fluoropyrimidin-4-ylamino)methyl)pyrrolidine-1-carboxylate (4.9 g).

Step 2

A mixture of tert-butyl 2-((2-chloro-5-fluoropyrimidin-4-ylamino)methyl)pyrrolidine-1-carboxylate (331 mg, 1.0 mmol) and 6-morpholinopyridin-3-amine (197 mg, 1.1 mmol) in n-BuOH (5 mL) was cooled to 0° C. and then TFA (57 mg, 0.5 mmol) was added slowly. The mixture was heated to 120° C. for 4 h. The reaction mixture was concentrated and the residue was purified by preparative TLC to give tert-butyl 2-((5-fluoro-2-(6-morpholinopyridin-3-ylamino)pyrimidin-4-ylamino)methyl)pyrrolidine-1-carboxylate (380 mg).

Step 3

HCl/MeOH (3 mL, 4 N) was added to tert-butyl 2-((5-fluoro-2-(6-morpholinopyridin-3-ylamino)-pyrimidin-4-ylamino)methyl)pyrrolidine-1-carboxylate (380 mg, 0.80 mmol) at 0° C. slowly. The mixture was stirred for 0.5 h 0° C. and then warmed to room temperature and stirred for another 1 h. The resulting yellow solid was filtered and washed with EtOAc. The solid was dissolved in 0.5N NaOH (pH=8) and extracted with CH$_2$Cl$_2$. The combined organic layers were dried over anhydrous Na$_2$SO$_4$, filtered and concentrated to give 5-fluoro-N2-(6-morpholinopyridin-3-yl)-N4-(pyrrolidin-2-ylmethyl)-pyrimidine-2,4-diamine (250 mg).

Step 4

To a mixture of 5-fluoro-N2-(6-morpholinopyridin-3-yl)-N4-(pyrrolidin-2-ylmethyl)-pyrimidine-2,4-diamine (200 mg, 0.52 mmol), 2-cyanoacetic acid (48 mg, 0.57 mmol) and HATU (290 mg, 0.78 mmol) in CH$_2$Cl$_2$ (5 mL) at 0° C. was added DIEPA (200 mg, 0.16 mmol) slowly. The mixture was stirred for 0.5 h at room temperature. The solvent was removed and purified by preparative TLC to give 3-(2-((5-fluoro-2-(6-morpholinopyridin-3-ylamino)pyrimidin-4-ylamino)methyl)-pyrrolidin-1-yl)-3-oxopropanenitrile (80 mg, 33% yield).

Step 5

A mixture of 3-(2-((5-fluoro-2-(6-morpholinopyridin-3-ylamino)pyrimidin-4-ylamino)methyl)-pyrrolidin-1-yl)-3-oxopropanenitrile (80 mg, 0.18 mmol), cyclopropanecarbaldehyde (25 mg, 0.36 mol) and piperidine acetate (78 mg, 0.54 mmol) in anhydrous EtOH (1.5 mL) was heated to reflux for 5 h. After cooling, the solvent was removed and the obtained residue was purified by preparative TLC (EA/PE=2/1) to give the title compound (24 mg, 27% yield). LCMS: m/z, 493.2 (M+H)$^+$.

Example 40

Synthesis of 3-cyclopropyl-2-(3-((5-fluoro-2-(phenylamino)pyrimidin-4-yl)amino)piperidine-1-carbonyl)acrylonitrile

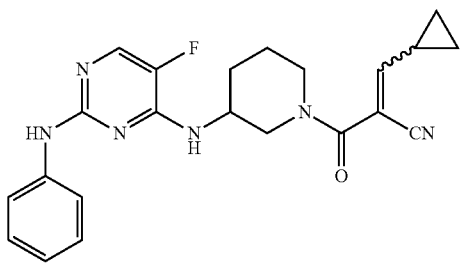 [SMILES: N#CC(=CC1CC1)C(=O)N1CCCC(Nc2nc(Nc3ccccc3)ncc2F)C1]

Step 1

To a solution of 2,4-dichloro-5-fluoropyrimidine (2.70 g) and DIPEA (4.18 g) in THF (40 mL) at −78° C. was added tert-butyl 3-aminopiperidine-1-carboxylate (3.40 g). The resulted mixture was stirred at RT overnight. The mixture was concentrated and purified on silica gel (eluting with 10% EA in PE) to afford tert-butyl 3-(2-chloro-5-fluoropyrimidin-4-ylamino)piperidine-1-carboxylate as a clear oil (4.2 g, 78% in yield).

Step 2

To a solution of tert-butyl 3-(2-chloro-5-fluoropyrimidin-4-ylamino)piperidine-1-carboxylate (0.5 g) in DIPEA (10 mL) was added aniline (0.6 g) and TFA. The mixture was stirred at 100° C. for 48 h. The mixture was concentrated and purified by preparative TLC (eluted with 5% MeOH in DCM) to afford tert-butyl 3-(5-fluoro-2-(phenylamino)pyrimidin-4-ylamino)piperidine-1-carboxylate as a yellow solid (500 mg, 87% in yield).

Step 3

To a solution of tert-butyl 3-(5-fluoro-2-(phenylamino)pyrimidin-4-ylamino)piperidine-1-carboxylate (0.5 g) in DCM (3 mL) was added TFA (1.5 mL). The mixture was stirred at RT for 1 h. The solvent was removed under reduced pressure. Saturated NaHCO$_3$ and DCM was added to the residue. The organic layer was dried and concentrated to afford 5-fluoro-N$^2$-phenyl-N$^4$-(piperidin-3-yl)pyrimidine-2,4-diamine as a white solid (300 mg, 81% in yield).

Step 4

To a solution of 5-fluoro-N$^2$-phenyl-N$^4$-(piperidin-3-yl)pyrimidine-2,4-diamine (0.15 g) and cyanoacetic acid ethyl ester (1.0 mL) in DCM (10 mL) was added and DBU (0.1 mL). The mixture was stirred at RT for 12 h. Solvent was removed and purified by preparative TLC (50% EA in PE) to afford 3-(3-(5-fluoro-2-(phenylamino)pyrimidin-4-ylamino)piperidin-1-yl)-3-oxopropanenitrile as a white solid (100 mg, 54% in yield).

Step 5

To a solution of 3-(3-(5-fluoro-2-(phenylamino)pyrimidin-4-ylamino)piperidin-1-yl)-3-oxopropanenitrile (0.1 g) in EtOH (5 mL) was added cyclopropanecarbaldehyde (0.1 g) and piperidine acetate (5 mg). The resulted solution was stirred at 70° C. for 2 h. The mixture was concentrated and purified by preparative TLC (50% EtOAc in PE) to afford the title compound. LCMS: m/z 407.2 (M+H)$^+$.

Example 41

Synthesis of 3-cyclopropyl-2-(2-(((5-fluoro-2-(phenylamino)pyrimidin-4-yl)amino)methyl)-pyrrolidine-1-carbonyl)acrylonitrile

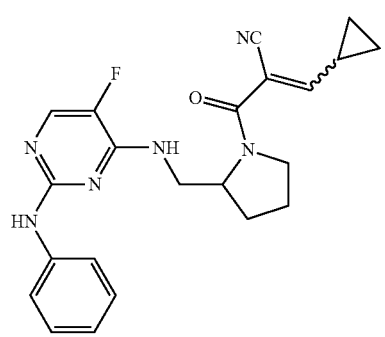 [SMILES: N#CC(=CC1CC1)C(=O)N1CCCC1CNc1nc(Nc2ccccc2)ncc1F]

Step 1

A mixture of tert-butyl 2-((2-chloro-5-fluoropyrimidin-4-ylamino)methyl)pyrrolidine-1-carboxylate (331 mg, 1.0 mmol) and aniline (10 2 mg, 1.1 mmol) in n-BuOH (5 mL) was cooled to 0° C. and then TFA (57 mg, 0.5 mmol) was added slowly. The mixture was heated to 120° C. for 4 h. The reaction mixture was concentrated and the residue was purified by preparative TLC to give 2-((5-fluoro-2-(phenylamino)-pyrimidin-4-ylamino)methyl)pyrrolidine-1-carboxylate (280 mg, 72% yield).

Step 2

HCl/MeOH (3 mL, 4 N) was added to tert-butyl 2-((5-fluoro-2-(phenylamino)pyrimidin-4-yl-amino)-methyl)pyrrolidine-1-carboxylate (280 mg, 0.72 mmol) at 0° C. slowly. The mixture was stirred for 0.5 h 0° C. and then warmed to room temperature and stirred for another 1 h. A yellow solid was precipitated out, filtered and washed with EtOAc. The solid was dissolved in 0.5N NaOH (pH=8), extracted with CH$_2$Cl$_2$. The combined organic layer was dried over anhydrous Na$_2$SO$_4$, filtered and concentrated to give 5-fluoro-N2-phenyl-N4-(pyrrolidin-2-ylmethyl)pyrimidine-2,4-diamine (200 mg, 82% yield).

Step 3

A mixture of 5-fluoro-N2-phenyl-N4-(pyrrolidin-2-ylmethyl)pyrimidine-2,4-diamine (200 mg, 0.69 mmol), 2-cyanoacetic acid (64 mg, 0.76 mol) and HATU (379 mg, 1.0 mmol) in CH$_2$Cl$_2$ (4 mL) at 0° C. was added DIPEA (267 mg, 2.07 mmol). The mixture was stirred for 0.5 h at room temperature. The solvent was removed and obtained residue was purified by preparative TLC to give 5-fluoro-N2-phenyl-N4-(pyrrolidin-2-ylmethyl)pyrimidine-2,4-diamine (110 mg, 45% yield).

Step 4

A mixture of 3-(2-((5-fluoro-2-(phenylamino)pyrimidin-4-ylamino)methyl)pyrrolidin-1-yl)-3-oxopropanenitrile (110 mg, 0.31 mmol), cyclopropanecarbaldehyde (24 mg, 0.34 mol) and piperidine acetate (135 mg, 0.93 mmol) in anhydrous EtOH (3 mL) was heated to reflux for 5 h. After cooling, the solvent was removed and the obtained residue was purified by preparative TLC (EtOAc/PE=1/1) to give the title compound (33 mg, 27% yield). LCMS: m/z, 407.1 (M+H)$^+$.

Example 42

Synthesis of N-(3-(5-fluoro-4-(phenylamino)pyrimidin-2-ylamino)-4-methoxyphenyl)-2-cyano-3-cyclopropylacrylamide

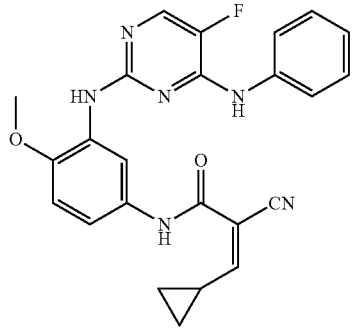 [SMILES: COc1ccc(NC(=O)/C(C#N)=C\C2CC2)cc1Nc1ncc(F)c(Nc2ccccc2)n1]

Step 1

A mixture of 2,4-dichloropyrimidine (500 mg, 3.36 mmol), aniline (313 mg, 3.36 mmol) and DIEA (2.17 g, 16.78 mmol) in n-BuOH (10 ml) was heated to 100° C. for 2 h. The mixture was cooled to room temperature and the precipitate was collected to give the 2-chloro-N-phenylpyrimidin-4-amine (350 mg, 51%).

Step 2

A mixture of 2-chloro-5-fluoro-N-phenylpyrimidin-4-amine (500 mg, 2.24 mmol), 2-methoxy-5-nitrobenzenamine (451 mg, 2.68 mmol) and TFA (0.5 mL) in IPA (20 mL) was heated to reflux for 3 days. The mixture was diluted with ETOAc and washed with a Na$_2$CO$_3$ solution. The organic layer was concentrated to give the crude product, which was purified by column chromatography to give 5-fluoro-N2-(2-methoxy-5-nitrophenyl)-N4-phenylpyrimidine-2,4-diamine (370 mg, 47%).

Step 3

To a solution of 5-fluoro-N2-(2-methoxy-5-nitrophenyl)-N4-phenylpyrimidine-2,4-diamine (370 mg, 1.04 mmol) in CH$_3$OH (20 mL) was added Pd/C (100 mg), and the mixture was stirred under a H$_2$ atmosphere overnight. The catalyst was filtered and the filtrate was concentrated to give N2-(5-amino-2-methoxyphenyl)-5-fluoro-N4-phenylpyrimidine-2,4-diamine (270 mg, 80%) which was subjected to the next step without any further purification.

Step 4

To a solution of N2-(5-amino-2-methoxyphenyl)-5-fluoro-N4-phenylpyrimidine-2,4-diamine (230 mg, 0.707 mmol) and 2-cyanoacetic acid (75 mg, 0.849 mmol) in CH$_2$Cl$_2$ (20 mL) at room temperature was added HATU (403 mg, 1.06 mmol) and DIEA (183 mg, 1.41 mmol). The formed mixture was stirred for 2 h. The precipitate was collected to give N-(3-(5-fluoro-4-(phenylamino)pyrimidin-2-yl-amino)-4-methoxyphenyl)-2-cyanoacetamide (270 mg, 97%).

Step 5

To a solution of N-(3-(5-fluoro-4-(phenylamino)pyrimidin-2-ylamino)-4-methoxyphenyl)-2-cyanoacetamide (90 mg, 0.229 mmol) in EtOH (5 mL) was added cyclopropanecarbaldehyde (20 mg, 0.275 mmol) and piperidine acetate (5 mg). The formed mixture was heated to reflux for 1 h. The precipitate was collected to give the title compound. LCMS m/z 445 (M+H)$^+$.

Following the synthesis in Example 42 above and using appropriate starting materials the following compounds were synthesized.

2-cyano-3-cyclopropyl-N-(3-((4-phenylpyrimidin-2-yl)amino)phenyl)acrylamide; LCMS m/z 382 (M+H)$^+$.

2-cyano-3-cyclopropyl-N-(4-methoxy-3-((4-phenylpyrimidin-2-yl)amino)phenyl)acrylamide; LCMS m/z 412 (M+H)$^+$.

2-cyano-4-(dimethylamino)-N-(4-methoxy-3-((4-phenylpyrimidin-2-yl)amino)phenyl)-4-methylpent-2-enamide; LCMS m/z 457 (M+H)$^+$.

2-cyano-3-cyclopropyl-N-(3-((4-(phenylamino)pyrimidin-2-yl)amino)phenyl)acrylamide; LCMS m/z 397 (M+H)$^+$.

2-cyano-3-cyclopropyl-N-(4-methoxy-3-((4-(phenylamino)pyrimidin-2-yl)amino)phenyl)acrylamide; LCMS m/z 427 (M+H)$^+$.

2-cyano-4-(dimethylamino)-4-methyl-N-(3-((4-(phenylamino)pyrimidin-2-yl)amino)phenyl)pent-2-enamide; LCMS m/z 442 (M+H)$^+$.

2-cyano-4-(dimethylamino)-N-(4-methoxy-3-((4-(phenylamino)pyrimidin-2-yl)amino)phenyl)-4-methylpent-2-enamide; LCMS m/z 472 (M+H)$^+$.

2-cyano-3-cyclopropyl-N-(3-((4-phenoxypyrimidin-2-yl)amino)phenyl)acrylamide; LCMS m/z 398 (M+H)$^+$.

2-cyano-3-cyclopropyl-N-(4-methoxy-3-((4-phenoxypyrimidin-2-yl)amino)phenyl)acrylamide; LCMS m/z 428 (M+H)$^+$.

2-cyano-4-(dimethylamino)-4-methyl-N-(3-((4-phenoxypyrimidin-2-yl)amino)phenyl)pent-2-enamide; LCMS m/z 443 (M+H)$^+$.

2-cyano-4-(dimethylamino)-4-methyl-N-(4-methoxy-3-((4-phenoxypyrimidin-2-yl)amino)phenyl)pent-2-enamide; LCMS m/z 473 (M+H)$^+$.

2-cyano-3-cyclopropyl-N-(3-((4-(phenylthio)pyrimidin-2-yl)amino)phenyl)acrylamide; LCMS m/z 414 (M+H)$^+$.

2-cyano-3-cyclopropyl-N-(4-methoxy-3-((4-(phenylthio)pyrimidin-2-yl)amino)phenyl)acrylamide; LCMS m/z 444 (M+H)$^+$.

2-cyano-4-(dimethylamino)-4-methyl-N-(3-((4-(phenylthio)pyrimidin-2-yl)amino)phenyl)pent-2-enamide; LCMS m/z 459 (M+H)$^+$.

2-cyano-4-(dimethylamino)-N-(4-methoxy-3-((4-(phenylthio)pyrimidin-2-yl)amino)phenyl)-4-methylpent-2-enamide; LCMS m/z 489 (M+H)$^+$.

2-cyano-3-cyclopropyl-N-(3-((5-fluoro-4-phenylpyrimidin-2-yl)amino)phenyl)acrylamide; LCMS m/z 400 (M+H)$^+$.

2-cyano-3-cyclopropyl-N-(4-methoxy-3-((5-fluoro-4-phenylpyrimidin-2-yl)amino)phenyl)acrylamide; LCMS m/z 430 (M+H)$^+$.

2-cyano-4-(dimethylamino)-N-(3-((5-fluoro-4-phenylpyrimidin-2-yl)amino)phenyl)-4-methylpent-2-enamide; LCMS m/z 445 (M+H)$^+$.

2-cyano-4-(dimethylamino)-N-(4-methoxy-3-((5-fluoro-4-phenylpyrimidin-2-yl)amino)phenyl)-4-methylpent-2-enamide; LCMS m/z 475 (M+H)+.

2-cyano-3-cyclopropyl-N-(3-((5-fluoro-4-(phenylamino)pyrimidin-2-yl)amino)phenyl)acrylamide; LCMS m/z 415 (M+H)+.

2-cyano-4-(dimethylamino)-N-(3-((5-fluoro-4-(phenylamino)pyrimidin-2-yl)amino)phenyl)-4-methylpent-2-enamide; LCMS m/z 460 (M+H)+.

2-cyano-4-(dimethylamino)-N-(4-methoxy-3-((5-fluoro-4-(phenylamino)pyrimidin-2-yl)amino)phenyl)-4-methylpent-2-enamide; LCMS m/z 490 (M+H)+.

2-cyano-3-cyclopropyl-N-(3-((5-fluoro-4-phenoxypyrimidin-2-yl)amino)phenyl)acrylamide; LCMS m/z 416 (M+H)+.

2-cyano-3-cyclopropyl-N-(4-methoxy-3-((5-fluoro-4-phenoxypyrimidin-2-yl)amino)phenyl)acrylamide; LCMS m/z 446 (M+H)+.

2-cyano-4-(dimethylamino)-N-(3-((5-fluoro-4-phenoxypyrimidin-2-yl)amino)phenyl)-4-methylpent-2-enamide; LCMS m/z 461 (M+H)+.

2-cyano-4-(dimethylamino)-N-(4-methoxy-3-((5-fluoro-4-phenoxypyrimidin-2-yl)amino)phenyl)-4-methylpent-2-enamide; LCMS m/z 491 (M+H)+.

2-cyano-3-cyclopropyl-N-(3-((5-fluoro-4-(phenylthio)pyrimidin-2-yl)amino)phenyl)acrylamide; LCMS m/z 432 (M+H)+.

2-cyano-3-cyclopropyl-N-(3-((5-fluoro-4-(phenylthio)pyrimidin-2-yl)amino)-4-methoxyphenyl)acrylamide; LCMS m/z 462 (M+H)+.

2-cyano-4-(dimethylamino)-N-(3-((5-fluoro-4-(phenylthio)pyrimidin-2-yl)amino)phenyl)-4-methyl-pent-2-enamide; LCMS m/z 477 (M+H)+.

2-cyano-4-(dimethylamino)-N-(3-((5-fluoro-4-(phenylthio)pyrimidin-2-yl)amino)-4-methoxyphenyl)-4-methylpent-2-enamide; LCMS m/z 507 (M+H)+.

Example 43

Synthesis of 5-(4-(2-cyano-3-cyclopropylacrylamido)benzylamino)-7-(3,5-dimethoxyphenylamino)-imidazo[1,2-c]pyrimidine-8-carboxamide

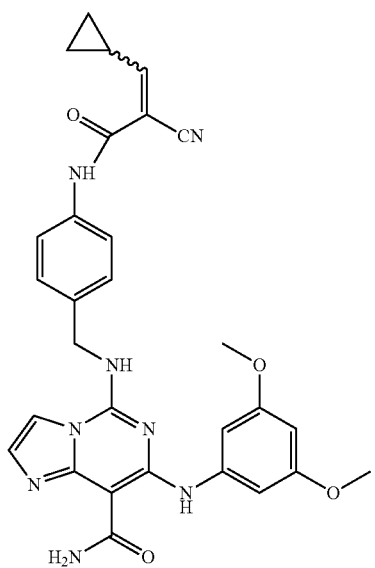 [SMILES: COc1cc(Nc2nc(NCc3ccc(NC(=O)C(C#N)=CC4CC4)cc3)n3ccnc3c2C(N)=O)cc(OC)c1]

Step 1

To a solution of 4,6-dichloro-2-(methylthio)pyrimidine-5-carbonitrile (14 g, 63.6 mmol, 1.0 eq) and 3,5-dimethoxyaniline (9.94 g, 63.6 mmol, 1.0 eq) in THF (300 mL) at 0° C., was added DIEA (12.32 g, 95.4 mmol, 1.5 eq). The resulted mixture was stirred at RT for 4 h. The reaction mixture was diluted with water (30 mL), filtered and dried to give 4-chloro-6-(3,5-dimethoxy-phenylamino)-2-methylsulfanyl-pyrimidine-5-carbonitrile (19 g, 89% in yield).

Step 2

To a solution of 4-chloro-6-(3,5-dimethoxyphenylamino)-2-(methylthio)pyrimidine-5-carbonitrile (14 g, 41.57 mmol, 1.0 eq) in DMF (200 mL) was added NH$_4$OH (20 g). The resulted mixture was stirred at RT for 2 h. The mixture was diluted with ice water (200 mL), filtered and dried to give 4-amino-6-(3,5-dimethoxy-phenylamino)-2-methylsulfanyl-pyrimidine-5-carbonitrile (11 g, 83% in yield).

Step 3

To a solution of 4-amino-6-(3,5-dimethoxyphenylamino)-2-(methylthio)pyrimidine-5-carbonitrile (11 g, 34.66 mmol, 1.0 eq) in DMSO (150 mL) and EtOH (150 mL) at 0° C. was added 5 M NaOH (66 mL) and H$_2$O$_2$ (37 mL). The resulting mixture was stirred at RT for 1 h. The mixture was poured into ice water, filtered and dried to give a white solid. The solid was suspended in EtOAc (60 mL) and stirred at 110° C. for 1 h. The resulting mixture was then cooled to RT, filtered and dried to give 4-amino-6-(3,5-dimethoxy-phenylamino)-2-methylsulfanyl-pyrimidine-5-carboxylic acid amide as a white solid (6.8 g, 58% in yield).

Step 4

To a solution of 4-amino-6-(3,5-dimethoxyphenylamino)-2-(methylthio)pyrimidine-5-carboxamide (6.8 g, 20.30 mmol, 1.0 eq) in DMF (80 mL) at 0° C. was added chloro-acetaldehyde (11.95 g, 60.9 mmol, 3.0 eq). The resulted mixture was stirred at 60° C. for 6 h. The mixture was poured into ice water, filtered and dried to give 7-(3,5-dimethoxy-phenylamino)-5-methylsulfanyl-imidazo[1,2-c]pyrimidine-8-carboxylic acid amide as a yellow solid (3.94 g, 54.7% in yield).

Step 5

A mixture of 7-(3,5-dimethoxyphenylamino)-5-(methylthio)imidazo[1,2-c]pyrimidine-8-carboxamide (500 mg, 1.40 mmol), DIPEA (720 mg, 5.55 mmol) and 4-(aminomethyl)aniline (340 mg, 2.80 mmol) in 15 ml of NMP was heated at 90° C. overnight. The mixture was cooled to room temperature, diluted with water, extracted with EtOAc and the combined organic layers were washed with brine, evaporated and purified by silica gel column eluted with EtOAc to give 5-(4-aminobenzylamino)-7-(3,5-dimethoxyphenylamino)imidazo[1,2-c]pyrimidine-8-carboxamide (500 mg, 83%).

Step 6

To a mixture of 5-(4-aminobenzylamino)-7-(3,5-dimethoxyphenylamino)imidazo[1,2-c]-pyrimidine-8-carboxamide (200 mg, 0.46 mmol), 2-cyanoacetic acid (48 mg, 0.56 mmol) and DIPEA (180 mg, 1.38 mmol) in 15 ml DCM was added HATU (261 mg, 0.70 mmol), then the mixture was stirred for 5 h at room temperature under N$_2$. The mixture was filtered to give 5-(4-(2-cyanoacetamido)benzylamino)-7-(3,5-dimethoxyphenylamino)imidazo[1,2-c]pyrimidine-8-carboxamide as a grey solid (140 mg, 61%).

Step 7

A mixture of 5-(4-aminobenzylamino)-7-(3,5-dimethoxyphenylamino)imidazo[1,2-c]-pyrimidine-8-carboxamide (140 mg, 0.32 mmol), cyclopropanecarbaldehyde (45 mg, 0.64 mmol) and piperidine acetate (5 mg, 0.032 mmol) in 15 ml of EtOH was heated at reflux for 1 h. The mixture was cooled to room temperature and evaporated to afford the residue which was purified by prep-HPLC to afford the title compound (21 mg, 13%). LCMS m/z 553.1 (M+H)$^+$.

Example 44

Synthesis of 5-(3-(2-cyano-3-cyclopropylacrylamido)benzylamino)-7-(3,5-dimethoxyphenylamino)

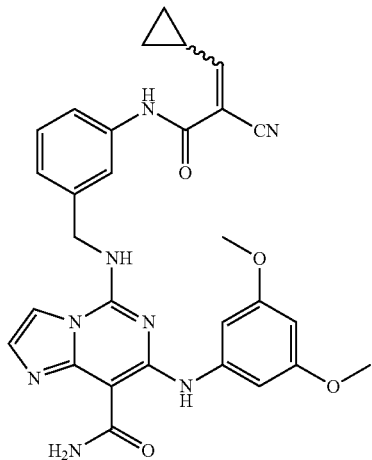 [SMILES: COc1cc(Nc2nc(NCc3cccc(NC(=O)C(C#N)=CC4CC4)c3)n3ccnc3c2C(N)=O)cc(OC)c1]

Step 1

To an NMP solution (10 mL) of 7-(3,5-dimethoxyphenylamino)-5-(methylthio)imidazo-[1,2-c]pyrimidine-8-carboxamide (500.00 mg, 1.39 mmol, 1.0 equiv) was added 3-(aminomethyl)aniline (425.00 mg, 3.49 mmol, 2.5 equiv) at 27° C. After 5 min, DIPEA (897.00 mg, 6.94 mmol) was added. The reaction was stirred at 100° C. for 3 h. The mixture was added to water and extracted with EtOAc. The organic layer was washed with water, dried over Na$_2$SO$_4$ and evaporated to dryness to give 5-(3-amino-benzylamino)-7-(3,5-dimethoxy-phenylamino)-imidazo[1,2-c]pyrimidine-8-carboxylic acid amide (500 mg, 82.9% in yield).

Step 2

To a mixture of 5-(3-aminobenzylamino)-7-(3,5-dimethoxyphenylamino)imidazo[1,2-c]-pyrimidine-8-carboxamide (100 mg, 0.23 mmol), 2-cyanoacetic acid (24 mg, 0.28 mmol) and DIPEA (104 mg, 0.80 mmol) in 5 ml DCM was added HATU (153 mg, 0.40 mmol), then the mixture was stirred for 5 h at room temperature under N$_2$. LCMS showed that the reaction was complete. The reaction mixture was filtered, and the solid was washed with DCM and dried under vacuum to give 5-(3-(2-cyanoacetamido)benzylamino)-7-(3,5-dimethoxyphenylamino)imidazo[1,2-c]pyrimidine-8-carboxamide (41 mg, 35.7% in yield).

Step 3

A mixture of 5-(3-(2-cyanoacetamido)benzylamino)-7-(3,5-dimethoxyphenyl-amino)imidazo-[1,2-c]pyrimidine-8-carboxamide (41 mg, 0.081 mmol), cyclopropanecarbaldehyde (7 mg, 0.28 mmol) and piperidine acetate (2 mg, 0.008 mmol) in 5 mL THF was refluxed for 5 h. LCMS showed that the reaction was complete. The reaction mixture was added to water (5 mL), the organic layer washed with water, dried over Na$_2$SO$_4$, filtered, evaporated to dryness to provide crude product (45 mg). The crude product was purified by preparative TLC to provide the title compound (19 mg, 42.2% in yield). LCMS m/z 553.3 (M+H)$^+$.

Example 45

Synthesis of 5-((1-(2-cyano-3-cyclopropylacryloyl)piperidin-3-yl)methylamino)-7-(3,5-dimethoxyphenylamino)imidazo[1,2-c]pyrimidine-8-carboxamide

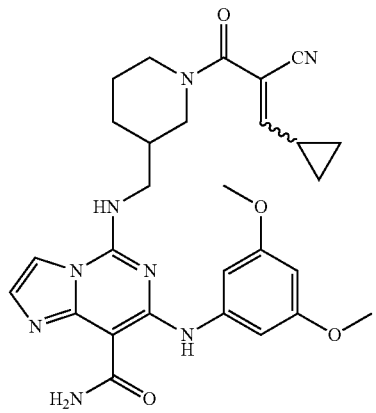 [SMILES: COc1cc(Nc2nc(NCC3CCCN(C(=O)C(C#N)=CC4CC4)C3)n3ccnc3c2C(N)=O)cc(OC)c1]

Step 1

To a solution of 7-(3,5-dimethoxyphenylamino)-5-(methylthio)imidazo[1,2-c]pyrimidine-8-carboxamide (1 g, 2.78 mmol) in NMP (15 mL) was added tert-butyl 3-(aminomethyl)piperidine-1-carboxylate (0.6 g, 3.34 mmol). The mixture was heated at 100° C. overnight, then the reaction mixture was concentrated to dryness to give tert-butyl 3-((8-carbamoyl-7-(3,5-dimethoxyphenyl-amino)imidazo[1,2-c]pyrimidin-5-ylamino)methyl)piperidine-1-carboxylate (1.1 g, yield: 75%), which was used directly for the next step without purification.

Step 2 t-Butyl 3-((8-carbamoyl-7-(3,5-dimethoxyphenylamino)imidazo[1,2-c]pyrimidin-5-ylamino)-methyl)piperidine-1-carboxylate (600 mg, 1.14 mmol) was dissolved in 4N HCl/MeOH (15 mL) at 0° C. The mixture was then stirred at room temperature for 1 h, then the reaction mixture was concentrated to dryness to give 7-(3,5-dimethoxyphenylamino)-5-(piperidin-3-ylmethylamino)imidazo[1,2-c]-pyrimidine-8-carboxamide (400 mg, yield: 82%) which was used directly for the next step without purification.

Step 3

A mixture of 7-(3,5-dimethoxyphenylamino)-5-(piperidin-3-ylmethylamino)-imidazo[1,2-c]pyrimidine-8-carboxamide (300 mg, 0.7 mmol), 2-cyanoacetic acid (60 mg, 0.7 mmol), HATU (266 mg, 0.7 mmol), DIEA (181 mg, 1.4 mmol) in 3 ml of DCM was stirred at room temperature for 1 h. The reaction mixture was filtered to give 100 mg of 5-((1-(2-cyanoacetyl)piperidin-3-yl)-methylamino)-7-(3,5-dimethoxyphenylamino)imidazo[1,2-c]pyrimidine-8-carboxamide as a crude solid.

Step 4

A mixture of 5-((1-(2-cyanoacetyl)piperidin-3-yl)methylamino)-7-(3,5-dimethoxyphenylamino)-imidazo[1,2-c]pyrimidine-8-carboxamide (100 mg, 0.20 mmol), cyclopropanecarbaldehyde (70 mg, 1.0 mmol), piperidine acetate (14.5 mg, 0.1 mmol) in 3 ml of THF was refluxed for 1 h. The reaction mixture was concentrated and the residue was purified by preparative TLC (DCM: MeOH=10:1) to give 12 mg of the title compound as a solid. LCMS m/z 545.3 (M+H)$^+$.

Proceeding as described in Example 15 above, but substituting tert-butyl 3-(aminomethyl)piperidine-1-carboxylate with tert-butyl 4-(aminomethyl)piperidine-1-carboxylate, 7-(3,5-dimethoxyphenylamino)-5-(piperidin-4-ylmethylamino)imidazo[1,2-c]pyrimidine-8-carboxamide was prepared.

Proceeding as described above, but substituting tert-butyl 3-(aminomethyl)piperidine-1-carboxylate with tert-butyl 3-(aminomethyl)pyrrolidine-1-carboxylate, 7-(3,5-dimethoxyphenylamino)-5-(pyrrolidin-3-ylmethylamino)imidazo[1,2-c]pyrimidine-8-carboxamide was prepared.

Proceeding as described above, but substituting tert-butyl 3-(aminomethyl)piperidine-1-carboxylate with tert-butyl 3-(aminomethyl)azetidine-1-carboxylate, 3-((8-carbamoyl-7-(3,5-dimethoxy-phenylamino)imidazo[1,2-d]pyrimidin-5-ylamino)azetidine-1-carboxylate was prepared which treatment with trifluoroacetic acid under hydrolysis condition gave 5-(azetidin-3-ylmethylamino)-7-(3,5-dimethoxyphenylamino)-imidazo[1,2-c]pyrimidine-8-carboxamide.

Example 46

Synthesis of 5-((1-(2-cyano-3-cyclopropylacryloyl)piperidin-4-yl)methylamino)-7-(3,5-dimethoxyphenylamino)imidazo[1,2-c]pyrimidine-8-carboxamide

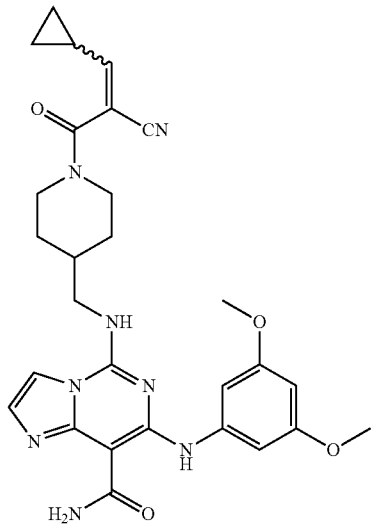 [SMILES: COc1cc(Nc2nc(NCC3CCN(C(=O)C(C#N)=CC4CC4)CC3)n3ccnc3c2C(N)=O)cc(OC)c1]

Step 1

To a solution of 7-(3,5-dimethoxyphenylamino)-5-(piperidin-4-ylmethylamino)-imidazo[1,2-c]pyrimidine-8-carboxamide (100 mg, 0.24 mmol) and cyano-acetic acid (24 mg, 0.28 mmol) in DCM (5 mL) was added HATU (137 mg, 0.36 mmol) and DIPEA (93 mg, 0.72 mmol). The reaction mixture was stirred at room temperature overnight. The reaction mixture was filtered and the filter cake was washed with DCM and dried under vacuum to give crude product, which was purified by silica gel chromatography eluted with PE:EtOAc=10:1 to give 5-((1-(2-cyanoacetyl)piperidin-4-yl)methylamino)-7-(3,5-dimethoxy-phenylamino)imidazo[1,2-c]pyrimidine-8-carboxamide (70 mg, yield: 60%) as a yellow solid.

Step 2

To a solution of 5-((1-(2-cyanoacetyl)piperidin-4-yl)methylamino)-7-(3,5-dimethoxyphenyl-amino)imidazo[1,2-c]pyrimidine-8-carboxamide (70 mg, 0.14 mmol) and cyclopropanecarbaldehyde (29 mg, 0.43 mmol) in EtOH (5 mL) was added piperidine acetate (62 mg, 0.43 mmol). The mixture was heated at 70° C. overnight. The solvent was removed to afford a residue, which was purified by Prep-TLC and HPLC to afford the title product (3.2 mg, yield: 3.2%) as a white solid. LCMS: m/z 544.3 (M+H)$^+$.

Example 47

Synthesis of 5-((1-(2-cyano-3-cyclopropylacryloyl)azetidin-3-yl)methylamino)-7-(3,5-dimethoxyphenylamino)imidazo[1,2-c]pyrimidine-8-carboxamide

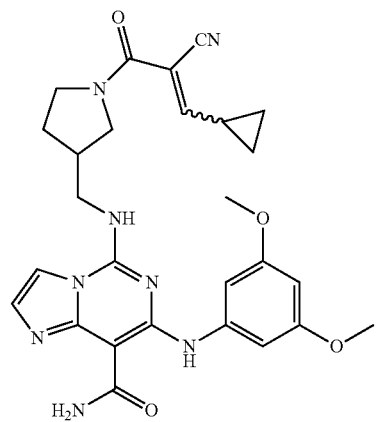 [SMILES: COc1cc(Nc2nc(NCC3CCN(C(=O)C(C#N)=CC4CC4)C3)n3ccnc3c2C(N)=O)cc(OC)c1]

Step 1

To a solution of 7-(3,5-dimethoxy-phenylamino)-5-[(pyrrolidin-3-ylmethyl)-amino]-imidazo[1,2-c]pyrimidine-8-carboxylic acid amide (300 mg, 0.73 mmol), 2-cyanoacetic acid (124 mg, 1.46 mmol), HOBt (197 mg, 1.46 mmol) and EDCI (279 mg, 1.46 mmol) in DCM (20 mL) was added DIEA (566 mg, 4.38 mmol). The resulted mixture was stirred at room temperature for 18 hours. The mixture was washed with H$_2$O (15 mL). The organic layer was dried and concentrated to give the crude product which was purified by prep-TLC to give 5-{[1-(2-cyano-acetyl)-pyrrolidin-3- ylmethyl]-amino}-7-(3,5-dimethoxy-phenylamino)-imidazo[1,2-c]pyrimidine-8-carboxylic acid amide (74 mg, 21% in yield).

Step 2

A solution of 5-{[1-(2-cyano-acetyl)-pyrrolidin-3-ylmethyl]-amino}-7-(3,5-dimethoxy-phenylamino)-imidazo[1,2-c]pyrimidine-8-carboxylic acid amide (74 mg, 0.15 mmol), cyclopropanecarbaldehyde (12 mg, 0.17 mmol) and piperidine acetate (64 mg, 0.45 mmol) in EtOH (10 mL) was heated at reflux for 18 hours. The mixture was concentrated and purified by pre-TLC to afford the title compound (20 mg, 25% in yield). LCMS: m/z 531.0 (M+H)$^+$.

Example 48

Synthesis of 5-((1-(2-cyano-3-cyclopropylacryloyl)azetidin-3-yl)methylamino)-7-(3,5-dimethoxy phenylamino)imidazo[1,2-c]pyrimidine-8-carboxamide

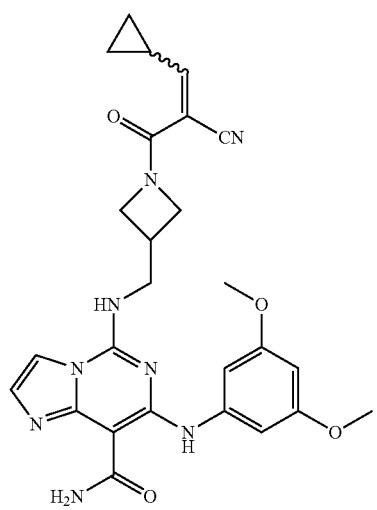 [SMILES: COc1cc(Nc2nc(NCC3CN(C(=O)C(C#N)=CC4CC4)C3)n3ccnc3c2C(N)=O)cc(OC)c1]

Step 1

A mixture of 5-(azetidin-3-ylmethylamino)-7-(3,5-dimethoxyphenylamino)-imidazo[1,2-c]pyrimidine-8-carboxamide (173 mg, 0.435 mmol), 2-cyanoacetic acid (51 mg, 0.478 mmol), HATU (182 mg, 0.478 mmol), DIEA (112 mg, 0.870 mmol) in 3 ml of DCM was stirred at room temperature for 1 h. The reaction mixture was filtered to give 130 mg of 5-((1-(2-cyanoacetyl)-azetidin-3-yl)methylamino)-7-(3,5-dimethoxyphenylamino)imidazo[1,2-c]pyrimidine-8-carboxamide.

Step 2

A mixture of 5-((1-(2-cyanoacetyl)azetidin-3-yl)methyl-amino)-7-(3,5-dimethoxyphenyl-amino)imidazo[1,2-c]pyrimidine-8-carboxamide (130 mg, 0.28 mmol), cyclopropanecarbaldehyde (71.4 mg, 1.4 mmol) and piperidine (25 mg, 0.14 mmol) in 3 ml of THF was refluxed for 1 h. The reaction mixture was concentrated and the residue was purified by preparative TLC (DCM:MeOH=10:1) to give 30 mg of 5-((1-(2-cyano-3-cyclopropylacryloyl)azetidin-3-yl)methylamino)-7-(3,5-dimethoxyphenylamino)imidazo[1,2-c]pyrimidine-8-carboxamide. LCMS m/z 517.2 (M+H)$^+$.

Example 49

Synthesis of 5-(3-(2-cyano-3-cyclopropylacrylamido)-2,2-dimethylpropylamino)-7-(3,5-dimethoxyphenylamino)imidazo[1,2-c]pyrimidine-8-carboxamide

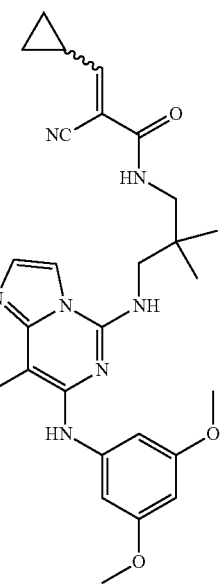

Step 1

To a mixture of cyclopropanecarboxaldehyde (2.4 mL, 32.1 mmol) and ethyl cyanoacetate (3.8 mL, 35.3 mmol) at 0° C. were added acetic acid (0.2 mL) and then piperidine (0.3 mL) was added dropwise. The ice bath was removed, and stirring was continued for 10 min. Additional acetic acid (0.2 mL) and piperidine (0.3 mL) were added, followed by addition of oven-dried 4 Å molecular sieves such that stirring was not impeded. The mixture was stirred for 12 h, and then partitioned between t-BuOMe and sat. NaHCO$_3$. The phases were separated, and the organic phase washed with brine, dried (Na$_2$SO$_4$), and concentrated. Flash chromatography of the residue (3-5-9% EtOAc/hexanes) furnished 2-cyano-3-cyclopropylacrylic acid ethyl ester (3.7 g, 70%) as a colorless oil.

Step 2

To 2-cyano-3-cyclopropylacrylic acid ethyl ester (1 g, 6.02 mmol) was added 5 mL of MeOH and then 5 mL of 10% NaOH (aq), and the mixture was stirred 12 h. The mixture was acidified to pH 2 by addition of 6 M HCl (aq)

and then concentrated to remove MeOH. The residue was filtered to afford 2-aminomethylbicyclopropyl-2-carboxylic acid (0.25 g, 34%) as a white solid.

Step 3

A mixture of 7-(3,5-dimethoxyphenylamino)-5-(methylthio)imidazo[1,2-c]pyrimidine-8-carboxamide (300 mg, 0.836 mmol), 2,2-dimethylpropane-1,3-diamine (426 mg, 4.18 mmol) in NMP (1 mL) was heated to 100° C. for 16 h. Water and EtOAc was added to the mixture. The aqueous layer was extracted with EtOAc. The EtOAc layers were washed with brine, dried over $Na_2SO_4$, concentrated in vacuo to give 5-(3-amino-2,2-dimethylpropylamino)-7-(3,5-dimethoxyphenylamino)imidazo-[1,2-c]pyrimidine-8-carboxamide (367 mg, crude) as a brown oil.

Step 4

A mixture of 5-(3-amino-2,2-dimethylpropylamino)-7-(3,5-dimethoxyphenylamino)-imidazo[1,2-c]pyrimidine-8-carboxamide (367 mg, 0.889 mmol), 2-cyano-3-cyclopropylacrylic acid (122 mg, 0.889 mmol), $Et_3N$ (224 mg, 2.22 mmol), EDCI (204 mg, 1.07 mmol) and HOBt (144 mg, 1.07 mmol) in DCM (5 mL) was stirred for 16 h. Water was added to the mixture and then filtered, the residue was purified by prep TLC (petroleum ether/EtOAc=1/1) and HPLC to obtain 5-(3-(2-cyano-3-cyclopropylacrylamido)-2,2-dimethylpropylamino)-7-(3,5-dimethoxyphenylamino)imidazo[1,2-c]pyrimidine-8-carboxamide (24 mg, 5%) as a white solid. LCMS: m/z 533.3 $(M+H)^+$.

Biological Examples

Example 1

General Procedure for In Vitro Kinase Activity Assay

General Procedure for Btk In Vitro Kinase Activity Assay.

Btk (human, full length) was purchased (Invitrogen, catalog number PV3363) and used following a procedure modified from the product literature. Btk (150 nM in kinase dilution buffer) was pre-activated by the addition of $MgCl_2$ (10 mM), ATP (100 μM), and $Zn(OAc)_2$ (10 μM) and incubated for 5 minutes at room temperature. Subsequently, Btk (5 nM final concentration) in kinase assay buffer supplemented with BSA (0.1 mg/mL) was pre-incubated with inhibitors (six or ten concentrations, in duplicate, 5% DMSO final concentration) for 30 minutes at room temperature. Kinase reactions were initiated by the addition of 0.16 μCi/μL of γ-$^{32}$P-ATP (6000 Ci/mmol, NEN) and 0.2 mg/mL substrate (poly[Glu:Tyr], 4:1 Glu:Tyr) and incubated for 30 minutes at room temperature. Kinase activity was determined by spotting 5 μL of each reaction onto sheets of phosphocellulose. Each blot was washed once with 10% AcOH solution, twice with 0.1% $H_3PO_4$ solution, and once with MeOH (5-10 minutes per wash). Dried blots were exposed for 30 minutes to a storage phosphor screen and scanned by a Typhoon imager (GE Life Sciences). The data were quantified using ImageQuant (v. 5.2, Molecular Dynamics) and plotted using GraphPad Prism 4.0 software.

TABLE 2

In vitro kinase activity assay data.

| Compound | Btk in vitro $IC_{50}$ |
|---|---|
| (structure) | +++ |
| (structure) | +++ |

TABLE 2-continued

In vitro kinase activity assay data.

| Compound | Btk in vitro IC$_{50}$ |
|---|---|
| (4-chlorophenyl pyrazolopyrimidine with (S)-pyrrolidine-N-CO-C(CN)=CH-cyclopropyl) | +++ |
| (4-chlorophenyl pyrazolopyrimidine with piperidine-N-CO-C(CN)=CH-cyclopropyl) | +++ |
| (4-phenoxyphenyl pyrazolopyrimidine with (S)-pyrrolidine-N-CO-C(CN)=CH-cyclopropyl) | ++ |
| (4-phenoxyphenyl pyrazolopyrimidine with (R)-pyrrolidine-N-CO-C(CN)=CH-cyclopropyl) | ++ |
| (4-phenoxyphenyl pyrazolopyrimidine with (R)-piperidine-N-CO-C(CN)=CH-cyclopropyl) | +++ |
| (4-phenoxyphenyl pyrazolopyrimidine with (R)-piperidine-N-CO-C(CN)=CH-C(CH$_3$)$_2$-N(CH$_3$)$_2$) | +++ |

TABLE 2-continued
In vitro kinase activity assay data.
| Compound | Btk in vitro IC$_{50}$ |
|---|---|
| 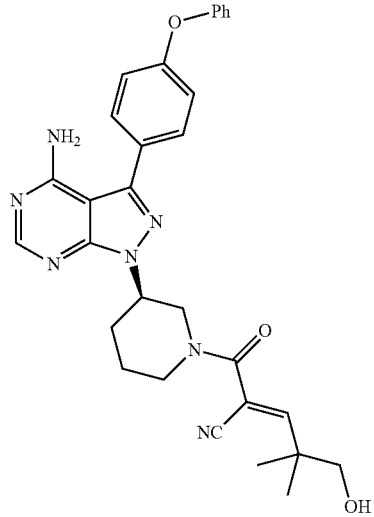 [SMILES: CC(C)(/C=C(\C#N)C(=O)N1CCC[C@@H](n2nc(-c3ccc(Oc4ccccc4)cc3)c3c(N)ncnc32)C1)CO] | ++ |
| 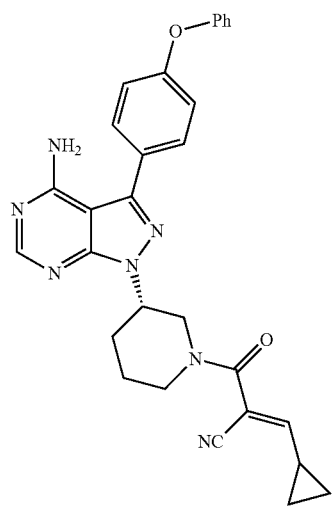 [SMILES: N#C/C(=C\C1CC1)C(=O)N1CCC[C@H](n2nc(-c3ccc(Oc4ccccc4)cc3)c3c(N)ncnc32)C1] | +++ |
| 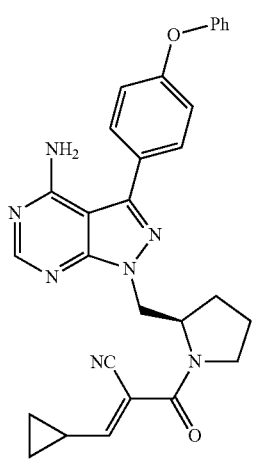 [SMILES: N#C/C(=C\C1CC1)C(=O)N1CCC[C@@H]1Cn1nc(-c2ccc(Oc3ccccc3)cc2)c2c(N)ncnc21] | +++ |
| 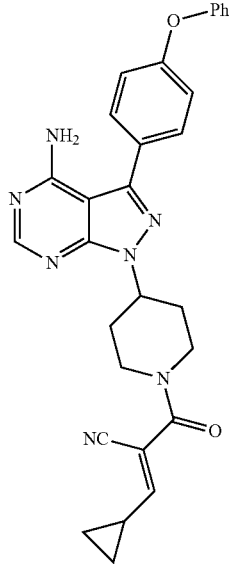 [SMILES: N#C/C(=C\C1CC1)C(=O)N1CCC(n2nc(-c3ccc(Oc4ccccc4)cc3)c3c(N)ncnc32)CC1] | ++ |
| 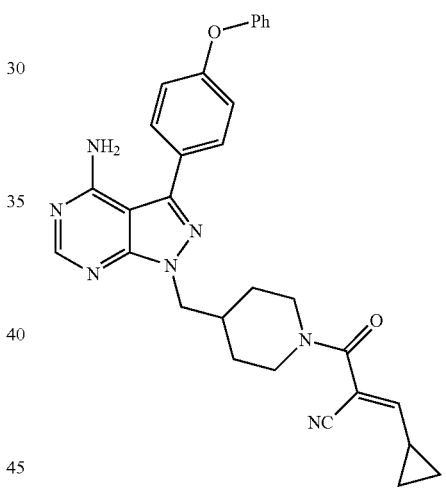 | ++ |
| 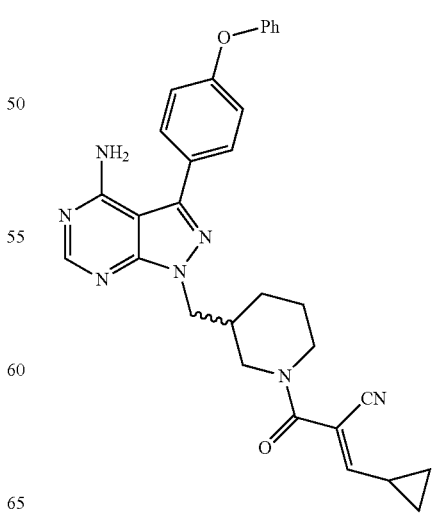 | ++ |

TABLE 2-continued

In vitro kinase activity assay data.

| Compound | Btk in vitro IC$_{50}$ |
|---|---|
| 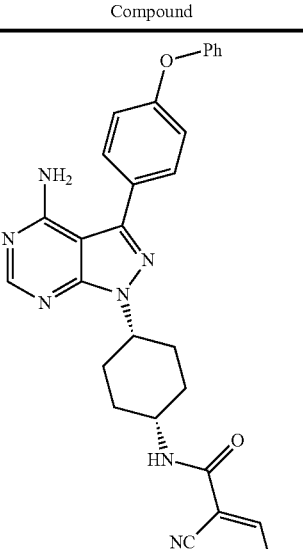 | ++ |

+++ for < 0.1 uM,
++ for < 1.0 uM,
+ for < 10 uM,
− for > 10 uM

Example 2

General Procedure for EGFR In Vitro Kinase Activity Assay

EGFR (ErbB1) kinase domain (human, GST-fusion) was purchased (Invitrogen, catalog number PV3872) and used following a procedure modified from the product literature. EGFR (4 nM final concentration) in kinase assay buffer supplemented with BSA (0.1 mg/mL) was pre-incubated with inhibitors (six or ten concentrations, in duplicate, 5% DMSO final concentration) for 30 minutes at room temperature. Kinase reactions were initiated by the addition of 0.16 µCi/βL of γ-$^{32}$P-ATP (6000 Ci/mmol, NEN) and 0.2 mg/mL substrate (poly[Glu:Tyr], 4:1 Glu:Tyr) and incubated for 30 minutes at room temperature. Kinase activity was determined by spotting 5 µL of each reaction onto sheets of phosphocellulose. Each blot was washed once with 10% AcOH solution, twice with 0.1% H$_3$PO$_4$ solution, and once with MeOH (5-10 minutes per wash). Dried blots were exposed for 30 minutes to a storage phosphor screen and scanned by a Typhoon imager (GE Life Sciences). The data were quantified using ImageQuant (v. 5.2, Molecular Dynamics) and plotted using GraphPad Prism 4.0 software. Cyanoacrylamide 33 inhibited EGFR kinase activity with an IC$_{50}$<0.1 µM.

Example 3

Inhibition of Mouse Collagen-Induced Arthritis

Inhibition of murine collagen-induced arthritis (mCIA) is a standard animal disease model for rheumatoid arthritis. Previous studies have demonstrated that inhibition of BTK is efficacious in blocking mCIA (see Honigberg L. A., et. al., *Proc Natl Acad Sci USA*. 107:13075-80. 2010). Starting on day 0 DBA/1 mice are injected with an emulsion of Type II collagen in Complete Freund's Adjuvant. Mice are boosted 21 days later to synchronize development of disease. After development of mild disease, animals are enrolled in the study and randomized. Dosing is oral, Q.D. typically for 11 days with test compound or dexamethasone (0.2 mg/kg) as control. One group receives vehicle alone. Clinical scoring (0-4) is based on the extent of swelling and severity of arthritis. Scores for all four paws are added for maximum score of 16. Anti-collagen antibodies and total Ig are measured for each animal by Elisa at the end of the study (Bolder BioPath, Boulder, Colo.).

Example 4

Recovery of Kinase Activity Upon Dialysis

Standard experimental methods to establish reversibility are known in the art. Protein dialysis is one such method. A solution containing a protein kinase that is inhibited by a compound of Formula I may be subjected to extensive dialysis to establish if the kinase inhibitor is reversible. Partial or complete recovery of protein kinase activity over time during dialysis is indicative of reversibility.

Method

A compound of Formula I described herein (1 uM) is added to a solution of protein kinase (50 nM, pre-activated if necessary) in a buffer containing 20 mM Hepes [pH 8.0], 10 mM MgCl2, 2.5 mM tris(2-carboxyethyl)phosphine (TCEP), 0.25 mg/mL BSA, and 100 uM ATP.

After 60 min at rt, the reactions is transferred to a dialysis cassette (0.1-0.5 mL Slide-A-Lyzer, MWCO 10 kDa, Pierce) and dialyzed against 2 L of buffer (20 mM Hepes [pH 8.0], 10 mM MgCl2, 1 mM DTT) at 4° C. The dialysis buffer is exchanged after 2 h, and then is exchanged every 24 h until the end of the experiment. Aliquots are removed from the dialysis cassettes every 24 h, flash frozen in liquid nitrogen, and subsequently analyzed for protein kinase activity in triplicate. Kinase activity for each sample is normalized to the DMSO control for that time point and expressed as the mean±SD.

Results

Kinase activity recovers from inhibition by reversible kinase inhibitors upon dialysis. Upon extensive dialysis at 4° C. or at room temperature, kinase activity partially or completely recovers in a time-dependent manner from inhibition by an excess (20 equiv, 1.0 uM) of reversible kinase inhibitor.

Example 5

Mass Spectral Analysis

A protein kinase that is inhibited by compound of Formula I may be subjected to mass spectral analysis to assess the formation of permanent, irreversible covalent adducts. Suitable analytical methods to examine intact full protein or peptide fragments generated upon tryptic cleavage of the protein kinase are generally known in the art. Such methods identify permanent, irreversible covalent protein adducts by observing a mass peak that corresponds to the mass of a control sample plus the mass of an irreversible adduct. Two such methods are described below.

Mass Spectral Analysis of Intact Full Kinase

Method

A protein kinase (5 uM) is incubated with a compound of Formula I (25 uM, 5 equiv) for 1 h at room temperature in buffer (20 mM Hepes [pH 8.0], 100 mM NaCl, 10 mM MgCl2).

A control sample is also prepared which does not have a compound of Formula I. The reaction is stopped by adding an equal volume of 0.4% formic acid, and the samples are analyzed by liquid chromatography (Microtrap C18 Protein column [Michrom Bioresources], 5% MeCN, 0.2% formic acid, 0.25 mL/min; eluted with 95% MeCN, 0.2% formic acid) and in-line ESI mass spectrometry (LCT Premier, Waters). Molecular masses of the protein kinase and any adducts may be determined with MassLynx deconvolution software.

Results

High-resolution intact mass spectrometry analysis of a kinase that is inhibited by a compound of Formula I will reveal a spectrum similar to the kinase in the absence of inhibitor (e.g. control sample). There will be no formation of a new peak in the mass spectrum corresponding to the molecular mass of the kinase plus the molecular mass of the compound of Formula I. On the basis of this experiment no permanent, irreversible protein adduct will be apparent to one skilled in the art.

Mass Spectral Analysis of Kinase Tryptic Digest

Method

A protein (10-100 pmols) is incubated with a compound of Formula I (100-1000 pmols, 10 equiv) for 3 hrs prior to tryptic digestion. Iodoacetamide may be used as the alkylating agent after compound incubation. A control sample is also prepared which does not the compound of Formula I. For tryptic digests a 1 ul aliquot (3.3 pmols) is diluted with 10 ul of 0.1% TFA prior to micro C18 Zip Tipping directly onto the MALDI target using alpha cyano-4-hydroxy cinnamic acid as the desorption matrix (5 mg/mol in 0.1% TFA:Acetonitrile 50:50) or Sinapinic acid as the desorption matrix (10 mg/mol in 0.1% TFA:Acetonitrile 50:50).

Results

High-resolution mass spectrometry analysis of the tryptic fragments of a kinase that is inhibited by a compound of Formula I will reveal a spectrum similar to the kinase in the absence of inhibitor (e.g. control sample). There will be no evidence of any modified peptides that are not present in the control sample. On the basis of this experiment, no permanent, irreversible protein adducts will be apparent to one skilled in the art.

Cellular assays are also optionally used to assess the inhibiting properties of a compound of Formula I provided herein or embodiments thereof. Cellular assays include cells from any appropriate source, including plant and animal cells (such as mammalian cells). The cellular assays are also optionally conducted in human cells. Cellular assays of BTK inhibition are well known in the art, and include methods in which an inhibitor is delivered into the cell (e.g. by electroporation, passive diffusion, microinjection and the like) and an activity endpoint is measured, such as the amount of phosphorylation of a cellular substrate, the amount of expression of a cellular protein, or some other change in the cellular phenotype known to be affected by the catalytic activity of BTK. For example, phosphorylation of a particular cellular substrate is optionally assessed using a detection antibody specific or the phosphorylated cellular substrate followed by western blotting techniques and visualization using any appropriate means (e.g. fluorescent detection of a fluorescently labeled antibody).

Measuring the reduction in the BTK catalytic activity in the presence of an inhibitor disclosed herein relative to the activity in the absence of the inhibitor is optionally performed using a variety of methods known in the art, such as described herein. Other methods for assaying BTK activity are known in the art.

Example 6

Determination of Drug-Kinase Residence Time
(Drug Off-Rate Assay)

The following is a protocol to distinguish whether a compound displays a slow or non-existent dissociation rate from BTK, such as typically would occur if a covalent bond is formed between the compound and the target. The readout for slow dissociation is the ability of the compound of interest to block binding of a high affinity fluorescent tracer molecule to the kinase active site, as detected using time-resolved fluorescence resonance energy transfer (TR-FRET). The experiment was conducted in a buffer consisting of 50 mM Hepes pH 7.5, 10 mM $MgCl_2$, 0.01% Triton X-100, and 1 mM EGTA.

The first step of the procedure was incubation of 500 nM BTK (Invitrogen Cat. #PV3587) with 1.5 uM of a compound of Formula (IA) for 30 minutes in a volume of 10 uL. The mixture was then diluted 5-fold by addition of 40 uL of buffer. A 10 uL volume of the diluted kinase/compound solution was then added to a well of a small volume 384 well plate (such as Greiner Cat. #784076). In order to probe for reversibility of the kinase-compound binding interaction, a competition solution containing both a high affinity fluorescent tracer and an antibody coupled to Europium was prepared. For BTK, the competition solution contained 1.5 uM Tracer 178 (Invitrogen Cat. #PV5593), which is a proprietary high affinity ligand for BTK coupled to the fluorophore AlexaFluor 647. The competition solution also contained 80 nM of an Anti-polyhistidine antibody coupled to Europium (Invitrogen Cat. #PV5596) which is designed to bind the polyhistidine purification tag in BTK.

After addition of 10 uL of the competition solution to the Greiner plate, the mixture was incubated for one hour or greater to allow time for dissociation of non-covalent inhibitors and binding of the high affinity tracer. It was expected that covalent and slow dissociating inhibitors will block binding of the tracer while rapidly dissociating non-covalent inhibitors will not. Binding of the tracer to BTK was detected using TR-FRET between the Europium moiety of the Anti-histidine antibody and the AlexaFluor 647 group of Tracer 178. Binding was evaluated using a Perkin Elmer Envision instrument (Model 2101) equipped with filters and mirrors compatible with LANCE-type TR-FRET experiments. Data were plotted at percentage of signal obtained in the absence of competitor compound. The background signal was obtained by omission of BTK from the reaction.

Reversibility of Binding

The following approach was developed to differentiate compounds that form irreversible bonds with their targets, such as acrylamide compounds, from compound that bind reversibly. Reactions were prepared with the protein target at a higher concentration than the compounds of interest. Both irreversible and reversible compounds bound the target and became depleted from solution. The reactions were then treated with perturbations including both denaturation with 5 M guanidine hydrochloride and digestion with trypsin, disrupting proper folding of the target. It was found that the perturbation returned reversible compounds to solution due to dissociation from the target while irreversible compounds remained bound to the target. The concentration of compound in solution was assessed both preceding and following perturbation using high performance liquid chromatography (HPLC) coupled to tandem mass spectrometry. Using this technique, it was demonstrated that an acrylamide-containing compound 1 (shown in table below) was depleted from solution in both the native and perturbed state, while reversible compounds 1 and 27 were depleted in the folded state but returned to solution following perturbation of the target (See table below).

| Cpd | Compound in solution in the native state? | Compound in solution in the de-natured or digested state? |
|---|---|---|
| 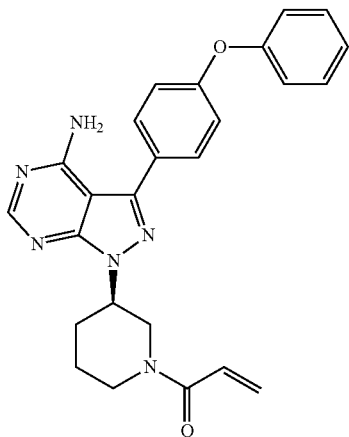 [SMILES: C=CC(=O)N1CCC[C@@H](n2nc(-c3ccc(Oc4ccccc4)cc3)c3c(N)ncnc32)C1]<br>Irreversible inhibitor | no | no |
| 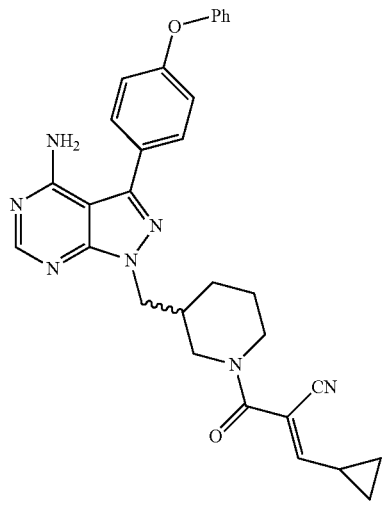 [SMILES: N#C/C(=C\C1CC1)C(=O)N1CCCC(Cn2nc(-c3ccc(Oc4ccccc4)cc3)c3c(N)ncnc32)C1] | no | yes |

Formulation Examples

The following are representative pharmaceutical formulations containing a compound of Formula (I).

Tablet Formulation

The following ingredients are mixed intimately and pressed into single scored tablets.

| Ingredient | Quantity per tablet mg |
|---|---|
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this invention | 200 |
| lactose spray dried | 148 |
| magnesium stearate | 2 |

Injectable Formulation

Compound of the invention (e.g., compound 1) in 2% HPMC, 1% Tween 80 in DI water, pH 2.2 with MSA, q.s. to at least 20 mg/mL The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound having the structure of Formula (XI):

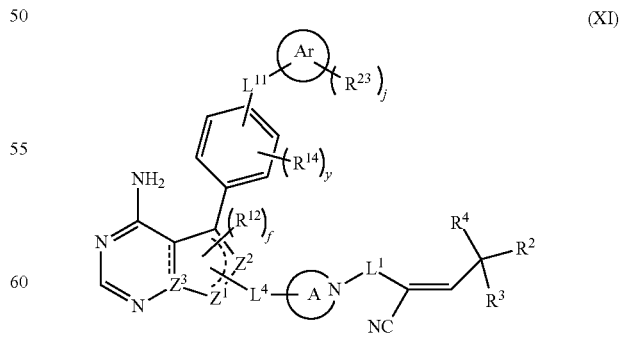

wherein:
the dashed lines are optionally a bond;
y is an integer from 0 to 2;
j is an integer from 0 to 3;
f is 0 or 1;

$Z^1$, $Z^2$, and $Z^3$ are —N— or —CH—, provided that at least one and not more than two of $Z^1$, $Z^2$, and $Z^3$ are simultaneously N;

Ar is a monocyclic or fused bicyclic ($C_6$-$C_{10}$) aryl, monocyclic or fused bicyclic 5-10 membered heteroaryl containing 1-4 heteroatoms selected from N, O or S, monocyclic ($C_3$-$C_{10}$)cycloalkyl or 4 to 8 membered heterocycloalkyl containing 1-4 heteroatoms selected from N, O or S and is optionally fused to monocyclic aryl or heteroaryl as defined above and can contain one to two —CO— groups in the ring;

$R^{12}$ is hydrogen, ($C_1$-$C_6$) unsubstituted saturated alkyl, hydroxy, unsubstituted saturated ($C_1$-$C_6$) alkoxy, halogen, halo substituted ($C_1$-$C_6$) saturated alkyl, or unsubstituted saturated ($C_1$-$C_6$) haloalkoxy;

$R^{14}$ is hydrogen, ($C_1$-$C_6$) unsubstituted saturated alkyl, hydroxy, —O($C_1$-$C_6$) unsubstituted saturated alkyl, halogen, unsubstituted saturated ($C_1$-$C_6$) haloalkyl, or unsubstituted saturated ($C_1$-$C_6$) haloalkoxy;

$L^1$ is —C(O)— or —$SO_2$—;

$L^4$ is a bond, —O—, —NH—, or methylene;

ring A is azetidinyl, pyrrolidinyl, piperidinyl, or piperazinyl optionally substituted with methyl or fluoro;

$L^{11}$ is —O—, —CO—, —$CH_2$—, —S—, —SO—, —$SO_2$—, —$NR^{15C}$—, —$NR^{15C}CO$—, —$CONR^{15C}$—, —$NR^{15C}SO_2$—, —$SO_2NR^{15C}$—, or —$NR^{15C}CONR^{15D}$—, wherein each $R^{15C}$ and $R^{15D}$ is independently hydrogen or $C_1$-$C_6$ unsubstituted saturated alkyl;

$R^{23}$ is hydrogen, ($C_1$-$C_6$) unsubstituted saturated alkyl, hydroxy, unsubstituted saturated ($C_1$-$C_6$) alkoxy, halo, unsubstituted saturated ($C_1$-$C_6$) haloalkyl, unsubstituted saturated ($C_1$-$C_6$) haloalkoxy, carboxy, —COO—($C_1$-$C_6$) unsubstituted saturated alkyl, cyano, —$CONH_2$, or —$NR^xR^y$ where $R^x$ is hydrogen and $R^y$ is hydrogen, ($C_1$-$C_6$) unsubstituted saturated alkyl, unsubstituted saturated ($C_3$-$C_6$) cycloalkyl, unsubstituted saturated ($C_3$-$C_6$)cycloalkyl-($C_1$-$C_6$) unsubstituted saturated alkyl, —COR wherein R is ($C_1$-$C_6$) unsubstituted saturated alkyl, or —$SO_2$—($C_1$-$C_6$) unsubstituted saturated alkyl;

$R^2$ and $R^3$ are independently ($C_1$-$C_6$) unsubstituted saturated alkyl, unsubstituted saturated ($C_1$-$C_6$) haloalkoxy, ($C_1$-$C_6$) saturated alkyl which is substituted with one, two, or three substituents independently selected from hydroxyl, unsubstituted saturated ($C_1$-$C_6$) alkoxy, carboxy, cyano, —COO—($C_1$-$C_6$) unsubstituted saturated alkyl, —S—($C_1$-$C_6$) unsubstituted saturated alkyl, —$SO_2$—($C_1$-$C_6$) unsubstituted saturated alkyl, halo, —CONR"R' or NR"R' where each R" is hydrogen, ($C_1$-$C_6$) unsubstituted saturated alkyl, ($C_3$-$C_6$) unsubstituted saturated cycloalkyl, ($C_1$-$C_6$) saturated alkyl substituted with one, two, or three hydroxy or one to three unsubstituted saturated ($C_1$-$C_6$) alkoxy and R' is hydrogen, ($C_1$-$C_6$) unsubstituted saturated alkyl, unsubstituted saturated ($C_3$-$C_6$) cycloalkyl or 4 to 8 membered heterocycloalkyl containing 1-4 heteroatoms selected from N, O or S and which is optionally substituted with one or two groups independently selected from ($C_1$-$C_6$) unsubstituted saturated alkyl, hydroxyl, unsubstituted saturated ($C_1$-$C_6$) alkoxy, —S—($C_1$-$C_6$) unsubstituted saturated alkyl, —$SO_2$—($C_1$-$C_6$) unsubstituted saturated alkyl, or halo, or $R^2$ and $R^3$ together with the carbon atom to which they are attached form ($C_3$-$C_6$) unsubstituted saturated cycloalkyl; and $R^4$ is $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl, wherein $R^{18}$ is independently halogen, —CN, —OH, —SH, —$NH_2$, —COOH, —$NO_2$, —$CONH_2$, —$CF_3$, unsubstituted alkyl, unsubstituted heteroalkyl, unsubstituted cycloalkyl, unsubstituted heterocycloalkyl, unsubstituted aryl, or unsubstituted heteroaryl.

2. The compound of claim 1, wherein $L^{11}$ is —O—.

3. The compound of claim 2, wherein $R^{12}$ is absent, methyl, fluoro, or trifluoromethyl.

4. The compound of claim 3, wherein $R^{14}$ is independently absent, unsubstituted saturated ($C_1$-$C_6$) alkyl, unsubstituted saturated ($C_1$-$C_6$) alkoxy, halo, unsubstituted saturated ($C_1$-$C_6$) haloalkyl or unsubstituted saturated ($C_1$-$C_6$) haloalkoxy.

5. The compound of claim 4, wherein $R^{23}$ is independently absent, unsubstituted saturated ($C_1$-$C_6$) alkyl, unsubstituted saturated ($C_1$-$C_6$) alkoxy, halo, unsubstituted saturated ($C_1$-$C_6$) haloalkyl, unsubstituted saturated ($C_1$-$C_6$) haloalkoxy, or cyano.

6. The compound of claim 5, wherein $L^4$ is a bond or methylene.

7. The compound of claim 6, wherein $L^1$ is —C(O)— and ring A is piperidinyl optionally substituted with methyl or fluoro.

8. The compound of claim 7, wherein $R^2$ and $R^3$ are independently unsubstituted saturated $C_1$-$C_6$ alkyl or together form ($C_3$-$C_6$) unsubstituted saturated cycloalkyl.

9. The compound of claim 8, wherein Ar is unsubstituted phenyl or phenyl substituted at least one of a meta or para position.

10. A pharmaceutical composition comprising a compound of claim 1 or a pharmaceutically acceptable salt thereof, and a pharmaceutically acceptable excipient.

11. A method for treating leukemia, multiple myeloma, lymphoma, non-small cell lung cancer, pancreatic cancer or rheumatoid arthritis, said method comprising administering to a subject in need thereof an effective amount of a compound of claim 1.

12. The compound according to claim 1, said compound selected from the group consisting of:

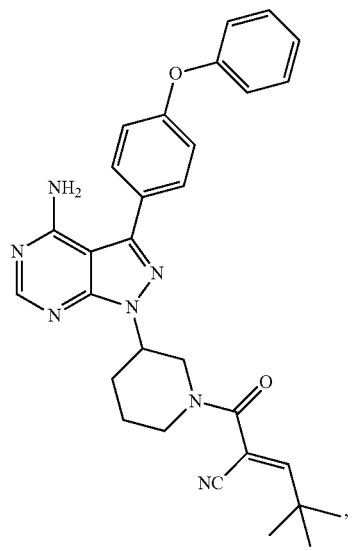

195
-continued
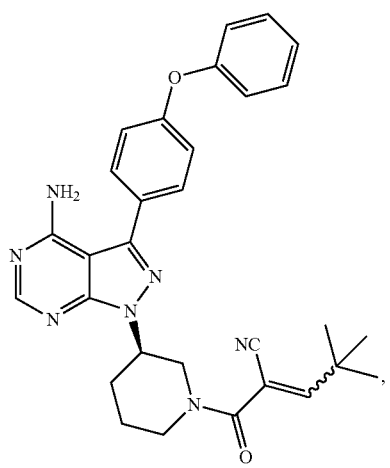
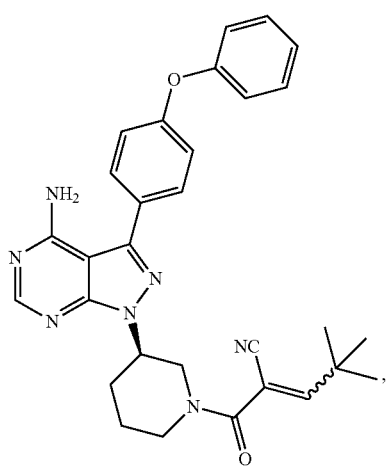
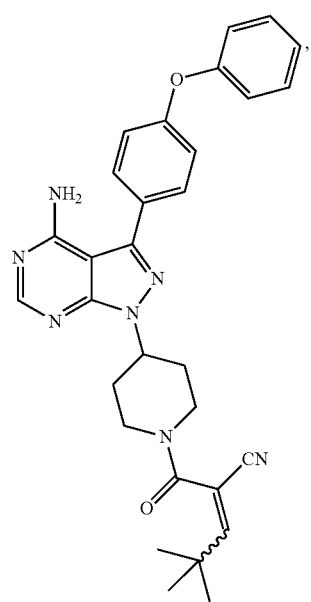
196
-continued
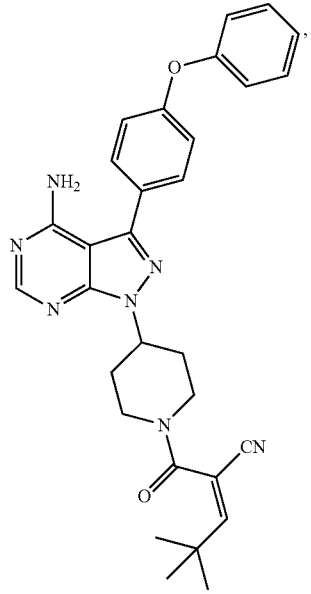
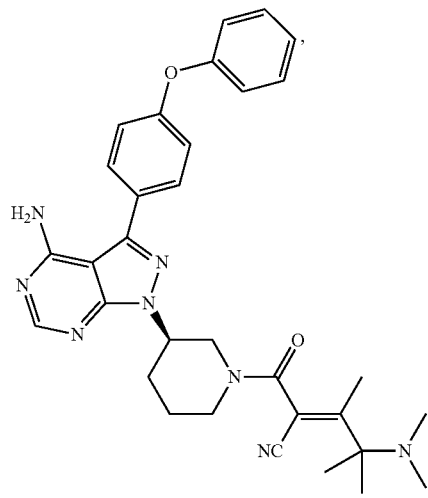
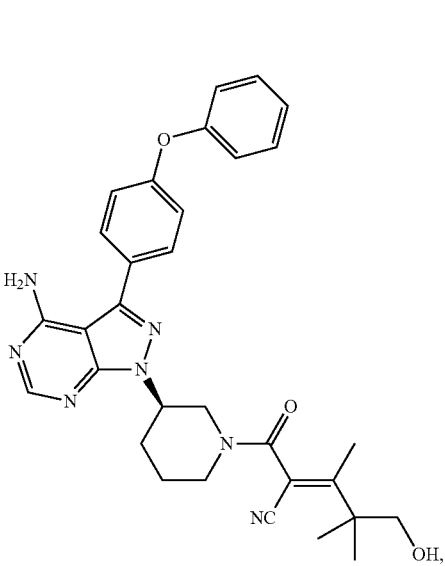

197
-continued
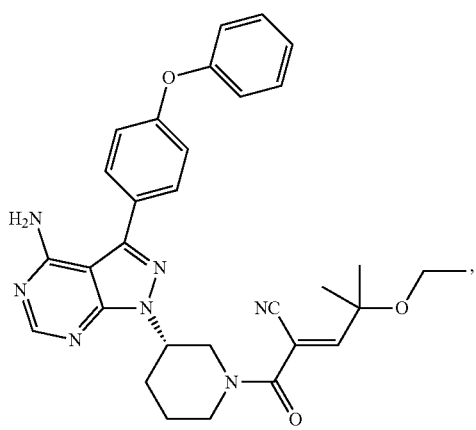
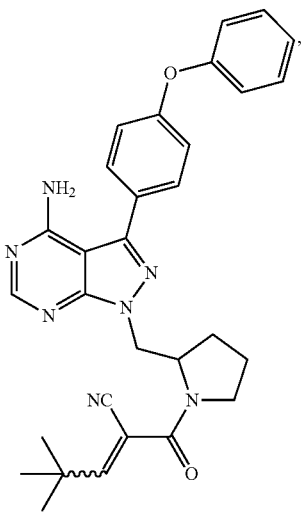
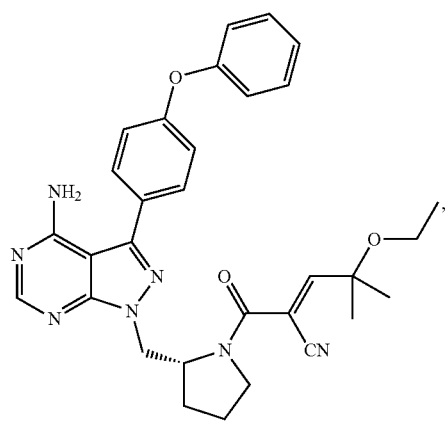
198
-continued
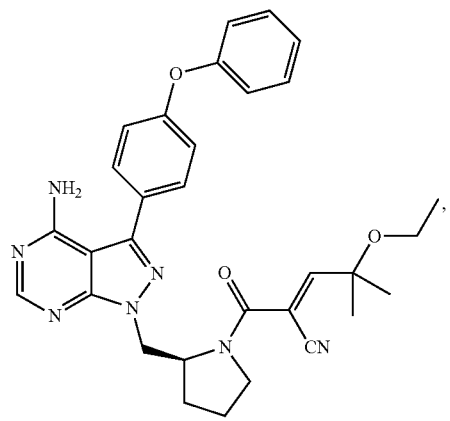
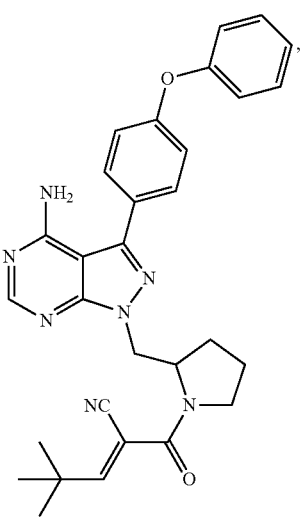
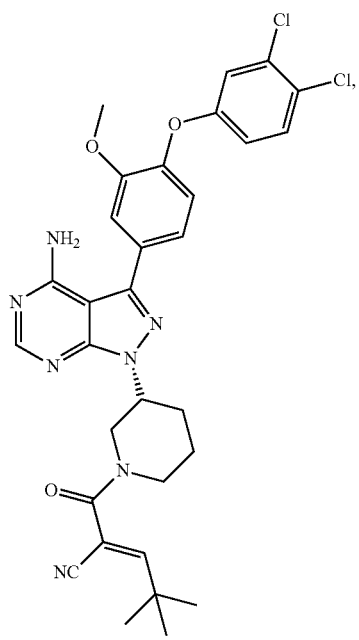

199
-continued
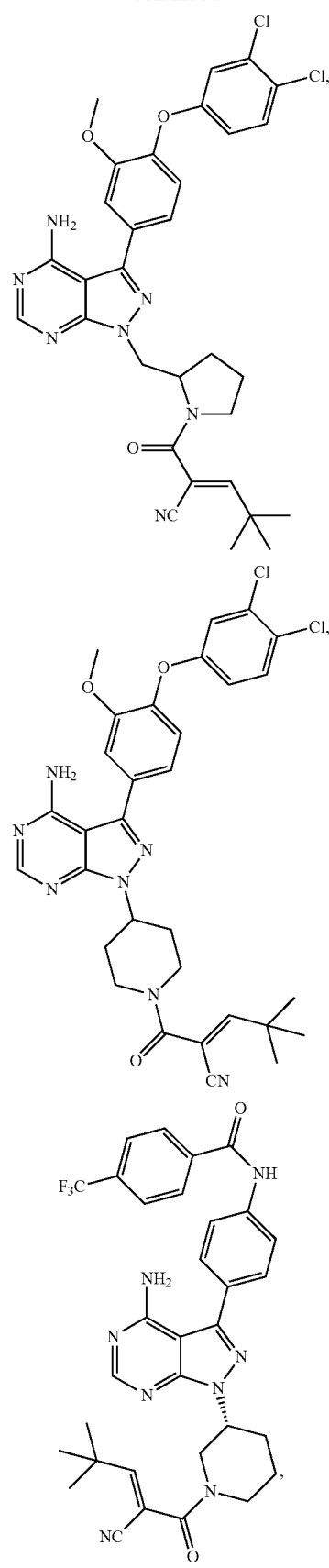
200
-continued
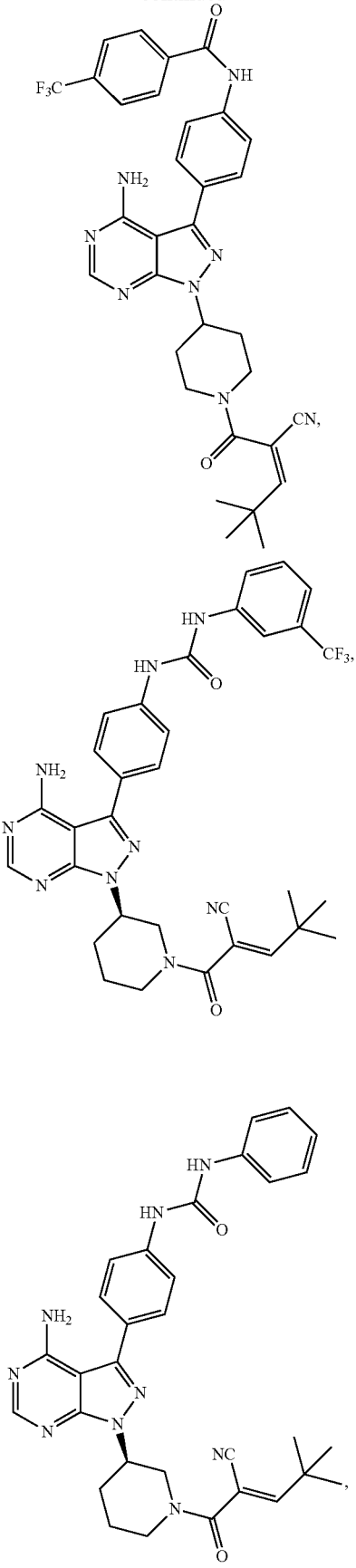

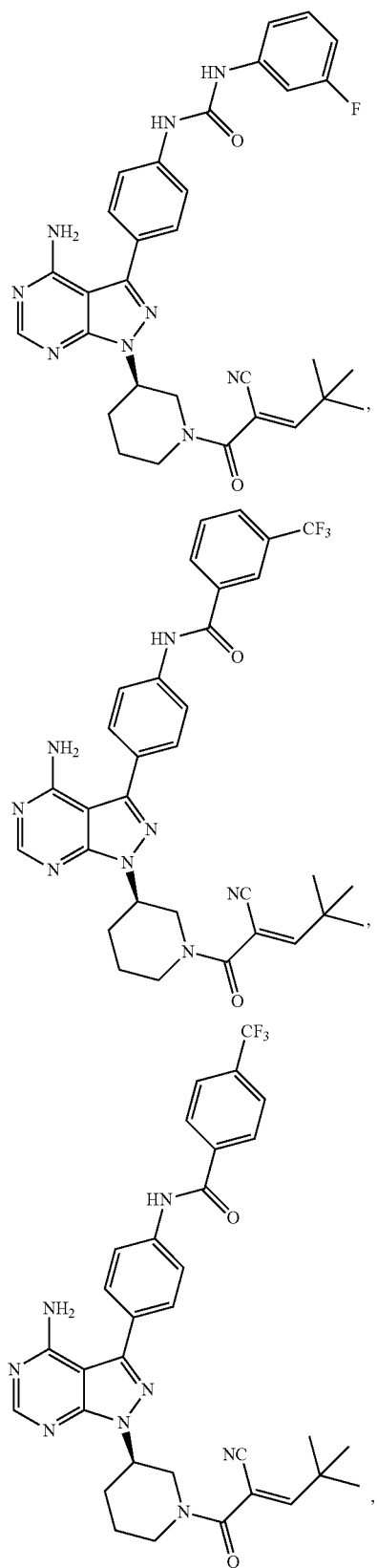
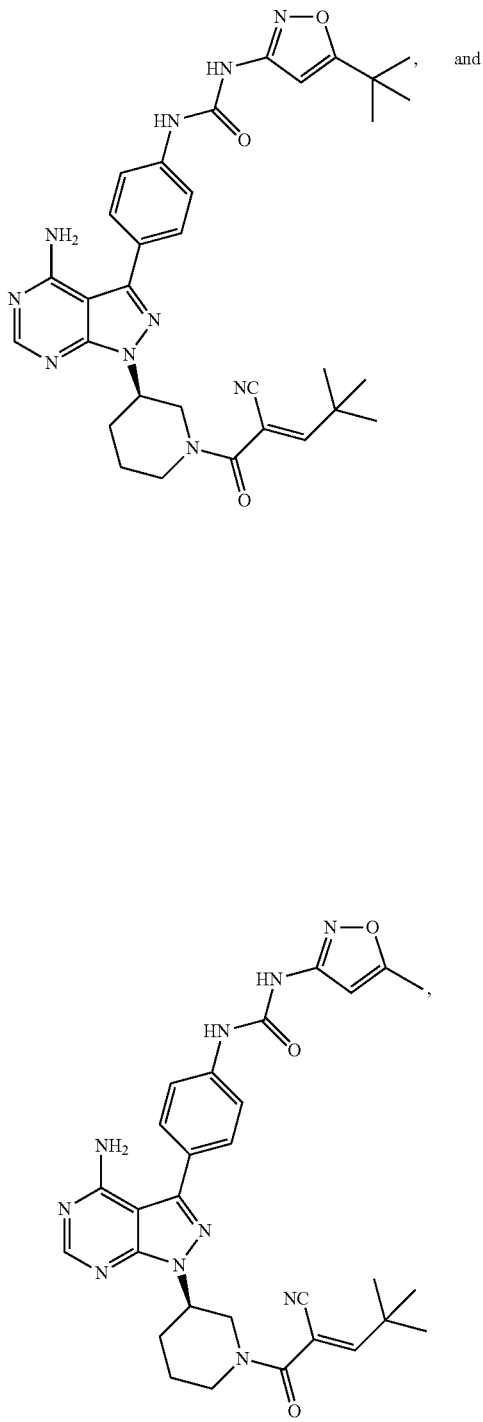
* * * * *

UNITED STATES PATENT AND TRADEMARK OFFICE
CERTIFICATE OF CORRECTION

PATENT NO. : 9,580,427 B2
APPLICATION NO. : 14/118541
DATED : February 28, 2017
INVENTOR(S) : John William Taunton, Jr. et al.

It is certified that error appears in the above-identified patent and that said Letters Patent is hereby corrected as shown below:

In the Specification

At Column 193, Line 1, delete "-N- or -CH-," and insert the following: --N or C,--

Signed and Sealed this
Sixth Day of May, 2025

Coke Morgan Stewart
*Acting Director of the United States Patent and Trademark Office*